US011261192B2

(12) United States Patent
Huang et al.

(10) Patent No.: US 11,261,192 B2
(45) Date of Patent: Mar. 1, 2022

(54) SUBSTITUTED 1,2-DIHYDRO-3H-PYRAZOLO[3,4-D] PYRIMIDIN-3-ONES

(71) Applicant: Recurium IP Holdings, LLC, San Diego, CA (US)

(72) Inventors: Peter Qinhua Huang, San Diego, CA (US); Kevin Duane Bunker, Escondido, CA (US); Brant Clayton Boren, San Diego, CA (US); Sayee Gajanan Hegde, San Diego, CA (US); Hui Liu, San Diego, CA (US); Aditya Krishnan Unni, San Diego, CA (US); Sunny Abraham, San Diego, CA (US); Chad Daniel Hopkins, San Diego, CA (US); Sunil Paliwal, Monroe Township, NJ (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/971,254

(22) PCT Filed: Feb. 26, 2019

(86) PCT No.: PCT/US2019/019557
§ 371 (c)(1),
(2) Date: Aug. 19, 2020

(87) PCT Pub. No.: WO2019/173082
PCT Pub. Date: Sep. 12, 2019

(65) Prior Publication Data
US 2021/0139482 A1 May 13, 2021

Related U.S. Application Data

(60) Provisional application No. 62/641,149, filed on Mar. 9, 2018, provisional application No. 62/755,163, filed on Nov. 2, 2018.

(51) Int. Cl.
*C07D 487/04* (2006.01)
*C07D 491/048* (2006.01)

(52) U.S. Cl.
CPC ....... *C07D 487/04* (2013.01); *C07D 491/048* (2013.01)

(58) Field of Classification Search
CPC .......................... C07D 487/04; C07D 491/048
See application file for complete search history.

(56) References Cited

U.S. PATENT DOCUMENTS

| 7,507,748 | B2 | 3/2009 | Yuan |
| 2007/0254892 | A1 | 11/2007 | Sagara et al. |
| 2010/0003191 | A1 | 1/2010 | Ono |
| 2010/0029707 | A1 | 2/2010 | Uchikawa et al. |
| 2013/0182202 | A1 | 7/2013 | Archetti et al. |
| 2017/0174703 | A1 | 6/2017 | Wu et al. |
| 2017/0294582 | A1 | 10/2017 | Stoessel et al. |
| 2018/0130964 | A1 | 5/2018 | Kim et al. |
| 2018/0179238 | A1 | 6/2018 | Lee et al. |
| 2018/0254418 | A1 | 9/2018 | Yoon et al. |
| 2018/0305386 | A1 | 10/2018 | Lee et al. |
| 2018/0337350 | A1 | 11/2018 | Li et al. |
| 2019/0106427 | A1 | 4/2019 | Chakravarty et al. |
| 2020/0308207 | A1 | 10/2020 | Kim et al. |

FOREIGN PATENT DOCUMENTS

| AU | 2008315048 | 4/2009 |
| AU | 2008315048 A1 | 4/2009 |
| CN | 103864792 | 6/2014 |
| CN | 108794484 | 11/2018 |
| CN | 108794493 | 11/2018 |
| CN | 109651337 | 4/2019 |
| EP | 3244466 | 11/2017 |
| EP | 3544076 | 9/2019 |
| KR | 2020029946 | 3/2020 |
| WO | WO 2005/028434 | 3/2005 |
| WO | WO 2005/095387 | 10/2005 |
| WO | WO 2006/064251 | 6/2006 |
| WO | WO 2007/035963 | 3/2007 |
| WO | WO 2007/126122 | 11/2007 |
| WO | WO 2008/051493 | 5/2008 |
| WO | WO 2008/068974 | 6/2008 |
| WO | WO 2008/069311 | 6/2008 |
| WO | WO 2009/054332 | 4/2009 |
| WO | WO 2009/076502 | 6/2009 |
| WO | WO 2010/045306 | 4/2010 |
| WO | WO 2010/132015 | 11/2010 |
| WO | WO 2011/146401 | 11/2011 |
| WO | WO 2012/038026 | 3/2012 |
| WO | WO 2013/000994 | 1/2013 |
| WO | WO 2013/059396 | 4/2013 |

(Continued)

OTHER PUBLICATIONS

CAS Reg. No. 955365-80-7, Entered Nov. 21, 2007.
Matheson et al., "A WEE1 Inhibitor Analog of AZD1775 Maintains Synergy with Cisplatin and Demonstrates Reduced Single-Agent Cytotoxicity in Medulloblastoma Cells" ACS Chemical Biology (2016) 11(4):921-930.
Matheson et al., "A WEE1 Inhibitor Analog of AZD1775 Maintains Synergy with Cisplatin and Demonstrates Reduced Single-Agent Cytotoxicity in Medulloblastoma Cells" ACS Chemical Biology (2016) 11(7):2066-2067.

(Continued)

Primary Examiner — Erich A Leeser
(74) Attorney, Agent, or Firm — Knobbe, Martens, Olson & Bear, LLP

(57) ABSTRACT

Compounds of Formula (I) are provided herein. Such compounds, as well as pharmaceutically acceptable salts and compositions thereof, are useful for treating diseases or conditions, including conditions characterized by excessive cellular proliferation, such as breast cancer.

27 Claims, No Drawings

(56) References Cited

FOREIGN PATENT DOCUMENTS

| WO | WO 2014/062454 | | 4/2014 | | |
|---|---|---|---|---|---|
| WO | WO 2014/134240 | | 9/2014 | | |
| WO | WO 2014/134308 | | 9/2014 | | |
| WO | WO 2014/183825 | | 11/2014 | | |
| WO | WO 2015/144001 | | 10/2015 | | |
| WO | WO 2016/022626 | | 2/2016 | | |
| WO | WO 2016/034262 | | 3/2016 | | |
| WO | WO 2016/138821 | | 9/2016 | | |
| WO | WO 2017/075629 | | 5/2017 | | |
| WO | WO 2017/161028 | | 9/2017 | | |
| WO | WO 2017/214491 | | 12/2017 | | |
| WO | WO 2018/011569 | | 1/2018 | | |
| WO | WO 2018/133829 | | 7/2018 | | |
| WO | WO 2019/028008 | | 2/2019 | | |
| WO | WO 2019/037678 | * | 2/2019 | ........... | C07D 471/04 |
| WO | WO 2019/096322 | | 5/2019 | | |
| WO | WO 2019/134539 | | 7/2019 | | |
| WO | WO 2019/165204 | | 8/2019 | | |
| WO | WO 2019/169065 | | 9/2019 | | |
| WO | WO 2019/173082 | | 9/2019 | | |
| WO | WO 2020/210320 | | 10/2020 | | |
| WO | WO 2020/259724 | | 12/2020 | | |
| WO | WO 2021/127044 | | 6/2021 | | |
| WO | WO 2021/127045 | | 6/2021 | | |
| WO | WO 2021/127047 | | 6/2021 | | |

OTHER PUBLICATIONS

Matheson et al., "Development of Potent Pyrazolopyrimidinone-Based WEE1 Inhibitors with Limited Single-Agent Cytotoxicity for Cancer Therapy" Chem. Med. Chem. (2018) 13(16):1681-1694.
Sutherland et al., "A Robust High-Content Imaging Approach for Probing the Mechanism of Action and Phenotypic Outcomes of Cell-Cycle Modulators" Molecular Cancer Therapeutics (2011) 10(2):242-254.
Wright et al., "Dual Targeting of WEE1 and PLK1 by AZD1775 Elicits Single Agent Cellular Anticancer Activity" ACS Chemical Biology (2017) 12(7), 1883-1892.
Matheson et al., "A WEE1 Inhibitor Analog of AZD1775 Maintains Synergy with Cisplatin and Demonstrates Reduced Single-Agent Cytotoxicity in Medulloblastoma Cells" ACS Chem. Biol. (2016) 11:2066-2067.
International Search Report and Written Opinion dated May 16, 2019 for PCT Application No. PCT/US2019/019557; dated Feb. 26, 2019.
International Preliminary Report on Patentability dated Sep. 15, 2020 for PCT Application No. PCT/US2019/019557; dated Feb. 26, 2019.

* cited by examiner

SUBSTITUTED 1,2-DIHYDRO-3H-PYRAZOLO[3,4-D] PYRIMIDIN-3-ONES

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Applications Nos. 62/641,149, filed Mar. 9, 2018, and 62/755,163, filed Nov. 2, 2018.

FIELD

The present application relates to compounds that are WEE1 inhibitors and methods of using them to treat conditions characterized by excessive cellular proliferation, such as cancer.

DESCRIPTION

WEE1 kinase plays a role in the G2-M cell-cycle checkpoint arrest for DNA repair before mitotic entry. Normal cells repair damaged DNA during G1 arrest. Cancer cells often have a deficient G1-S checkpoint and depend on a functional G2-M checkpoint for DNA repair. WEE1 is overexpressed in various cancer types.

SUMMARY

Some embodiments provide a compound of Formula (I), or a pharmaceutically acceptable salt thereof.

Some embodiments disclosed herein relate to a pharmaceutical composition that can include an effective amount of one or more of compounds of Formula (I), or a pharmaceutically acceptable salt thereof, and a pharmaceutically acceptable carrier, diluent, excipient or combination thereof.

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating or treating a cancer described herein that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating or treating a cancer described herein that can include contacting a malignant growth or a tumor, wherein the malignant growth or tumor is due to a cancer described herein.

Some embodiments described herein relate to a method for inhibiting the activity of WEE1 in a cell (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

Some embodiments described herein relate to a method for ameliorating or treating a cancer described herein that can include inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) using an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

DETAILED DESCRIPTION

WEE1 is a tyrosine kinase that is a critical component of the ATR-mediated G2 cell cycle checkpoint control that prevents entry into mitosis in response to cellular DNA damage. ATR phosphorylates and activates CHK1, which in turn activates WEE1, leading to the selective phosphorylation of cyclin-dependent kinase 1 (CDK1) at Tyr15, thereby stabilizing the CDK1-cyclin B complex and halting cell-cycle progression. This process confers a survival advantage by allowing tumor cells time to repair damaged DNA prior to entering mitosis. Inhibition of WEE1 abrogates the G2 checkpoint, promoting cancer cells with DNA damage to enter into unscheduled mitosis and undergo cell death via mitotic catastrophe. Therefore, WEE1 inhibition has the potential to sensitize tumors to DNA-damaging agents, such as cisplatin, and to induce tumor cell death.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, hydroxyalkyl, haloalkoxy, an amino, a mono-substituted amine group, a di-substituted amine group and an amine ($C_1$-$C_6$ alkyl).

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

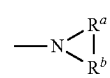

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups and cycloalkenyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

As used herein, "lower alkylene groups" are straight-chained —CH$_2$-tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group

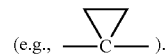

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (iso-propoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—NO$_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —NH$_2$ group.

A "mono-substituted amine" group refers to a "—NHR$_A$" group in which R$_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The R$_A$ may be substituted or unsubstituted. Examples of mono-substituted amino groups include, but are not limited to, —NH(methyl), —NH(phenyl) and the like.

A "di-substituted amine" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_A$ and R$_B$ can independently be substituted or unsubstituted. Examples of di-substituted amino groups include, but are not limited to, —N(methyl)$_2$, —N(phenyl)(methyl), —N(ethyl)(methyl) and the like.

As used herein, "amine(alkyl)" group refers to an -(alkylene)-NR'R" radical where R' and R" are independently hydrogen or alkyl as defined herein. An amine(alkyl) may be substituted or unsubstituted. Examples of amine(alkyl) groups include, but are not limited to, —CH$_2$NH(methyl), —CH$_2$NH(phenyl), —CH$_2$CH$_2$NH(methyl), —CH$_2$CH$_2$NH(phenyl), —CH$_2$N(methyl)$_2$, —CH$_2$N(phenyl)(methyl), —NCH$_2$(ethyl)(methyl), —CH$_2$CH$_2$N(methyl)$_2$, —CH$_2$CH$_2$N(phenyl)(methyl), —NCH$_2$CH$_2$(ethyl)(methyl) and the like.

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine and salts with amino acids such as arginine and lysine. For compounds of Formula (I), those skilled in the art understand that when a salt is formed by protonation of a nitrogen-based group (for example, NH$_2$), the nitrogen-based group can be associated with a positive charge (for example, NH$_2$ can become NH$_3^+$) and the positive charge can be balanced by a negatively charged counterion (such as Cl$^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to a compound of Formula (I), or a pharmaceutically acceptable salt thereof, having the structure:

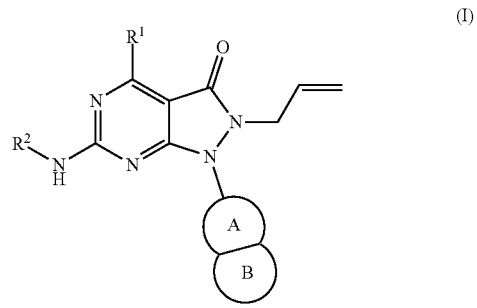

wherein: $R^1$ can be selected from hydrogen, halogen and a substituted or unsubstituted $C_1$-$C_6$ alkyl; Ring A can be selected from a substituted or unsubstituted phenyl and a substituted or unsubstituted 5-6 membered monocyclic heteroaryl; Ring B can be selected from a substituted or unsubstituted monocyclic 5-7 membered carbocyclyl and a substituted or unsubstituted 5-7 membered monocyclic heterocyclyl; $R^2$ can be selected from

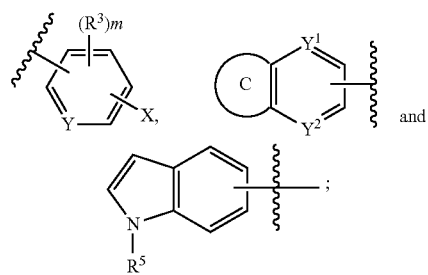

m can be 0, 1, 2 or 3; $R^3$ can be selected from halogen and a substituted or unsubstituted $C_1$-$C_6$ alkyl; X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl; Y can be CH or N (nitrogen); $Y^1$ can be $CR^{4A}$ or N (nitrogen); $Y^2$ can be $CR^{4B}$ or N (nitrogen); Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl; $R^{4A}$ and $R^{4B}$ can be independently selected from hydrogen, halogen and an unsubstituted $C_{1-4}$ alkyl; and $R^5$ can be a substituted or unsubstituted 5-7 membered monocyclic heterocyclyl.

Some embodiments disclosed herein relate to a compound of Formula (I), or a pharmaceutically acceptable salt thereof, wherein: $R^1$ can be selected from hydrogen, halogen and a substituted or unsubstituted $C_1$-$C_6$ alkyl; Ring A can be selected from a substituted or unsubstituted phenyl and a substituted or unsubstituted 5-6 membered monocyclic heteroaryl; Ring B can be selected from a substituted or unsubstituted monocyclic 5-7 membered carbocyclyl and a substituted or unsubstituted 5-7 membered monocyclic heterocyclyl; $R^2$ can be selected from

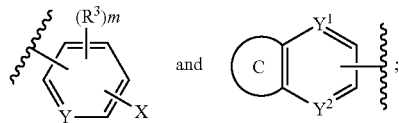

m can be 0, 1, 2 or 3; $R^3$ can be selected from halogen and a substituted or unsubstituted $C_1$-$C_6$ alkyl; X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl; Y can be CH or N (nitrogen); $Y^1$ can be $CR^{4A}$ or N (nitrogen); $Y^2$ can be $CR^{4B}$ or N (nitrogen); Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl; and $R^{4A}$ and $R^{4B}$ can be independently selected from hydrogen, halogen and an unsubstituted $C_1$-4 alkyl.

In some embodiments, $R^1$ can be selected from the group consisting of hydrogen, halogen and a substituted or unsubstituted $C_1$-$C_6$ alkyl. In some embodiments, Ring A can be selected from the group consisting of a substituted or unsubstituted phenyl and a substituted or unsubstituted 5-6 membered monocyclic heteroaryl. In some embodiments, Ring B can be selected from the group consisting of a substituted or unsubstituted monocyclic 5-7 membered carbocyclyl and a substituted or unsubstituted 5-7 membered monocyclic heterocyclyl. In some embodiments, $R^2$ can be selected from the group consisting of

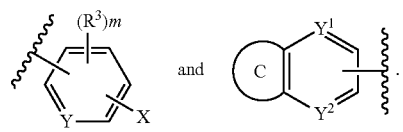

In some embodiments, m can be 0, 1, 2 or 3. In some embodiments, $R^3$ can be selected from the group consisting of halogen and a substituted or unsubstituted $C_1$-$C_6$ alkyl. In some embodiments, X can be selected from the group consisting of hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl. In some embodiments, Y can be CH or N. In some embodiments, $Y^1$ can be $CR^{4A}$ or N. In some embodiments, $Y^2$ can be $CR^{4B}$ or N. In some embodiments, Ring C can be selected from the group consisting of a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl. In some embodiments, $R^{4A}$ and $R^{4B}$ are independently selected from the group consisting of hydrogen, halogen and an unsubstituted $C_{1-4}$ alkyl.

In some embodiments, $R^1$ can be selected from hydrogen, halogen and $C_1$-$C_6$ alkyl. In some embodiments, $R^1$ can be hydrogen. In other embodiments, $R^1$ can be halogen. In some embodiments, $R^1$ can be fluoro. In still other embodiments, $R^1$ can be an unsubstituted $C_1$-$C_6$ alkyl (such as methyl, ethyl, n-propyl, iso-propyl, n-butyl, iso-butyl, sec-butyl, t-butyl, pentyl (straight chain or branched) or hexyl (straight chain or branched)). In some embodiments, $R^1$ can be an unsubstituted methyl. In some embodiments, $R^1$ can be a substituted $C_1$-$C_6$ alkyl, such as those described herein. In some embodiments, $R^1$ can be an unsubstituted $C_1$-$C_6$ haloalkyl (such as a $C_1$-$C_6$ fluoroalkyl, a $C_1$-$C_6$ chloroalkyl or a $C_1$-$C_6$ chlorofluoroalkyl). In some embodiments, $R^1$ can be —$CHF_2$, —$CF_3$, —$CF_2CH_3$ or —$CH_2CF_3$.

In some embodiments, Ring A can be selected from a substituted or unsubstituted phenyl and a substituted or unsubstituted 5-6 membered monocyclic heteroaryl.

In some embodiments, Ring A can be a substituted phenyl. In other embodiments, Ring A can be an unsubstituted phenyl.

In some embodiments, Ring A can be a substituted 5-6 membered monocyclic heteroaryl. In some embodiments, Ring A can be an unsubstituted 5-6 membered monocyclic heteroaryl. In some embodiments, Ring A can be selected from a substituted or unsubstituted pyrrole, a substituted or unsubstituted furan, a substituted or unsubstituted thiophene, a substituted or unsubstituted imidazole, a substituted or unsubstituted pyrazole, a substituted or unsubstituted oxazole, a substituted or unsubstituted thiazole, a substituted or unsubstituted pyridine, a substituted or unsubstituted pyrazine, a substituted or unsubstituted pyrimidine and a substituted or unsubstituted pyridazine.

When substituted, Ring A can be substituted with one or more substituents selected from halogen, an unsubstituted $C_1$-$C_4$ haloalkyl and an unsubstituted $C_1$-$C_4$ alkyl. In some embodiments, Ring A is mono-substituted with a halogen (for example, fluoro).

In some embodiments,

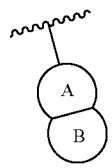

can be selected from:

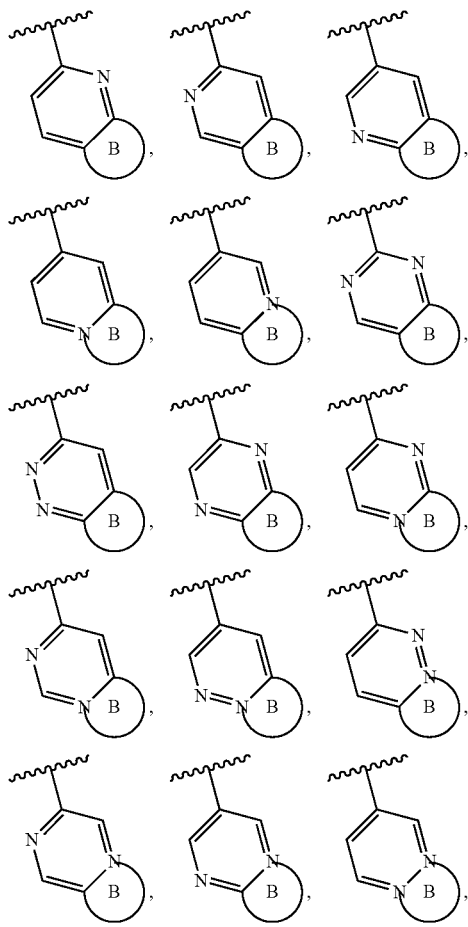

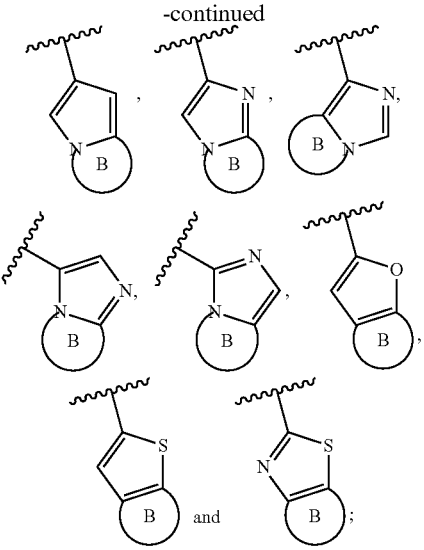

wherein each of the aforementioned groups are substituted or unsubstituted. In some embodiments,

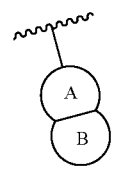

can be a substituted or unsubstituted

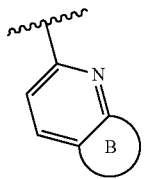

In some embodiments,

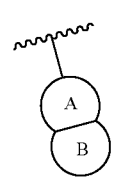

can be a substituted or unsubstituted

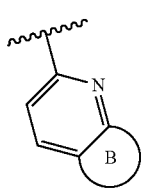

wherein the Ring A is unsubstituted. In other embodiments,

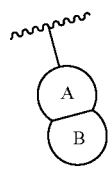

can be selected from a substituted or unsubstituted

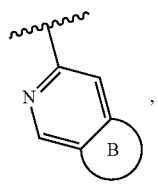

a substituted or unsubstituted

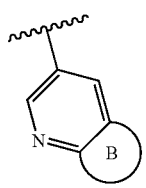

and a substituted or unsubstituted

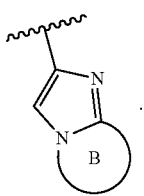

As described herein, the Ring A portion of

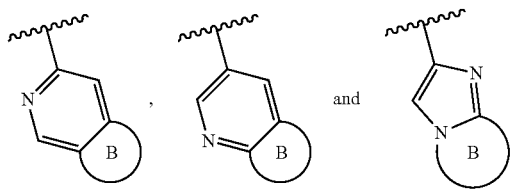

can be unsubstituted.

In some embodiments, Ring B can be selected from a substituted or unsubstituted monocyclic 5-7 membered carbocyclyl and a substituted or unsubstituted 5-7 membered monocyclic heterocyclyl.

In some embodiments, Ring B can be a substituted or unsubstituted monocyclic 5-7 membered carbocyclyl. In some embodiments, Ring B can be a substituted or unsubstituted monocyclic 5 membered carbocyclyl. In other embodiments, Ring B can be a substituted or unsubstituted monocyclic 6 membered carbocyclyl. In still other embodiments, Ring B can be a substituted or unsubstituted monocyclic 7 membered carbocyclyl.

In some embodiments,

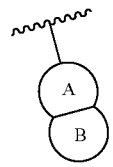

can be selected from:

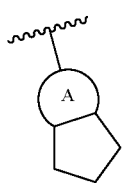, 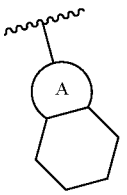 and 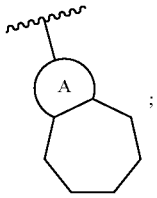;

wherein each of the aforementioned groups are substituted or unsubstituted.

In some embodiments, Ring B can be a substituted or unsubstituted monocyclic 5-7 membered heterocyclyl. In some embodiments, Ring B can be a substituted or unsubstituted monocyclic 5 membered heterocyclyl. In other embodiments, Ring B can be a substituted or unsubstituted monocyclic 6 membered heterocyclyl. In still other embodiments, Ring B can be a substituted or unsubstituted monocyclic 7 membered heterocyclyl.

In some embodiments,

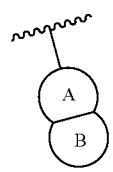

can be selected from:

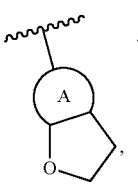, , 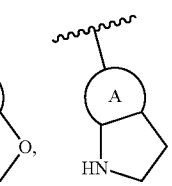,

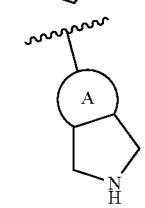, 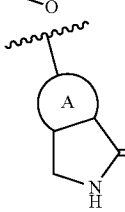

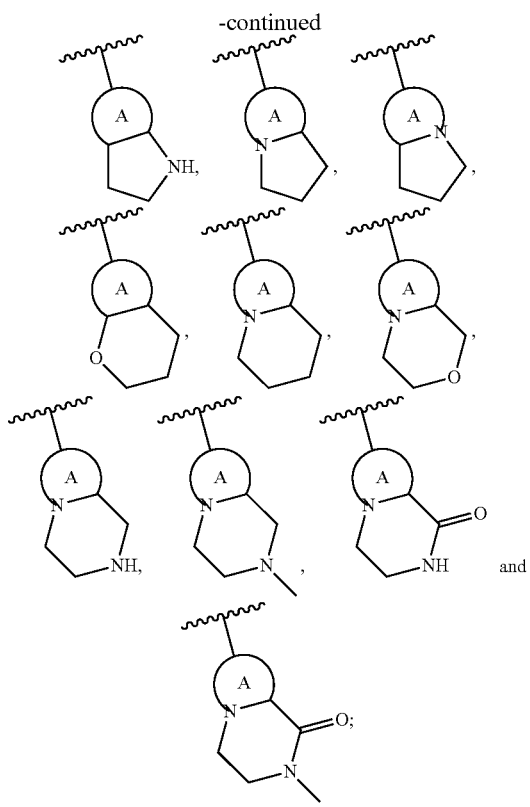

wherein each of the aforementioned groups are substituted or unsubstituted, including any —NH group.

In some embodiments, Ring B can be selected from

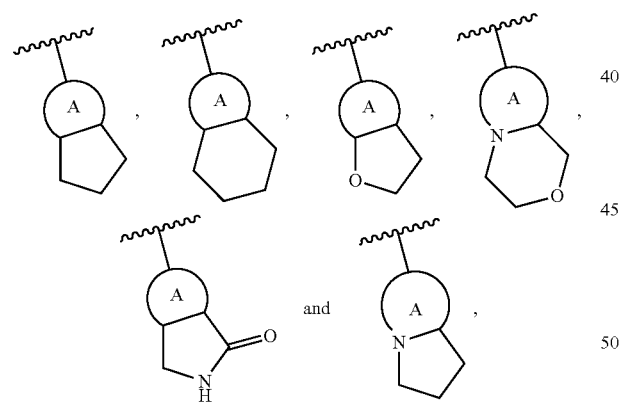

wherein each of the aforementioned groups are substituted or unsubstituted, including any —NH group. In some embodiments, Ring B can be a substituted or unsubstituted

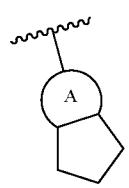

In some embodiments, when Ring B is substituted, Ring B can be substituted with 1, 2 or 3 substituents independently selected from halogen, hydroxy, amino, an unsubstituted N-linked amido (for example, —NHC(O)C$_1$-C$_6$ alkyl), an unsubstituted C$_1$-C$_6$ haloalkyl (such as those described herein) and a substituted or unsubstituted C$_1$-C$_6$ alkyl (such as those described herein). In some embodiments, when Ring B is substituted, Ring B can be substituted with 1, 2 or 3 substituents independently selected from halogen, hydroxy, amino, an unsubstituted N-linked amido (for example, —NHC(O)C$_1$-C$_6$ alkyl) and a substituted or unsubstituted C$_1$-C$_6$ alkyl (such as those described herein). In some embodiments, Ring B can be substituted with 1, 2 or 3 substituents independently selected from fluoro, hydroxy, amino, an unsubstituted —NHC(O)C$_1$-C$_6$ alkyl, an unsubstituted C$_1$-C$_6$ haloalkyl (such as those described herein) and an unsubstituted C$_1$-C$_6$ alkyl (such as those described herein). In some embodiments, Ring B can be substituted with 1 or 2 substituents independently selected from fluoro, hydroxy, —CF$_3$, —CHF$_2$, —CF$_2$CH$_3$, an unsubstituted methyl, an unsubstituted ethyl and —NHC(O)CH$_3$.

In some embodiments,

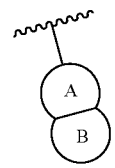

can be selected from:

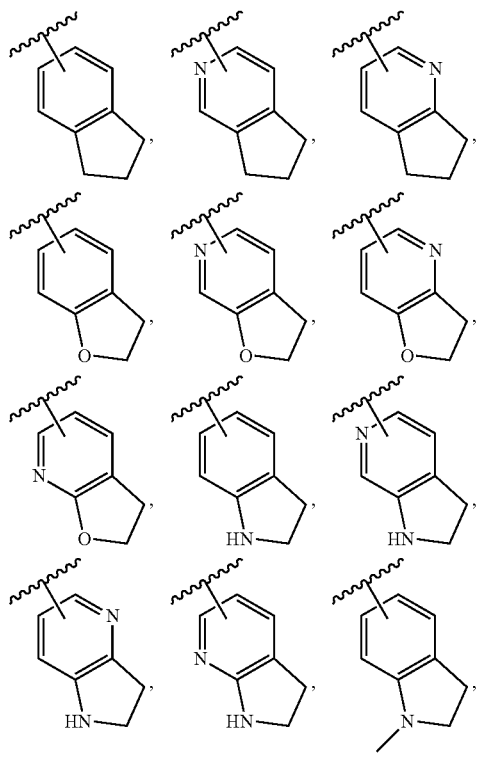

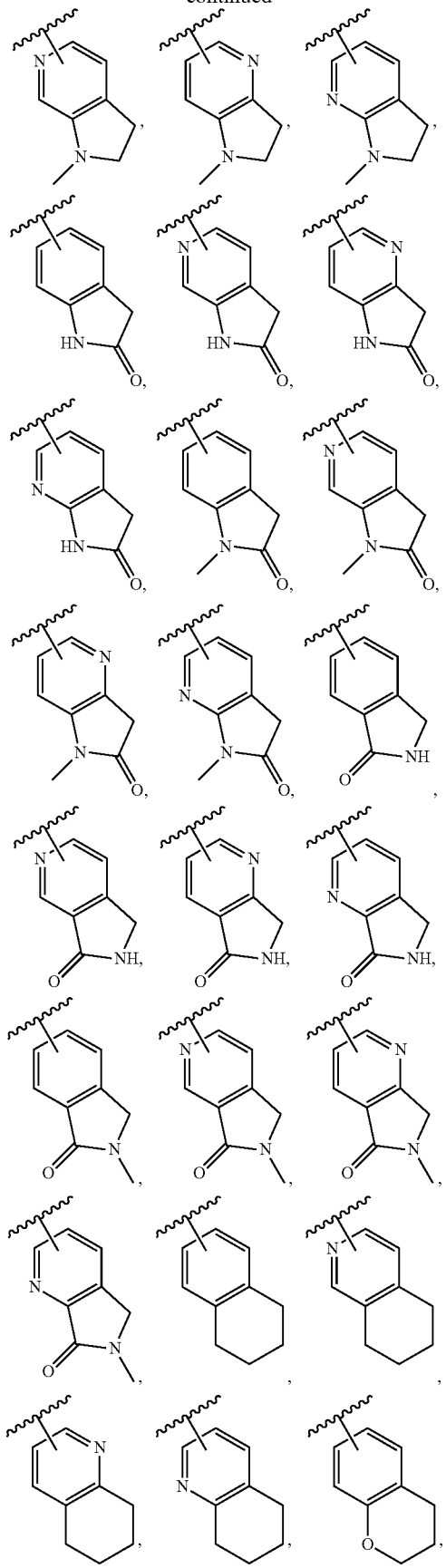
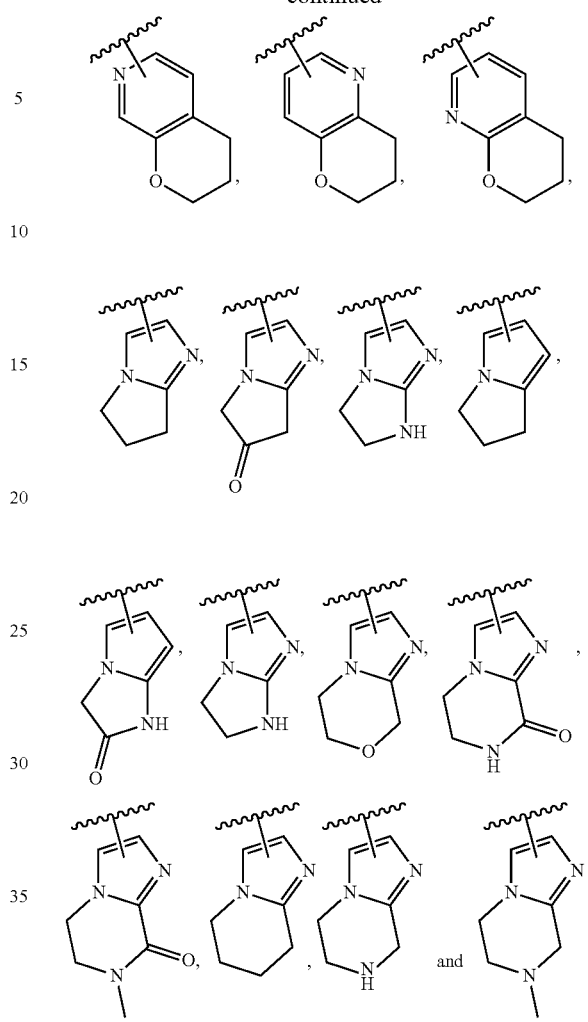
wherein each of the aforementioned groups are substituted or unsubstituted, including any —NH group.
In some embodiments,
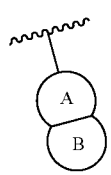
can be selected from:
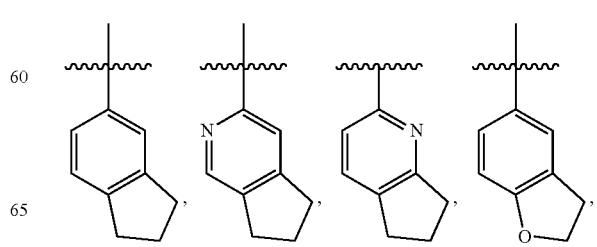

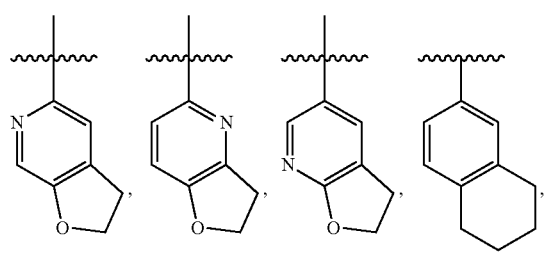
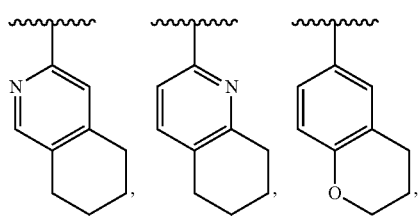
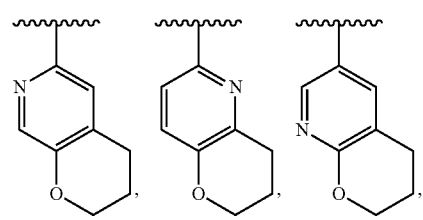
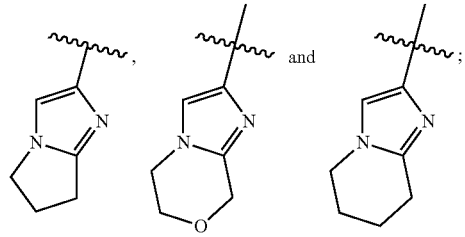
wherein each of the aforementioned groups are substituted or unsubstituted. In some embodiments,
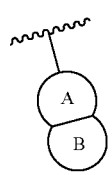
can be selected from:
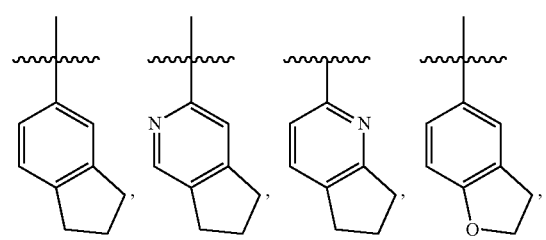
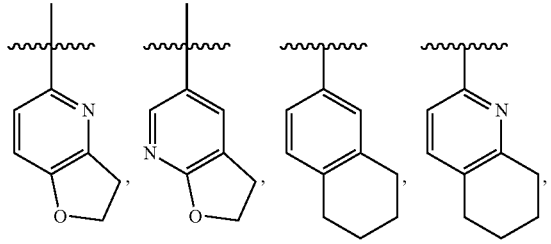
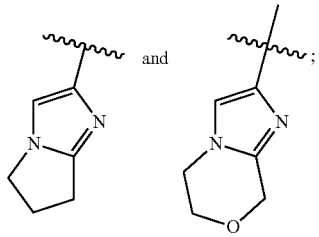
wherein each of the aforementioned groups are substituted or unsubstituted. In some embodiments,
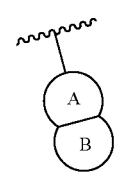
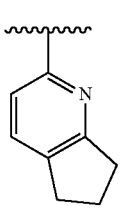
In some embodiments,
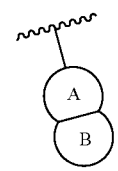
can be a substituted or
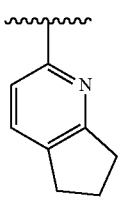
Both Ring A and Ring B can be substituted or unsubstituted. In some embodiments, Ring A and Ring B of

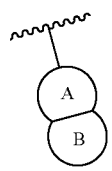

can be independently substituted or unsubstituted. In some embodiments, Ring A and Ring B of

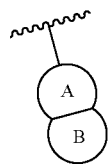

can be both unsubstituted. In some embodiments, Ring A and Ring B of

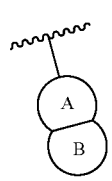

can be both independently substituted. In some embodiments, Ring A of

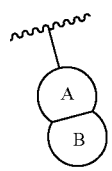

can be substituted and Ring B of

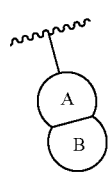

can be unsubstituted. In some embodiments, Ring A of

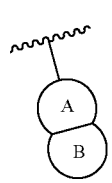

can be unsubstituted and Ring B of

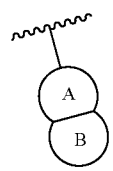

can be substituted. In some embodiments, Ring A of

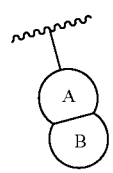

can be unsubstituted and Ring B of

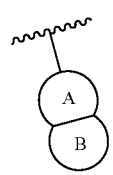

can be substituted with 1, 2 or 3 substituents independently selected from halogen, hydroxy and a substituted or unsubstituted $C_1$-$C_6$ alkyl (such as those described herein). In some embodiments, Ring A of

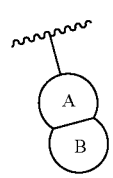

can be unsubstituted and Ring B of

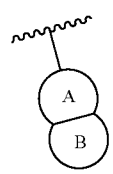

can be substituted with 1, 2 or 3 substituents independently selected from fluoro, hydroxy, amino, an unsubstituted N-linked amido (for example, —NHC(O)$C_1$-$C_6$ alkyl), an unsubstituted $C_1$-$C_6$ haloalkyl (such as those described herein) and an unsubstituted $C_1$-$C_6$ alkyl (such as those described herein). In some embodiments, Ring A of can be unsubstituted and Ring B of

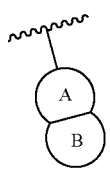

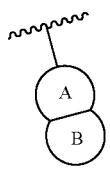

can be substituted with 1 or 2 substituents independently selected from fluoro, hydroxy, amino, —$CF_3$, —$CHF_2$, —$CF_2CH_3$, an unsubstituted methyl, an unsubstituted ethyl and —$NHC(O)CH_3$.

In some embodiments, $R^2$ can be selected from

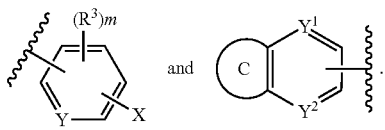

In some embodiments, $R^2$ can be

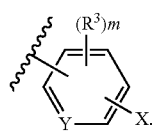

In some embodiments, $R^2$ can be

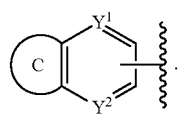

In some embodiments, Y can be CH or N (nitrogen). In some embodiments, Y can be CH. In some embodiments, Y can be N (nitrogen).

In some embodiments, $R^3$ can be selected from halogen and a substituted or unsubstituted $C_1$-$C_6$ alkyl (such as those described herein). In some embodiments, $R^3$ can be halogen. In some embodiments, $R^3$ can be a substituted $C_1$-$C_6$ alkyl (such as those described herein). In some embodiments, $R^3$ can be an unsubstituted $C_1$-$C_6$ alkyl (such as those described herein).

In some embodiments, m can be 0, 1, 2 or 3. In some embodiments, m can be 0. In some embodiments, m can be 1. In some embodiments, m can be 2. In some embodiments, m can be 3. When m is 2 or 3, the $R^3$ groups can be the same or different from each other.

In some embodiments, X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl (such as those described herein), a substituted or unsubstituted $C_1$-$C_6$ alkoxy (such as methoxy, ethoxy, n-propoxy, iso-propoxy, n-butoxy, iso-butoxy, sec-butoxy, t-butoxy, pentoxy (straight chain or branched) or hexoxy (straight chain or branched)), a substituted or unsubstituted $C_3$-$C_6$ cycloalkoxy (such as cyclopropoxy, cyclobutoxy, cyclopentoxy or cyclohexoxy), a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl.

In some embodiments, X can be hydrogen. In other embodiments, X can be halogen. In some embodiments, X can be fluoro. In some embodiments, X can be chloro. In still other embodiments, X can be hydroxy. In yet still other embodiments, X can be cyano. In some embodiments, X can be an amino.

In some embodiments, X can be an unsubstituted $C_1$-$C_6$ alkyl (such as those described herein). In some embodiments, X can be an unsubstituted methyl, an unsubstituted ethyl or an unsubstituted iso-propyl. In some embodiments, X can be a substituted $C_1$-$C_6$ alkyl (such as those described herein). In some embodiments, X can be an unsubstituted $C_1$-$C_6$ haloalkyl (such as a $C_1$-$C_6$ fluoroalkyl, a $C_1$-$C_6$ chloroalkyl or a $C_1$-$C_6$ chlorofluoroalkyl). In some embodiments, X can be selected from —$CHF_2$, —$CF_3$, —$CF_2CH_3$ and —$CH_2CF_3$. In some embodiments, X can be an unsubstituted $C_1$-$C_6$ hydroxyalkyl (such as a $C_1$-$C_6$ mono-hydroxyalkyl or a $C_1$-$C_6$ di-hydroxyalkyl). In some embodiments, X can be selected from —$CH_2OH$, —$CH_2CH_2OH$, —$CH(OH)CH_3$ and —$C(OH)(CH_3)_2$. In some embodiments, X can be an unsubstituted $C_1$-$C_6$ cyanoalkyl (such as a $C_1$-$C_6$ mono-cyanoalkyl or a $C_1$-$C_6$ di-cyanoalkyl). In some embodiments, X can be selected from

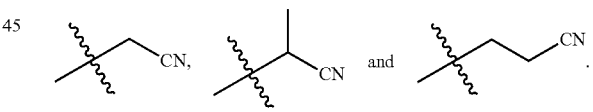

In some embodiments, X can be an unsubstituted $C_1$-$C_6$ alkoxyalkyl (such as a $C_1$-$C_6$ mono-alkoxyalkyl or a $C_1$-$C_6$ di-alkoxyalkyl). In some embodiments, X can be selected from

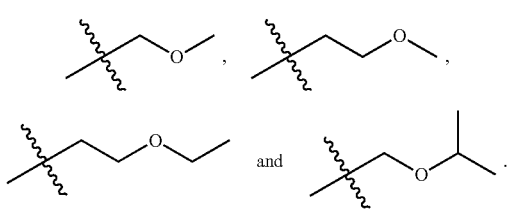

In some embodiments, X can be a substituted $C_1$-$C_6$ alkyl selected from

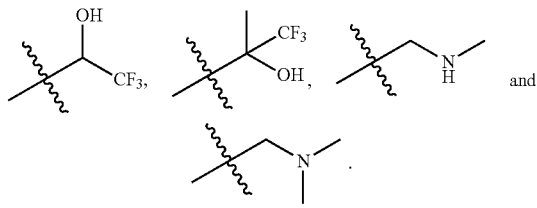

In some embodiments, X can be an unsubstituted $C_1$-$C_6$ alkoxy (such as those described herein). In some embodiments, X can be an unsubstituted methoxy, an unsubstituted ethoxy or an unsubstituted iso-propoxy. In some embodiments, X can be a substituted $C_1$-$C_6$ alkoxy (such as those described herein). In some embodiments, X can be a $C_1$-$C_6$ alkoxy substituted with 1, 2 or 3 substituents independently selected from halogen, an amino, a mono-substituted amine (such as those described herein) and a di-substituted amine (such as those described herein). In some embodiments, X can be a $C_1$-$C_6$ alkoxy substituted with 1 substituent selected from halogen, an amino, a mono-substituted amine (such as those described herein) and a di-substituted amine (such as those described herein).

In some embodiments, X can be selected from

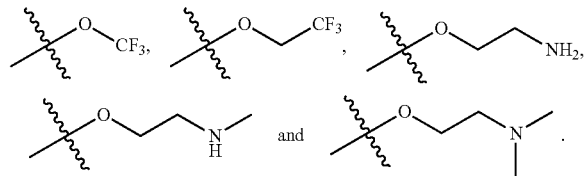

In some embodiments, X can be a substituted $C_3$-$C_6$ cycloalkoxy (such as those described herein). In some embodiments, X can be an unsubstituted $C_3$-$C_6$ cycloalkoxy (such as those described herein).

In some embodiments, X can be a substituted ($C_1$-$C_6$ alkyl)acyl, such as a substituted —(CO)—$CH_3$. In some embodiments, X can be an unsubstituted ($C_1$-$C_6$ alkyl)acyl, such as an unsubstituted —(CO)—$CH_3$.

In some embodiments, X can be a substituted 4-6 membered monocyclic heterocyclyl. In some embodiments, X can be an unsubstituted 4-6 membered monocyclic heterocyclyl. In some embodiments, X can be selected from azetidine, oxetane, diazetidine, azaoxetane, pyrrolidine, tetrahydrofuran, imidazoline, pyrazolidine, piperidine, tetrahydropyran, piperazine, morpholine and dioxane; wherein each of the aforementioned groups are substituted or unsubstituted, including any —NH group. In some embodiments, X can be selected from

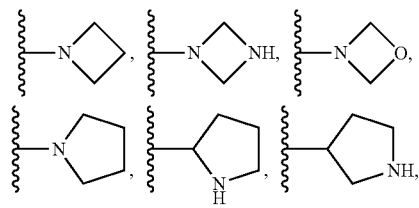

-continued

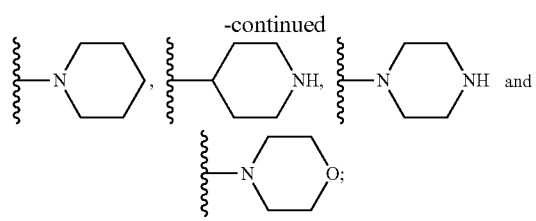

wherein each of the aforementioned groups are substituted or unsubstituted, including any —NH group.

In some embodiments, X can be a 4-6 membered monocyclic heterocyclyl (such as those described herein) substituted with 1 or 2 substituents independently selected from halogen, a substituted or unsubstituted $C_1$-$C_6$ alkyl (such as those described herein), a mono-substituted amine (such as those described herein), a di-substituted amine (such as those described herein), an amino, substituted or unsubstituted amine($C_1$-$C_6$ alkyl) and a substituted or unsubstituted ($C_1$-$C_6$ alkyl)acyl. In some embodiments, X can be a 4-6 membered monocyclic heterocyclyl substituted with 1 or 2 substituents independently selected from fluoro, an unsubstituted methyl, an unsubstituted ethyl, an unsubstituted iso-propyl, —$CH_2OH$ and —$N(CH_3)_2$. In some embodiments, X can be selected from

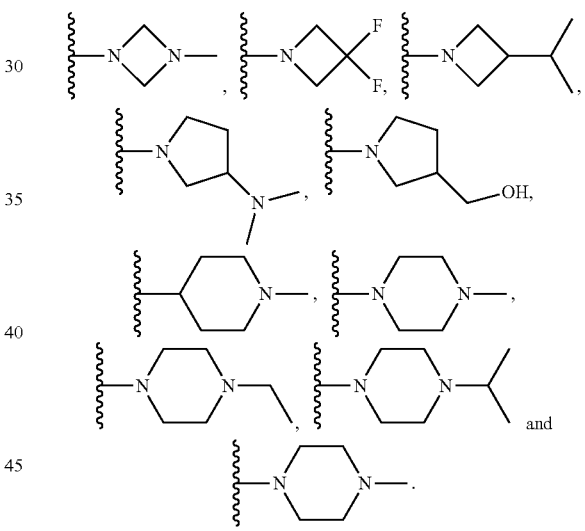

In some embodiments, X can be a substituted amine($C_1$-$C_6$ alkyl). In some embodiments, X can be an unsubstituted amine($C_1$-$C_6$ alkyl). In some embodiments, X can be selected from

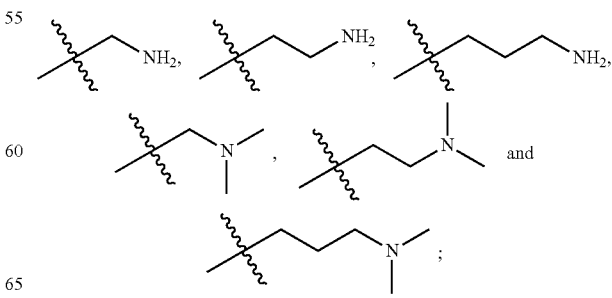

wherein each of the aforementioned groups are substituted or unsubstituted, including any —NH group.

In some embodiments, X can be a substituted —NH—$(CH_2)_{1-6}$-amine. In some embodiments, X can be an unsubstituted —NH—$(CH_2)_{1-6}$-amine. In some embodiments, X can be selected from

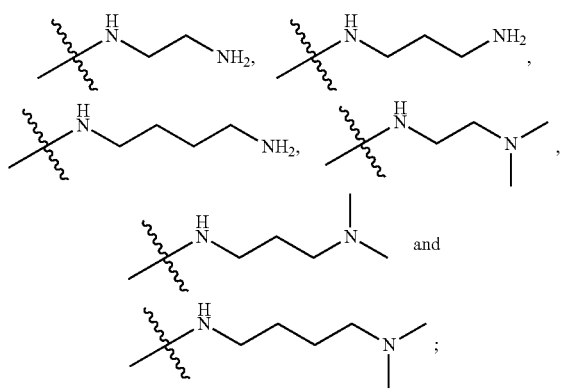

wherein each of the aforementioned groups are substituted or unsubstituted, including any —NH group.

In some embodiments, X can be a mono-substituted amine. In some embodiments, the substituent of the mono-substituted amine is an unsubstituted $C_1$-$C_6$ alkyl (such as those as described herein) or an unsubstituted $C_3$-$C_6$ cycloalkyl (such as cyclopropyl, cyclobutyl, cyclopentyl and cyclohexyl).

In some embodiments, X can be a di-substituted amine. In some embodiments, the two substituents of the di-substituted amine are independently selected from an unsubstituted $C_1$-$C_6$ alkyl (such as those as described herein) and an unsubstituted $C_3$-$C_6$ cycloalkyl (such as those as described herein).

In some embodiments, X can be selected from

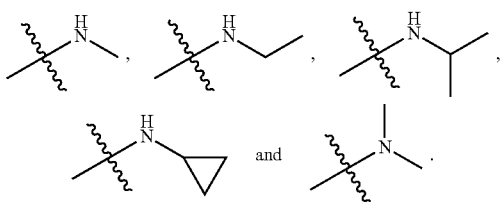

In some embodiments, X can be a substituted or unsubstituted C-amido. In some embodiments, X can be a substituted or unsubstituted N-amido. In some embodiments, X can be a substituted or unsubstituted C-carboxy. In some embodiments, X can be a substituted or unsubstituted O-carboxy. In some embodiments, X can be a substituted or unsubstituted O-carbamyl. In some embodiments, X can be a substituted or unsubstituted N-carbamyl. In some embodiments, X can be mono-substituted with an unsubstituted $C_1$-$C_6$ hydroxyalkyl (such as those described herein).

In some embodiments, $Y^1$ can be $CR^{4A}$ or N (nitrogen). In some embodiments, $Y^1$ can be $CR^{4A}$. In some embodiments, $Y^1$ can be N (nitrogen).

In some embodiments, $Y^2$ can be $CR^{4B}$ or N (nitrogen). In some embodiments, $Y^2$ can be $CR^{4B}$. In some embodiments, $Y^2$ can be N (nitrogen).

In some embodiments, $Y^1$ and $Y^2$ can each be N (nitrogen). In some embodiments, $Y^1$ can be $CR^{4A}$ and $Y^2$ can be $CR^{4B}$. In some embodiments, $Y^1$ can be $CR^{4A}$ and $Y^2$ can be N (nitrogen). In some embodiments, $Y^1$ can be N (nitrogen) and $Y^2$ can be $CR^{4B}$.

In some embodiments, $R^{4A}$ can be hydrogen. In some embodiments, $R^{4A}$ can be halogen. In some embodiments, $R^{4A}$ can be an unsubstituted $C_1$-4 alkyl (such as those described herein).

In some embodiments, $R^{4B}$ can be hydrogen. In some embodiments, $R^{4B}$ can be halogen. In some embodiments, $R^{4B}$ can be an unsubstituted $C_1$-4 alkyl (such as those described herein).

In some embodiments, $R^{4A}$ and $R^{4B}$ can each be hydrogen. In some embodiments, $R^{4A}$ and $R^{4B}$ can each be halogen (wherein the halogens can be the same or different from each other). In some embodiments, $R^{4A}$ and $R^{4B}$ can each be an unsubstituted $C_1$-4 alkyl (such as those described herein, and wherein the $C_1$-4 alkyls can be the same or different from each other). In some embodiments, one of $R^{4A}$ and $R^{4B}$ can be hydrogen and the other of $R^{4A}$ and $R^{4B}$ can be halogen. In some embodiments, one of $R^{4A}$ and $R^{4B}$ can be hydrogen and the other of $R^{4A}$ and $R^{4B}$ can be an unsubstituted $C_1$-4 alkyl (such as those described herein). In some embodiments, one of $R^{4A}$ and $R^{4B}$ can be halogen and the other of $R^{4A}$ and $R^{4B}$ can be an unsubstituted $C_1$-4 alkyl (such as those described herein).

In some embodiments, $R^2$ can be

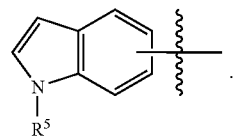

For example, $R^2$ can be

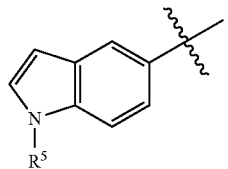

When $R^2$ is

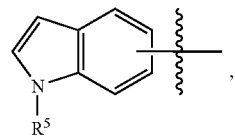

in some embodiments, $R^5$ can be a substituted 5-7 membered monocyclic heterocyclyl. In other embodiments, $R^5$ can be an unsubstituted 5-7 membered monocyclic heterocyclyl. Examples of $R^5$ groups include a substituted or unsubstituted piperidinyl, a substituted or unsubstituted pyrrolidinyl and a substituted or unsubstituted azepanyl. When substituted the $R^5$ group, possible substituents include an unsubstituted $C_{1-4}$ alkyl, halogen, hydroxy and unsubstituted $C_{1-4}$ haloalkyl.

In some embodiments, Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl.

In some embodiments, Ring C can be a substituted $C_6$-$C_{10}$ aryl. In some embodiments, Ring C can be an unsubstituted $C_6$-$C_{10}$ aryl. In some embodiments, Ring C can be a substituted $C_6$ aryl. In some embodiments, Ring C can be an unsubstituted $C_6$ aryl.

In some embodiments, Ring C can be a substituted 5-10 membered heteroaryl. In some embodiments, Ring C can be an unsubstituted 5-10 membered heteroaryl. In some embodiments, Ring C can be a substituted 5-6 membered heteroaryl. In some embodiments, Ring C can be an unsubstituted 5-6 membered heteroaryl. In some embodiments, Ring C can be selected from furan, thiophene, pyrrole, oxazole, thiazole, imidazole, benzimidazole, indole, pyrazole, isoxazole, pyridine, pyridazine, pyrimidine, pyrazine, purine, quinoline, isoquinoline, quinazoline and quinoxaline; wherein each of the aforementioned groups are substituted or unsubstituted, including any —NH group.

In some embodiments, Ring C can be a substituted or unsubstituted monocyclic 5 membered carbocyclyl. In some embodiments, Ring C can be a substituted or unsubstituted monocyclic 6 membered carbocyclyl. In some embodiments, Ring C can be a substituted or unsubstituted monocyclic 7 membered carbocyclyl.

In some embodiments, Ring C can be a Ring C can be a substituted or unsubstituted 5 membered monocyclic heterocyclyl. In some embodiments, Ring C can be a substituted or unsubstituted 6 membered monocyclic heterocyclyl. In some embodiments, Ring C can be a substituted or unsubstituted 7 membered monocyclic heterocyclyl. In some embodiments, Ring C can be selected from imidazoline, imidazolidine, isoxazoline, isoxazolidine, oxazoline, oxazolidine, oxazolidinone, thiazoline, thiazolidine, morpholine, piperidine, piperazine, pyrrolidine, pyrrolidone, 4-piperidone, pyrazoline, pyrazolidine, tetrahydropyran, azepine, oxepine and diazepine; wherein each of the aforementioned groups are substituted or unsubstituted, including any —NH group.

In some embodiments, Ring C can be a substituted or unsubstituted 7 membered bicyclic heterocyclyl (for example, a fused, a bridged or a spiro heterocyclyl). In some embodiments, Ring C can be a substituted or unsubstituted 8 membered bicyclic heterocyclyl, such as, a fused, a bridged or a spiro heterocyclyl. In some embodiments, Ring C can be a substituted or unsubstituted 9 membered bicyclic heterocyclyl (for example, a fused, a bridged or a spiro heterocyclyl). In some embodiments, Ring C can be a substituted or unsubstituted 10 membered bicyclic heterocyclyl, such as, a fused, a bridged or a spiro heterocyclyl. In some embodiments, Ring C can be selected from pyrrolizidine, indoline, 1,2,3,4 tetrahydroquinoline, 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane; wherein each of the aforementioned groups are substituted or unsubstituted, including any —NH group.

In some embodiments, Ring C can be substituted with one or more substituents independently selected from an unsubstituted $C_1$-$C_6$ alkyl (as described herein) and an unsubstituted ($C_1$-$C_6$ alkyl)acyl. In some embodiments, Ring C can be substituted with one substituent selected from an unsubstituted $C_1$-$C_6$ alkyl (as described herein) and an unsubstituted ($C_1$-$C_6$ alkyl)acyl.

In some embodiments, $R^2$ can be selected from:

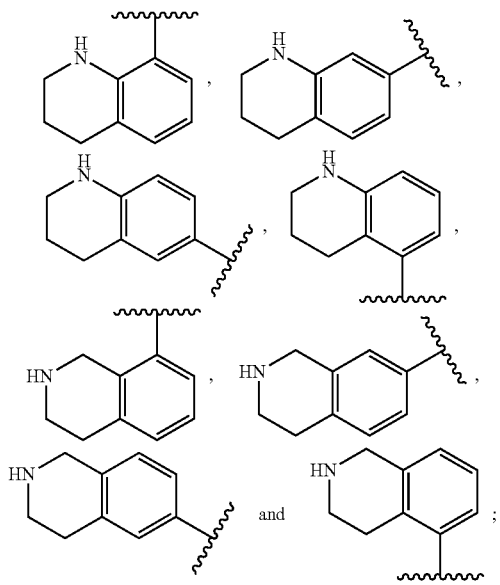

wherein each of the aforementioned groups can be substituted or unsubstituted.

Examples of a compound of Formula (I) include:

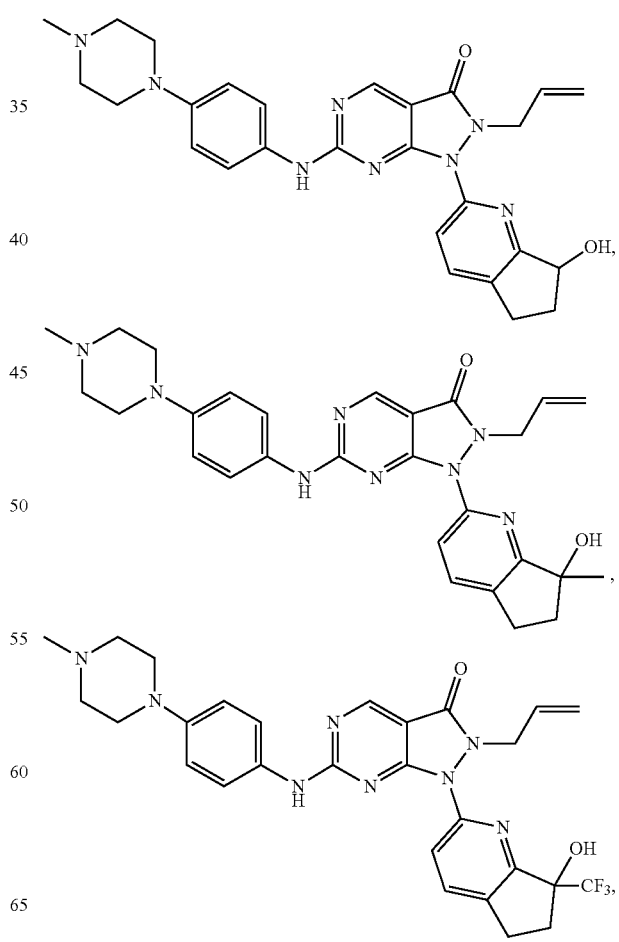

35
-continued
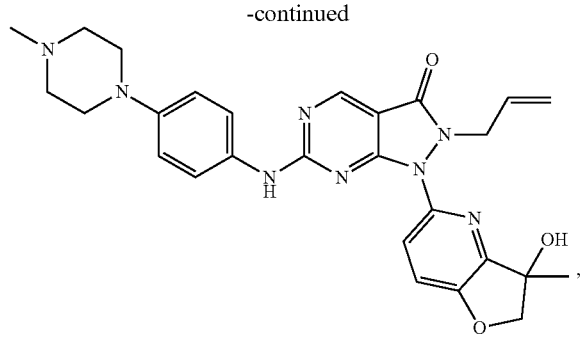
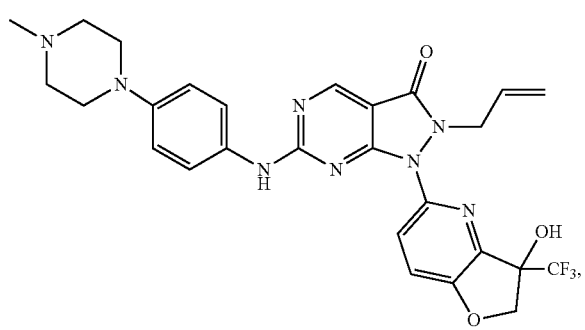
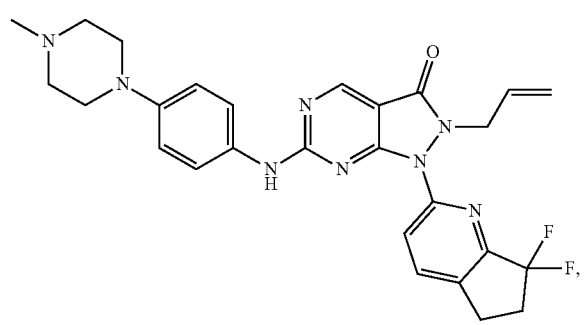
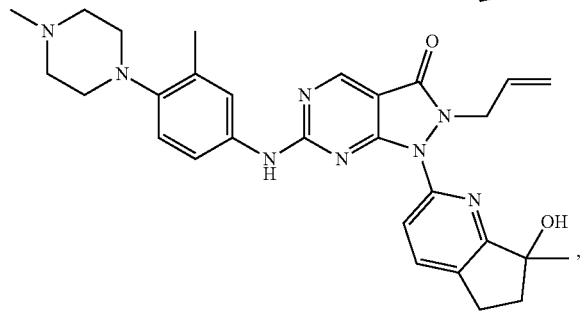
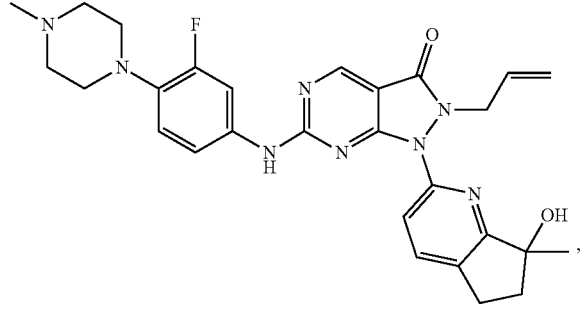
36
-continued
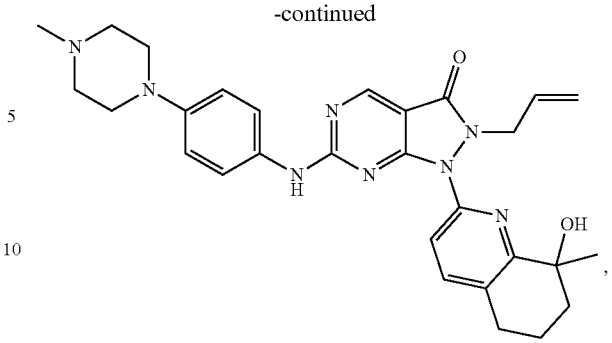
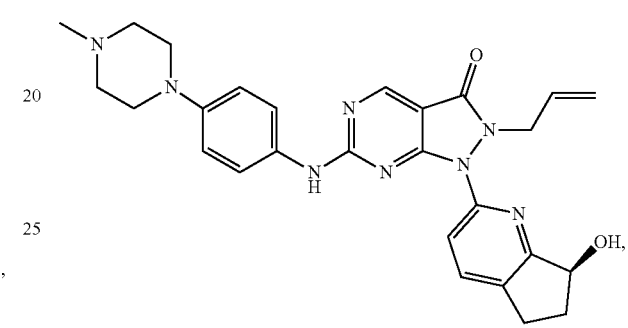
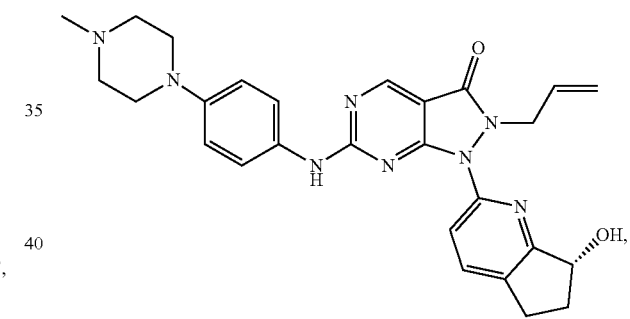
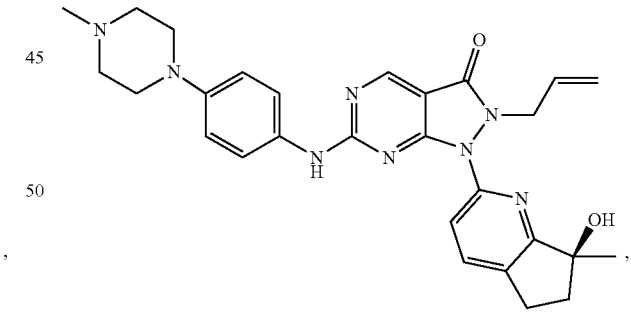
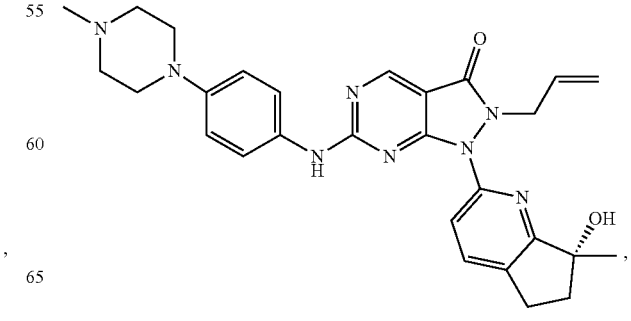

37
-continued
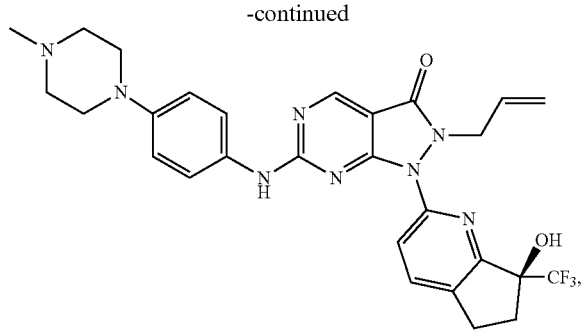
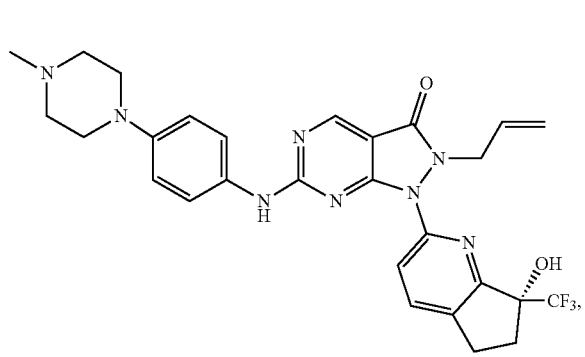
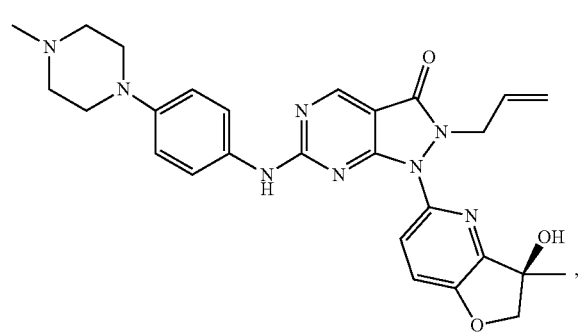
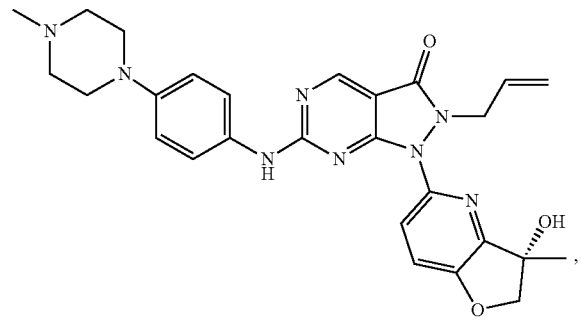
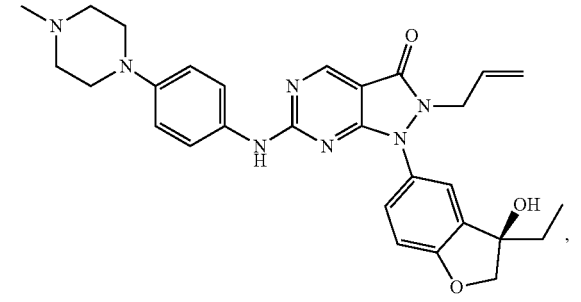
38
-continued
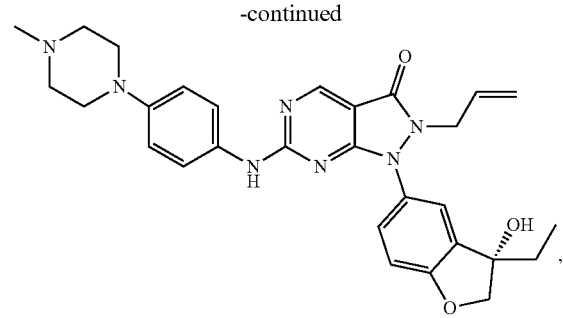
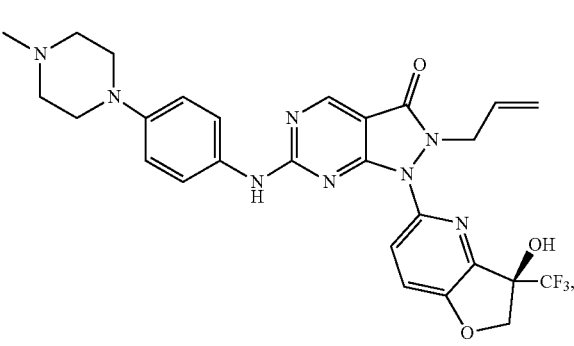
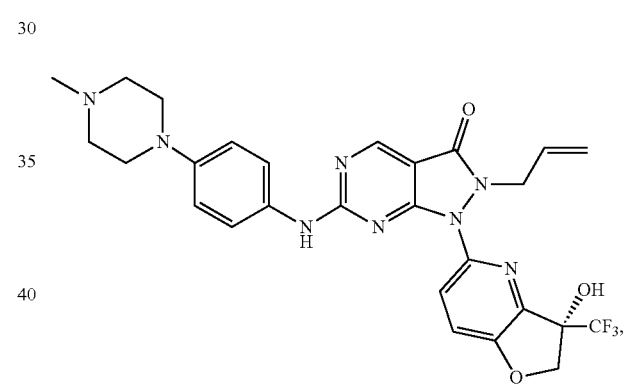
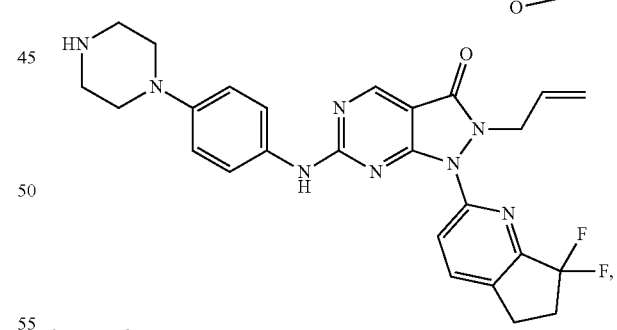
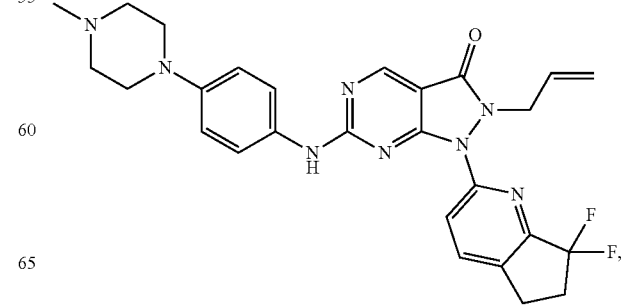

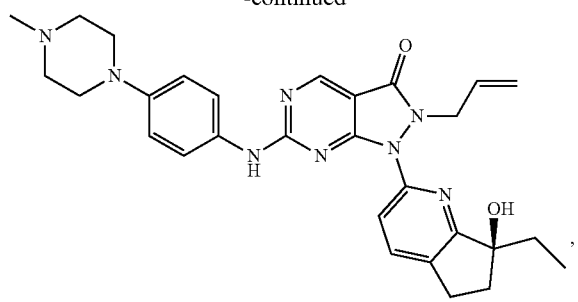,
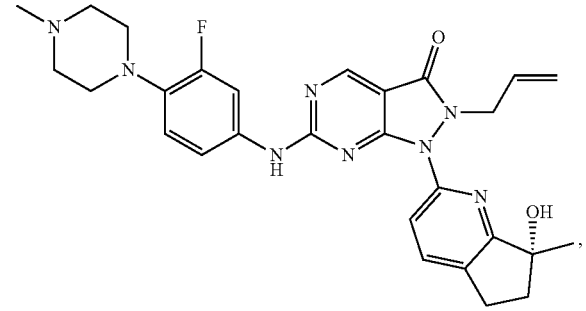,
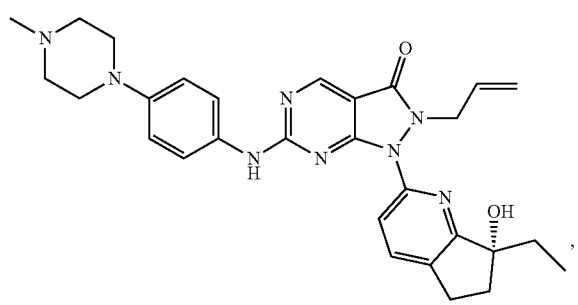,
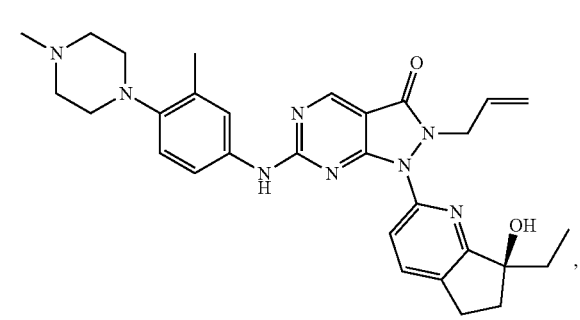,
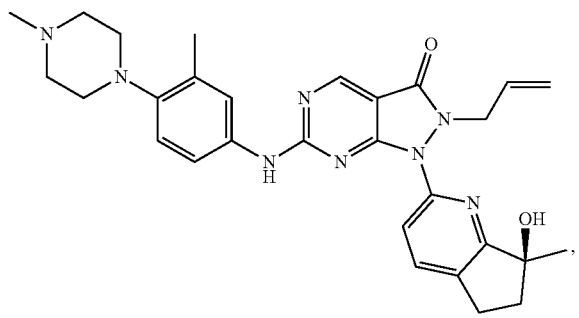,
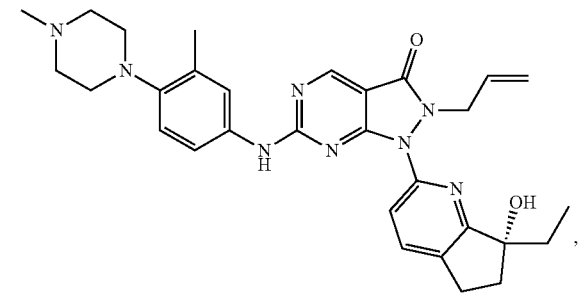,
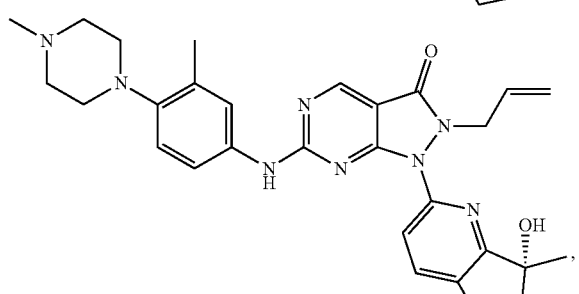,
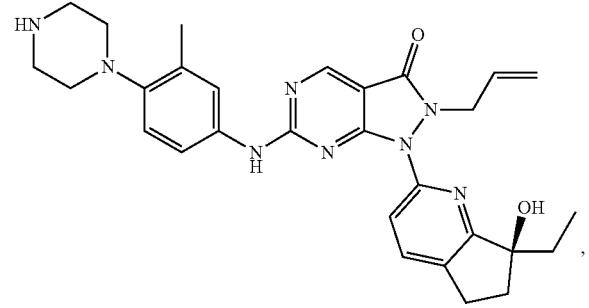,
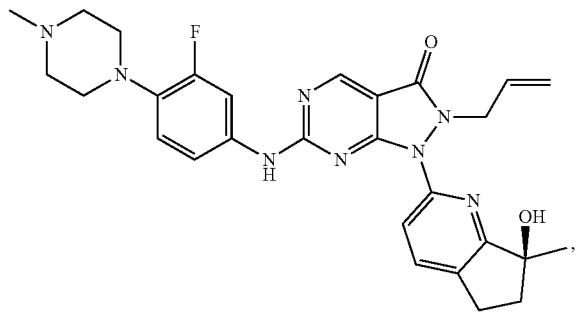,
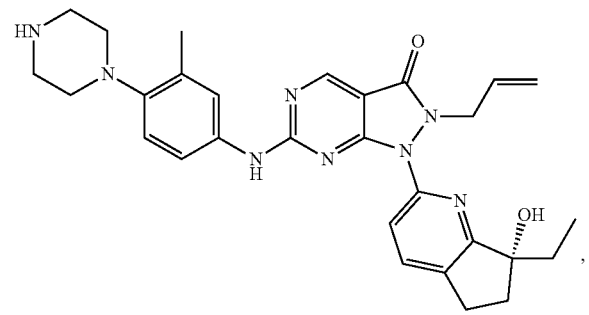, 41
-continued
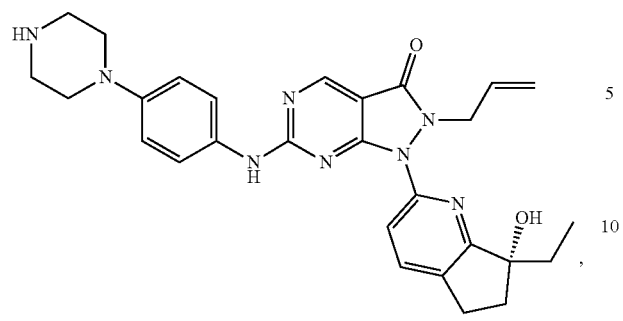
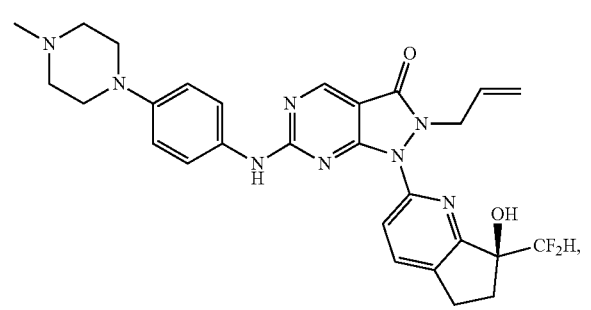
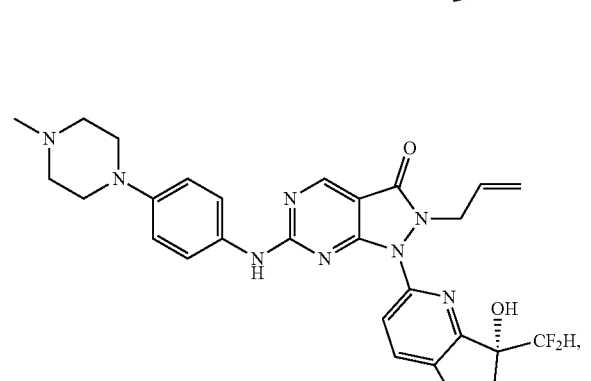
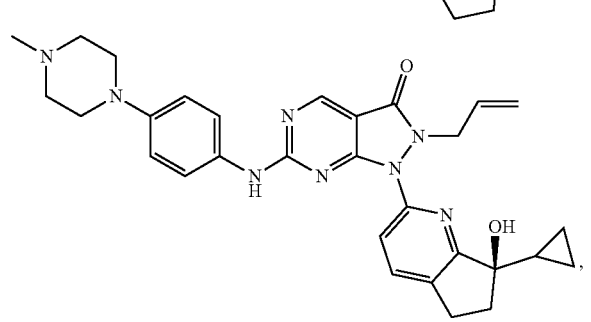
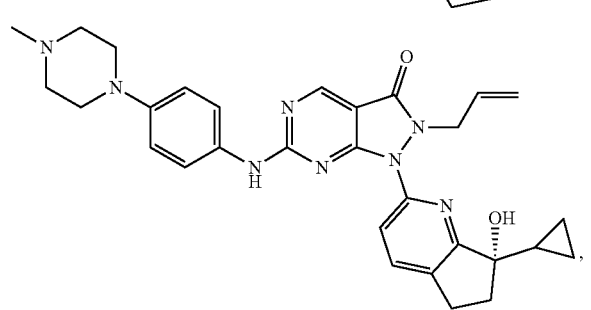
42
-continued
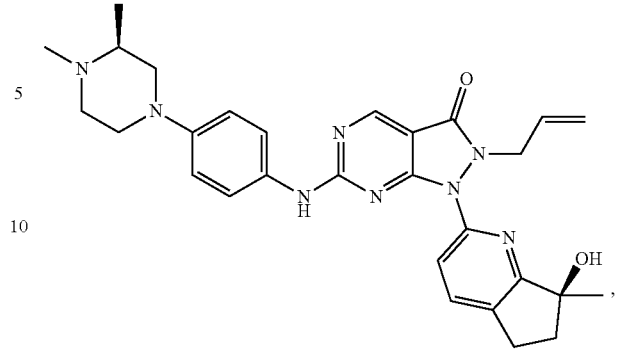
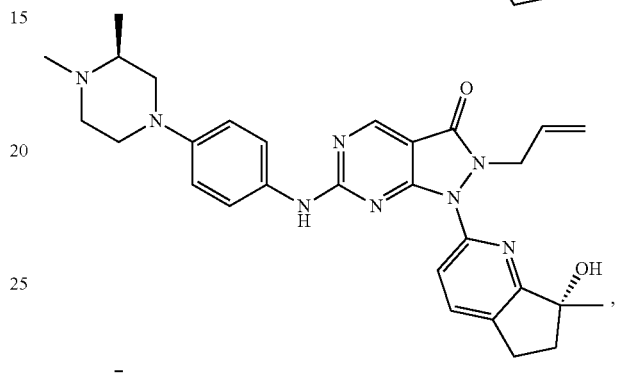
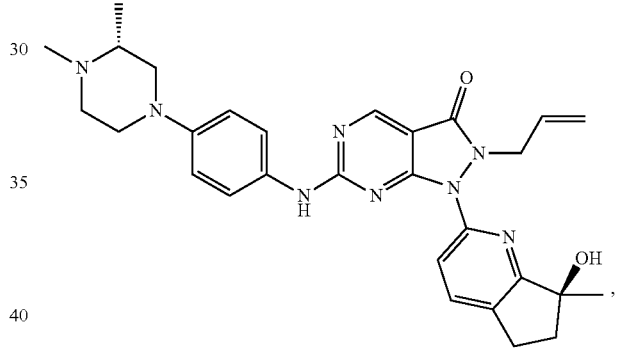
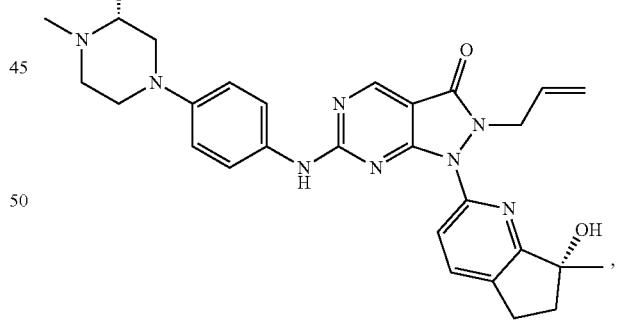
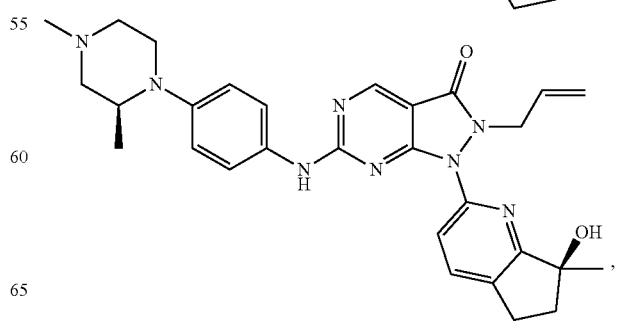

43
-continued
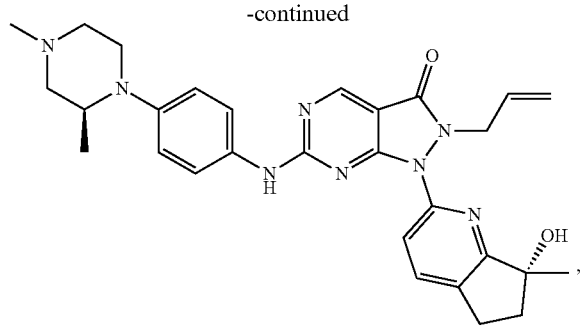
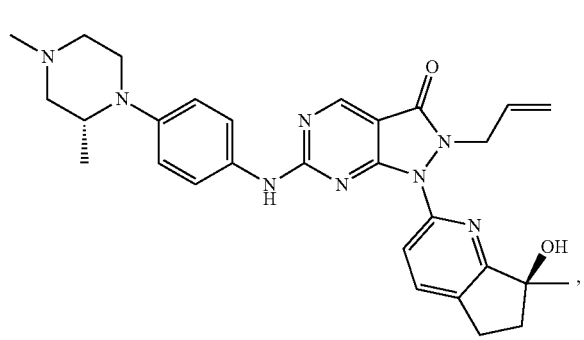
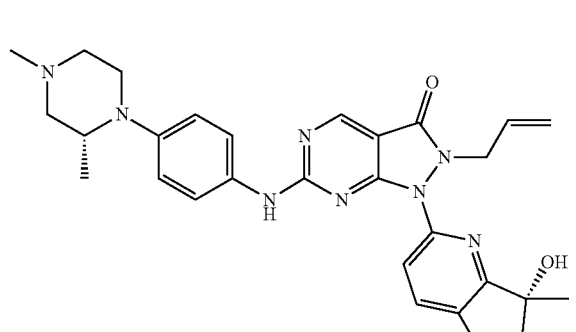
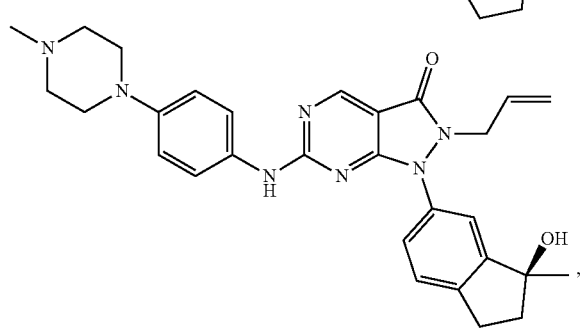
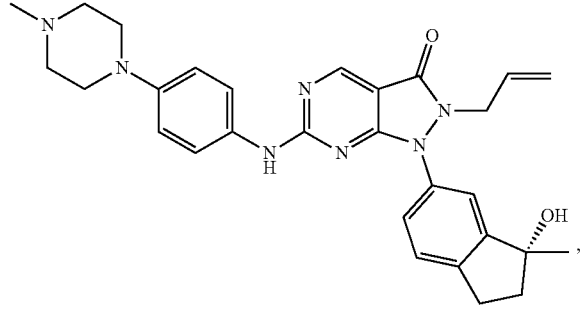
44
-continued
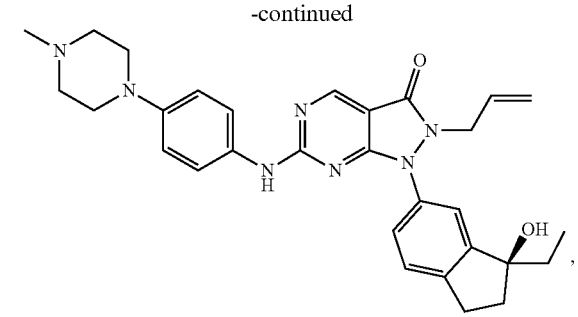
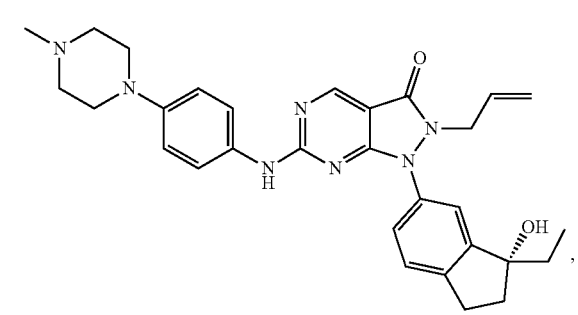
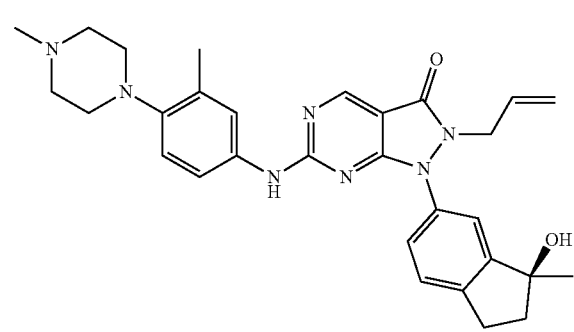
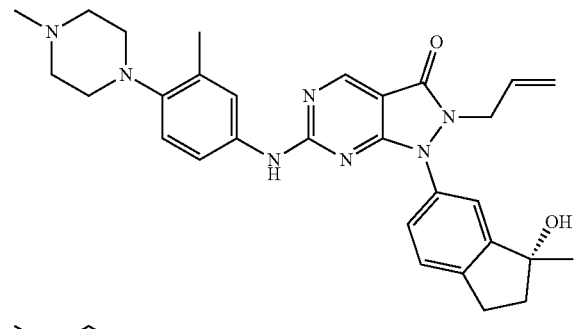
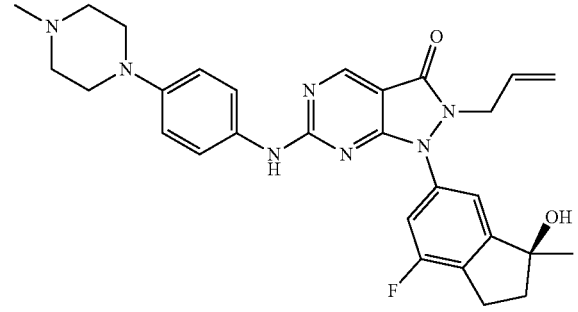

45
-continued
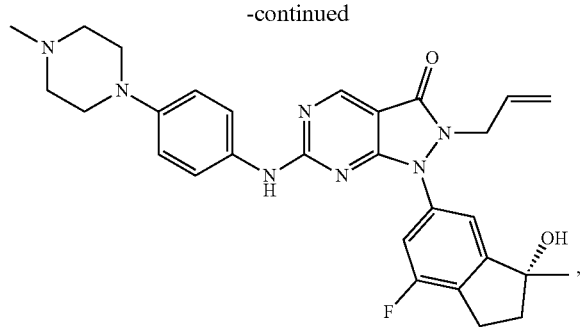
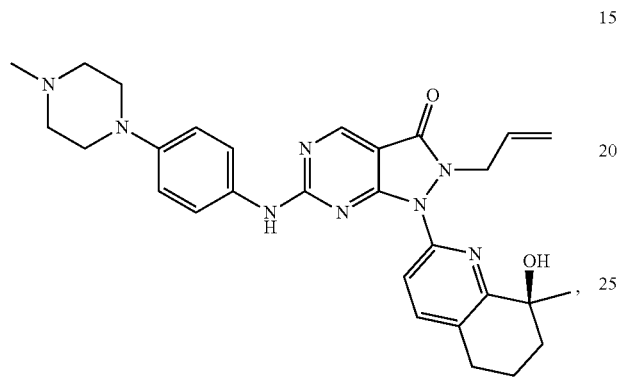
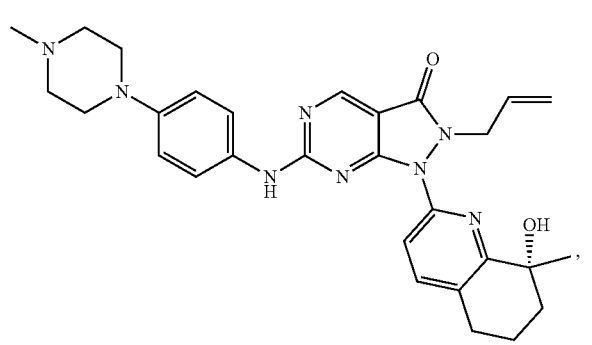
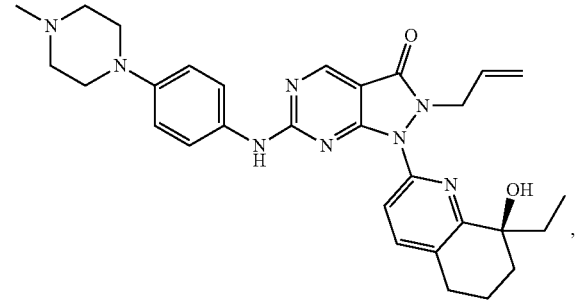
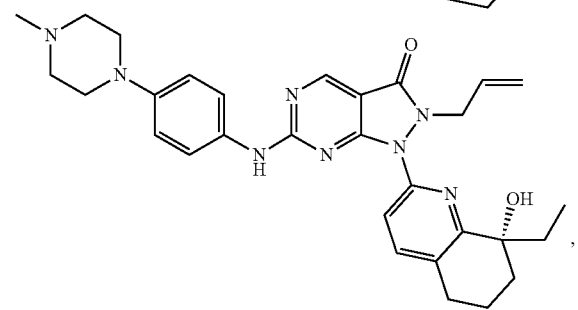
46
-continued
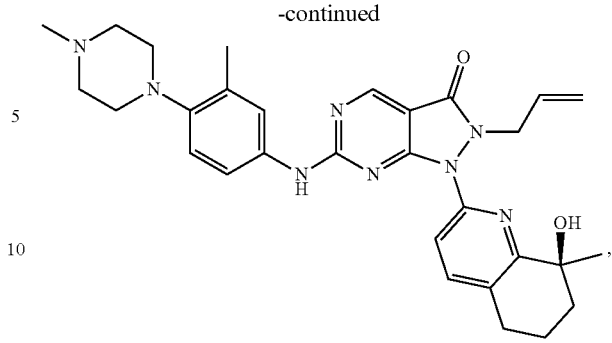
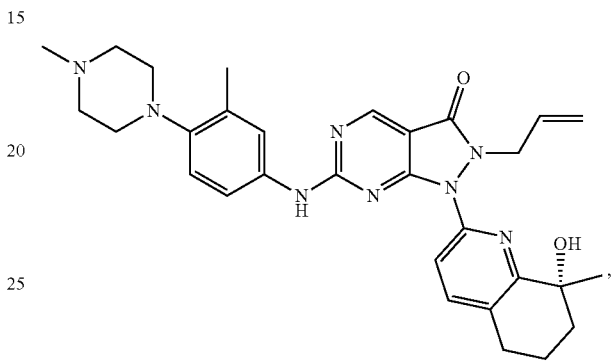
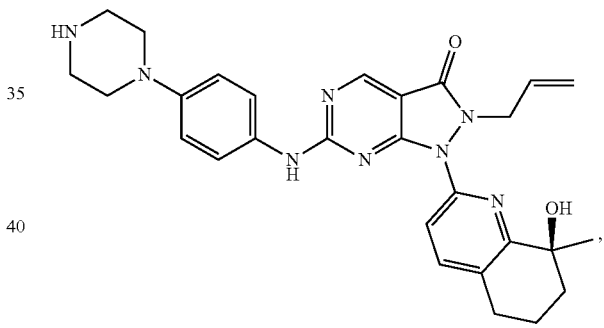
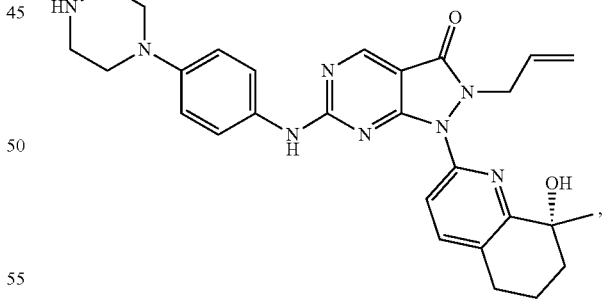
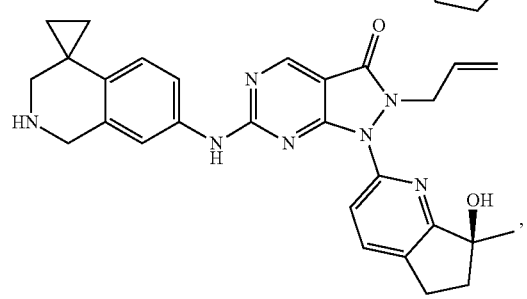

47
-continued
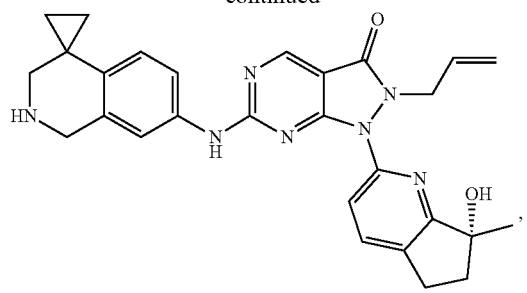
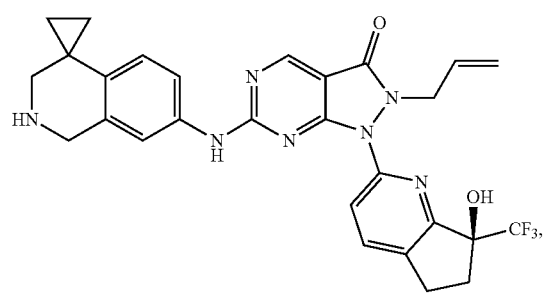
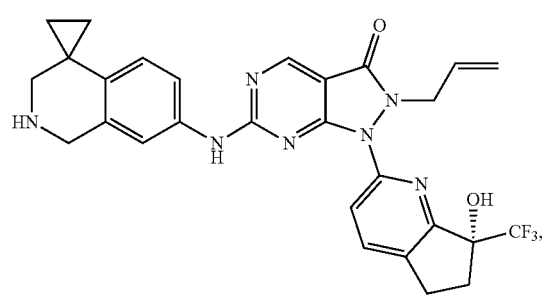
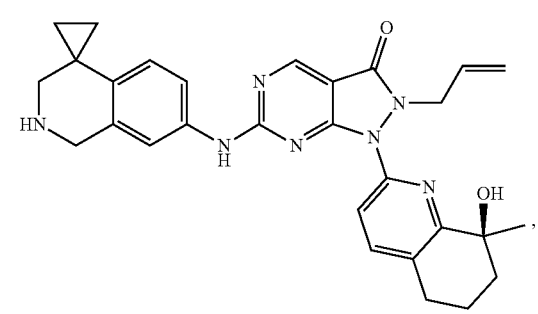
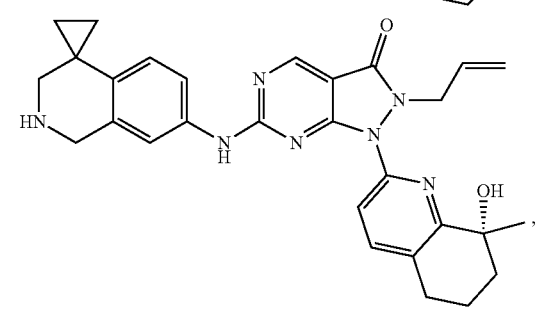
48
-continued
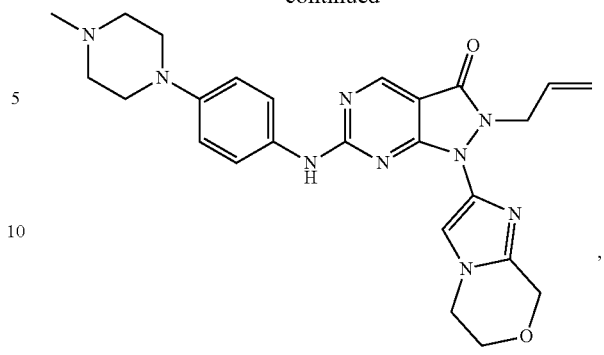
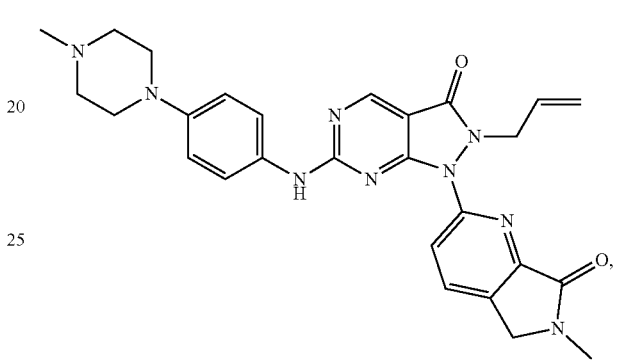
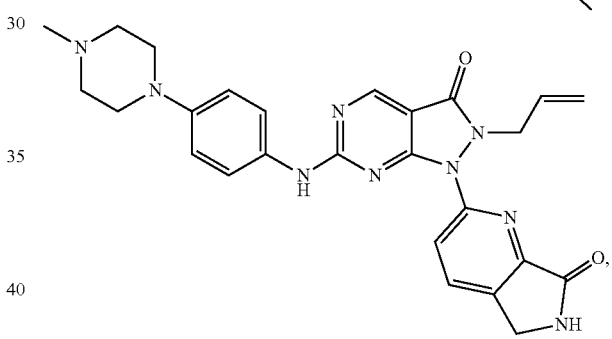
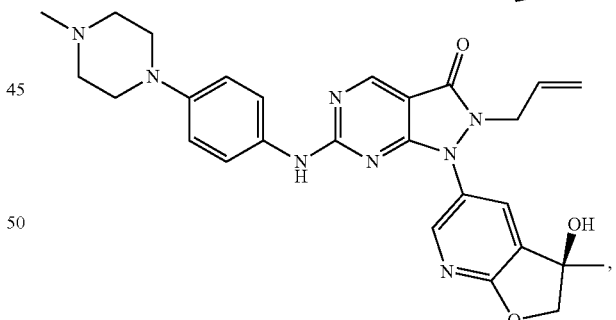
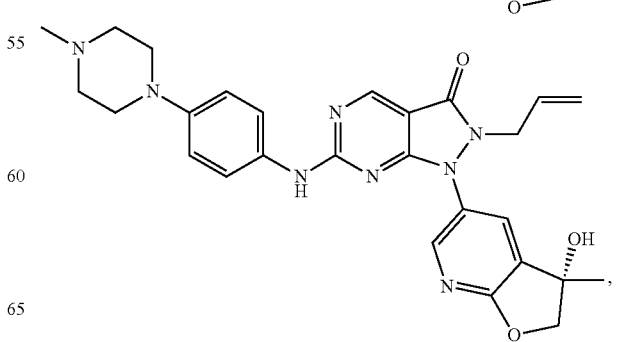

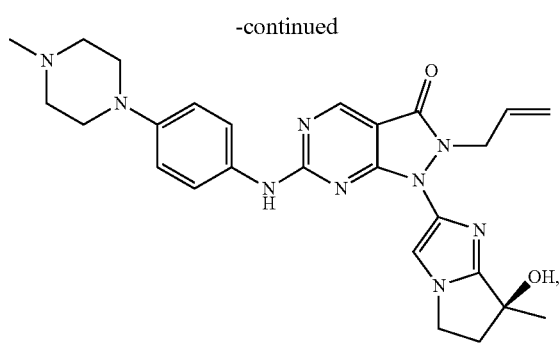
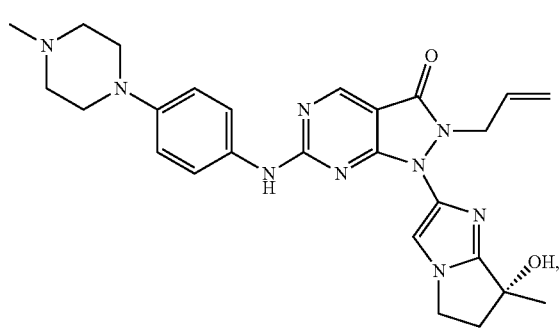
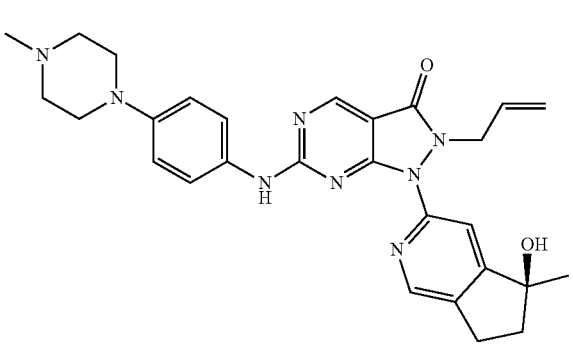
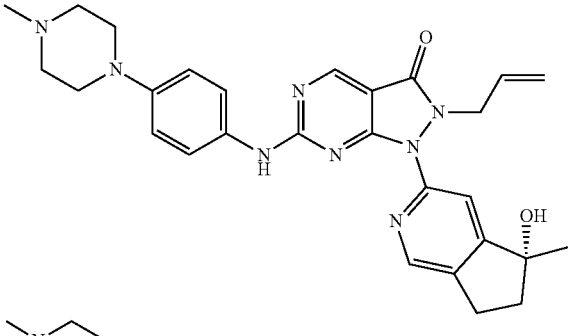
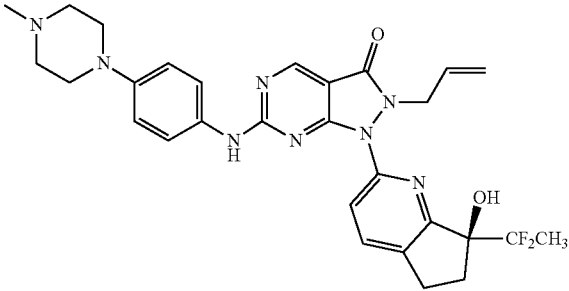
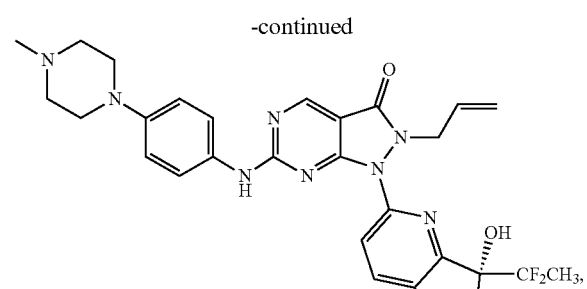
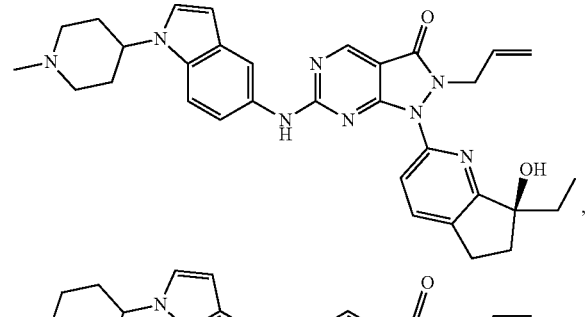
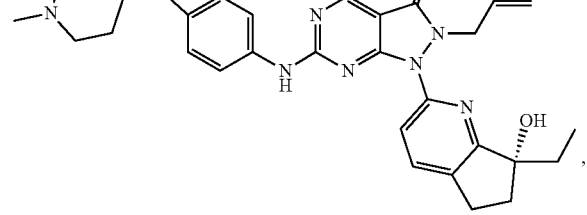
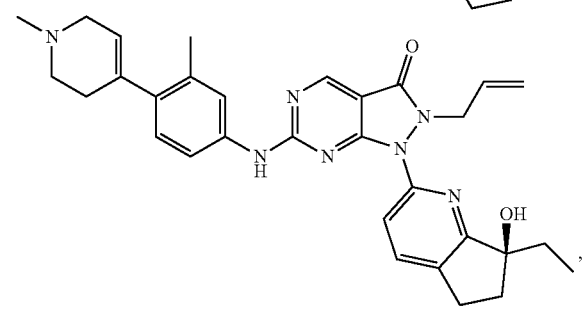
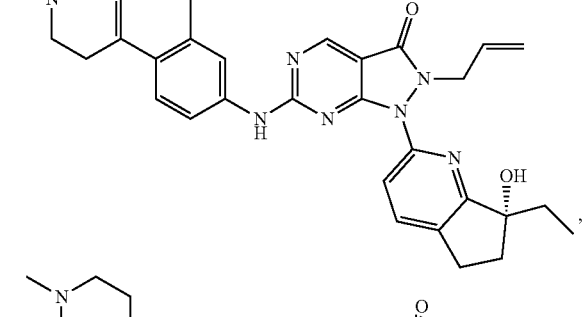
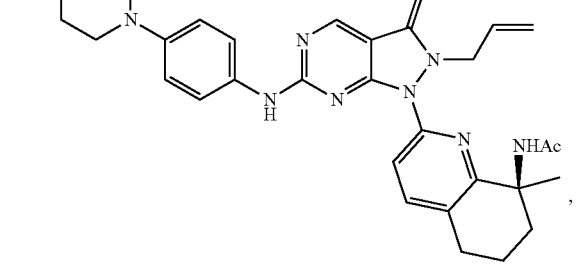

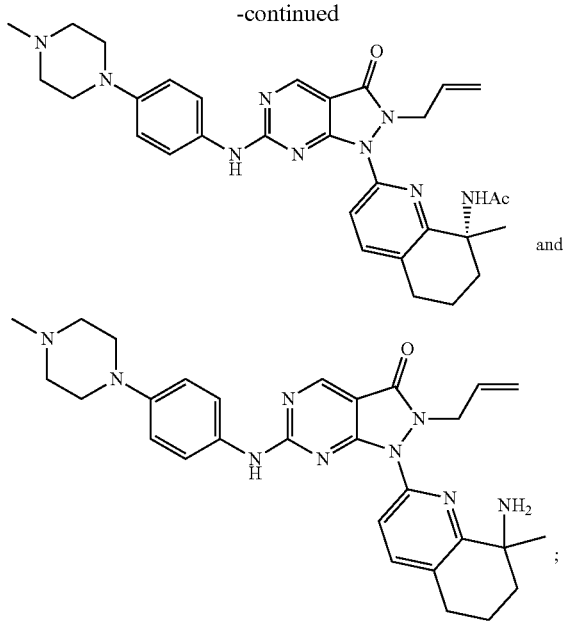

or a pharmaceutically acceptable salt of any of the foregoing.

Synthesis

Compounds of the Formula (I), or pharmaceutically acceptable salts thereof, can be made in various ways by those skilled using known techniques as guided by the detailed teachings provided herein. For example, in an embodiment, compounds of the Formula (I) are prepared in accordance with General Scheme 1 as shown herein.

In general, the coupling reaction reactions between compounds of the general Formulae A and B to form compounds of the Formula (I) as illustrated in General Scheme 1 can be carried out in a manner similar to the reactions as described herein in the Examples, by appropriate adjustment of the reagents and conditions described in the Examples. Any preliminary reaction steps required to form starting compounds of the general Formula A and B, or other precursors, can be carried out by those skilled in the art. In General Scheme 1, Ring A, Ring B, $R^1$ and $R^2$ can be as described herein.

General Scheme 1

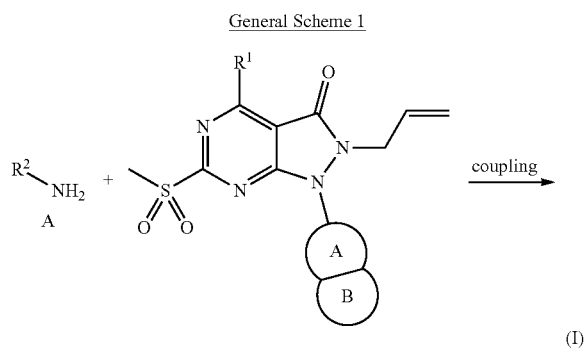

Pharmaceutical Compositions

Some embodiments described herein relate to a pharmaceutical composition, that can include an effective amount of one or more compounds described herein (for example, a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as antioxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

Uses and Methods of Treatment

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating or treating a cancer that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating or treating a cancer that can include contacting a malignant growth or a tumor, wherein the malignant growth or tumor is due to a cancer described herein.

Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a cancer cell from a cancer described herein. Other embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include contacting a cancer cell from a cancer described herein with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof), and thereby inhibiting the activity of WEE1.

Some embodiments described herein relate to a method for ameliorating or treating a cancer described herein that can include inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) using an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for ameliorating or treating a cancer described herein that can include contacting a cancer cell with an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof), wherein the compound inhibits the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

Some embodiments disclosed herein relate to a method for inhibiting the activity of WEE1 that can include providing an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) to a subject having a cancer described herein or a cancer cell from a cancer described herein. Other embodiments disclosed herein relate to the use of an effective amount of a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) in the manufacture of a medicament for inhibiting the activity of WEE1. Still other embodiments disclosed herein relate to a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) for inhibiting the activity of WEE1.

Examples of suitable cancers include, but are not limited to: brain cancers, cervicocerebral cancers, esophageal cancers, thyroid cancers, small cell cancers, non-small cell cancers, breast cancers, lung cancers (for example non-small cell lung cancer and small cell lung cancer), stomach cancers, gallbladder/bile duct cancers, liver cancers, pancreatic cancers, colon cancers, rectal cancers, ovarian cancers, choriocarcinomas, uterus body cancers, uterocervical cancers, renal pelvis/ureter cancers, bladder cancers, prostate cancers, penis cancers, testicular cancers, fetal cancers, Wilms' cancer, skin cancers, malignant melanoma, neuroblastomas, osteosarcomas, Ewing's tumors, soft part sarcomas, acute leukemia, chronic lymphatic leukemias, chronic myelocytic leukemias, polycythemia vera, malignant lymphomas, multiple myeloma, Hodgkin's lymphomas, and non-Hodgkin's lymphomas.

As described herein, a cancer can become resistant to one or more anti-cancer agents. In some embodiments, a compound described herein (for example, a compound of Formula (I), or a pharmaceutically acceptable salt thereof) or a pharmaceutical composition that includes an effective amount of a compound described herein (for example, a compound of Formula (I), or a pharmaceutically acceptable salt thereof) can be used to treat and/or ameliorate a cancer that has become resistant to one or more anti-cancer agents (such as one or more WEE1 inhibitors). Examples of anti-cancer agents that a subject may have developed resistance to include, but are not limited to, WEE1 inhibitors (such as AZD1775). In some embodiments, the cancer that has become resistant to one or more anti-cancer agents can be a cancer described herein.

Several known WEE1 inhibitors can cause one or more undesirable side effects in the subject being treated. Examples of undesirable side effects include, but are not limited to, thrombocytopenia, neutropenia, anemia, diarrhea, vomiting, nausea, abdominal pain, and constipation. In some embodiments, a compound described herein (for example, a compound of Formula (I), or a pharmaceutically acceptable salt thereof) can decrease the number and/or severity of one or more side effects associated with a known WEE1 inhibitor. In some embodiments, a compound of Formula (I), or a pharmaceutically acceptable salt thereof, can result in a severity of a side effect (such as one of those described herein) that is 25% less than compared to the severity of the same side effect experienced by a subject receiving a known WEE1 inhibitor (such as AZD1775, formally known as MK1775 (CAS No.: 955365-80-7, 2-allyl-1-(6-(2-hydroxypropan-2-yl)pyridin-2-yl)-6-(4-(4-methylpiperazin-1-yl)phenylamino)-1,2-dihydropyrazolo[3,4-d]pyrimidin-3-one)). In some embodiments, a compound of Formula (I), or a pharmaceutically acceptable salt thereof, results in a number of side effects that is 25% less than compared to the number of side effects experienced by a subject receiving a known WEE1 inhibitor (for example, AZD1775). In some embodiments, a compound of Formula (I), or a pharmaceutically acceptable salt thereof, results in a severity of a side effect (such as one of those described herein) that is less in the range of about 10% to about 30% compared to the severity of the same side effect experienced by a subject receiving a known WEE1 inhibitor (such as AZD1775) In some embodiments, a compound of Formula (I), or a pharmaceutically acceptable salt thereof, results in a number of side effects that is in the range of about 10% to about 30% less than compared to the number of side effects experienced by a subject receiving a known WEE1 inhibitor (for example, AZD1775).

The one or more compounds of Formula (I), or a pharmaceutically acceptable salt thereof, that can be used to treat, ameliorate and/or inhibit the growth of a cancer wherein inhibiting the activity of WEE1 is beneficial is provided in any of the embodiments under the heading titled "Compounds."

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an WEE1 inhibitor is the amount which results in the reduction in WEE1 activity and/or phosphorylation (such as phosphorylation of CDC2). The reduction in WEE1 activity is known to those skilled in the art and can be determined by the analysis of WEE1 intrinsic kinase activity and downstream substrate phosphorylation.

The amount of the compound of Formula (I), or a pharmaceutically acceptable salt thereof, required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day, or any amount in between. The compound may be administered in unit dosage form; for example, containing 1 to 500 mg, 10 to 100 mg, 5 to 50 mg or any amount in between, of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of Formula (I), or pharmaceutically acceptable salts thereof, can be determined by comparing their in vitro activity, and in vivo activity in animal models. Such comparison can be done by comparison against an established drug, such as cisplatin and/or gemcitabine)

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

2-Allyl-6-(methylthio)-1,2-dihydro-3H-pyrazolo[3,4-d]pyrimidin-3-one

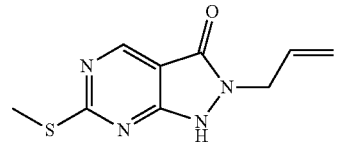

Intermediate 1 was prepared following a procedure described in Matheson et al., ACS Chem. Biol. (2016) 11:2066-2067. MS (LCMS) 223.0 [M+H]$^+$.

Intermediate 2

2-Bromo-6,7-dihydro-5H-cyclopenta[b]pyridine-7-ol

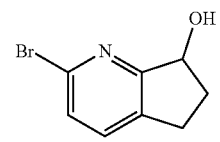

Step 1. A mixture of propiolamide (62 g, 898.55 mmol), ethyl 2-oxocyclopentanecarboxylate (140.35 g, 898.55 mmol) and Na$_2$CO$_3$ (94.3 g, 898.55 mmol) in water (2.25 L) was stirred at rt for 18 h. The mixture was extracted with EtOAc (3×500 mL). The combined organic layers were washed with brine, dried (Na$_2$SO$_4$) and concentrated to afford ethyl 1-(3-amino-3-oxoprop-1-enyl)-2-oxocyclopentanecarboxylate (40 g, 20%) as an off white solid. MS (LCMS) 226.3 [M+H]$^+$.

Step 2. A solution of ethyl 1-(3-amino-3-oxoprop-1-enyl)-2-oxocyclopentanecarboxylate (39 g, 173.33 mmol) in conc. HCl (390 mL) was stirred in a sealed tube at 110° C. for 18 h. The solvent was removed and aq. NaHCO$_3$ solution was added to adjust pH to 8-9 at 0° C. The resulting solid was filtered and washed with Et$_2$O (2×100 mL) to afford 6,7-dihydro-1H-cyclopenta[b]pyridin-2(5H)-one (15 g, 64% yield) as an off white solid. MS (LCMS) 135.9 [M+H]$^+$.

Step 3. A solution of 6,7-dihydro-1H-cyclopenta[b]pyridin-2(5H)-one (18 g, 133.33 mmol) in PBr$_3$ (180 mL) was heated at 180° C. for 18 h. The reaction was then allowed to cool to rt and was poured into ice-cold water. The pH was adjusted to 8-9 with saturated NaHCO₃. The resulting solution was filtered through a Celite pad. The filtrate was extracted with EtOAc (2×500 mL). The combined organic extracts were dried (Na₂SO₄) and concentrated to afford the 2-bromo-6,7-dihydro-5H-cyclopenta[b]pyridine (7 g, 26%) as an off white solid. MS (LCMS) 197.8 [M+H]⁺.

Step 4. To a stirred solution of 2-bromo-6,7-dihydro-5H-cyclopenta[b]pyridine (4 g, 20.41 mmol) in DCM (120 mL) was added m-CPBA (10.5 g, 61.22 mmol). The mixture was heated at reflux for 16 h, quenched with sat. NaHCO₃ and extracted with 5% MeOH/DCM (2×100 mL). The combined organic layers were dried (Na₂SO₄) and concentrated to afford 2-bromo-6,7-dihydro-5H-cyclopenta[b]pyridine 1-oxide (3.3 g, 76% yield) as an off white solid. MS (LCMS) 213.8 [M+H]⁺.

Step 5. A solution of 2-bromo-6,7-dihydro-5H-cyclopenta[b]pyridine-1-oxide (3.2 g, 15.09 mmol) in Ac₂O (30 mL) was heated at 100° C. for 16 h. Ac₂O was removed under reduced pressure. The residue was purified by flash chromatography (SiO₂, 7% EtOAc/pet ether) to afford 2-bromo-6,7-dihydro-5H-cyclopenta[b]pyridine-7-yl acetate (2 g, 52%) as an oil. MS (LCMS) 255.9 [M+H]⁺.

Step 6. To a stirred solution of 2-bromo-6,7-dihydro-5H-cyclopenta[b]pyridine-7-yl acetate (2 g, 7.84 mmol) in THF/H₂O (20 mL, 1:1) was added LiOH.H₂O (0.755 g, 31.49 mmol) at rt. The reaction was stirred for 3 h and was then diluted with water and extracted with EtOAc (2×50 mL). The combined organic layers were dried (Na₂SO₄) and concentrated. The residue was purified by flash chromatography (SiO₂, 40% EtOAc/pet ether) to afford Intermediate 2 (1.2 g, 71%) as a brown solid. MS (LCMS) 214.1 [M+H]⁺.

Intermediate 3

2-Allyl-1-(7-hydroxy-6,7-dihydro-5H-cyclopenta[b]pyridin-2-yl)-6-(methylthio)-1H-pyrazolo[3,4-d]pyrimidin-3(2H)-one

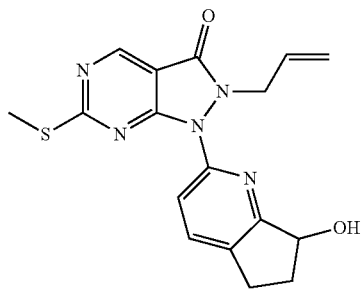 [SMILES: C=CCn1c(=O)c2cnc(SC)nc2n1-c1ccc2c(n1)C(O)CC2]

To a solution of Intermediate 1 (450 mg, 2.02 mmol), Intermediate 2 (558 mg, 2.62 mmol), CuI (384 mg, 2.02 mmol) and K₂CO₃ (390 mg, 2.83 mmol) in 1,4-dioxane (30 mL), N,N'-Dimethylethylenediamine (0.43 mL, 4.02 mmol) was added at 80° C. The suspension was heated at 95° C. for 18 h. The mixture was cooled to rt, diluted with aq. NH₄OH (30 mL) and extracted with EtOAc (2×50 mL). The combined organic extracts were washed with brine (20 mL), dried (Na₂SO₄) and evaporated to dryness. The residue was purified by flash chromatography (SiO₂, 40% EtOAc/pet ether) to afford Intermediate 3 (280 mg, 38%) as a pale yellow oil. MS (ESI) 356.4 [M+H]⁺.

Example 1A (S)-2-Allyl-1-(7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

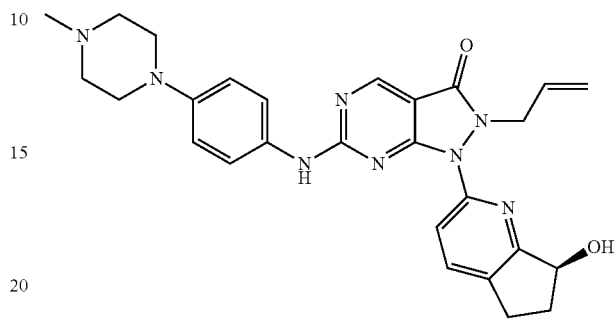

Example 1B (R)-2-Allyl-1-(7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

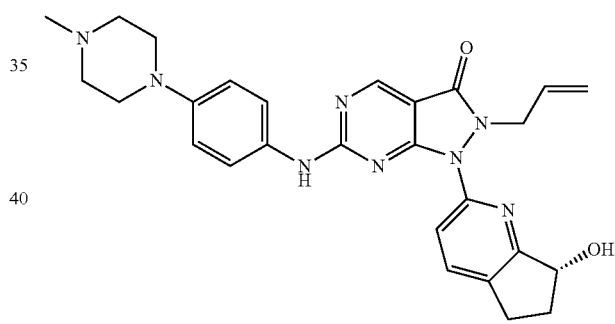

To a solution of Intermediate 3 (280 mg, 0.79 mmol) in toluene (20 mL), m-CPBA (201 mg, 1.17 mmol) was added and the mixture was stirred at rt for 1 h. DIPEA (0.69 mL, 3.94 mmol) and 4-(4-methyl piperazine-1-yl)aniline (178 mg, 0.93 mmol) were added and the mixture was stirred at rt for 18 h. Saturated NaHCO₃(25 mL) was added and the mixture was extracted with EtOAc (2×30 mL). The combined organic extracts were washed with brine (20 mL), dried (Na₂SO₄) and concentrated. The residue was purified by reverse phase HPLC (acetonitrile/water) to afford racemic 2-allyl-1-(7-hydroxy-6,7-dihydro-5H-cyclopenta[b]pyridin-2-yl)-6-(4-(4-methylpiperazin-1-yl)phenylamino)-1H-pyrazolo[3,4-d]pyrimidin-3(2H)-one (87 mg, 30% yield) as yellow solid. The enantiomers were separated by SFC chromatography (Chiralpak AD-H, 40% (0.5% DEA in ethanol)) to afford Peak 1 (Example 1A, 19 mg) and Peak 2 (Example 1B, 25 mg). Example 1A: a yellow solid; ¹H NMR (DMSO-d₆, 400 MHz) δ 10.08 (brs, 1H), 8.81 (s, 1H), 7.93 (d, J=8.0 Hz, 1H), 7.66 (d, J=8.4 Hz, 1H), 7.60-7.53 (m, 2H), 6.90 (d, J=8.8 Hz, 2H), 5.73-5.62 (m, 1H), 5.57-5.39 (m, 1H), 5.04-4.86 (m, 3H), 4.68-4.52 (m, 2H), 3.13-3.06 (m, 4H), 3.05-2.94 (m, 1H), 2.86-2.75 (m, 1H), 2.47-2.37 (m, 5H), 2.22 (s, 3H), 1.92-1.83 (m, 1H); MS (LCMS) 499.3 [M+H]+. Example 1B: a yellow solid; ¹H NMR (DMSO-d₆, 400 MHz) δ 10.05 (brs, 1H), 8.80 (s, 1H), 7.93 (d, J=8.0 Hz, 1H), 7.66 (d, J=8.0 Hz, 1H), 7.60-7.53 (m, 2H), 6.90 (d, J=8.8 Hz, 2H), 5.73-5.62 (m, 1H), 5.57-5.39 (m, 1H), 5.04-4.86 (m, 3H), 4.68-4.52 (m, 2H), 3.13-3.06 (m, 4H), 3.05-2.94 (m, 1H), 2.86-2.75 (m, 1H), 2.47-2.37 (m, 5H), 2.22 (s, 3H), 1.91-1.83 (m, 1H); MS (LCMS) 499.3 [M+H]+. The absolute stereochemistry was arbitrarily assigned for Example 1A and Example 1B.

Intermediate 4

2-Bromo-7-methyl-6,7-dihydro-5H-cyclopenta[b]pyridin-7-ol

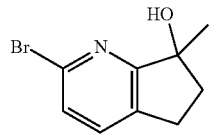

Step 1. To a stirred solution of racemic 2-bromo-6,7-dihydro-5H-cyclopenta[b]pyridin-7-ol (1.4 g, 6.60 mmol) in DCM (15 mL) was added Dess-Martin periodinane (3.0 g, 7.26 mmol). The mixture was stirred at rt for 16 h, quenched with aq. saturated NaHCO₃ solution and extracted with DCM (2×30 mL). The combined organic layers were concentrated under reduced pressure. The residue was purified by flash chromatography (SiO₂, 40% EtOAc/pet ether) to afford 2-bromo-5H-cyclopenta[b]pyridin-7(6H)-one (780 mg, 60%) as an off white solid. MS (LCMS) 212.0 [M+H]+.

Step 2. To a stirred solution of 2-bromo-5H-cyclopenta[b]pyridin-7(6H)-one (400 mg, 1.90 mmol) in THF (10 mL) was added methyl magnesium iodide (2M THF, 7.5 mL) at 0° C. The reaction was stirred from 0° C. to rt for 16 h, quenched with aq. saturated NH₄Cl and extracted with EtOAc (2×40 mL). The combined organic layers were concentrated under reduced pressure and the residue purified by flash chromatography (SiO₂, 30% EtOAc/pet ether) to afford Intermediate 4 (200 mg, 46%) as an off white solid. MS (LCMS) 227.9 [M+H]+.

Intermediate 5

2-allyl-1-(7-hydroxy-7-methyl-6,7-dihydro-5H-cyclopenta[b]pyridin-2-yl)-6-(methylthio)-1,2-dihydro-3H-pyrazolo[3,4-d]pyrimidin-3-one

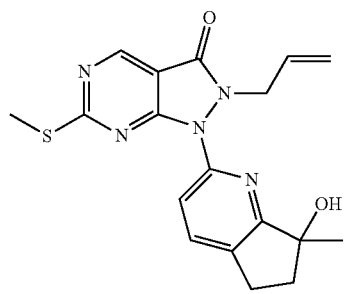

Intermediate 5 was prepared following a procedure described for Intermediate 3 using Intermediate 1 and Intermediate 4. MS (LCMS) 370.1 [M+H]+.

Example 2A (S)-2-Allyl-1-(7-hydroxy-7-methyl-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

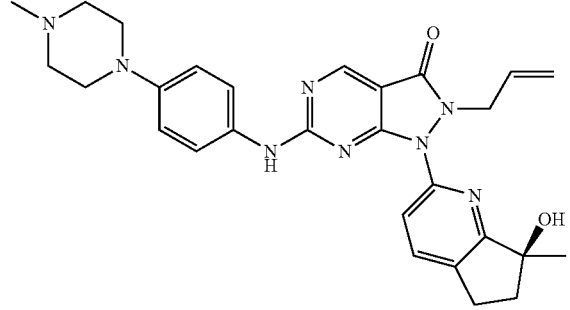

Example 2B (R)-2-Allyl-1-(7-hydroxy-7-methyl-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

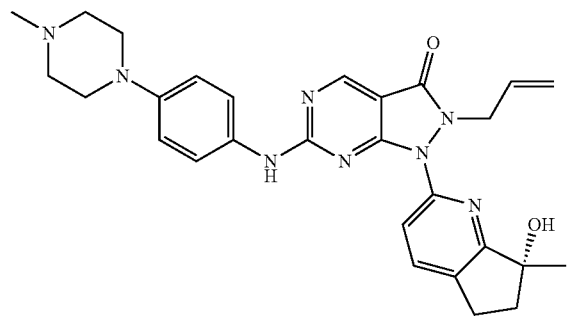

To a stirred solution Intermediate 5 (330 mg, 0.89 mmol) in THF/H₂O (20 mL, 1:1) was added Oxone (673 mg, 2.68 mmol) and the mixture was stirred at rt for 1 h, diluted with water (50 mL) and extracted with EtOAc (2×50 mL). The combined organic layers were dried (Na₂SO₄), filtered and concentrated under reduced pressure to afford a mixture of the sulfoxide and sulfone (330 mg, 0.822 mmol) as a semi-solid. To the mixture of the sulfoxide and sulfone (330 mg, 0.82 mmol) in toluene (10 mL), were added DIPEA (0.43 mL, 2.46 mmol) followed by 4-(4-methylpiperazin-1-yl)aniline (188 mg, 0.99 mmol) and the reaction was stirred at rt for 16 h. The mixture was diluted with EtOAc (50 mL) and washed with water (50 mL). The organic layer was dried (Na₂SO₄), filtered and concentrated under reduced pressure and the residue purified by flash chromatography (neutral alumina, 5% methanol/DCM) to afford racemic 2-allyl-1-(7-hydroxy-7-methyl-6,7-dihydro-5H-cyclopenta[b]pyridin-2-yl)-6-((4-(4-methylpiperazin-1-yl)phenyl)amino)-1,2- dihydro-3H-pyrazolo[3,4-d]pyrimidin-3-one (260 mg) as an off-white solid. The enantiomers were separated by SFC chromatography (Chiralpak AD-H, 15% (15 mM Ammonia in Methanol)) to afford Peak 1 (Example 2A, 105 mg) and Peak 2 (Example 2B, 96 mg). Example 2A: a yellow solid; $^1$H NMR (400 MHz, DMSO-$d_6$) δ 10.16 (s, 1H), 8.81 (s, 1H), 7.92 (d, J=6.8 Hz, 1H), 7.68 (d, J=8.0 Hz, 1H), 7.62-7.55 (m, 2H), 6.91 (d, J=9.2 Hz, 2H), 5.71-5.63 (m, 1H), 5.17 (s, 1H), 4.99 (d, J=9.6 Hz, 1H), 4.86 (d, J=17.2 Hz, 1H), 4.79-4.55 (m, 2H), 3.12-3.07 (m, 4H), 3.02-2.91 (m, 1H), 2.85-2.72 (m, 1H), 2.47-2.42 (m, 4H), 2.22 (s, 3H), 2.12 (t, J=7.2 Hz, 2H), 1.45 (s, 3H); MS (LCMS) 513.4 [M+H]$^+$. Example 2B: as a yellow solid; $^1$H NMR (400 MHz, DMSO-$d_6$) δ 10.16 (s, 1H), 8.82 (s, 1H), 7.97-7.89 (m, 1H), 7.68 (d, J=8.4 Hz, 1H), 7.62-7.55 (m, 2H), 6.91 (d, J=9.6 Hz, 2H), 5.71-5.63 (m, 1H), 5.17 (br s, 1H), 4.98 (d, J=9.6 Hz, 1H), 4.85 (d, J=16.4 Hz, 1H), 4.79-4.55 (m, 2H), 3.12-3.07 (m, 4H), 3.02-2.91 (m, 1H), 2.85-2.72 (m, 1H), 2.47-2.42 (m, 4H), 2.22 (s, 3H), 2.12 (t, J=7.2 Hz, 2H), 1.45 (s, 3H); MS (LCMS) 513.5 [M+H]$^+$. The absolute stereochemistry was arbitrarily assigned for Example 2A and Example 2B.

Intermediate 6

2-Bromo-7-(trifluoromethyl)-6,7-dihydro-5H-cyclopenta[b]pyridin-7-ol

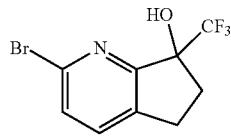 [SMILES: OC1(C(F)(F)F)CCc2ccc(Br)nc21]

To a stirred solution of 2-bromo-5,6-dihydro-7H-cyclopenta[b]pyridin-7-one (1.5 g, 7.08 mmol) in THF (20 mL) was added TMSCF$_3$ (3.2 ml, 21.23 mmol) followed by TBAF (1M in THF) (0.7 ml, 0.71 mmol) at 0° C. The reaction was stirred from 0° C. to rt for 12 h, quenched with 6N HCl and extracted with EtOAc (2×50 mL). The combined organic layers were dried (Na$_2$SO$_4$) and concentrated. The residue was purified by flash chromatography (SiO$_2$, 30% EtOAc/pet ether) to afford Intermediate 6 (825 mg, 41%) as a brown solid. MS (LCMS) 281.9 [M+H]$^+$.

Intermediate 7

2-allyl-1-(7-hydroxy-7-(trifluoromethyl)-6,7-dihydro-5H-cyclopenta[b]pyridin-2-yl)-6-(methylthio)-1,2-dihydro-3H-pyrazolo[3,4-d]pyrimidin-3-one

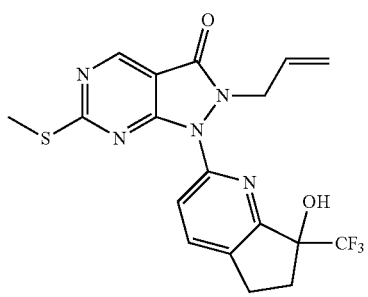 [SMILES: C=CCn1c(=O)c2cnc(SC)nc2n1-c1ccc2c(n1)C(O)(C(F)(F)F)CC2]

Intermediate 7 was prepared following a procedure described for Intermediate 3 using Intermediate 1 and Intermediate 6. MS (LCMS) 424.3 [M+H]$^+$.

Example 3A (S)-2-Allyl-1-(7-hydroxy-7-(trifluoromethyl)-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

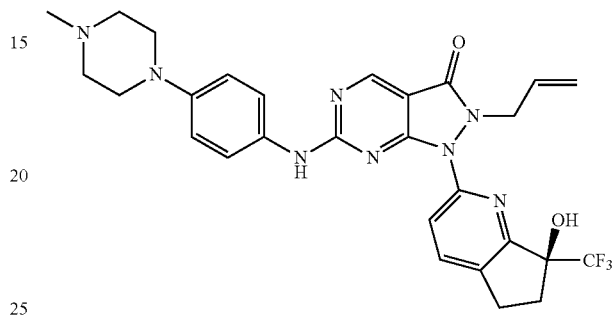

Example 3B (R)-2-Allyl-1-(7-hydroxy-7-(trifluoromethyl)-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

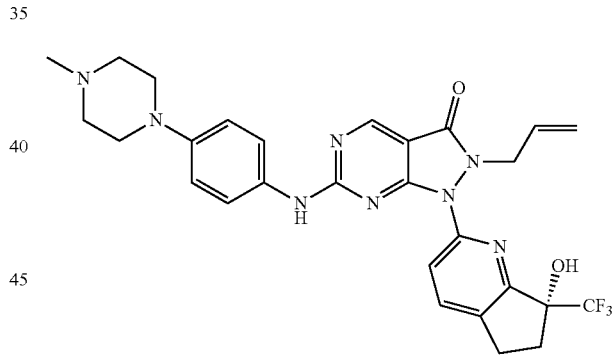

Examples 3A and 3B were prepared by following a procedure described for Examples 2A and 2B using Intermediate 7 to give racemic 2-allyl-1-(7-hydroxy-7-(trifluoromethyl)-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (330 mg). The enantiomers were separated by SFC chromatography (Chiralpak AD-H, 40% (15 mM Ammonia in Methanol)) to afford Peak 1 (Example 3A, 126 mg) and Peak 2 (Example 3B, 150 mg). Example 3A: a yellow solid; $^1$H NMR (400 MHz, DMSO-$d_6$) δ 10.20 (s, 1H), 8.84 (s, 1H), 8.07 (br s, 1H), 7.92 (d, J=8.0 Hz, 1H), 7.65-7.58 (m, 2H), 6.94 (d, J=8.8 Hz, 2H), 6.79 (s, 1H), 5.68-5.60 (m, 1H), 4.96 (d, J=10.0 Hz, 1H), 4.79 (d, J=16.4 Hz, 2H), 4.61-4.53 (m, 1H), 3.14-3.02 (m, 5H), 3.00-2.90 (m, 1H), 2.61-2.60 (m, 1H), 2.49-2.44 (m, 4H), 2.22 (br s, 4H); MS (LCMS) 567.5 [M+H]$^+$. Example 3B: a yellow solid; $^1$HNMR (400 MHz, DMSO-$d_6$) δ 10.20 (s, 1H), 8.84 (s, 1H), 8.07 (br s, 1H), 7.92

(d, J=8.0 Hz, 1H), 7.65-7.58 (m, 2H), 6.94 (d, J=8.8 Hz, 2H), 6.79 (s, 1H), 5.70-5.60 (m, 1H), 4.96 (d, J=10.0 Hz, 1H), 4.79 (d, J=16.4 Hz, 2H), 4.61-4.53 (m, 1H), 3.16-3.02 (m, 5H), 3.00-2.90 (m, 1H), 2.61-2.56 (m, 1H), 2.49-2.44 (m, 4H), 2.25 (br s, 4H); MS (LCMS) 567.6 [M+H]$^+$. The absolute stereochemistry was arbitrarily assigned for Example 3A and Example 3B.

Intermediate 8

5-Bromo-3-methyl-2,3-dihydrofuro[3,2-b]pyridin-3-ol

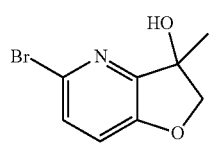

Step 1. 2,3-Dihydrofuro[3,2-b]pyridin-5-amine was prepared according to WO Publication No. 2008/069311. MS (LCMS) 137.1 [M+H]$^+$.

Step 2. To a stirred solution of 2,3-dihydrofuro[3,2-b]pyridin-5-amine (9.0 g, 66.17 mmol) in CH$_2$Br$_2$ (200 mL) was added CuBr$_2$ (7.303 g, 33.08 mmol) and followed by addition of isoamyl nitrite (8.515 g, 72.78 mmol) drop-wise. The reaction was stirred for at rt for 2 h, quenched with saturated aq. NaHCO$_3$ (50 mL) and filtered through a Celite pad. The filtrate was extracted with DCM (3×50 mL). The combined organic layers were dried (Na$_2$SO$_4$), filtered and concentrated. The residue was purified by flash chromatography (SiO$_2$, EtOAc/pet ether) to afford 5-bromo-2,3-dihydrofuro[3,2-b]pyridine (6.0 g, 45%) as a brown solid. MS (ESI) 200.2 [M+H]$^+$.

Step 3. To a stirred solution of 5-bromo-2,3-dihydrofuro[3,2-b]pyridine (6.0 g, 30.15 mmol) in DCM (100 mL) was added m-CPBA (6.27 g, 36.18 mmol) at 0° C. and the mixture was stirred at rt for 16 h. The reaction mixture was concentrated under reduced pressure and the residue was triturated with n-pentane and dried to afford crude 5-bromo-2,3-dihydrofuro[3,2-b]pyridine 4-oxide (9.5 g) as an off-white solid. MS (ESI) 216.2 [M+H]$^+$. Acetic anhydride (100 mL) was added to 5-bromo-2,3-dihydrofuro[3,2-b]pyridine 4-oxide (9.5 g, 44.18 mmol) and heated at 90° C. for 1 h. The reaction was cooled to rt, concentrated under reduced pressure and the residue was diluted with saturated aq. NaHCO$_3$ (100 mL) and extracted with EtOAc (3×60 mL). The combined organic layers were dried (Na$_2$SO$_4$), filtered and concentrated under reduced pressure. The residue was purified by flash chromatography (SiO$_2$, EtOAc/pet ether) to afford 5-bromo-2,3-dihydrofuro[3,2-b]pyridin-3-yl acetate (5.0 g, 65%) as a brown solid. MS (ESI) 258.2 [M+H]$^+$.

Step 4. To a stirred solution of 5-bromo-2,3-dihydrofuro[3,2-b]pyridin-3-yl acetate (5.0 g, 19.45 mmol) in THF/H$_2$O (1:1, 30 mL) was added LiOH.H$_2$O (2.45 g, 58.35 mmol) and stirred at rt for 2 h. The mixture was extracted with EtOAc (3×100 mL) and the combined organic layers were washed with water (100 mL) and brine (100 mL). The organic layer was dried (Na$_2$SO$_4$), filtered and concentrated under reduced pressure to afford 5-bromo-2,3-dihydrofuro[3,2-b]pyridin-3-ol (2.5 g, 59%) as an off-white solid. MS (ESI) 216.1 [M+H]$^+$.

Step 5. To a stirred solution of 5-bromo-2,3-dihydrofuro[3,2-b]pyridin-3-ol (2.6 g, 12.09 mmol) in acetone (30 mL), was added freshly prepared Jones reagent (25 mL, CrO$_3$ (3 eq.) and aq. H$_2$SO$_4$ (3 eq.) at 0° C., and the reaction was stirred at 0° C. for 30 min. The reaction was diluted with EtOAc (60 mL), washed with ice-cold water (50 mL) and brine (50 mL). The organic layer was dried (Na$_2$SO$_4$), filtered and concentrated under reduced pressure to afford 5-bromofuro[3,2-b]pyridin-3(2H)-one (1.2 g, 46% yield) as a brown solid. MS (ESI) 214.4 [M+H]$^+$.

Step 6. To a 0° C. solution of 5-bromofuro[3,2-b]pyridin-3(2H)-one (1.1 g, 5.16 mmol) in Et$_2$O (15 mL) was added methyl magnesium iodide (8.6 mL, 3.0 M in Et$_2$O, 25.80 mmol). The reaction was stirred at 0° C. for 1 h, quenched with aq. NH$_4$Cl (30 mL) and extracted with EtOAc (2×30 mL). The combined organic layers were dried (Na$_2$SO$_4$), filtered and concentrated under reduced pressure. The residue was purified by flash chromatography (SiO$_2$, 30% EtOAc/pet ether) to Intermediate 8 (510 mg, 43% yield) as a brown solid. MS (ESI) 230.3 [M+H]$^+$.

Intermediate 9

2-Allyl-1-(3-hydroxy-3-methyl-2,3-dihydrofuro[3,2-b]pyridin-5-yl)-6-(methylthio)-1,2-dihydro-3H-pyrazolo[3,4-d]pyrimidin-3-one

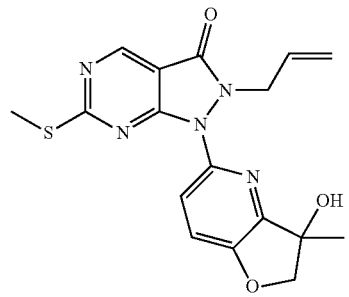

Intermediate 9 was prepared following the procedure described for Intermediate 3 using Intermediate 1 and Intermediate 8; MS (ESI) 372.6 [M+H]$^+$.

Example 4A (S)-2-Allyl-1-(3-hydroxy-3-methyl-2,3-dihydrofuro[3,2-b]pyridin-5-yl)-6-((4-(4-methylpiperazin-1-yl)phenyl)amino)-1,2-dihydro-3H-pyrazolo[3,4-d]pyrimidin-3-one

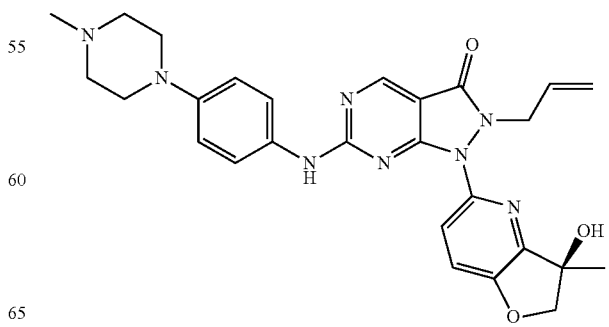

Example 4B (R)-2-Allyl-1-(3-hydroxy-3-methyl-2,3-dihydrofuro[3,2-b]pyridin-5-yl)-6-((4-(4-methylpiperazin-1-yl)phenyl)amino)-1,2-dihydro-3H-pyrazolo[3,4-d]pyrimidin-3-one

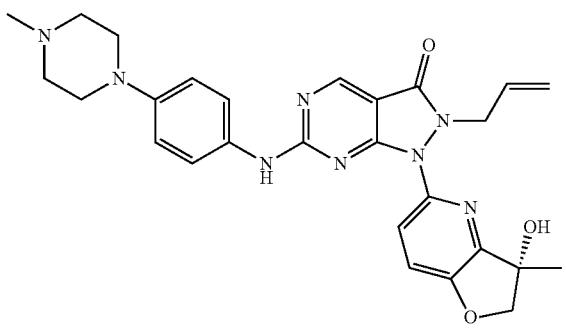

Examples 4A and 4B were prepared following a procedure described for Examples 2A and 2B using Intermediate 9 to give racemic 2-allyl-1-(3-hydroxy-3-methyl-2,3-dihydrofuro[3,2-b]pyridin-5-yl)-6-((4-(4-methylpiperazin-1-yl)phenyl)-amino)-1,2-dihydro-3H-pyrazolo[3,4-d]pyrimidin-3-one (350 mg). The enantiomers were separated by SFC chromatography (Chiralpak AD-H, 40% (0.5% DEA in Ethanol)) to afford Peak 1 (Example 4A, 120 mg) and Peak 2 (Example 4B, 120 mg). Example 4A: a yellow solid; $^1$H NMR (400 MHz, DMSO-$d_6$) δ 10.10 (br s, 1H), 8.81 (s, 1H), 7.70-7.53 (m, 4H), 6.85 (d, J=16.8 Hz, 2H), 5.81 (s, 1H), 5.71-5.64 (m, 1H), 5.01 (d, J=9.2 Hz, 1H), 4.89 (d, J=17.2 Hz, 1H), 4.50-4.43 (m, 4H), 3.07 (t, J=4.4 Hz, 4H), 2.44 (t, J=4.4 Hz, 4H), 2.21 (s, 3H), 1.55 (s, 3H); MS (ESI) 515.6 [M+H]$^+$. Example 4B: as a yellow solid; $^1$H NMR (400 MHz, DMSO-$d_6$) δ 10.10 (br s, 1H), 8.81 (s, 1H), 7.70-7.53 (m, 4H), 6.85 (d, J=16.8 Hz, 2H), 5.81 (s, 1H), 5.71-5.64 (m, 1H), 5.01 (d, J=9.2 Hz, 1H), 4.89 (d, J=17.2 Hz, 1H), 4.50-4.43 (m, 4H), 3.07 (t, J=4.4 Hz, 4H), 2.44 (t, J=4.4 Hz, 4H), 2.21 (s, 3H), 1.55 (s, 3H); MS (ESI) 515.5 [M+H]$^+$. The absolute stereochemistry was arbitrarily assigned for Example 4A and Example 4B.

Intermediate 10

3-ethyl-5-iodo-2,3-dihydrobenzofuran-3-ol

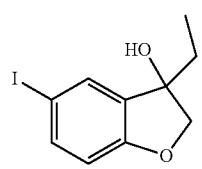

Step 1. 5-iodobenzofuran-3(2H)-one was prepared according to WO Publication No. 2008/068974. MS (ESI) m/z 260.9 [M+H]$^+$.

Step 2. To a stirred, 0° C. solution of 5-iodobenzofuran-3(2H)-one (2 g, 7.69 mmol) in toluene (20 mL) was added 3.0 M EtMgBr (12.82 mL, 38.46 mmol) drop-wise. The mixture was allowed to warm to rt and stirred for 16 h. After completion by TLC, the reaction was quenched with water (50 mL) and extracted with EtOAc (2×100 mL). The combined organic layers were dried (Na$_2$SO$_4$), filtered and concentrated under reduced pressure. The residue was purified by flash chromatography (SiO$_2$, 20% EtOAc/pet ether) to afford Intermediate 10 (1.5 g, 67%) as a yellow solid. MS (ESI) 272.9 [M+H—H$_2$O]$^+$.

Intermediate 11

2-allyl-1-(3-ethyl-3-hydroxy-2,3-dihydrobenzofuran-5-yl)-6-(methylthio)-1,2-dihydro-3H-pyrazolo[3,4-d]pyrimidin-3-one

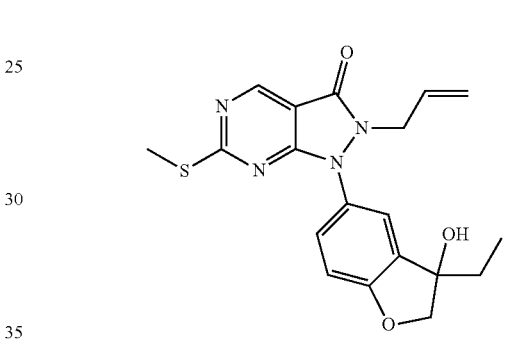

Intermediate 11 was prepared following the procedure described for Intermediate 3 using Intermediate 1 and Intermediate 10. MS (ESI) 385.1 [M+H]$^+$.

Example 5A (R)-2-allyl-1-(3-ethyl-3-hydroxy-2,3-dihydrobenzofuran-5-yl)-6-((4-(4-methylpiperazin-1-yl)phenyl)amino)-1,2-dihydro-3H-pyrazolo[3,4-d]pyrimidin-3-one

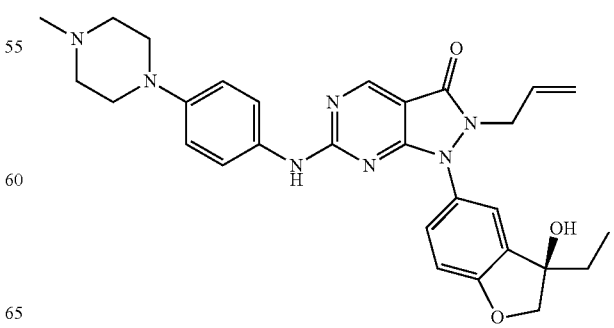

Example 5B (S)-2-allyl-1-(3-ethyl-3-hydroxy-2,3-dihydrobenzofuran-5-yl)-6-((4-(4-methylpiperazin-1-yl)phenyl)amino)-1,2-dihydro-3H-pyrazolo[3,4-d]pyrimidin-3-one

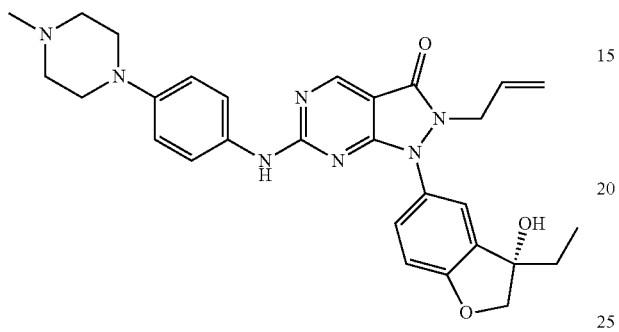

Examples 5A and 5B were prepared following a procedure described for Examples 2A and 2B using Intermediate 11 to give racemic 2-allyl-1-(3-ethyl-3-hydroxy-2,3-dihydrobenzofuran-5-yl)-6-((4-(4-methylpiperazin-1-yl)phenyl)amino)-1,2-dihydro-3H-pyrazolo[3,4-d]pyrimidin-3-one (380 mg). The enantiomers were separated by SFC chromatography (Chiralpak AD-H, 45% (0.5% DEA in Ethanol)) to afford Peak 1 (Example 5A, 123 mg) and Peak 2 (Example 5B, 141 mg). Example 5A: a yellow solid; $^1$H NMR (400 MHz, DMSO-$d_6$) δ 9.95 (br s, 1H), 8.77 (s, 1H), 7.51 (d, J=2 Hz, 2H), 7.30-7.28 (m, 2H), 6.97 (d, J=8.8 Hz, 1H), 6.82 (d, J=8.8 Hz, 2H), 5.70-5.64 (m, 1H), 5.55 (s, 1H), 5.08 (d, J=10.4 Hz, 1H), 4.93 (d, J=10.4 Hz, 1H), 4.46 (d, J=10.4 Hz, 1H), 4.32 (d, J=10.4 Hz, 1H), 4.20 (s, 2H), 3.05-3.03 (m, 4H), 2.44-2.42 (m, 4H), 2.20 (s, 3H), 1.91-1.82 (m, 2H), 0.84 (t, J=7.2 Hz, 3H); MS (ESI) 528.2 [M+H]$^+$. Example 5B: a yellow solid; $^1$H NMR (400 MHz, DMSO-$d_6$) δ 9.95 (brs, 1H), 8.77 (s, 1H), 7.51 (d, J=2 Hz, 2H), 7.30-7.28 (m, 2H), 6.97 (d, J=8.8 Hz, 1H), 6.82 (d, J=8.8 Hz, 2H), 5.70-5.64 (m, 1H), 5.55 (s, 1H), 5.08 (d, J=10.4 Hz, 1H), 4.93 (d, J=10.4 Hz, 1H), 4.46 (d, J=10.4 Hz, 1H), 4.32 (d, J=10.4 Hz, 1H), 4.20 (s, 2H), 3.05-3.03 (m, 4H), 2.44-2.42 (m, 4H), 2.20 (s, 3H), 1.91-1.82 (m, 2H), 0.84 (t, J=7.2 Hz, 3H); MS (ESI) 528.2 [M+H]$^+$. The absolute stereochemistry was arbitrarily assigned for Example 5A and Example 5B.

Intermediate 12

5-bromo-3-(trifluoromethyl)-2,3-dihydrofuro[3,2-b]pyridin-3-ol

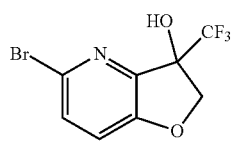 [SMILES: OC1(C(F)(F)F)COc2ccc(Br)nc21]

A 1/1 mixture of KOH/Celite by weight was finely ground. The KOH/Celite mixture (720 mg) was packed into a glass dropper. 5-bromofuro[3,2-b]pyridin-3(2H)-one (500 mg, 2.35 mmol) and Me$_3$SiCF$_3$ (666 mg, 4.69 mmol) were dissolved in DMF (2.0 mL). The solution was added to the glass dropper using the syringe. The product was eluted with 4.0 mL of DMF. The reaction was repeated on 4×500 mg scale. The combined reaction mixtures were quenched with saturated NH$_4$Cl (50 mL). The aqueous layer was extracted with Et$_2$O (2×75 mL) and the combined organic layers were washed with brine (2×100 mL), dried (Na$_2$SO$_4$), filtered and concentrated under reduced pressure. The residue was purified by flash chromatography (SiO$_2$, 20% EtOAc/pet ether) to afford Intermediate 12 (530 mg, 16%) as an off-white solid. MS (ESI) 284.2 [M+H]$^+$.

Intermediate 13

2-allyl-1-(3-hydroxy-3-(trifluoromethyl)-2,3-dihydrofuro[3,2-b]pyridin-5-yl)-6-(methylthio)-1,2-dihydro-3H-pyrazolo[3,4-d]pyrimidin-3-one

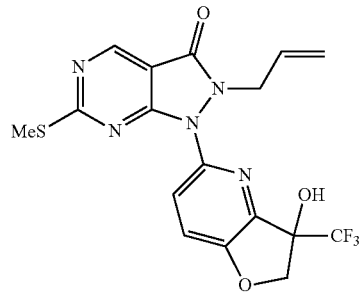 [SMILES: C=CCn1c(=O)c2cnc(SC)nc2n1-c1ccc2c(n1)C(O)(C(F)(F)F)CO2]

Intermediate 13 was prepared following the procedure described for Intermediate 3 using Intermediate 1 and Intermediate 12. MS (ESI) 426.4 [M+H]$^+$.

Example 6A (R)-2-allyl-1-(3-hydroxy-3-(trifluoromethyl)-2,3-dihydrofuro[3,2-b]pyridin-5-yl)-6-((4-(4-methylpiperazin-1-yl)phenyl)amino)-1,2-dihydro-3H-pyrazolo[3,4-d]pyrimidin-3-one

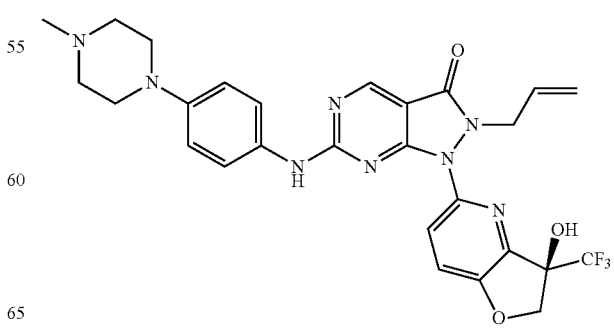

Example 6B (S)-2-allyl-1-(3-hydroxy-3-(trifluoromethyl)-2,3-dihydrofuro[3,2-b]pyridin-5-yl)-6-((4-(4-methylpiperazin-1-yl)phenyl)amino)-1,2-dihydro-3H-pyrazolo[3,4-d]pyrimidin-3-one

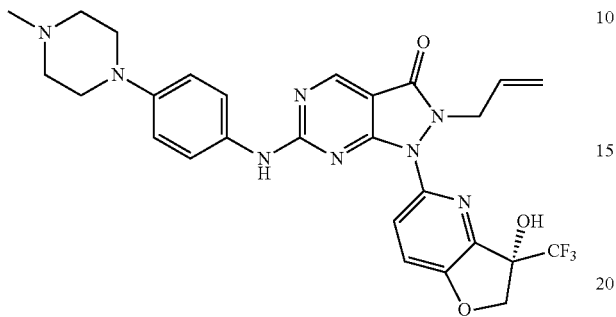

Examples 6A and 6B were prepared following a procedure described for Examples 2A and 2B using Intermediate 13 to give racemic 2-allyl-1-(3-hydroxy-3-(trifluoromethyl)-2,3-dihydrofuro[3,2-b]pyridin-5-yl)-6-((4-(4-methylpiperazin-1-yl)phenyl)amino)-1,2-dihydro-3H-pyrazolo[3,4-d]pyrimidin-3-one (170 mg). The enantiomers were separated by SFC chromatography (Chiral Pak IG, 40.0%, (0.5% DEA in MeOH)) to afford Peak 1 (Example 6A, 35 mg) and Peak 2 (Example 6B, 40 mg). Example 6A: a yellow solid; $^1$H NMR (400 MHz, DMSO-$d_6$) δ 10.2 (br s, 1H), 8.84 (s, 1H), 7.87-7.85 (m, 2H), 7.60-7.55 (m, 2H), 6.91 (d, J=9.2 Hz, 2H), 5.67-5.62 (m, 1H), 5.00-4.93 (m, 2H), 4.83 (d, J=16 Hz, 1H), 4.63 (d, J=12 Hz, 1H), 4.59 (d, J=12 Hz, 2H), 4.48-4.42 (m, 1H), 3.10-3.08 (m, 4H), 2.47-2.44 (m, 4H), 2.22 (s, 3H); MS (ESI) 569.2 [M+H]$^+$. Example 6B: a yellow solid; $^1$H NMR (400 MHz, DMSO-$d_6$) δ 10.2 (br s, 1H), 8.84 (s, 1H), 7.87-7.85 (m, 2H), 7.60-7.55 (m, 2H), 6.91 (d, J=9.2 Hz, 2H), 5.67-5.62 (m, 1H), 5.00-4.93 (m, 2H), 4.83 (d, J=16 Hz, 1H), 4.63 (d, J=12 Hz, 1H), 4.59 (d, J=12 Hz, 2H), 4.48-4.42 (m, 1H), 3.10-3.08 (m, 4H), 2.47-2.44 (m, 4H), 2.22 (s, 3H); MS (ESI) 569.2 [M+H]$^+$. The absolute stereochemistry was arbitrarily assigned for Example 6A and Example 6B.

Intermediate 14

2-Bromo-7,7-difluoro-6,7-dihydro-5H-cyclopenta[b]pyridine

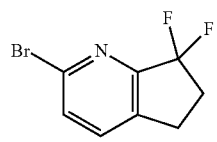 [SMILES: FC1(F)CCc2ccc(Br)nc21]

To a stirred rt solution of 2-bromo-5,6-dihydro-7H-cyclopenta[b]pyridin-7-one (2.0 g, 9.43 mmol) in DCM (50 mL) was added DAST (3.7 mL, 28.30 mmol) and the mixture was stirred at rt for 4 days. The reaction was quenched with aq. NaHCO$_3$ (25 mL) at 0° C. and extracted with DCM (3×30 mL). The organic layer was dried (Na$_2$SO$_4$), filtered and concentrated under reduced pressure. The residue was purified by flash chromatography (SiO$_2$, 3% EtOAc/pet ether) to afford Intermediate 14 (0.8 g, 36% yield) as an off-white solid. MS (ESI) 233.9 [M+H]$^+$.

Intermediate 15

2-Allyl-1-(7,7-difluoro-6,7-dihydro-5H-cyclopenta[b]pyridin-2-yl)-6-(methylthio)-1,2-dihydro-3H-pyrazolo[3,4-d]pyrimidin-3-one

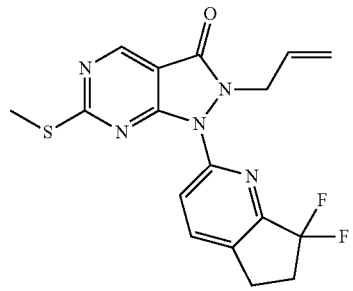 [SMILES: C=CCn1c(=O)c2cnc(SC)nc2n1-c1ccc2c(n1)C(F)(F)CC2]

Intermediate 15 was prepared following a procedure described for Intermediate 3 using Intermediate 1 and Intermediate 14; MS (ESI) 376.4 [M+H]$^+$.

Example 7

2-Allyl-1-(7,7-difluoro-6,7-dihydro-5H-cyclopenta[b]pyridin-2-yl)-6-((4-(piperazin-1-yl) phenyl)amino)-1,2-dihydro-3H-pyrazolo[3,4-d]pyrimidin-3-one

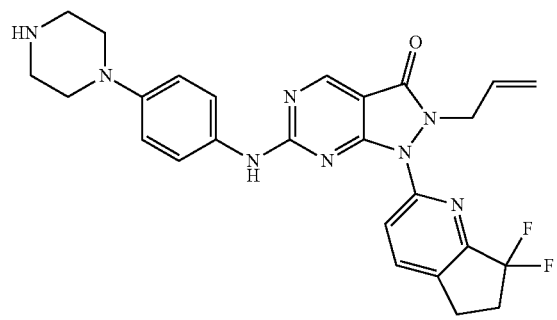 [SMILES: C=CCn1c(=O)c2cnc(Nc3ccc(N4CCNCC4)cc3)nc2n1-c1ccc2c(n1)C(F)(F)CC2]

Step 1. The employment of tert-butyl 4-(4-aminophenyl)piperazine-1-carboxylate and Intermediate 15 by following the procedure described for Examples 2A and 2B afforded tert-butyl 4-(4-((2-allyl-1-(7,7-difluoro-6,7-dihydro-5H-cyclopenta[b]pyridin-2-yl)-3-oxo-2,3-dihydro-1H-pyrazolo[3,4-d]pyrimidin-6-yl)amino)phenyl)piperazine-1-carboxylate (120 mg, 19% yield). MS (ESI) 605.2 [M+H]$^+$.

Step 2. To a stirred solution of tert-butyl 4-(4-((2-allyl-1-(7,7-difluoro-6,7-dihydro-5H-cyclopenta[b]pyridin-2-yl)-3-oxo-2,3-dihydro-1H-pyrazolo[3,4-d]pyrimidin-6-yl)amino)phenyl)piperazine-1-carboxylate (250 mg, 0.41 mmol) in Et$_2$O (10 mL) was added 2M HCl in Et$_2$O (5 mL) at 0° C. The mixture was stirred at rt for 4 h, concentrated under reduced pressure, and triturated with Et$_2$O to afford Example 7 in a hydrochloride salt form (94 mg, 42%) as a pale yellow solid. $^1$H NMR (400 MHz, DMSO-$d_6$) δ 10.28

(br s, 1H), 8.95 (br s, 2H), 8.87 (s, 1H), 8.17 (d, J=8.4 Hz, 1H), 8.05 (d, J=8.0 Hz, 1H), 7.62 (br s, 2H), 7.00 (d, J=8.8 Hz, 2H), 5.75-5.65 (m, 1H), 5.01 (d, J=10.4 Hz, 1H), 4.86 (d, J=17.6 Hz, 1H), 4.61 (d, J=5.6 Hz, 2H), 3.38-3.20 (m, 8H), 3.14-3.05 (m, 2H), 2.78-2.62 (m, 2H); MS (ESI) 505.4 [M+H]⁺.

Example 8

2-Allyl-1-(7,7-difluoro-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

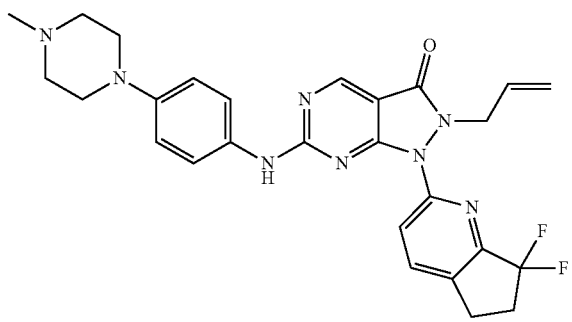 [SMILES: C=CCn1c(=O)c2cnc(Nc3ccc(N4CCN(C)CC4)cc3)nc2n1-c1ccc2c(n1)C(F)(F)CC2]

The employment of 4-(4-methylpiperazin-1-yl)aniline and Intermediate 15 by following the procedure described for Examples 2A and 2B afforded Example 8 (120 mg, 19%) as a yellow solid. ¹H NMR (400 MHz, DMSO-d₆) δ 10.24 (br s, 1H), 8.85 (s, 1H), 8.18 (br s, 1H), 8.06 (br s, 1H), 7.57 (br s, 2H), 6.94 (d, J=8.8 Hz, 2H), 5.75-5.65 (m, 1H), 5.00 (d, J=10.4 Hz, 1H), 4.85 (d, J=17.2 Hz, 1H), 4.61 (d, J=5.2 Hz, 2H), 3.10 (br s, 6H), 2.78-2.62 (m, 2H), 2.52-2.42 (m, 4H), 2.22 (s, 3H); MS (ESI) 519.3 [M+H]⁺.

Intermediate 16

2-bromo-7-ethyl-6,7-dihydro-5H-cyclopenta[b]pyridin-7-ol

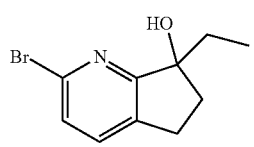

To a 0° C. solution of 2-bromo-5,6-dihydro-7H-cyclopenta[b]pyridin-7-one (2 g, 9.43 mmol) in PhMe (20 mL) was added EtMgBr 3M in DEE (9.4 mL, 28.29 mmol) drop-wise. The ice bath was removed and the reaction was stirred at rt for 16 h. After completion by TLC, the reaction was cooled to 0° C. and quenched with sat. NH₄Cl (30 mL) solution and extracted with EtOAc (2×50 mL). The organic layer was separated, dried (Na₂SO₄) and evaporated under reduced pressure. The residue was purified by flash chromatography (SiO₂, 30% EtOAc/Hexanes) to afford Intermediate 16 (860 mg, 38%) as an oil. MS (ESI) 244.2 [M+H]⁺.

Intermediate 17

2-allyl-1-(7-ethyl-7-hydroxy-6,7-dihydro-5H-cyclopenta[b]pyridin-2-yl)-6-(methylthio)-1,2-dihydro-3H-pyrazolo[3,4-d]pyrimidin-3-one

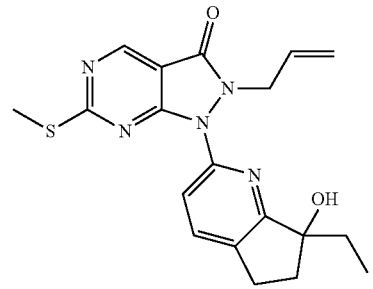 [SMILES: C=CCn1c(=O)c2cnc(SC)nc2n1-c1ccc2c(n1)C(O)(CC)CC2]

Intermediate 17 was prepared following a procedure described for Intermediate 3 using Intermediate 1 and Intermediate 16. MS (LCMS) 384.5 [M+H]⁺.

Example 9A (S)-2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

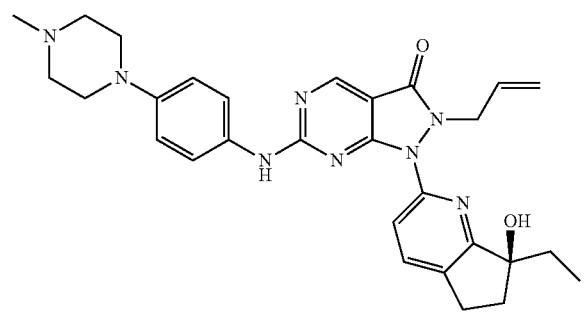 [SMILES: C=CCn1c(=O)c2cnc(Nc3ccc(N4CCN(C)CC4)cc3)nc2n1-c1ccc2c(n1)[C@](O)(CC)CC2]

Example 9B (R)-2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

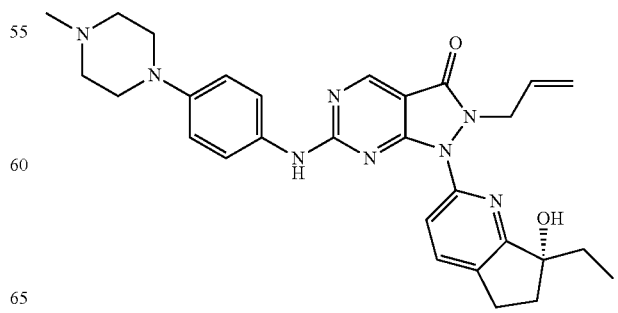

To a 0° C. solution of Intermediate 17 (4.5 g, 11.7 mmol) in toluene (90 mL) was added m-CPBA (3.7 g, 12.9 mmol). The ice bath was removed and the reaction was stirred for 30 min. After completion by TLC, 4-(4-methylpiperazin-1-yl)aniline (2.9 g, 15.2 mmol) and DIPEA (10.9 mL, 61.05 mmol) were added at 0° C. The ice bath was removed and the reaction was stirred at rt for 16 h. The reaction was determined to be complete by TLC and water (100 mL) was added to the reaction and extracted with EtOAc (3×100 mL). The combined organic layers were washed with sat. NaHCO$_3$ solution (250 mL), brine (300 mL), dried (Na$_2$SO$_4$) and evaporated under reduced pressure. The crude material was triturated with 30% Et$_2$O/pentane to afford racemic 2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (5.2 g, 84%). The racemic material (3.5 g) was separated by SFC chromatography (Chiralpak AD-H, 35% (0.5% DEA in Methanol)) to afford Peak 1 (Example 9A, 1.38 g) and Peak 2 (Example 9B, 1.26 g). Example 9A; a yellow solid; $^1$H NMR (400 MHz, DMSO-d$_6$) δ 10.05 (br s, 1H), 8.82 (s, 1H), 7.92 (br s, 1H), 7.70 (d, J=8.4 Hz, 1H), 7.58 (br s, 2H), 6.92 (d, J=8.8 Hz, 2H), 5.70-5.63 (m, 1H), 5.05 (s, 1H), 4.99 (d, J=10.4 Hz, 1H), 4.85 (d, J=17.6 Hz, 1H), 4.74 (br s, 1H), 4.56 (d, J=10.8 Hz, 1H) 3.09-3.08 (m, 4H) 3.01-2.81 (m, 1H), 2.80-2.74 (m, 1H), 2.46-2.44 (m, 4H), 2.22 (s, 3H), 2.20-2.17 (m, 1H), 2.03-1.98 (m, 1H), 1.91-1.86 (m, 1H), 1.73-1.67 (m, 1H), 0.87 (t, J=7.2 Hz, 3H); MS (ESI) 527.5 [M+H]$^+$. Example 9B; a yellow solid; $^1$H NMR (400 MHz, DMSO-d$_6$) δ 10.05 (br s, 1H), 8.82 (s, 1H), 7.92 (br s, 1H), 7.70 (d, J=8.4 Hz, 1H), 7.58 (br s, 2H), 6.92 (d, J=8.8 Hz, 2H), 5.70-5.63 (m, 1H), 5.05 (s, 1H), 4.99 (d, J=10.4 Hz, 1H), 4.85 (d, J=17.6 Hz, 1H), 4.74 (br s, 1H), 4.56 (d, J=10.8 Hz, 1H) 3.09-3.08 (m, 4H) 3.01-2.81 (m, 1H), 2.80-2.74 (m, 1H), 2.46-2.44 (m, 4H), 2.22 (s, 3H), 2.20-2.17 (m, 1H), 2.03-1.98 (m, 1H), 1.91-1.86 (m, 1H), 1.73-1.67 (m, 1H), 0.87 (t, J=7.2 Hz, 3H); MS (ESI) 527.5 [M+H]$^+$. The absolute stereochemistry was arbitrarily assigned for Example 9A and Example 9B.

Example 10A (S)-2-allyl-1-(7-hydroxy-7-methyl-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one

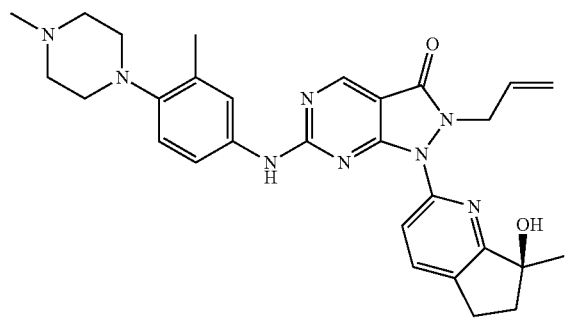

Example 10B (R)-2-allyl-1-(7-hydroxy-7-methyl-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one

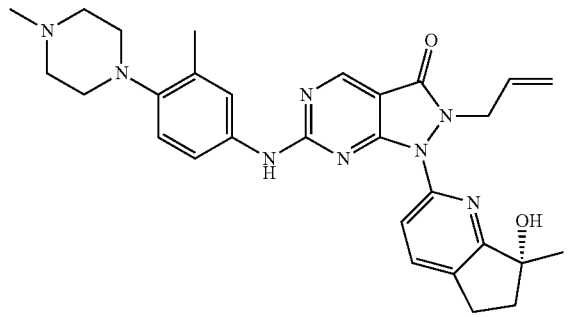

Examples 10A and 10B were prepared by following a procedure described for Examples 2A and 2B using Intermediate 5 to give racemic 2-allyl-1-(7-hydroxy-7-methyl-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one (400 mg). The enantiomers were separated by chiral SFC chromatography (Chiralpak AD-H, 20% (15 mM Ammonia in Methanol)) to give Peak 1 (Example 10A, 120 mg) and Peak 2 (Example 10B, 125 mg). Example 10A: yellow solid; $^1$H NMR (400 MHz, DMSO-d$_6$) δ 10.13 (br s, 1H), 8.84 (s, 1H), 7.90 (d, J=7.6 Hz, 1H), 7.71 (d, J=8.4 Hz, 1H), 7.66 (br s, 1H) 7.41 (d, J=8.8 Hz, 1H), 6.98 (d, J=8.4 Hz, 1H), 5.72-5.63 (m, 1H), 5.19 (s, 1H), 4.99 (d, J=10.0 Hz, 1H), 4.85 (d, J=17.2 Hz, 1H), 4.79-4.69 (m, 1H), 4.66-4.56 (m, 1H), 3.02-2.93 (m, 1H), 2.84-2.75 (m, 5H), 2.51-2.42 (m, 4H), 2.23 (s, 6H), 2.13 (t, J=6.8 Hz, 2H), 1.45 (s, 3H); MS (ESI) 527.5 [M+H]$^+$. Example 10B: yellow solid; $^1$H NMR (400 MHz, DMSO-d$_6$) δ 10.13 (br s, 1H), 8.84 (s, 1H), 7.90 (d, J=8.4 Hz, 1H), 7.71 (d, J=8.4 Hz, 1H), 7.66 (br s, 1H) 7.41 (q, J=8.4, 2 Hz, 1H), 6.98 (d, J=8.4 Hz, 1H), 5.72-5.63 (m, 1H), 5.19 (s, 1H), 4.99 (d, J=10.0 Hz, 1H), 4.85 (d, J=17.2 Hz, 1H), 4.78-4.68 (m, 1H), 4.64-4.56 (m, 1H), 2.99-2.93 (m, 1H), 2.82-2.77 (m, 5H), 2.51-2.42 (m, 4H), 2.24 (s, 3H), 2.23 (s, 3H), 2.13 (t, J=6.8 Hz, 2H), 1.44 (s, 3H); MS (ESI) 527.4 [M+H]$^+$. The absolute stereochemistry was arbitrarily assigned for Example 10A and Example 10B.

Example 11A (S)-2-allyl-6-((3-fluoro-4-(4-methylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one

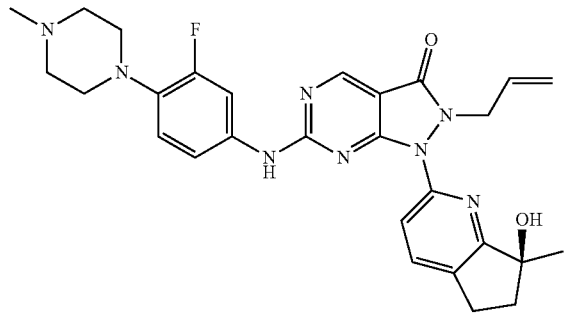

Example 11B (R)-2-allyl-6-((3-fluoro-4-(4-methylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one

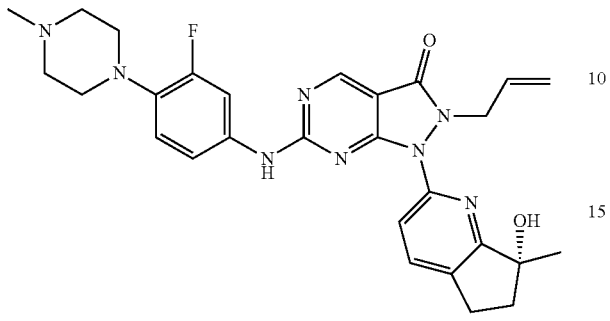

Examples 11A and 11B were prepared by following a procedure described for Examples 2A and 2B using Intermediate 5 to give racemic 2-allyl-6-((3-fluoro-4-(4-methylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one (370 mg). The enantiomers were separated by chiral SFC chromatography (Chiral Pak AD-H, 25% (0.5% DEA in EtOH)) to afford Peak 1 (Example 11A, 90 mg) and Peak 2 (Example 11B, 90 mg). Example 11A: yellow solid; $^1$H NMR (300 MHz, DMSO-$d_6$) δ 10.25 (br s, 1H), 8.88 (s, 1H), 7.91 (d, J=8.4 Hz, 1H), 7.75 (br s, 1H), 7.71 (d, J=7.8 Hz, 1H), 7.39 (d, J=8 Hz, 1H), 7.02 (t, J=9.6 Hz, 1H), 5.73-5.64 (m, 1H), 5.19 (s, 1H), 5.01 (d, J=10 Hz, 1H), 4.89 (d, J=17.2 Hz, 1H), 4.72-4.61 (m, 2H), 3.02-2.96 (m, 5H), 2.84-2.76 (m, 1H), 2.51-2.47 (m, 4H), 2.22 (s, 3H), 2.16 (t, J=6.6 Hz, 2H), 1.45 (s, 3H); MS (ESI) 531.4 [M+H]$^+$. Example 11B: $^1$H NMR (300 MHz, DMSO-$d_6$) δ 10.25 (br s, 1H), 8.88 (s, 1H), 7.91 (d, J=8.4 Hz, 1H), 7.75 (br s, 1H), 7.71 (d, J=7.8 Hz, 1H), 7.39 (d, J=8 Hz, 1H), 7.02 (t, J=9.6 Hz, 1H), 5.73-5.64 (m, 1H), 5.19 (s, 1H), 5.01 (d, J=10 Hz, 1H), 4.89 (d, J=17.2 Hz, 1H), 4.72-4.61 (m, 2H), 3.02-2.96 (m, 5H), 2.84-2.76 (m, 1H), 2.51-2.47 (m, 4H), 2.22 (s, 3H), 2.16 (t, J=6.6 Hz, 2H), 1.45 (s, 3H); MS (ESI) 531.4. The absolute stereochemistry was arbitrarily assigned for Example 11A and Example 11B.

Example 12A (S)-2-allyl-1-(7-ethyl-7-hydroxy-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one

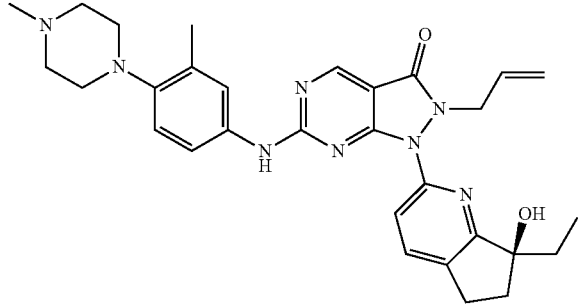

Example 12B (R)-2-allyl-1-(7-ethyl-7-hydroxy-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one

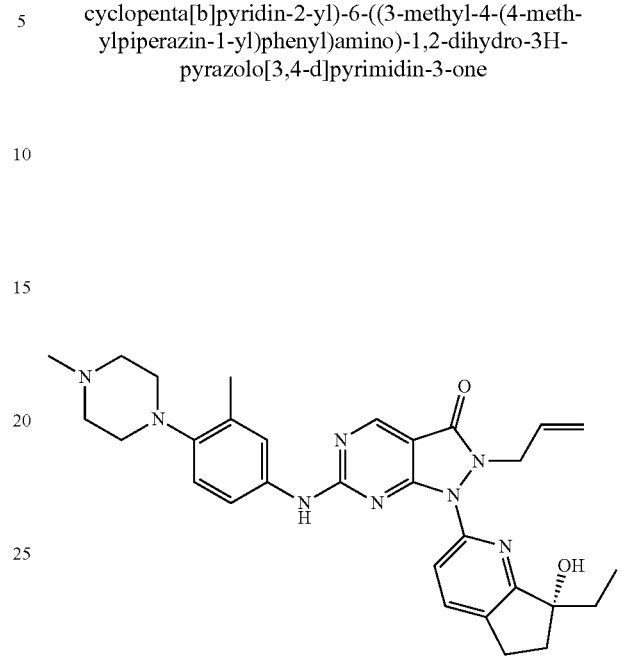

Examples 12A and 12b were prepared following a procedure described for Examples 9A and 9B using Intermediate 17 and 3-methyl-4-(4-methylpiperazin-1-yl)aniline to give racemic 2-allyl-1-(7-ethyl-7-hydroxy-6,7-dihydro-5H-cyclopenta[b]pyridin-2-yl)-6-((3-methyl-4-(4-methylpiperazin-1-yl)phenyl)amino)-1,2-dihydro-3H-pyrazolo[3,4-d]pyrimidin-3-one (500 mg). The enantiomers were separated by SFC chromatography (Chiral Pak AD-H, 35% (0.5% DEA in MeOH)) to afford Peak 1 (Example 12A, 169 mg) and Peak 2 (Example 12B, 166 mg). Example 12A: yellow solid; $^1$H NMR (400 MHz, DMSO-$d_6$) δ 10.05 (br s, 1H), 8.83 (s, 1H), 7.89 (d, J=8 Hz, 1H), 7.71 (d, J=8 Hz, 1H), 7.65 (br s, 1H), 7.42 (dd, J=8.4 Hz, J=8.4 Hz 1H), 6.98 (d, J=8.8 Hz, 1H), 5.70-5.63 (m, 1H), 5.04 (s, 1H), 4.99 (d, J=10.4 Hz, 1H), 4.85 (d, J=16.8 Hz, 1H), 4.77-4.74 (m, 1H), 4.56 (dd, J=16.4 Hz, J=6.4 Hz, 1H) 3.09-2.93 (m, 1H) 2.81-2.74 (m, 4H), 2.5-2.49 (m, 4H), 2.32-2.17 (m, 7H), 2.05-1.98 (m, 1H), 1.92-1.80 (m, 1H), 1.73-1.69 (m, 1H), 1.91-1.86 (m, 1H), 0.87 (t, J=7.6 Hz, 3H); MS (ESI) 541.3 [M+H]$^+$. Example 12b: yellow solid; $^1$H NMR (400 MHz, DMSO-$d_6$) δ 10.05 (br s, 1H), 8.83 (s, 1H), 7.89 (d, J=8 Hz, 1H), 7.71 (d, J=8 Hz, 1H), 7.65 (br s, 1H), 7.42 (dd, J=8.4 Hz, J=8.4 Hz 1H), 6.98 (d, J=8.8 Hz, 1H), 5.70-5.63 (m, 1H), 5.04 (s, 1H), 4.99 (d, J=10.4 Hz, 1H), 4.85 (d, J=16.8 Hz, 1H), 4.77-4.74 (m, 1H), 4.56 (dd, J=16.4 Hz, J=6.4 Hz, 1H) 3.09-2.93 (m, 1H) 2.81-2.74 (m, 4H), 2.5-2.49 (m, 4H), 2.32-2.17 (m, 7H), 2.05-1.98 (m, 1H), 1.91-1.80 (m, 1H), 1.73-1.67 (m, 1H), 1.91-1.86 (m, 1H), 0.86 (t, J=7.6 Hz, 3H); MS (ESI) 541.3 [M+H]$^+$. The absolute stereochemistry was arbitrarily assigned for Example 12A and Example 12B.

Example 13A (S)-2-allyl-1-(7-ethyl-7-hydroxy-6,7-dihydro-5H-cyclopenta[b]pyridin-2-yl)-6-((3-methyl-4-(piperazin-1-yl)phenyl)amino)-1,2-dihydro-3H-pyrazolo[3,4-d]pyrimidin-3-one

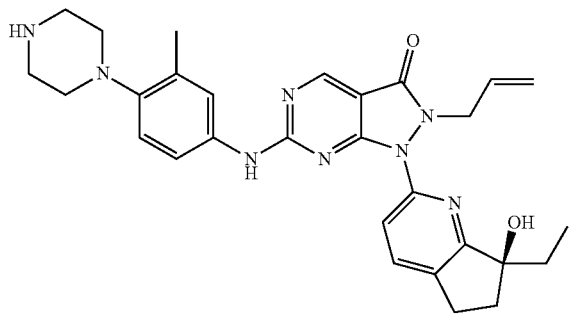 [SMILES: C=CCn1c(=O)c2cnc(Nc3ccc(N4CCNCC4)c(C)c3)nc2n1-c1ccc2c(n1)[C@@](O)(CC)CC2]

Example 13B (R)-2-allyl-1-(7-ethyl-7-hydroxy-6,7-dihydro-5H-cyclopenta[b]pyridin-2-yl)-6-((3-methyl-4-(piperazin-1-yl)phenyl)amino)-1,2-dihydro-3H-pyrazolo[3,4-d]pyrimidin-3-one

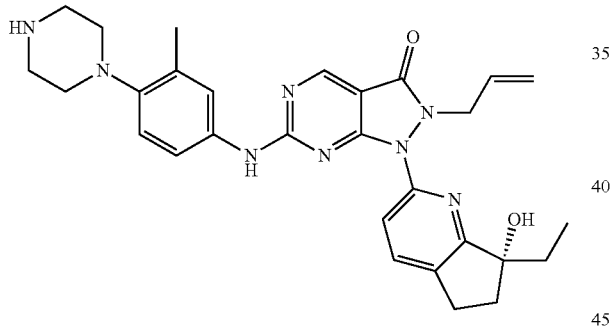

Step 1: 2-allyl-1-(7-ethyl-7-hydroxy-6,7-dihydro-5H-cyclopenta[b]pyridin-2-yl)-6-((3-methyl-4-(4-(2,2,2-trifluoroacetyl)piperazin-1-yl)phenyl)amino)-1,2-dihydro-3H-pyrazolo[3,4-d]pyrimidin-3-one was prepared following a procedure described for Examples 9A and 9B using Intermediate 17 and 1-(4-(4-amino-2-methylphenyl)piperazin-1-yl)-2,2,2-trifluoroethan-1-one. MS (ESI) 623.2 [M+H]$^+$.

Step 2: To a stirred solution of 2-allyl-1-(7-ethyl-7-hydroxy-6,7-dihydro-5H-cyclopenta[b]pyridin-2-yl)-6-((3-methyl-4-(4-(2,2,2-trifluoroacetyl)piperazin-1-yl)phenyl)amino)-1,2-dihydro-3H-pyrazolo[3,4-d]pyrimidin-3-one (900 mg, 1.45 mmol) in methanol (15 mL) was added $K_2CO_3$ (399 mg, 2.89 mmol). The reaction was stirred at rt for 4 h. After completion by TLC, the solvent was evaporated. The reaction was diluted with water (30 mL) and solid compound was filtered to afford racemic 2-allyl-1-(7-ethyl-7-hydroxy-6,7-dihydro-5H-cyclopenta[b]pyridin-2-yl)-6-((3-methyl-4-(piperazin-1-yl)phenyl)amino)-1,2-dihydro-3H-pyrazolo[3,4-d]pyrimidin-3-one (500 mg, 86%) as a pale yellow solid. The enantiomers were separated by chiral SFC chromatography (Chiral Pak AD-H, 40% (0.5% DEA in MeOH)) to afford Peak 1 (Example 13A, 162 mg) and Peak 2 (Example 13B, 108 mg). Example 13A: yellow solid; $^1$H NMR (400 MHz, DMSO-$d_6$) δ 10.12 (brs, 1H), 8.84 (s, 1H), 7.89 (d, J=8.4 Hz, 1H), 7.71 (d, J=8.1 Hz, 1H), 7.67 (brs, 1H), 7.41 (d, J=8.4 Hz, 1H), 6.96 (d, J=8.4 Hz, 1H), 5.67-5.66 (m, 1H), 5.05 (s, 1H), 4.99 (d, J=10.5 Hz, 1H), 4.85 (d, J=18 Hz, 1H), 4.77-4.74 (m, 1H), 4.56 (dd, J=6.3, 6.6 Hz, 1H), 3.39-3.32 (m, 1H), 2.84-2.83 (m, 1H), 2.79-2.71 (m, 9H), 2.24 (s, 3H), 2.22-2.19 (m, 1H), 2.02-2.01 (m, 1H), 1.89-1.86 (m, 1H), 1.73-1.69 (m, 1H), 0.86 (t, J=7.2 Hz, 3H); MS (ESI) 527.2 [M+H]$^+$. Example 13B: yellow solid; $^1$H NMR (400 MHz, DMSO-$d_6$) δ 10.12 (brs, 1H), 8.84 (s, 1H), 7.89 (d, J=8.4 Hz, 1H), 7.71 (d, J=8.1 Hz, 1H), 7.67 (brs, 1H), 7.41 (d, J=8.4 Hz, 1H), 6.96 (d, J=8.4 Hz, 1H), 5.67-5.66 (m, 1H), 5.05 (s, 1H), 4.99 (d, J=10.5 Hz, 1H), 4.85 (d, J=18 Hz, 1H), 4.77-4.74 (m, 1H), 4.56 (dd, J=6.3, 6.6 Hz, 1H), 3.39-3.32 (m, 1H), 2.84-2.83 (m, 1H), 2.79-2.71 (m, 9H), 2.24 (s, 3H), 2.22-2.19 (m, 1H), 2.02-2.01 (m, 1H), 1.89-1.86 (m, 1H), 1.73-1.69 (m, 1H), 0.86 (t, J=7.2 Hz, 3H); MS (ESI) 527.4 [M+H]$^+$. The absolute stereochemistry was arbitrarily assigned for Example 13A and Example 13B.

Intermediate 18

(S)-2-bromo-7-ethyl-6,7-dihydro-5H-cyclopenta[b]pyridin-7-ol

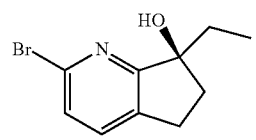

Intermediate 19

(R)-2-bromo-7-ethyl-6,7-dihydro-5H-cyclopenta[b]pyridin-7-ol

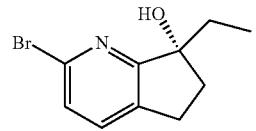

Racemic Intermediate 16 (6 g, 24.79 mmol) was purified by SFC purification (Lux Cellulose-2, 10% Ethanol) Intermediate 18 (1.9 g, 7.88 mmol) and Intermediate 19 (1.8 g, 7.47 mmol). Intermediate 18: colorless oil; $[\alpha]_D^{25}$ (c=0.5, CHCl$_3$)−27.31°; MS (ESI) 242.3 [M+H]$^+$. Intermediate 19: colorless oil; $[\alpha]_D^{25}$ (c=0.5, CHCl$_3$)+35.53°; MS (ESI) 242.3 [M+H]$^+$.

Intermediate 20

(R)-2-allyl-1-(7-ethyl-7-hydroxy-6,7-dihydro-5H-cyclopenta[b]pyridin-2-yl)-6-(methylthio)-1,2-dihydro-3H-pyrazolo[3,4-d]pyrimidin-3-one

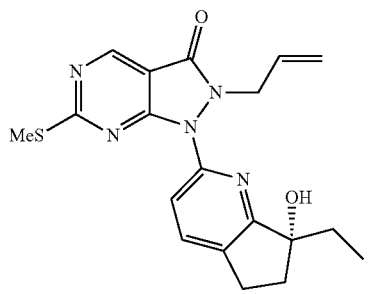 [SMILES: C=CCn1c(=O)c2cnc(SC)nc2n1-c1ccc2c(n1)[C@@](O)(CC)CC2]

Intermediate 20 was prepared following a procedure described for Intermediate 3 using Intermediate 1 and Intermediate 19. $[\alpha]_D^{25}$ (c=0.1, CHCl$_3$)+17.84°; MS (LCMS) 384.5 [M+H]$^+$.

Example 14

(R)-2-allyl-1-(7-ethyl-7-hydroxy-6,7-dihydro-5H-cyclopenta[b]pyridin-2-yl)-6-((4-(piperazin-1-yl)phenyl)amino)-1,2-dihydro-3H-pyrazolo[3,4-d]pyrimidin-3-one

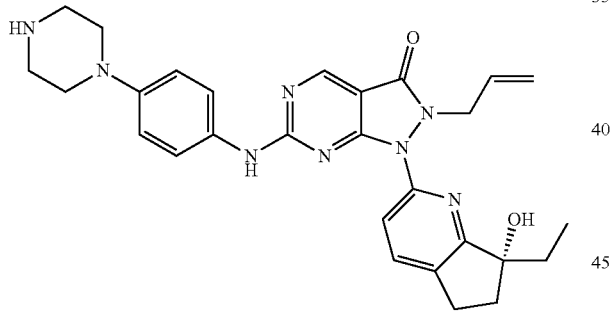

Step 1: (R)-2-allyl-1-(7-ethyl-7-hydroxy-6,7-dihydro-5H-cyclopenta[b]pyridin-2-yl)-6-((4-(4-(2,2,2-trifluoroacetyl)piperazin-1-yl)phenyl)amino)-1,2-dihydro-3H-pyrazolo[3,4-d]pyrimidin-3-one was prepared following a procedure described for Examples 9A and 9B using Intermediate 20. MS (ESI) 609.6 [M+H]$^+$.

Step 2: To a stirred solution of (R)-2-allyl-1-(7-ethyl-7-hydroxy-6,7-dihydro-5H-cyclopenta[b]pyridin-2-yl)-6-((4-(4-(2,2,2-trifluoroacetyl)piperazin-1-yl)phenyl)amino)-1H-pyrazolo[3,4-d]pyrimidin-3(2H)-one (350 mg, 0.575 mmol) in MeOH (6 mL) was added K$_2$CO$_3$ (238 mg, 1.72 mmol) at 0° C. The ice bath was removed and the reaction was stirred at rt for 16 h. After completion by TLC, the reaction was concentrated under reduced pressure. Water (15 mL) was added and the mixture was stirred for 10 minutes. The mixture was diluted with sat. NaHCO$_3$ and extracted with EtOAc (3×40 mL). The combined organic layers were dried (Na$_2$SO$_4$), filtered and concentrated under reduced pressure. The crude mixture was purified by prep-HPLC (Water/CH$_3$CN) to afford Example 14 (220 mg, 74%) as an off white solid. $^1$H NMR (400 MHz, DMSO-d$_6$) 10.25 (brs, 1H), 8.81 (s, 1H), 7.90 (d, J=7.2 Hz, 1H), 7.69 (d, J=8.4 Hz, 1H), 7.57 (brs, 2H), 6.90 (d, J=8.8 Hz, 2H), 5.70-5.63 (m, 1H), 5.04 (s, 1H), 4.99 (d, J=9.2 Hz, 1H), 4.85 (d, J=17.2 Hz, 1H), 4.74 (brs, 1H), 4.57-4.54 (m, 1H), 3.02-2.93 (m, 5H), 2.86-2.74 (m, 5H), 2.22-2.06 (m, 1H), 2.05-1.99 (m, 1H), 1.91-1.86 (m, 1H), 1.73-1.67 (m, 1H), 0.8 (t, J=7.2 Hz, 3H); MS (ESI) 513.3 [M+H]$^+$.

Intermediate 21

2-bromo-7-(difluoromethyl)-6,7-dihydro-5H-cyclopenta[b]pyridin-7-ol

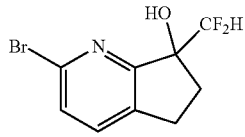

To a stirred solution of Me$_3$SiCF$_2$H (1.175 g, 9.48 mmol) in 1,2-DME (10 mL) were added 18-crown-6 (625 mg, 2.37 mmol) and CsF (715 mg, 4.739 mmol) at 0° C. and the reaction was stirred for 15 min. To reaction was added 2-bromo-5,6-dihydro-7H-cyclopenta[b]pyridin-7-one (1 g, 4.74 mmol) at 0° C. The ice bath was removed and the reaction was stirred at rt for 16 h. The reaction was determined to be complete by TLC and the reaction was diluted with water (30 mL) and extracted with EtOAc (2×50 mL). The separated organic layers were washed with brine, dried (Na$_2$SO$_4$), filtered and concentrated under reduced pressure to afford crude compound. The above reaction was repeated on 4×1 g scale. The residue was purified by flash chromatography (SiO$_2$, EtOAc/pet ether) to afford Intermediate 21 (470 mg) as an off-white solid; MS (ESI) 266.3 [M+H]$^+$.

Intermediate 22

2-allyl-1-(7-(difluoromethyl)-7-hydroxy-6,7-dihydro-5H-cyclopenta[b]pyridin-2-yl)-6-(methylthio)-1,2-dihydro-3H-pyrazolo[3,4-d]pyrimidin-3-one

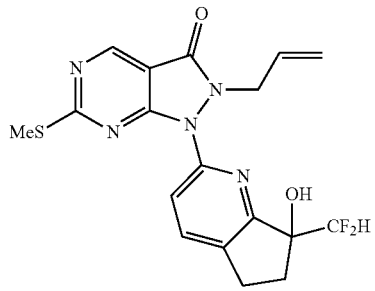 [SMILES: C=CCn1c(=O)c2cnc(SC)nc2n1-c1ccc2c(n1)C(O)(C(F)F)CC2]

Intermediate 22 was prepared following a procedure described for Intermediate 3 using Intermediate 1 and Intermediate 21; MS (ESI) 406.3 [M+H]$^+$.

Example 15A (S)-2-allyl-1-(7-(difluoromethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

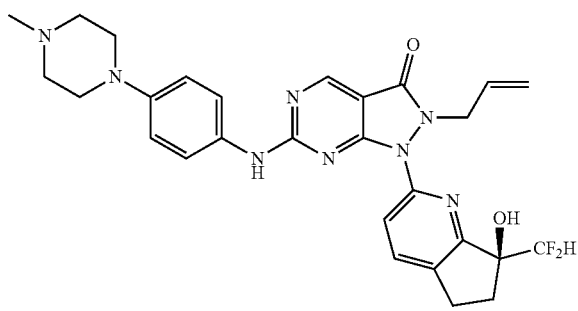 [SMILES: C=CCn1c(=O)c2cnc(Nc3ccc(N4CCN(C)CC4)cc3)nc2n1-c1ccc2c(n1)[C@](O)(C(F)F)CC2]

Example 15B (R)-2-allyl-1-(7-(difluoromethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

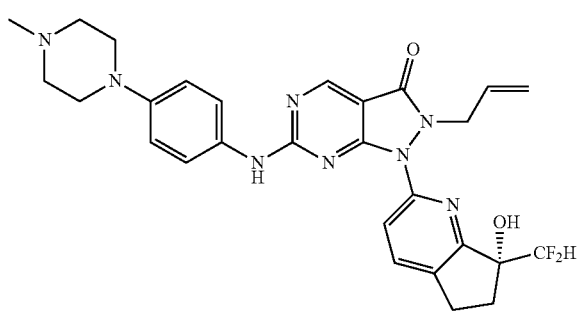 [SMILES: C=CCn1c(=O)c2cnc(Nc3ccc(N4CCN(C)CC4)cc3)nc2n1-c1ccc2c(n1)[C@@](O)(C(F)F)CC2]

Examples 15A and 15B were prepared following a procedure described for Examples 9A and 9B using Intermediate 22 to give racemic 2-allyl-1-(7-(difluoromethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (120 mg). The enantiomers were separated by SFC chromatography (Chiral Pak AD-H, 30.0% (0.5% DEA in Methanol)) to afford Peak 1 (Example 15A, 35 mg) and Peak 2 (Example 15B, 35 mg). Example 15A: yellow solid; $^1$H NMR (400 MHz, DMSO-$d_6$) δ 10.2 (br s, 1H), 8.83 (s, 1H), 8.02 (br s, 1H), 7.82 (d, J=8.4 Hz, 1H), 7.57 (br s, 2H), 6.93 (d, J=8.7 Hz, 2H), 6.26 (t, J=59.1 Hz, 1H), 6.22 (s, 1H), 5.68-5.61 (m, 1H), 4.97 (d, J=9.9 Hz, 1H), 4.82 (d, J=17.4 Hz, 1H), 4.74 (br s, 1H), 4.60-4.54 (m, 1H), 3.10-2.90 (m, 6H), 2.47-2.46 (m, 5H), 2.22 (s, 3H), 2.11-2.04 (m, 1H); MS (ESI) 549.2 [M+H]$^+$. Example 15B: yellow solid; $^1$H NMR (400 MHz, DMSO-$d_6$) δ 10.2 (br s, 1H), 8.83 (s, 1H), 8.02 (br s, 1H), 7.82 (d, J=8.4 Hz, 1H), 7.57 (br s, 2H), 6.93 (d, J=8.7 Hz, 2H), 6.26 (t, J=59.1 Hz, 1H), 6.22 (s, 1H), 5.68-5.61 (m, 1H), 4.97 (d, J=9.9 Hz, 1H), 4.82 (d, J=17.4 Hz, 1H), 4.74 (br s, 1H), 4.60-4.54 (m, 1H), 3.10-2.90 (m, 6H), 2.47-2.46 (m, 5H), 2.22 (s, 3H), 2.11-2.04 (m, 1H); MS (ESI) 549.2 [M+H]$^+$. The absolute stereochemistry was arbitrarily assigned for Example 15A and Example 15B.

Intermediate 23

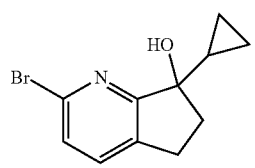 [SMILES: OC1(C2CC2)CCc2ccc(Br)nc21]

To a 0° C. solution of 2-bromo-5H-cyclopenta[b]pyridin-7(6H)-one (4 g, 18.80 mmol) in THF (50 mL) was added 3M cyclopropyl magnesium bromide solution in THF (31 mL, 94.3 mmol). The ice bath was removed and the reaction was stirred at rt for 16 h. After completion by TLC, the reaction was quenched with aq. NH$_4$Cl (200 mL). The mixture was extracted with EtOAc (2×200 mL). The combined organic layers were dried (Na$_2$SO$_4$), filtered and concentrated under reduced pressure. The crude product was purified by flash column chromatography (SiO$_2$, 30% EtOAc/pet. ether) to afford 2-Intermediate 23 (3 g, 63%) as a colorless oil. MS (ESI) 255.9 [M+H]$^+$.

Intermediate 24

2-allyl-1-(7-cyclopropyl-7-hydroxy-6,7-dihydro-5H-cyclopenta[b]pyridin-2-yl)-6-(methylthio)-1,2-dihydro-3H-pyrazolo[3,4-d]pyrimidin-3-one

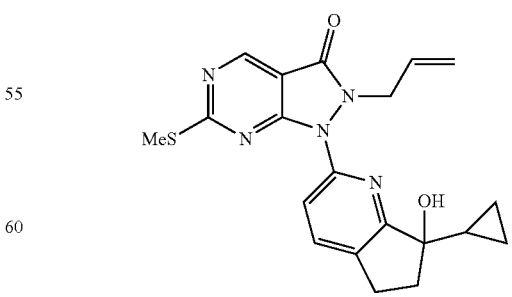

Intermediate 24 was prepared following a procedure described for Intermediate 3 using Intermediate 1 and Intermediate 23. MS (ESI) 396.5 [M+H]$^+$.

Example 16A (R)-2-allyl-1-(7-cyclopropyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

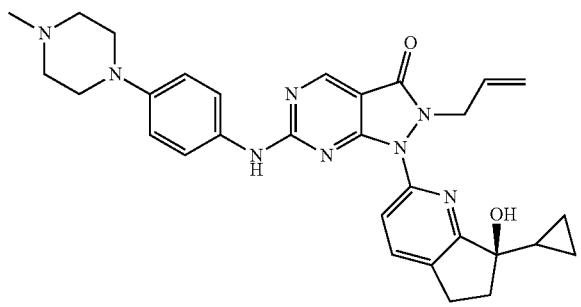

Example 16B (S)-2-allyl-1-(7-cyclopropyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

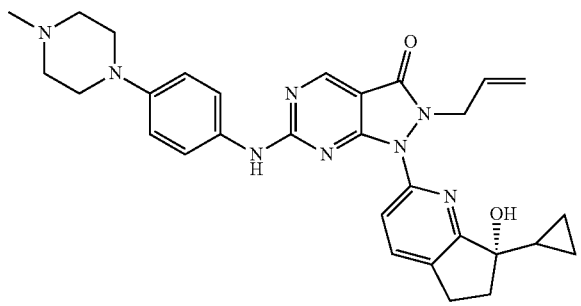 [SMILES: C=CCn1c(=O)c2cnc(Nc3ccc(N4CCN(C)CC4)cc3)nc2n1-c1ccc2c(n1)[C@@](O)(C1CC1)CC2]

Examples 16A and 16B were prepared by following a procedure described for Examples 2A and 2B using Intermediate 24 to give racemic 2-allyl-1-(7-cyclopropyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (400 mg). The enantiomers were separated by chiral SFC chromatography (Chiral Pak AD-H, 45% (0.5% DEA in Methanol)) to afford Peak 1 (Example 16A, 159 mg) and Peak 2 (Example 16B, 111 mg). Example 16A: yellow solid; $^1$H NMR (400 MHz, DMSO-$d_6$) δ 10.13 (br s, 1H), 8.82 (s, 1H), 7.92 (m, 1H), 7.71 (d, J=7.6 Hz, 1H), 7.58 (m, 2H), 6.92 (J=7.6 Hz, 2H), 5.70-5.64 (m, 1H), 5.04 (s, 1H), 4.98 (d, J=10 Hz, 1H), 4.87-4.77 (m, 2H), 4.65 (m, 1H), 3.09 (s, 4H), 2.93-2.79 (m, 2H), 2.46 (m, 4H), 2.22 (s, 3H), 2.09-1.99 (m, 2H), 1.22-1.21 (m, 1H), 0.44-0.30 (m, 4H); MS (ESI) 539.5 [M+H]$^+$. Example 16B: yellow solid; $^1$H NMR (400 MHz, DMSO-$d_6$) δ 10.13 (br s, 1H), 8.82 (s, 1H), 7.92 (m, 1H), 7.71 (d, J=8.4 Hz, 1H), 7.58 (m, 2H), 6.92 (J=8.7 Hz, 2H), 5.70-5.64 (m, 1H), 5.04 (s, 1H), 4.98 (d, J=9.6 Hz, 1H), 4.87-4.77 (m, 2H), 4.65 (m, 1H), 3.09 (s, 4H), 2.93-2.79 (m, 2H), 2.46 (m, 4H), 2.22 (s, 3H), 2.09-1.99 (m, 2H), 1.22-1.21 (m, 1H), 0.44-0.30 (m, 4H); MS (ESI) 539.5 [M+H]$^+$. The absolute stereochemistry was arbitrarily assigned for Example 16A and Example 16B.

Example 17A 2-allyl-6-((4-((S)-3,4-dimethylpiperazin-1-yl)phenyl)amino)-1-((S)-7-hydroxy-7-methyl-6,7-dihydro-5H-cyclopenta[b]pyridin-2-yl)-1,2-dihydro-3H-pyrazolo[3,4-d]pyrimidin-3-one

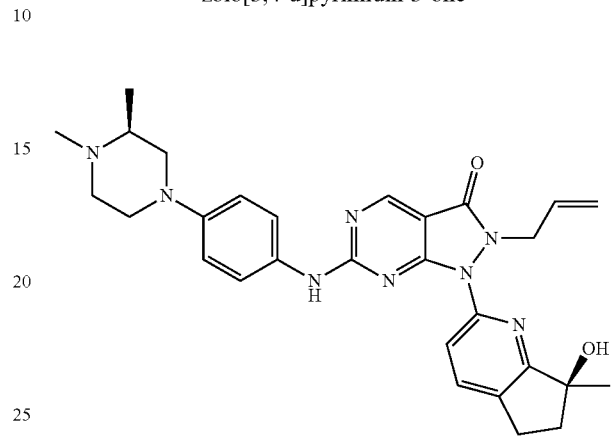

Example 17B 2-allyl-6-((4-((S)-3,4-dimethylpiperazin-1-yl)phenyl)amino)-1-((R)-7-hydroxy-7-methyl-6,7-dihydro-5H-cyclopenta[b]pyridin-2-yl)-1,2-dihydro-3H-pyrazolo[3,4-d]pyrimidin-3-one

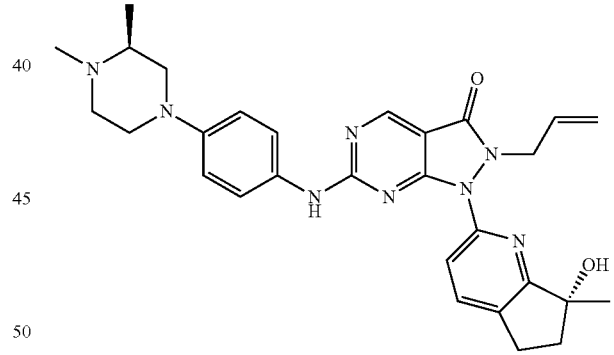

Examples 17A and 17B were prepared following a procedure described for Examples 9A and 9B using Intermediate 5 and (S)-4-(3,4-dimethylpiperazin-1-yl)aniline to give a mixture of diastereomers 2-allyl-6-((4-((S)-3,4-dimethylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one (500 mg). The diastereomers were separated by chiral SFC chromatography (Chiral Pak IG, (0.5% DEA in Methanol:Hexane (80:20)) to afford Peak 1 (Example 17A, 130 mg) and Peak 2 (Example 17B, 75 mg). Example 17A: yellow solid; $^1$H NMR (400 MHz, DMSO-$d_6$) δ 10.1 (br s, 1H), 8.82 (s, 1H), 7.92 (d, J=6.8 Hz, 1H), 7.69 (d, J=8.0 Hz, 1H), 7.57 (br s, 2H), 6.91 (d, J=8.8 Hz, 2H), 5.71-5.63 (m, 1H), 5.17 (s, 1H), 4.99 (d, J=10.0 Hz, 1H), 4.86 (d, J=17.6 Hz, 1H), 4.78-4.71

(m, 1H), 4.65-4.57 (m, 1H), 3.47 (t, J=10.8 Hz, 2H), 3.00-2.93 (m, 1H), 2.83-2.67 (m, 3H), 2.34-2.22 (m, 5H), 2.13 (t, J=6.8 Hz, 3H), 1.45 (s, 3H), 1.05 (d, J=6.0 Hz, 3H); MS (ESI) 527.3 [M+H]+. Example 17B: yellow solid; $^1$H NMR (400 MHz, DMSO-d$_6$) δ 10.1 (br s, 1H), 8.82 (s, 1H), 7.93 (d, J=7.2 Hz, 1H), 7.68 (d, J=8.8 Hz, 1H), 7.57 (br s, 2H), 6.91 (d, J=8.8 Hz, 2H), 5.71-5.63 (m, 1H), 5.17 (s, 1H), 4.99 (d, J=10.0 Hz, 1H), 4.86 (d, J=17.2 Hz, 1H), 4.76-4.70 (m, 1H), 4.65-4.57 (m, 1H), 3.52-3.47 (m, 2H), 3.01-2.93 (m, 1H), 2.83-2.67 (m, 3H), 2.36-2.11 (m, 8H), 1.45 (s, 3H), 1.05 (d, J=6.0 Hz, 3H); MS (ESI) 527.3 [M+H]+. The absolute stereochemistry was arbitrarily assigned for Example 17A and Example 17B.

Example 18A 2-allyl-6-((4-((R)-3,4-dimethylpiperazin-1-yl)phenyl)amino)-1-((S)-7-hydroxy-7-methyl-6,7-dihydro-5H-cyclopenta[b]pyridin-2-yl)-1,2-dihydro-3H-pyrazolo[3,4-d]pyrimidin-3-one

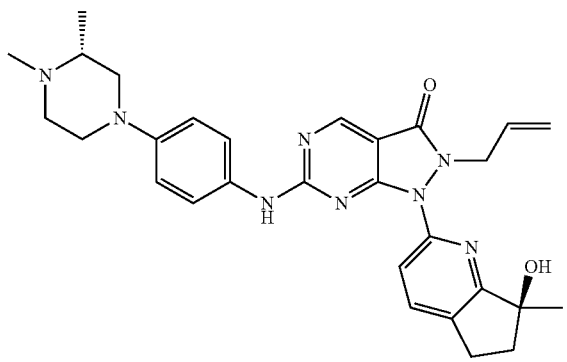

Example 18B 2-allyl-6-((4-((R)-3,4-dimethylpiperazin-1-yl)phenyl)amino)-1-((R)-7-hydroxy-7-methyl-6,7-dihydro-5H-cyclopenta[b]pyridin-2-yl)-1,2-dihydro-3H-pyrazolo[3,4-d]pyrimidin-3-one

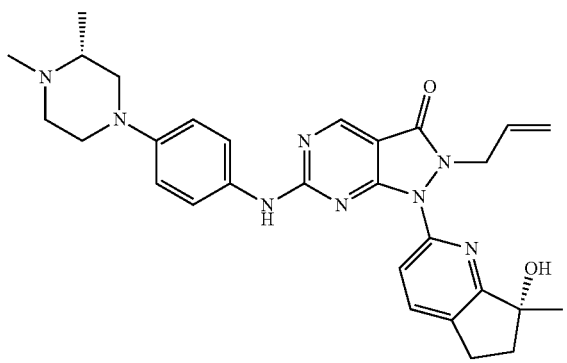

Examples 18A and 18B were prepared following a procedure described for Examples 9A and 9B using Intermediate 5 and (R)-4-(3,4-dimethylpiperazin-1-yl)aniline to give a mixture of diastereomers 2-allyl-6-((4-((R)-3,4-dim-ethylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one. The diastereomers were separated by chiral SFC chromatography (Chiralpak AD-H, 20.0% (0.5% DEA in Methanol)) to afford Peak 1 (Example 18A, 94 mg) and Peak 2 (Example 18B, 85 mg). Example 18A: yellow solid; $^1$H NMR (400 MHz, DMSO-d$_6$) δ 10.09 (br s, 1H), 8.81 (s, 1H), 7.92 (d, J=6.8 Hz, 1H), 7.68 (d, J=8.0 Hz, 1H), 7.57 (m, 2H), 6.91 (d, J=8.8 Hz, 2H), 5.71-5.62 (m, 1H), 5.16 (s, 1H), 4.99 (d, J=10.0 Hz, 1H), 4.86 (d, J=16.8 Hz, 1H), 4.78-4.55 (m, 2H), 3.47 (t, J=10.4 Hz, 2H), 3.31-2.93 (m, 1H), 2.83-2.67 (m, 3H), 2.36-2.11 (m, 8H), 1.45 (s, 3H), 1.05 (d, J=5.6 Hz, 3H); MS (ESI) 527.3 [M+H]+. Example 18B: yellow solid; $^1$H NMR (400 MHz, DMSO-d$_6$) δ 10.10 (br s, 1H), 8.82 (s, 1H), 7.92 (d, J=6.8 Hz, 1H), 7.68 (d, J=8.0 Hz, 1H), 7.57 (m, 2H), 6.91 (d, J=9.2 Hz, 2H), 5.72-5.62 (m, 1H), 5.16 (s, 1H), 4.99 (d, J=10.0 Hz, 1H), 4.86 (d, J=16.8 Hz, 1H), 4.76-4.70 (m, 1H), 4.61-4.58 (m, 1H), 3.48 (m, 2H), 3.01-2.93 (m, 1H), 2.83-2.71 (m, 3H), 2.32-2.11 (m, 8H), 1.45 (s, 3H), 1.07 (m, 3H); MS (ESI) 527.3 [M+H]+. The absolute stereochemistry on tertiary alcohol was arbitrarily assigned for Example 18A and Example 18B.

Example 19A 2-allyl-6-((4-((S)-2,4-dimethylpiperazin-1-yl)phenyl)amino)-1-((S)-7-hydroxy-7-methyl-6,7-dihydro-5H-cyclopenta[b]pyridin-2-yl)-1,2-dihydro-3H-pyrazolo[3,4-d]pyrimidin-3-one

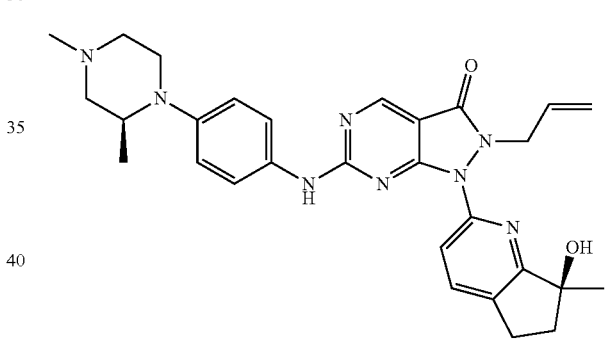

Example 19B 2-allyl-6-((4-((S)-2,4-dimethylpiperazin-1-yl)phenyl)amino)-1-((R)-7-hydroxy-7-methyl-6,7-dihydro-5H-cyclopenta[b]pyridin-2-yl)-1,2-dihydro-3H-pyrazolo[3,4-d]pyrimidin-3-one

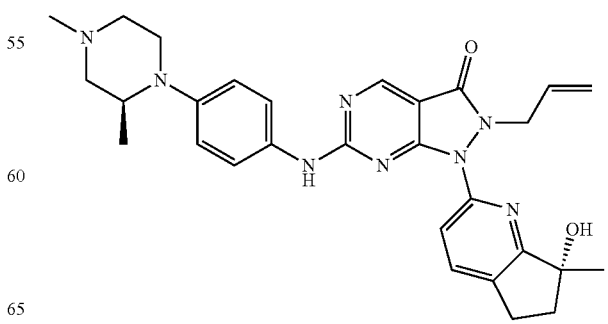

Examples 19A and 19B were prepared following a procedure described for Examples 9A and 9B using Intermediate 5 and (S)-4-(2,4-dimethylpiperazin-1-yl)aniline to give a mixture of diastereomers 2-allyl-6-((4-((S)-2,4-dimethylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one (400 mg). The diastereomers were separated by chiral SFC chromatography (Chiralpak AD-H, 25.0% (0.5% DEA in MeOH)) to afford Peak 1 (Example 19A, 158 mg) and Peak 2 (Example 19B, 103 mg). Example 19A: yellow solid; ¹H NMR (400 MHz, DMSO-d₆) δ 10.1 (br s, 1H), 8.82 (s, 1H), 7.92 (d, J=7.6 Hz, 1H), 7.69 (d, J=8.4 Hz, 1H), 7.57 (br s, 2H), 6.88 (d, J=9.2 Hz, 2H), 5.71-5.63 (m, 1H), 5.18 (s, 1H), 4.99 (d, J=10.4 Hz, 1H), 4.86 (d, J=17.2 Hz, 1H), 4.78-4.71 (m, 1H), 4.65-4.57 (m, 1H), 3.87 (br s, 1H), 3.21-3.16 (m, 1H), 3.00-2.93 (m, 2H), 2.83-2.72 (m, 2H), 2.58-2.51 (m, 1H), 2.34-2.28 (m, 1H), 2.20 (s, 3H), 2.12 (t, J=6.8 Hz, 3H), 1.45 (s, 3H), 0.97 (d, J=6.4 Hz, 3H); MS (ESI) 527.3 [M+H]⁺. Example 19B: yellow solid; ¹H NMR (400 MHz, DMSO-d₆) δ 10.1 (br s, 1H), 8.82 (s, 1H), 7.92 (d, J=7.2 Hz, 1H), 7.69 (d, J=8.0 Hz, 1H), 7.57 (br s, 2H), 6.88 (d, J=8.0 Hz, 2H), 5.71-5.64 (m, 1H), 5.18 (s, 1H), 4.99 (d, J=10.4 Hz, 1H), 4.86 (d, J=17.2 Hz, 1H), 4.78-4.71 (m, 1H), 4.65-4.57 (m, 1H), 3.87 (br s, 1H), 3.21-3.16 (m, 1H), 3.00-2.92 (m, 2H), 2.83-2.72 (m, 2H), 2.58-2.51 (m, 1H), 2.34-2.28 (m, 1H), 2.20 (s, 3H), 2.13 (t, J=7.2 Hz, 3H), 1.45 (s, 3H), 0.96 (d, J=6.4 Hz, 3H); MS (ESI) 527.2 [M+H]⁺. The absolute stereochemistry on tertiary alcohol was arbitrarily assigned for Example 19A and Example 19B.

Example 20A 2-allyl-6-((4-((R)-2,4-dimethylpiperazin-1-yl)phenyl)amino)-1-((S)-7-hydroxy-7-methyl-6,7-dihydro-5H-cyclopenta[b]pyridin-2-yl)-1,2-dihydro-3H-pyrazolo[3,4-d]pyrimidin-3-one Example 20B 2-allyl-6-((4-((R)-2,4-dimethylpiperazin-1-yl)phenyl)amino)-1-((R)-7-hydroxy-7-methyl-6,7-dihydro-5H-cyclopenta[b]pyridin-2-yl)-1,2-dihydro-3H-pyrazolo[3,4-d]pyrimidin-3-one

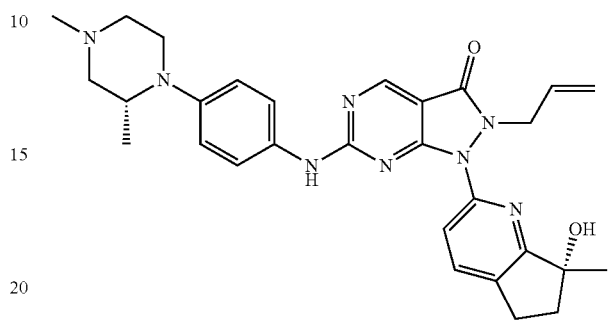

Examples 20A and 20B were prepared following a procedure described for Examples 9A and 9B using Intermediate 5 and (R)-4-(2,4-dimethylpiperazin-1-yl)aniline to give a mixture of diastereomers 2-allyl-6-((4-((R)-2,4-dimethylpiperazin-1-yl)phenyl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one (400 mg). The diastereomers were separated by chiral SFC chromatography (Chiralpak AD-H, 20.0% (0.5% DEA in MeOH)) to afford Peak 1 (Example 20A, 170 mg) and Peak 2 (Example 20B, 170 mg). Example 20A: yellow solid; ¹H NMR (400 MHz, DMSO-d₆) δ 10.1 (br s, 1H), 8.82 (s, 1H), 7.92 (d, J=7.6 Hz, 1H), 7.69 (d, J=8.4 Hz, 1H), 7.57 (br s, 2H), 6.88 (d, J=8.8 Hz, 2H), 5.71-5.63 (m, 1H), 5.18 (s, 1H), 4.99 (d, J=10.4 Hz, 1H), 4.86 (d, J=17.2 Hz, 1H), 4.78-4.71 (m, 1H), 4.65-4.57 (m, 1H), 3.87 (br s, 1H), 3.21-3.16 (m, 1H), 3.00-2.93 (m, 2H), 2.83-2.72 (m, 2H), 2.59-2.52 (m, 1H), 2.34-2.28 (m, 1H), 2.20 (s, 3H), 2.12 (t, J=7.2 Hz, 3H), 1.45 (s, 3H), 0.96 (d, J=6.4 Hz, 3H); MS (ESI) 527.2 [M+H]⁺. Example 20B: yellow solid; ¹H NMR (400 MHz, DMSO-d₆) δ 10.1 (br s, 1H), 8.82 (s, 1H), 7.92 (d, J=7.6 Hz, 1H), 7.69 (d, J=8.4 Hz, 1H), 7.57 (br s, 2H), 6.88 (d, J=8.8 Hz, 2H), 5.71-5.63 (m, 1H), 5.18 (s, 1H), 4.99 (d, J=10 Hz, 1H), 4.86 (d, J=17.2 Hz, 1H), 4.78-4.71 (m, 1H), 4.65-4.57 (m, 1H), 3.87 (br s, 1H), 3.21-3.16 (m, 1H), 3.00-2.93 (m, 2H), 2.83-2.72 (m, 2H), 2.59-2.51 (m, 1H), 2.34-2.28 (m, 1H), 2.20 (s, 3H), 2.12 (t, J=7.2 Hz, 3H), 1.45 (s, 3H), 0.96 (d, J=6.4 Hz, 3H); MS (ESI) 527.3 [M+H]⁺. The absolute stereochemistry on tertiary alcohol was arbitrarily assigned for Example 20A and Example 20B.

Intermediate 25

6-bromo-1-methyl-2,3-dihydro-1H-inden-1-ol

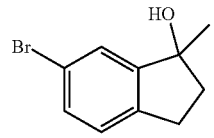

A suspension of anhydrous CeCl₃ (17.5 g, 71.08 mmol) in THF (100 mL) was stirred at rt for 1 h and cooled down to −78° C. 1.6 M MeLi in DEE (44 mL, 71.08 mmol) was added at −78° C. and the reaction was stirred for 30 min. To this, was added a solution of 6-bromo-2,3-dihydro-1H-inden-1-one (10 g, 47.39 mmol) in THF (100 mL) at −78° C. The ice bath was removed and the reaction was stirred at rt for 2 h. After completion by TLC, the reaction was quenched with aq. NH₄Cl (200 mL). The mixture was extracted with EtOAc (2×200 mL). The combined organic layers were dried (Na₂SO₄), filtered and concentrated under reduced pressure. The crude product was purified by column chromatography (SiO₂, 30% EtOAc/pet. ether) to afford Intermediate 25 (6 g, 55%) as a colorless oil. ¹H NMR (400 MHz, DMSO-d₆) δ 7.43 (d, J=2.0 Hz, 1H), 7.35 (dd, J=8.0, 2.0 Hz, 1H), 7.16 (d, J=8.0 Hz, 1H), 5.14 (s, 1H) 2.89-2.81 (m, 1H), 2.75-2.66 (m, 1H), 2.07 (t, J=4.4 Hz, 2H), 1.40 (s, 3H).

Intermediate 26

2-allyl-1-(3-hydroxy-3-methyl-2,3-dihydro-1H-inden-5-yl)-6-(methylthio)-1,2-dihydro-3H-pyrazolo[3,4-d]pyrimidin-3-one

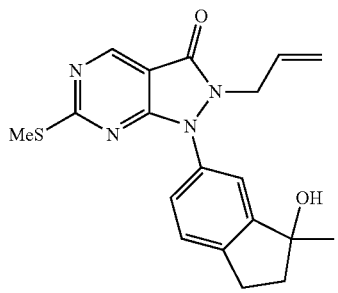 [SMILES: C=CCn1c(=O)c2cnc(SC)nc2n1-c1ccc2c(c1)C(C)(O)CC2]

Intermediate 26 was prepared following a procedure described for Intermediate 3 using Intermediate 1 and Intermediate 25. MS (ESI) 369.4 [M+H]⁺.

Example 21A (S)-2-allyl-1-(3-hydroxy-3-methyl-2,3-dihydro-1H-inden-5-yl)-6-((4-(4-methylpiperazin-1-yl)phenyl)amino)-1,2-dihydro-3H-pyrazolo[3,4-d]pyrimidin-3-one

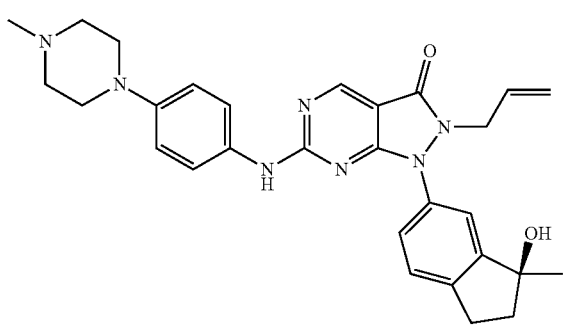

Example 21B (R)-2-allyl-1-(3-hydroxy-3-methyl-2,3-dihydro-1H-inden-5-yl)-6-((4-(4-methylpiperazin-1-yl)phenyl)amino)-1,2-dihydro-3H-pyrazolo[3,4-d]pyrimidin-3-one

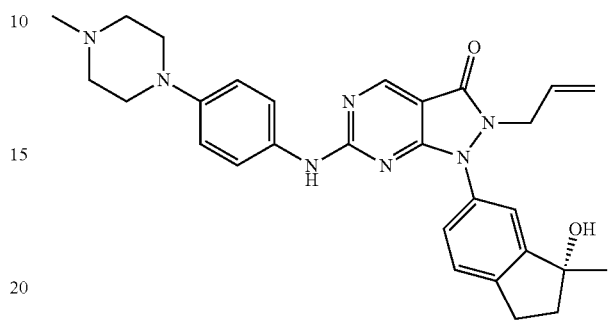

Examples 21A and 21B were prepared by following a procedure described for Examples 2A and Examples 2B using Intermediate 26 to give racemic 2-allyl-1-(3-hydroxy-3-methyl-2,3-dihydro-1H-inden-5-yl)-6-((4-(4-methylpiperazin-1-yl)phenyl)-amino)-1,2-dihydro-3H-pyrazolo[3,4-d]pyrimidin-3-one (350 mg). The enantiomers were separated by chiral SFC chromatography (Chiralpak IG, 40.0% (0.5% DEA in Methanol)) to give Peak 1 (Example 21A, 70 mg) and Peak 2 (Example 21B, 71 mg). Example 21A: yellow solid; ¹H NMR (400 MHz, DMSO-d₆) δ 10.03 (br s, 1H), 8.79 (s, 1H), 7.54 (br s, 2H), 7.38-7.34 (m, 2H), 7.27 (dd, J=8.0, 2.0 Hz, 1H), 6.86 (d, J=9.2 Hz, 2H), 5.68-5.62 (m, 1H), 5.15 (s, 1H), 5.09 (d, J=9.6 Hz, 1H), 4.93 (d, J=17.6 Hz, 1H), 4.24 (br s, 2H), 3.05 (s, 4H), 2.99-2.92 (m, 1H), 2.85-2.77 (m, 1H), 2.50-2.46 (m, 4H), 2.22 (s, 3H), 2.11 (t, J=6.8 Hz, 2H), 1.43 (s, 3H); MS (ESI) 512.3 [M+H]⁺. Example 21B: yellow solid; ¹H NMR (400 MHz, DMSO-d₆) δ 10.03 (br s, 1H), 8.79 (s, 1H), 7.54 (br s, 2H), 7.38-7.34 (m, 2H), 7.27 (dd, J=8.0, 2.0 Hz, 1H), 6.86 (d, J=9.2 Hz, 2H), 5.68-5.62 (m, 1H), 5.15 (s, 1H), 5.09 (d, J=9.6 Hz, 1H), 4.93 (d, J=17.6 Hz, 1H), 4.24 (br s, 2H), 3.05 (s, 4H), 2.99-2.92 (m, 1H), 2.85-2.77 (m, 1H), 2.50-2.46 (m, 4H), 2.22 (s, 3H), 2.11 (t, J=6.8 Hz, 2H), 1.43 (s, 3H); MS (ESI) 512.3 [M+H]⁺. The absolute stereochemistry was arbitrarily assigned for Example 21A and Example 21B.

Intermediate 27

6-bromo-1-ethyl-2,3-dihydro-1H-inden-1-ol

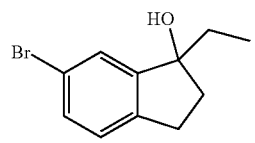

To a stirred solution of 6-bromo-2,3-dihydro-1H-inden-1-one (5.0 g, 23.68 mmol) in toluene (50 mL) was added EtMgBr (23.70 mL, 71.07 mmol) drop-wise at 0° C. The ice bath was removed and the reaction was stirred at rt for 16 h. The reaction was quenched with sat. aq. NH₄Cl (50 mL) and extracted with EtOAc (3×50 mL). The combined organic layers were dried (Na₂SO₄) and the solvent was evaporated under reduced pressure. The crude product was purified by column chromatography (SiO₂, 20% EtOAc/pet. ether) to afford Intermediate 27 (4 g, 70%) as a colorless liquid. MS (ESI) 223.1 [M+H—H₂O]⁺.

Intermediate 28

2-allyl-1-(3-ethyl-3-hydroxy-2,3-dihydro-1H-inden-5-yl)-6-(methylthio)-1,2-dihydro-3H-pyrazolo[3,4-d]pyrimidin-3-one

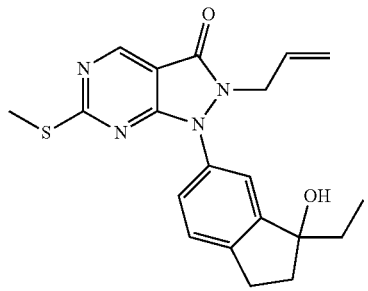 [SMILES: C=CCn1c(=O)c2cnc(SC)nc2n1-c1ccc2c(c1)C(O)(CC)CC2]

Intermediate 28 was prepared following a procedure described for Intermediate 3 using Intermediate 1 and Intermediate 27. MS (ESI) 383.4 [M+H]⁺.

Example 22A (S)-2-allyl-1-(3-ethyl-3-hydroxy-2,3-dihydro-1H-inden-5-yl)-6-((4-(4-methylpiperazin-1-yl)phenyl)amino)-1,2-dihydro-3H-pyrazolo[3,4-d]pyrimidin-3-one

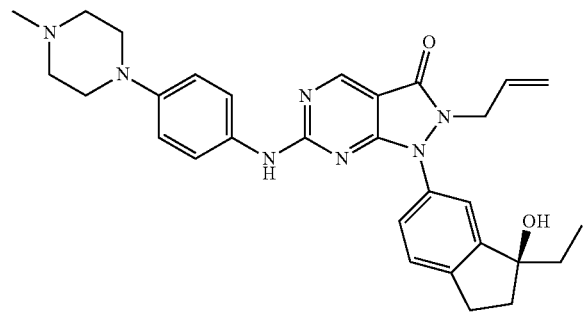 [SMILES: C=CCn1c(=O)c2cnc(Nc3ccc(N4CCN(C)CC4)cc3)nc2n1-c1ccc2c(c1)[C@](O)(CC)CC2]

Example 22B (R)-2-allyl-1-(3-ethyl-3-hydroxy-2,3-dihydro-1H-inden-5-yl)-6-((4-(4-methylpiperazin-1-yl)phenyl)amino)-1,2-dihydro-3H-pyrazolo[3,4-d]pyrimidin-3-one

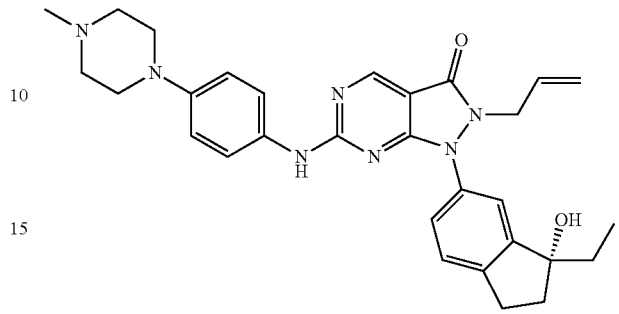

Examples 22A and 22B were prepared following a procedure described for Examples 9A and 9B using Intermediate 28 to give racemic 2-allyl-1-(3-ethyl-3-hydroxy-2,3-dihydro-1H-inden-5-yl)-6-((4-(4-methylpiperazin-1-yl)phenyl)amino)-1,2-dihydro-3H-pyrazolo[3,4-d]pyrimidin-3-one (340 mg). The enantiomers were separated by chiral SFC chromatography (Chiralpak IG, 35.0% (0.5% DEA in Methanol)) to give Peak 1 (Example 22A, 102 mg) and Peak 2 (Example 22B, 91 mg). Example 22A: yellow solid; ¹H NMR (400 MHz, DMSO-d₆) δ 10.01 (br s, 1H), 8.79 (s, 1H), 7.55 (br s, 2H), 7.38 (d, J=8.4 Hz, 1H), 7.28 (d, J=6.8 Hz, 2H), 6.85 (d, J=9.2 Hz, 2H), 5.71-5.62 (m, 1H), 5.08 (d, J=10.4 Hz, 1H), 5.02 (s, 1H), 4.92 (d, J=17.2 Hz, 1H), 4.23-4.19 (m, 2H), 3.06-3.04 (m, 4H), 2.98-2.91 (m, 1H), 2.81-2.75 (m, 1H), 2.44-2.32 (m, 4H), 2.21-2.16 (m, 4H), 2.05-1.98 (m, 1H), 1.82-1.75 (m, 1H), 1.69-1.62 (m, 1H), 0.86 (t, J=7.6 Hz, 3H); MS (ESI) 526.2 [M+H]⁺. Example 22B: ¹H NMR (400 MHz, DMSO-d₆) δ 10.01 (br s, 1H), 8.79 (s, 1H), 7.55 (br s, 2H), 7.38 (d, J=8.4 Hz, 1H), 7.28 (d, J=6.8 Hz, 2H), 6.85 (d, J=9.2 Hz, 2H), 5.67-5.63 (m, 1H), 5.09 (d, J=10.4 Hz, 1H), 5.02 (s, 1H), 4.92 (d, J=17.2 Hz, 1H), 4.23-4.22 (m, 2H), 3.06-3.04 (m, 4H), 2.94-2.91 (m, 1H), 2.81-2.77 (m, 1H), 2.45-2.42 (m, 4H), 2.21-2.16 (m, 4H), 2.03-2.00 (m, 1H), 1.82-1.75 (m, 1H), 1.67-1.64 (m, 1H), 0.86 (t, J=7.6 Hz, 3H); MS (ESI) 526.3 [M+H]⁺. The absolute stereochemistry was arbitrarily assigned for Example 22A and Example 22B.

Example 23A (S)-2-allyl-1-(3-hydroxy-3-methyl-2,3-dihydro-1H-inden-5-yl)-6-((3-methyl-4-(4-methylpiperazin-1-yl)phenyl)amino)-1,2-dihydro-3H-pyrazolo[3,4-d]pyrimidin-3-one

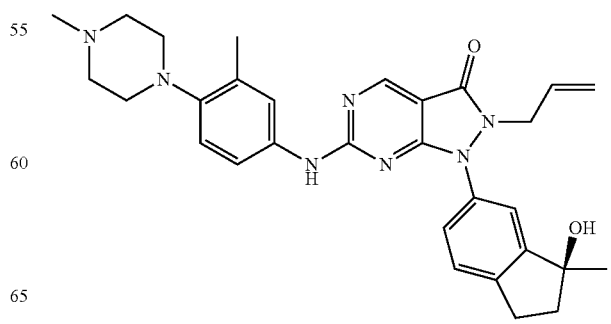

Example 23B (R)-2-allyl-1-(3-hydroxy-3-methyl-2,3-dihydro-1H-inden-5-yl)-6-((3-methyl-4-(4-methylpiperazin-1-yl)phenyl)amino)-1,2-dihydro-3H-pyrazolo[3,4-d]pyrimidin-3-one

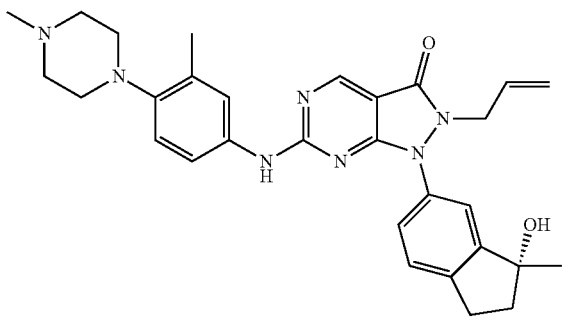

Examples 23A and 24b were prepared following a procedure described for Examples 9A and 9B using Intermediate 26 and 3-methyl-4-(4-methylpiperazin-1-yl)aniline to give racemic 2-allyl-1-(3-hydroxy-3-methyl-2,3-dihydro-1H-inden-5-yl)-6-((3-methyl-4-(4-methylpiperazin-1-yl)phenyl)amino)-1,2-dihydro-3H-pyrazolo[3,4-d]pyrimidin-3-one (635 mg). The enantiomers were separated by SFC chromatography (Chiral Pak AD-H, 40% (0.5% isopropyl amine in isopropyl alcohol)) to afford Peak 1 (Example 23A, 223 mg) and Peak 2 (Example 23B, 223 mg). Example 23A: yellow solid; $^1$H NMR (400 MHz, DMSO-$d_6$) δ 10.00 (brs, 1H), 8.81 (s, 1H), 7.47-7.29 (m, 5H), 6.93 (d, J=8.4 Hz, 1H), 5.71-5.64 (m, 1H), 5.14 (s, 1H), 5.09 (d, J=10.4 Hz, 1H), 4.93 (d, J=17.2 Hz, 1H), 4.25 (brs, 2H), 2.99-2.91 (m, 1H), 2.85-2.76 (m, 5H), 2.45 (brs, 4H), 2.22 (s, 3H), 2.17 (s, 3H), 2.12-2.09 (m, 2H), 1.42 (s, 3H); MS (ESI) 526.3 [M+H]$^+$. Example 23B: yellow solid; $^1$H NMR (400 MHz, DMSO-$d_6$) δ 10.00 (brs, 1H), 8.81 (s, 1H), 7.47-7.29 (m, 5H), 6.93 (d, J=8.4 Hz, 1H), 5.71-5.64 (m, 1H), 5.14 (s, 1H), 5.09 (d, J=10.4 Hz, 1H), 4.93 (d, J=17.2 Hz, 1H), 4.25 (brs, 2H), 2.99-2.91 (m, 1H), 2.85-2.76 (m, 5H), 2.45 (brs, 4H), 2.22 (s, 3H), 2.17 (s, 3H), 2.12-2.09 (m, 2H), 1.42 (s, 3H); MS (ESI) 526.7 [M+H]$^+$. The absolute stereochemistry was arbitrarily assigned for Example 23A and Example 23B.

Intermediate 29

6-bromo-4-fluoro-1-methyl-2,3-dihydro-1H-inden-1-ol

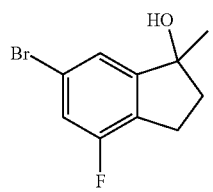

Step 1: 6-bromo-4-fluoro-2,3-dihydro-1H-inden-1-one was prepared according to WO Publication No. 2005/095387. $^1$H NMR (400 MHz, CDCl3-$d_6$) δ 7.70 (s, 1H), 7.42 (d, J=9.6 Hz, 1H), 3.10 (t, J=6.0 Hz, 2H), 2.75 (t, J=6.4 Hz, 2H).

Step 2: To a 0° C. solution of 6-bromo-4-fluoro-2,3-dihydro-1H-inden-1-one (6 g, 26 mmol) in diethyl ether (60 mL) was added 3.0 M MeMgBr in DEE (87 mL, 262 mmol) drop-wise. The ice bath was removed and the reaction was stirred at rt for 16 h. After completion by TLC, the reaction was quenched with water (50 mL) and extracted with EtOAc (2×100 mL). The combined organic layers were washed with water (150 mL), brine (150 mL), dried (Na$_2$SO$_4$), filtered and concentrated under reduced pressure. The crude product was purified by column chromatography (SiO$_2$, 10% EtOAc/pet. ether) to afford 6-bromo-4-fluoro-1-methyl-2,3-dihydro-1H-inden-1-ol (3 g, 47%) as a yellow oil. $^1$H NMR (400 MHz, CDCl3) δ 7.28 (d, J=1.6 Hz, 1H), 7.11 (dd, J=10.0, 4.8 Hz, 1H), 3.03-2.95 (m, 1H), 2.85-2.74 (m, 1H), 2.30-2.18 (m, 2H), 1.58 (s, 3H).

Intermediate 30

2-allyl-1-(7-fluoro-3-hydroxy-3-methyl-2,3-dihydro-1H-inden-5-yl)-6-(methylthio)-1,2-dihydro-3H-pyrazolo[3,4-d]pyrimidin-3-one

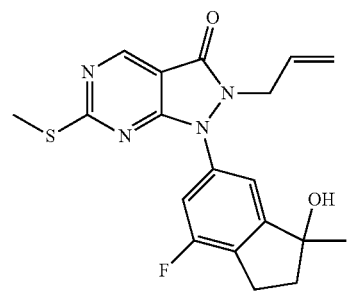

Intermediate 30 was prepared following a procedure described for Intermediate 3 using Intermediate 1 and Intermediate 29. MS (ESI) 387.3 [M+H]$^+$.

Example 24A (S)-2-allyl-1-(7-fluoro-3-hydroxy-3-methyl-2,3-dihydro-1H-inden-5-yl)-6-((4-(4-methylpiperazin-1-yl)phenyl)amino)-1,2-dihydro-3H-pyrazolo[3,4-d]pyrimidin-3-one

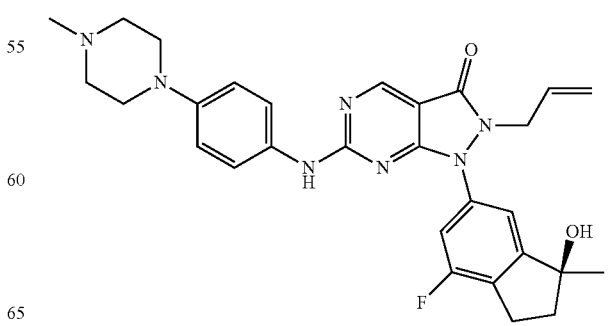

Example 24B (R)-2-allyl-1-(7-fluoro-3-hydroxy-3-methyl-2,3-dihydro-1H-inden-5-yl)-6-((4-(4-methylpiperazin-1-yl)phenyl)amino)-1,2-dihydro-3H-pyrazolo[3,4-d]pyrimidin-3-one

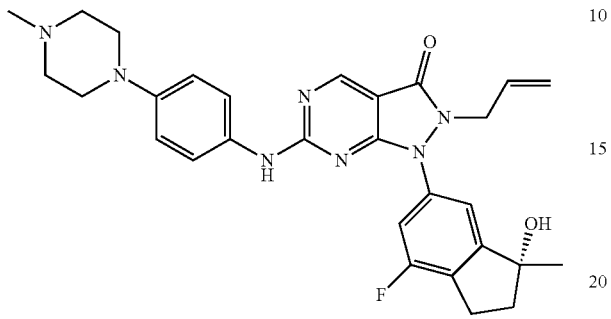

Examples 24A and 24B were prepared following a procedure described for Examples 9A and 9B using Intermediate 30 to give racemic 2-allyl-1-(7-fluoro-3-hydroxy-3-methyl-2,3-dihydro-1H-inden-5-yl)-6-((4-(4-methylpiperazin-1-yl)phenyl)-amino)-1,2-dihydro-3H-pyrazolo[3,4-d]pyrimidin-3-one (165 mg). The enantiomers were separated by SFC chromatography (Chiral Pak AD-H, 30% (0.5% isopropylamine in IPA)) to afford Peak 1 (Example 24A, 43 mg) and Peak 2 (Example 24B, 47 mg). Example 24A: yellow solid; 1H NMR (400 MHz, DMSO-d$_6$) δ 10.10 (brs, 1H), 8.81 (s, 1H), 7.55 (brs, 2H), 7.21 (d, J=9.2 Hz, 2H), 6.86 (d, J=9.2 Hz, 2H), 5.71-5.64 (m, 1H), 5.31 (s, 1H), 5.09 (d, J=10.8 Hz, 1H), 4.96 (d, J=17.2 Hz, 1H), 4.28 (brs, 2H)), 3.05-2.78 (m, 6H), 2.50-2.45 (m, 4H), 2.22 (s, 3H), 2.16-2.13 (m, 2H), 1.44 (s, 3H); MS (ESI) 530.3 [M+H]$^+$. Example 24B: yellow solid; 1H NMR (400 MHz, DMSO-d$_6$) δ 10.10 (br s, 1H), 8.81 (s, 1H), 7.55 (br s, 2H), 7.21 (d, J=9.6 Hz, 2H), 6.86 (d, J=9.2 Hz, 2H), 5.71-5.64 (m, 1H), 5.31 (s, 1H), 5.09 (d, J=10.4 Hz, 1H), 4.96 (d, J=16.8 Hz, 1H), 4.28 (br s, 2H)), 3.05-2.78 (m, 6H), 2.50-2.45 (m, 4H), 2.22 (s, 3H), 2.16-2.13 (m, 2H), 1.44 (s, 3H); MS (ESI) 530.3 [M+H]$^+$.]$^+$. The absolute stereochemistry was arbitrarily assigned for Example 24A and Example 24B.

Intermediate 31

2-bromo-8-methyl-5,6,7,8-tetrahydroquinolin-8-ol

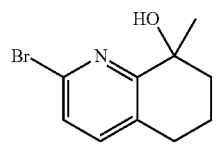

Step 1: To a stirred solution of 2-chloro-6,7-dihydroquinolin-8(5H)-one (1.7 g, 9.39 mmol) in CH$_3$CN (30 mL), was added TMS-Br (2.86 g, 18.78 mmol) and the reaction was heated at 150° C. in CEM-microwave for 20 min. After completion by TLC, the reaction was diluted with DCM (100 mL), washed with aq. NaHCO$_3$(50 mL). The organic layer was dried (Na$_2$SO$_4$), filtered and concentrated under reduced pressure. The crude product was purified by flash column chromatography (SiO$_2$, 20% EtOAc/pet. ether) to afford 2-bromo-6,7-dihydroquinolin-8(5H)-one (1.2 g, 57%) as a brown oil. MS (ESI) 226.3 [M+H].

Step 2: To a 0° C. solution of 2-bromo-6,7-dihydroquinolin-8(5H)-one (1.20 g, 5.33 mmol) in DEE (30 mL), was added 3.0 M CH$_3$MgI in DEE, (8.88 mL, 26.65 mmol) drop-wise. The mixture was allowed to warm to rt and stirred for 16 h. After completion by TLC, the reaction was quenched with water (25 mL) and extracted with EtOAc (2×50 mL). The combined organic layers were dried (Na$_2$SO$_4$), filtered and concentrated under reduced pressure. The crude product was purified by flash chromatography (SiO$_2$, 20% EtOAc/pet. ether) to afford Intermediate 31 (900 mg, 70%) as an off-white solid. MS (ESI) 241.9 [M+H]$^+$.

Intermediate 32

2-allyl-1-(8-hydroxy-8-methyl-5,6,7,8-tetrahydroquinolin-2-yl)-6-(methylthio)-1,2-dihydro-3H-pyrazolo[3,4-d]pyrimidin-3-one

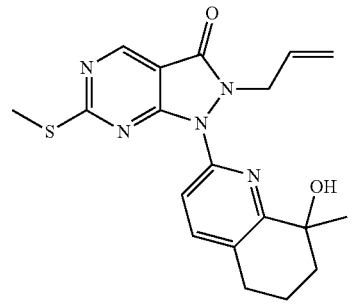

Intermediate 32 was prepared following a procedure described for Intermediate 3 using Intermediate 1 and Intermediate 31. MS (ESI) 384.1 [M+H]$^+$.

Example 25A (S)-2-allyl-1-(8-hydroxy-8-methyl-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one

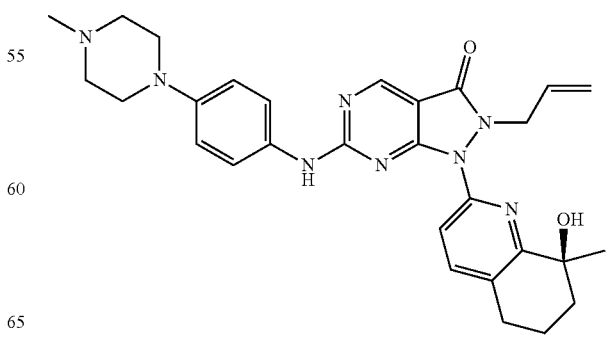

Example 25B (R)-2-allyl-1-(8-hydroxy-8-methyl-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one

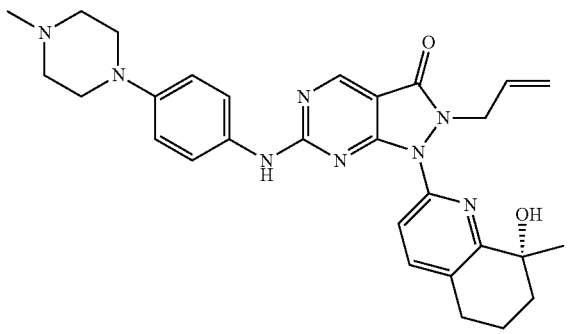

Examples 25A and 25B were prepared by following a procedure described for Examples 2A and 2B using Intermediate 32 to give racemic 2-allyl-1-(8-hydroxy-8-methyl-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one (450 mg). The enantiomers were separated by chiral SFC chromatography (Chiral Pak AD-H, 45% (0.5% DEA in Methanol)) to give Peak 1 (Example 25A, 160 mg) and Peak 2 (Example 25B, 165 mg). Example 25A: yellow solid; $^1$H NMR (400 MHz, DMSO-$d_6$) δ 10.04 (br s, 1H), 8.81 (s, 1H), 7.77 (d, J=7.2 Hz, 1H), 7.69 (d, J=8.4 Hz, 1H), 7.57 (d, J=6.8 Hz, 2H), 6.92 (d, J=8.8 Hz, 2H), 5.72-5.61 (m, 1H), 4.98 (d, J=10.4 Hz, 1H), 4.89 (s, 1H), 4.84 (s, 1H), 4.81 (br s, 1H), 4.65 (dd, J=16.0, 5.2 Hz, 1H), 3.14-3.07 (m, 4H), 2.83-2.75 (m, 2H), 2.49-2.43 (m, 4H), 2.23 (s, 3H), 1.98-1.87 (m, 2H), 1.82 (d, J=10.8 Hz, 1H), 1.77-1.68 (m, 1H), 1.49 (s, 3H); MS (ESI) 527.3 [M+H]$^+$. Example 25B: a yellow solid; $^1$H NMR (400 MHz, DMSO-$d_6$) δ 10.04 (br s, 1H), 8.81 (s, 1H), 7.77 (d, J=8.4 Hz, 1H), 7.69 (d, J=7.6 Hz, 1H), 7.56 (d, J=6.8 Hz, 2H), 6.92 (d, J=8.8 Hz, 2H), 5.71-5.61 (m, 1H), 4.98 (d, J=10.4 Hz, 1H), 4.89 (s, 1H), 4.84 (s, 1H), 4.81 (s, 1H), 4.66 (dd, J=15.6, 5.2 Hz, 1H), 3.09 (s, 4H), 2.86-2.72 (m, 2H), 2.47-2.44 (m, 4H), 2.22 (s, 3H), 1.96-1.93 (m, 2H), 1.83-177 (m, 1H), 1.73-1.70 (m, 1H), 1.49 (s, 3H); MS (ESI) 527.3 [M+H]$^+$. The absolute stereochemistry was arbitrarily assigned for Example 25A and Example 25B.

Intermediate 33

2-bromo-8-ethyl-5,6,7,8-tetrahydroquinolin-8-ol

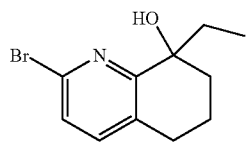

To a 0° C. solution of 2-bromo-6,7-dihydroquinolin-8(5H)-one (2.00 g, 8.88 mmol) in diethyl ether (40 mL) was added 3.0 M EtMgBr in DEE (14.82 mL, 44.44 mmol) drop-wise. The ice bath was removed and the mixture was allowed to warm to rt and stirred for 16 h. After completion by TLC, the reaction was quenched with water (50 mL) and extracted with EtOAc (2×30 mL). The combined organic layers were washed with water, brine, (Na$_2$SO$_4$), filtered and concentrated under reduced pressure. The crude product was purified by column chromatography (SiO$_2$, 10% EtOAc/pet. ether) to afford Intermediate 33 (900 mg, 40%) as a pale yellow oil. MS (ESI) 256.2 [M+H]$^+$.

Intermediate 34

2-allyl-1-(8-ethyl-8-hydroxy-5,6,7,8-tetrahydroquinolin-2-yl)-6-(methylthio)-1,2-dihydro-3H-pyrazolo[3,4-d]pyrimidin-3-one

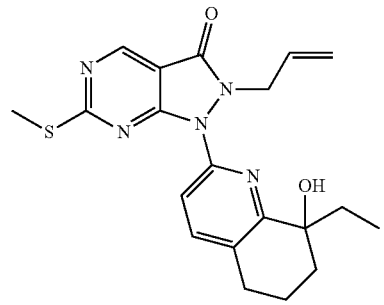 [SMILES: C=CCn1c(=O)c2cnc(SC)nc2n1-c1ccc2c(n1)C(O)(CC)CCC2]

Intermediate 34 was prepared following a procedure described for Intermediate 3 using Intermediate 1 and Intermediate 33. MS (ESI) 398.0 [M+H]$^+$.

Example 26A (S)-2-allyl-1-(8-ethyl-8-hydroxy-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one

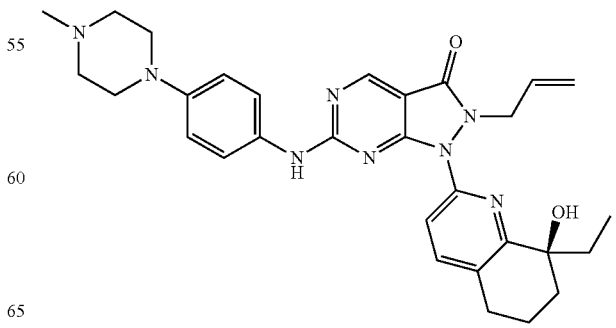

Example 26B (R)-2-allyl-1-(8-ethyl-8-hydroxy-5,6,7,8-tetrahydro-quinolin-2-yl)-6-((4-(4-methylpiperazin-1-yl)phenyl)amino)-1,2-dihydro-3H-pyrazolo[3,4-d]pyrimidin-3-one

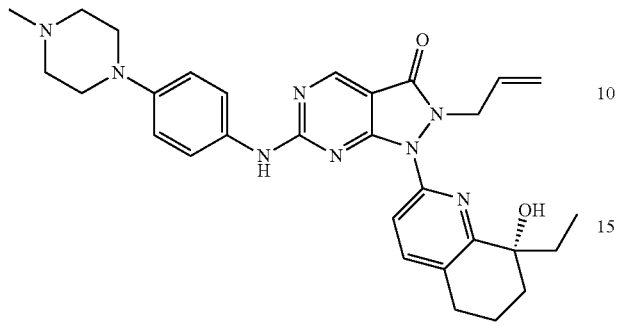

Examples 26A and 26B were prepared by following a procedure described for Examples 2A and 2B using Intermediate 34 to give racemic 2-allyl-1-(8-ethyl-8-hydroxy-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one (600 mg). The enantiomers were separated by chiral SFC chromatography (Chiral Pak AD-H, 35% (0.5% DEA in Methanol)) to give Peak 1 (Example 26A, 160 mg) and Peak 2 (Example 26B, 136 mg). Example 26A: yellow solid. $^1$H NMR (400 MHz, DMSO-d$_6$) δ 10.11 (br s, 1H), 8.81 (s, 1H), 7.78 (d, J=8.4 Hz, 1H), 7.69 (d, J=7.8 Hz, 1H), 7.60-754 (m, 2H), 6.93 (d, J=8.8 Hz, 2H), 5.70-5.61 (m, 1H), 4.99 (d, J=9.6 Hz, 1H), 4.86 (d, J=17.2 Hz, 1H), 4.81 (br s, 1H), 4.73 (s, 1H), 4.59 (dd, J=16, 5.6 Hz, 1H), 3.12-3.06 (m, 4H), 2.85-2.67 (m, 2H), 2.49-2.40 (m, 4H), 2.22 (s, 3H), 1.96-1.71 (m, 6H), 0.78 (t, J=7.6 Hz, 3H); MS (ESI) 541.3 Example 26B: yellow solid; $^1$H NMR (400 MHz, DMSO-d$_6$) δ 10.11 (br s, 1H), 8.81 (s, 1H), 7.78 (d, J=8.4 Hz, 1H), 7.69 (d, J=7.8 Hz, 1H), 7.60-754 (m, 2H), 6.93 (d, J=8.8 Hz, 2H), 5.70-5.61 (m, 1H), 4.99 (d, J=9.6 Hz, 1H), 4.86 (d, J=17.2 Hz, 1H), 4.81 (br s, 1H), 4.73 (s, 1H), 4.59 (dd, J=16, 5.6 Hz, 1H), 3.12-3.06 (m, 4H), 2.85-2.67 (m, 2H), 2.49-2.40 (m, 4H), 2.22 (s, 3H), 1.96-1.71 (m, 6H), 0.78 (t, J=7.6 Hz, 3H). MS (ESI) 541.3 [M+H]$^+$. The absolute stereochemistry was arbitrarily assigned for Example 26A and Example 26B.

Example 27A (S)-2-allyl-1-(8-hydroxy-8-methyl-5,6,7,8-tetrahydroquinolin-2-yl)-6-((3-methyl-4-(4-methylpiperazin-1-yl)phenyl)amino)-1,2-dihydro-3H-pyrazolo[3,4-d]pyrimidin-3-one

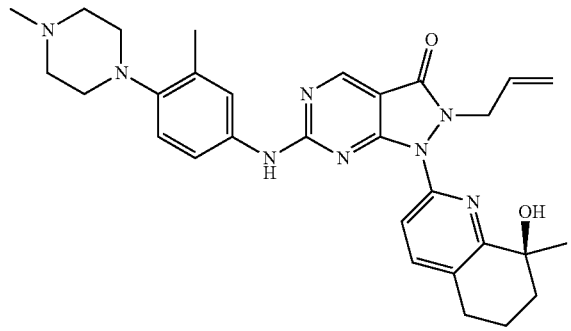

Example 27B (R)-2-allyl-1-(8-hydroxy-8-methyl-5,6,7,8-tetrahydroquinolin-2-yl)-6-((3-methyl-4-(4-methylpiperazin-1-yl)phenyl)amino)-1,2-dihydro-3H-pyrazolo[3,4-d]pyrimidin-3-one

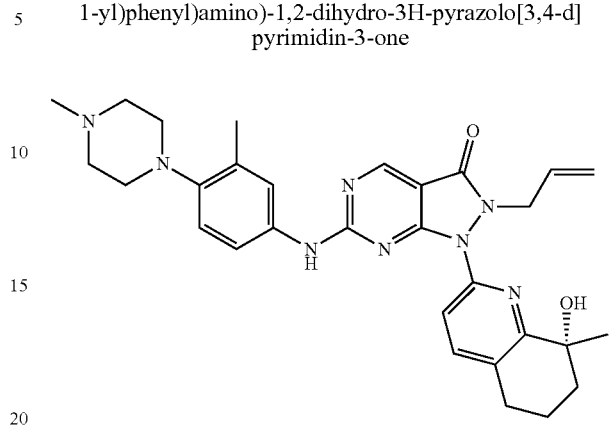

Examples 27A and 27B were prepared by following a procedure described for Examples 2A and 2B using Intermediate 32 and 3-methyl-4-(4-methylpiperazin-1-yl)aniline to give racemic 2-allyl-1-(8-hydroxy-8-methyl-5,6,7,8-tetrahydroquinolin-2-yl)-6-((3-methyl-4-(4-methylpiperazin-1-yl)phenyl)amino)-1,2-dihydro-3H-pyrazolo[3,4-d]pyrimidin-3-one (800 mg). The enantiomers were separated by chiral SFC chromatography (Chiral Pak AD-H, 50% (0.5% DEA in Methanol)) to give Peak 1 (Example 27A, 69 mg) and Peak 2 (Example 27B, 68 mg). Example 27A: yellow solid; $^1$H NMR (400 MHz, DMSO-d$_6$) δ 10.12 (brs, 1H), 8.84 (s, 1H), 7.75-7.67 (m, 3H), 7.39 (d, J=8.8 Hz, 1H), 6.99 (d, J=8.8 Hz, 1H), 5.71-5.61 (m, 1H), 4.98 (d, J=10 Hz, 1H), 4.89 (d, J=8.4 Hz, 2H), 4.84-4.80 (m, 1H), 4.67-4.61 (m, 1H), 2.85-2.67 (m, 6H), 2.52-2.48 (m, 4H) 2.47 (s, 6H), 1.96-1.92 (m, 2H), 1.83-1.70 (m, 2H), 1.49 (s, 3H); MS (ESI) 541.2 [M+H]$^+$. Example 27B: yellow solid; $^1$H NMR (400 MHz, DMSO-d$_6$) δ 10.12 (brs, 1H), 8.84 (s, 1H), 7.75-7.67 (m, 3H), 7.39 (d, J=8.8 Hz, 1H), 6.99 (d, J=8.8 Hz, 1H), 5.71-5.61 (m, 1H), 4.98 (d, J=10 Hz, 1H), 4.89 (d, J=8.4 Hz, 2H), 4.84-4.80 (m, 1H), 4.67-4.61 (m, 1H), 2.85-2.67 (m, 6H), 2.52-2.48 (m, 4H), 2.25-2.24 (m, 6H), 1.96-1.92 (m, 2H), 1.83-1.70 (m, 2H), 1.49 (s, 3H); MS (ESI) 541.2 [M+H]$^+$. The absolute stereochemistry was arbitrarily assigned for Example 27A and Example 27B.

Example 28A (S)-2-allyl-1-(8-hydroxy-8-methyl-5,6,7,8-tetrahydroquinolin-2-yl)-6-((4-(piperazin-1-yl)phenyl)amino)-1,2-dihydro-3H-pyrazolo[3,4-d]pyrimidin-3-one

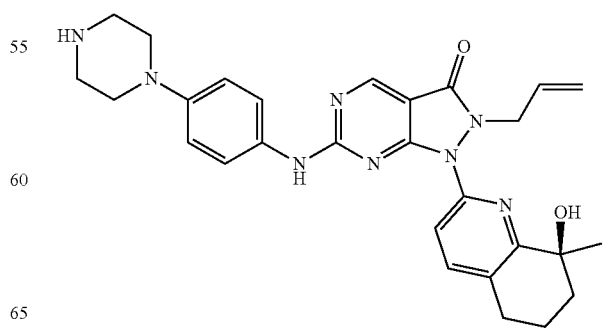

Example 28B (R)-2-allyl-1-(8-hydroxy-8-methyl-5,6,7,8-tetrahydroquinolin-2-yl)-6-((4-(piperazin-1-yl)phenyl)amino)-1,2-dihydro-3H-pyrazolo[3,4-d]pyrimidin-3-one

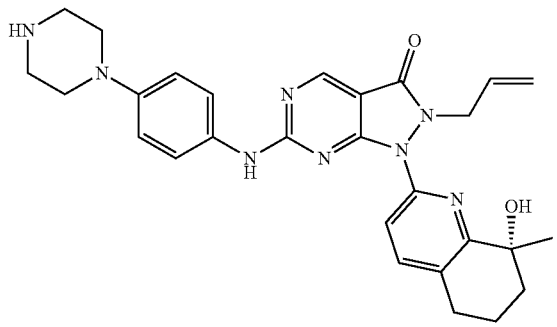 [SMILES: C=CCn1c(=O)c2cnc(Nc3ccc(N4CCNCC4)cc3)nc2n1-c1ccc2c(n1)[C@](C)(O)CCC2]

Step 1: 2-allyl-1-(8-hydroxy-8-methyl-5,6,7,8-tetrahydroquinolin-2-yl)-6-((4-(4-(2,2,2-trifluoroacetyl)piperazin-1-yl)phenyl)amino)-1,2-dihydro-3H-pyrazolo[3,4-d]pyrimidin-3-one was synthesized using a procedure described for Example 9A and Example 9B using Intermediate 32. MS (ESI) 609.5 [M+H]$^+$.

Step 2: To a 0° C. solution of 2-allyl-1-(8-hydroxy-8-methyl-5,6,7,8-tetrahydroquinolin-2-yl)-6-((4-(4-(2,2,2-trifluoroacetyl)piperazin-1-yl)phenyl)amino)-1H-pyrazolo[3,4-d]pyrimidin-3(2H)-one (400 mg, 0.66 mmol) in MeOH (6 mL) was added K$_2$CO$_3$ (272 mg, 1.97 mmol). The ice bath was removed and the reaction was stirred at rt for 16 h. After completion by TLC, the reaction was concentrated under reduced pressure. Water (10 mL) was added and the mixture was stirred for 10 minutes. The resulting solid was filtered and dried under vacuum to afford racemic 2-allyl-1-(8-hydroxy-8-methyl-5,6,7,8-tetrahydroquinolin-2-yl)-6-((4-(piperazin-1-yl)phenyl)-amino)-1H-pyrazolo[3,4-d]pyrimidin-3(2H)-one (260 mg). The enantiomers were separated by chiral SFC chromatography (Chiral Pak AD-n, 40% (0.5% DEA in Methanol)) to give Peak 1 (Example 28A, 39 mg) and Peak 2 (Example 28B, 33 mg). Example 28A: yellow solid; $^1$H NMR (400 MHz, DMSO-d$_6$) δ 10.10 (br s, 1H), 8.81 (s, 1H), 7.76 (d, J=8.4 Hz, 1H), 7.69 (d, J=8.4 Hz, 1H), 7.56 (brs, 2H), 6.90 (d, J=8.8 Hz, 2H), 5.69-5.62 (m, 1H), 4.98 (d, J=10.0 Hz, 1H), 4.88 (s, 1H), 4.84-4.80 (m, 2H), 4.67-4.61 (m, 1H), 3.00-2.99 (m, 4H), 2.83-2.76 (m, 6H), 1.96-1.91 (m, 2H), 1.83-1.70 (m, 2H), 1.49 (s, 3H); MS (ESI) 513.3 [M+H]$^+$. Example 28B: yellow solid; $^1$H NMR (400 MHz, DMSO-d$_6$) δ 10.09 (br s, 1H), 8.81 (s, 1H), 7.77 (d, J=8.4 Hz, 1H), 7.69 (d, J=8.0 Hz, 1H), 7.57 (d, J=7.2 Hz, 2H), 6.90 (d, J=8.8 Hz, 2H), 5.71-5.621 (m, 1H), 4.98 (d, J=9.2 Hz, 1H), 4.88 (s, 1H), 4.84-4.81 (m, 2H), 4.67-4.62 (s, 1H), 3.01-2.99 (m, 4H), 2.84-2.74 (m, 6H), 1.96-1.92 (m, 2H), 1.83-1.70 (m, 2H), 1.49 (s, 3H); MS (ESI) 513.3 [M+H]$^+$. The absolute stereochemistry was arbitrarily assigned for Example 28A and Example 28B.

Intermediate 35

1-(7'-amino-1'H-spiro[cyclopropane-1,4'-isoquinolin]-2'(3'H)-yl)-2,2,2-trifluoroethan-1-one

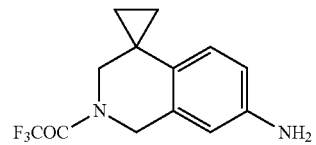

Step 1: 7'-nitro-2',3'-dihydro-1'H-spiro[cyclopropane-1,4'-isoquinoline] was prepared according to U.S. Pat. No. 7,507,748.

Step 2: To a stirred solution of 7'-nitro-2',3'-dihydro-1'H-spiro[cyclopropane-1,4'-isoquinoline] (2.5 g, 12.25 mmol) in DCM (40 mL) were added TEA (3.69 g, 36.75 mmol) and trifluoroacetic anhydride (3.08 g, 14.70 mmol) at 0° C. The ice bath was removed and the reaction was stirred at rt 16 h. After completion by TLC, the reaction was diluted with DCM (100 mL), washed with water (100 mL) and brine (50 mL). The organic layer was dried (Na$_2$SO$_4$), filtered and concentrated under reduced pressure. The crude product was purified by column chromatography (SiO$_2$, 10% EtOAc/pet. ether) to afford 2,2,2-trifluoro-1-(7'-nitro-1'H-spiro[cyclopropane-1,4'-isoquinolin]-2'(3'H)-yl)ethan-1-one (1.7 g, 46%) as a yellow oil. $^1$H NMR (300 MHz, DMSO-d$_6$) δ 8.26 (dd, J=20.7 Hz, 2.4 Hz, 1H), 8.05-8.00 (m, 1H), 7.13 (d, J=8.7 Hz, 1H), 5.04 (d, J=12.3 Hz, 2H), 3.74 (d, J=6.9 Hz, 2H), 1.24-1.15 (m, 4H).

Step 3: To a stirred solution of 2,2,2-trifluoro-1-(7'-nitro-1'H-spiro[cyclopropane-1,4'-isoquinolin]-2'(3'H)-yl)ethan-1-one (1.7 g, 5.66 mmol) in EtOH (17 mL) were added SnCl$_2$ (6.44 g, 33.99 mmol) and NH$_4$Cl (1.81 g, 33.99 mmol). The reaction was heated at 80° C. for 2 h. After completion by TLC, the reaction was concentrated under reduced pressure and the residue was dissolved in water (50 mL), basified to pH-8 using sat NaHCO$_3$ and extracted with EtOAc (2×50 mL). The combined organic layers were dried (Na$_2$SO$_4$), filtered and concentrated under reduced pressure to afford Intermediate 35 (1.4 g, 91%) as a pale yellow solid. MS (ESI) 270.9 [M+H]$^+$.

Example 29A (S)-2-allyl-6-((2',3'-dihydro-1'H-spiro[cyclopropane-1,4'-isoquinolin]-7'-yl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one

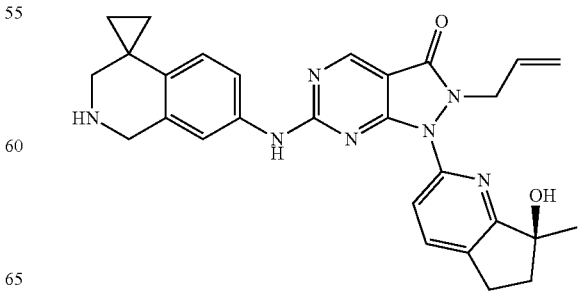

Example 29B (R)-2-allyl-6-((2',3'-dihydro-1'H-spiro[cyclopropane-1,4'-isoquinolin]-7'-yl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one

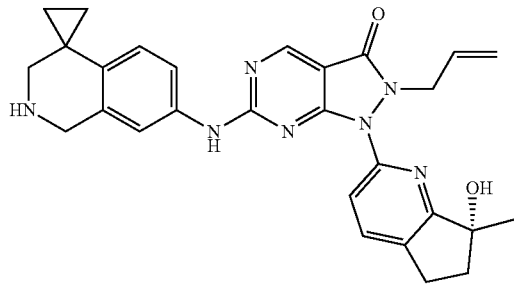 [SMILES: C=CCn1c(=O)c2cnc(Nc3ccc4c(c3)CNCC43CC3)nc2n1-c1ccc2c(n1)[C@](C)(O)CC2]

Step 1: 2-allyl-1-(7-hydroxy-7-methyl-6,7-dihydro-5H-cyclopenta[b]pyridin-2-yl)-6-((2'-(2,2,2-trifluoroacetyl)-2',3'-dihydro-1'H-spiro[cyclopropane-1,4'-isoquinolin]-7'-yl)amino)-1,2-dihydro-3H-pyrazolo[3,4-d]pyrimidin-3-one was prepared following a procedure described for Examples 9A and 9B using Intermediate 5 and Intermediate 35. MS (ESI) 592.4 [M+H]+.

Step 2: To a 0° C. solution of 2-allyl-1-(7-hydroxy-7-methyl-6,7-dihydro-5H-cyclopenta[b]pyridin-2-yl)-6-((2'-(2,2,2-trifluoroacetyl)-2',3'-dihydro-1'H-spiro[cyclopropane-1,4'-isoquinolin]-7'-yl)amino)-1,2-dihydro-3H-pyrazolo[3,4-d]pyrimidin-3-one (135 mg, 0.23 mmol) in MeOH (6 mL) was added K₂CO₃ (94 mg, 0.68 mmol). The ice bath was removed and the reaction was stirred at rt for 16 h. After completion by TLC, the reaction was concentrated under reduced pressure. Water (10 mL) was added to the crude compound and stirred for 10 minutes. The precipitate was filtered and dried under vacuum to afford racemic 2-allyl-6-((2',3'-dihydro-1'H-spiro[cyclopropane-1,4'-isoquinolin]-7'-yl)amino)-1-(7-hydroxy-7-methyl-6,7-dihydro-5H-cyclopenta[b]pyridin-2-yl)-1,2-dihydro-3H-pyrazolo[3,4-d]pyrimidin-3-one (85 mg) as an off white solid. The enantiomers were separated by chiral SFC chromatography (Chiral Pak IA, 45% (0.5% DEA in Methanol)) to give Peak 1 (Example 29A, 30 mg) and Peak 2 (Example 29B, 25 mg). Example 29A: yellow solid; ¹H NMR (400 MHz, DMSO-d₆) 10.16 (brs, 1H), 8.85 (s, 1H), 7.90 (d, J=8.4 Hz, 1H), 7.70 (d, J=8.4 Hz, 1H), 7.55 (brs, 1H), 7.32 (d, J=8.0 Hz, 1H), 6.66 (d, J=8.4 Hz, 1H), 5.71-5.63 (m, 1H), 5.18 (s, 1H), 4.99 (d, J=9.6 Hz, 1H), 4.85 (d, J=17.6 Hz, 1H), 4.74 (d, J=10.0 Hz, 1H), 4.60 (dd, J=16.4, 6.0 Hz, 1H), 3.91 (s, 2H), 3.03-2.94 (m, 1H), 2.87-2.72 (m, 3H), 2.13 (t, J=6.8 Hz, 2H), 1.45 (s, 3H), 0.88 (s, 2H), 0.77 (s, 2H). MS (ESI) 496.2 [M+H]+. Example 29B: yellow solid; ¹H NMR (400 MHz, DMSO-d₆) 10.16 (brs, 1H), 8.85 (s, 1H), 7.90 (d, J=8.4 Hz, 1H), 7.70 (d, J=8.4 Hz, 1H), 7.55 (brs, 1H), 7.32 (d, J=8.8 Hz, 1H), 6.66 (d, J=8.4 Hz, 1H), 5.71-5.63 (m, 1H), 5.18 (s, 1H), 4.99 (d, J=10.4 Hz, 1H), 4.85 (d, J=18 Hz, 1H), 4.74 (d, J=14 Hz, 1H), 4.60 (dd, J=16 Hz, 5.2 Hz, 1H), 3.91 (s, 2H), 3.01-2.96 (m, 1H), 2.84-2.67 (m, 3H), 2.13 (t, J=6.8 Hz, 2H), 1.45 (s, 3H), 0.88 (s, 2H), 0.77 (s, 2H). MS (ESI) 496.2 [M+H]+. The absolute stereochemistry was arbitrarily assigned for Example 29A and Example 29B.

Intermediate 36 tert-butyl 7'-amino-1'H-spiro[cyclopropane-1,4'-isoquinoline]-2'(3'H)-carboxylate

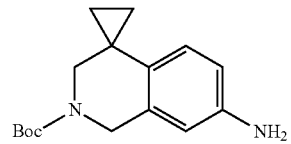

Step 1: To a stirred solution of 7'-nitro-2',3'-dihydro-1'H-spiro[cyclopropane-1,4'-isoquinoline] (3 g, 14.63 mmol) in 1,4-dioxane:H₂O (45 mL, 2:1) was added 1 N NaOH (15 mL) at 0° C. After 5 mins, di-tert-butyl dicarbonate (3.7 mL, 16.91 mmol) was added at 0° C., and the reaction was stirred at rt for 2 h. The reaction was acidified with KHSO₄ (pH: 2-3), then the mixture was extracted with ethyl acetate (2×100 mL). The combined organic layers were washed with water (25 mL), dried (Na₂SO₄) and concentrated. The resulting crude mixture was purified by column chromatography (SiO₂, 20% EA/pet. ether) to afford tert-butyl 7'-nitro-1'H-spiro[cyclopropane-1,4'-isoquinoline]-2'(3'H)-carboxylate (2.5 g, 56%) as a pale yellow solid. MS (LCMS) 249.0 [M-C₄H₁₀]+.

Step 2: To a stirred solution of tert-butyl 7'-nitro-1'H-spiro[cyclopropane-1,4'-isoquinoline]-2'(3'H)-carboxylate (1.0 g, 3.28 mmol) in EtOH (50 mL) was added SnCl₂ (3.74 g, 19.67 mmol) followed by NH₄Cl (1.04 g, 19.67 mmol) at rt. The reaction was stirred at 70° C. for 1 h. After completion by LCMS, the crude reaction was concentrated under reduced pressure, diluted with water (50 mL) and basified with sat. NaHCO₃ (pH: 8-9). The mixture was then filtered through a celite pad, extracted with 30% MeOH:DCM (3×100 mL). The combined organic layers were dried (Na₂SO₄) and concentrated to afford Intermediate 36 (615 mg, 93%) as an off-white solid. MS (LCMS) 275.4 [M+H]+.

Intermediate 37A tert-butyl (S)-7'-((2-allyl-1-(7-hydroxy-7-(trifluoromethyl)-6,7-dihydro-5H-cyclopenta[b]pyridin-2-yl)-3-oxo-2,3-dihydro-1H-pyrazolo[3,4-d]pyrimidin-6-yl)amino)-1'H-spiro[cyclopropane-1,4'-isoquinoline]-2'(3'H)-carboxylate

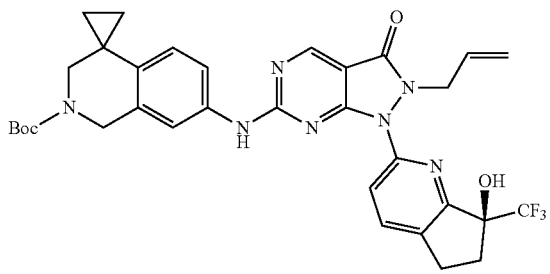 [SMILES: C=CCn1c(=O)c2cnc(Nc3ccc4c(c3)CN(C(=O)OC(C)(C)C)CC43CC3)nc2n1-c1ccc2c(n1)[C@](O)(C(F)(F)F)CC2]

Intermediate 37B tert-butyl (R)-7'-((2-allyl-1-(7-hydroxy-7-(trifluoromethyl)-6,7-dihydro-5H-cyclopenta[b]pyridin-2-yl)-3-oxo-2,3-dihydro-1H-pyrazolo[3,4-d]pyrimidin-6-yl)amino)-1'H-spiro[cyclopropane-1,4'-isoquinoline]-2'(3'H)-carboxylate

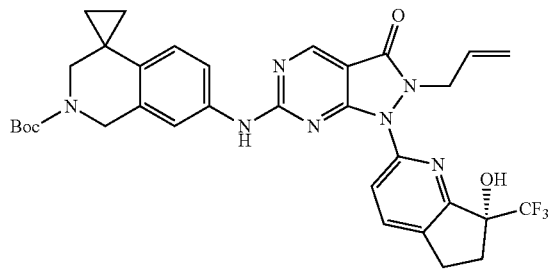 [SMILES: C=CCn1c(=O)c2cnc(Nc3ccc4c(c3)CN(C(=O)OC(C)(C)C)CC43CC3)nc2n1-c1ccc2c(n1)[C@@](O)(C(F)(F)F)CC2]

Intermediates 37A and 37B were prepared by following a procedure described for Examples 2A and 2B using Intermediate 7 and Intermediate 36 to give racemic tert-butyl-7'-((2-allyl-1-(7-hydroxy-7-(trifluoromethyl)-6,7-dihydro-5H-cyclopenta[b]-pyridine-2-yl)-3-oxo-2,3-dihydro-1H-pyrazolo[3,4-d]pyrimidin-6-yl)amino)-1'H-spiro-[cyclopropane-1,4'-isoquinoline]-2'(3'H)-carboxylate (364 mg). The enantiomers were separated by chiral SFC chromatography (Chiralpak IC, 35% Methanol) to give Peak 1 (Intermediate 37A, 140 mg) and Peak 2 (Intermediate 37B, 135 mg). Intermediate 37A: yellow solid; MS (ESI) 650.5 [M+H]$^+$. Intermediate 37B: yellow solid; MS (ESI) 650.5 [M+H]$^+$. The absolute stereochemistry was arbitrarily assigned for Intermediate 37A and Intermediate 37B.

Example 30A (S)-2-allyl-6-((2',3'-dihydro-1'H-spiro[cyclopropane-1,4'-isoquinolin]-7'-yl)amino)-1-(7-hydroxy-7-(trifluoromethyl)-6,7-dihydro-5H-cyclopenta[b]pyridin-2-yl)-1,2-dihydro-3H-pyrazolo[3,4-d]pyrimidin-3-one

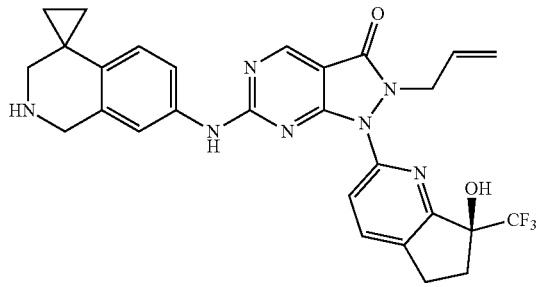 [SMILES: C=CCn1c(=O)c2cnc(Nc3ccc4c(c3)CNCC43CC3)nc2n1-c1ccc2c(n1)[C@](O)(C(F)(F)F)CC2]

To a stirred solution of Intermediate 37A (140 mg, 0.22 mmol) in DCM (4 mL) was added 2M HCl in Et$_2$O (1 mL) at 0° C. The ice bath was removed and the reaction was stirred at rt for 4 h. The reaction was concentrated under reduced pressure and triturated with diethyl ether to afford Example 30A (60 mg, 50%) as an HCl salt after drying under high vacuum. $^1$H NMR (400 MHz, DMSO-d$_6$) δ 10.38 (brs, 1H), 9.39 (s, 2H), 8.91 (s, 1H), 8.08 (d, J=8.4 Hz, 1H), 7.95 (d, J=8.4 Hz, 1H), 7.73 (s, 1H), 7.47 (d, J=8.8 Hz, 1H), 6.85 (d, J=8.8 Hz, 2H), 5.70-5.60 (m, 1H), 4.97 (d, J=15.4 Hz, 1H), 4.81-4.77 (m, 2H), 4.60-4.55 (m, 1H), 4.43-4.33 (m, 2H), 3.26 (brs, 1H), 3.13-2.94 (m, 2H), 2.67-2.56 (m, 2H), 2.33-2.23 (s, 1H), 1.09 (s, 4H); MS (ESI) 550.5 [M+H]$^+$.

Example 30B

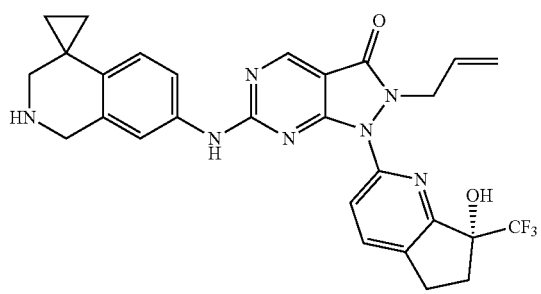 [SMILES: C=CCn1c(=O)c2cnc(Nc3ccc4c(c3)CNCC43CC3)nc2n1-c1ccc2c(n1)[C@@](O)(C(F)(F)F)CC2]

Example 30B was prepared according to the procedure for Example 30A as a hydrochloride salt. $^1$H NMR (400 MHz, DMSO-d$_6$) δ 10.38 (brs, 1H), 9.4 (s, 2H), 8.91 (s, 1H), 8.08 (d, J=8.4 Hz, 1H), 7.95 (d, J=8.4 Hz, 1H), 7.73 (s, 1H), 7.47 (d, J=8.8 Hz, 1H), 6.85 (d, J=8.8 Hz, 2H), 5.70-5.60 (m, 1H), 4.97 (d, J=15.4 Hz, 1H), 4.81-4.77 (m, 2H), 4.60-4.55 (m, 1H), 4.43-4.33 (m, 2H), 3.26 (brs, 1H), 3.13-2.94 (m, 2H), 2.67-2.56 (m, 2H), 2.33-2.23 (s, 1H), 1.09 (s, 4H); MS (ESI) 550.5 [M+H]$^+$. The absolute stereochemistry was arbitrarily assigned for Example 30A and Example 30B.

Example 31A (S)-2-allyl-6-((2',3'-dihydro-1'H-spiro[cyclopropane-1,4'-isoquinolin]-7'-yl)amino)-1-(8-hydroxy-8-methyl-5,6,7,8-tetrahydroquinolin-2-yl)-1,2-dihydro-3H-pyrazolo[3,4-d]pyrimidin-3-one

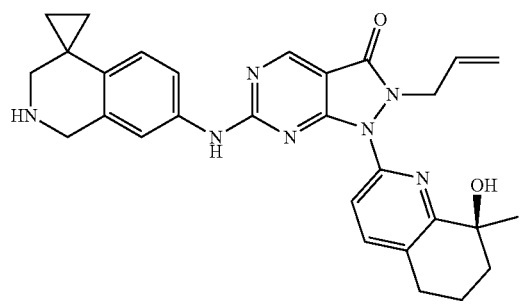 [SMILES: C=CCn1c(=O)c2cnc(Nc3ccc4c(c3)CNCC43CC3)nc2n1-c1ccc2c(n1)[C@](C)(O)CCC2]

Example 31B (R)-2-allyl-6-((2',3'-dihydro-1'H-spiro[cyclopropane-1,4'-isoquinolin]-7'-yl)amino)-1-(8-hydroxy-8-methyl-5,6,7,8-tetrahydroquinolin-2-yl)-1,2-dihydro-3H-pyrazolo[3,4-d]pyrimidin-3-one

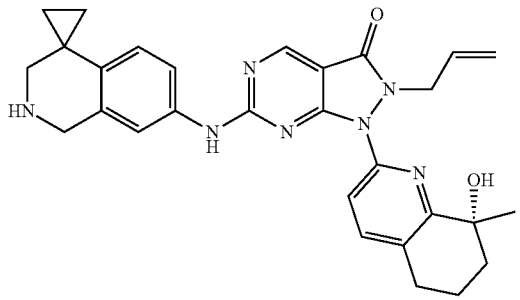

Step 1: 2-allyl-1-(8-hydroxy-8-methyl-5,6,7,8-tetrahydroquinolin-2-yl)-6-((2'-(2,2,2-trifluoroacetyl)-2',3'-dihydro-1'H-spiro[cyclopropane-1,4'-isoquinolin]-7'-yl)amino)-1,2-dihydro-3H-pyrazolo[3,4-d]pyrimidin-3-one (364 mg, 26%) was prepared by following a procedure described for Examples 2A and 2B using Intermediate 32 and Intermediate 35. MS (ESI) 606.4 [M+H]$^+$.

Step 2: To a stirred solution of 2-allyl-1-(8-hydroxy-8-methyl-5,6,7,8-tetrahydroquinolin-2-yl)-6-((2'-(2,2,2-trifluoroacetyl)-2',3'-dihydro-1'H-spiro[cyclopropane-1,4'-isoquinolin]-7'-yl)amino)-1,2-dihydro-3H-pyrazolo[3,4-d]pyrimidin-3-one (400 mg, 0.66 mmol) in MeOH (12 mL) was added K$_2$CO$_3$ (183 mg, 1.32 mmol) and the reaction was stirred at rt for 16 h. After completion by TLC, the solvent was evaporated. The reaction mixture was diluted with water (20 mL) and extracted with 10% MeOH in DCM (2×50 mL). The combined organic layers were dried (Na$_2$SO$_4$), filtered and concentrated under reduced pressure to afford racemic 2-allyl-6-((2',3'-dihydro-1'H-spiro[cyclopropane-1,4'-isoquinolin]-7'-yl)amino)-1-(8-hydroxy-8-methyl-5,6,7,8-tetrahydroquinolin-2-yl)-1,2-dihydro-3H-pyrazolo[3,4-d]pyrimidin-3-one (310 mg) as a pale yellow solid. The enantiomers were separated by chiral SFC chromatography (Chiralpak AD-H, (0.5% isopropylamine in IPA)) to give Peak 1 (Example 31A, 120 mg) and Peak 2 (Example 31B, 123 mg). Example 31A: yellow solid; $^1$H NMR (400 MHz, DMSO-d$_6$) δ 10.15 (br s, 1H), 8.85 (s, 1H), 7.75-7.69 (m, 2H), 7.56 (br s, 1H), 7.30 (d, J=8.0 Hz, 1H), 6.67 (d, J=8.8 Hz, 1H), 5.71-5.61 (m, 1H), 4.99 (d, J=9.2 Hz, 1H), 4.90-4.81 (m, 3H), 4.67-4.62 (dd, J=16 Hz, J=6.0 Hz, 1H), 3.92 (s, 2H), 2.86-2.66 (m, 4H), 1.96-1.92 (m, 2H), 1.84-1.71 (m, 2H), 1.49 (s, 3H), 0.88 (s, 2H), 0.78 (s, 2H); MS (ESI) 510.2 [M+H]$^+$. Example 31B: yellow solid; $^1$H NMR (400 MHz, DMSO-d$_6$) δ 10.15 (br s, 1H), 8.85 (s, 1H), 7.75-7.69 (m, 2H), 7.56 (br s, 1H), 7.30 (d, J=7.6 Hz, 1H), 6.67 (d, J=8.4 Hz, 1H), 5.70-5.63 (m, 1H), 4.99 (d, J=9.2 Hz, 1H), 4.89-4.80 (m, 3H), 4.67-4.62 (dd, J=16 Hz, J=5.6 Hz, 1H), 3.92 (s, 2H), 2.86-2.74 (m, 4H), 1.96-1.92 (m, 2H), 1.84-1.78 (m, 1H), 1.73-1.71 (m, 1H), 1.49 (s, 3H), 0.88 (s, 2H), 0.78 (s, 2H); MS (ESI) 510.2 [M+H]$^+$. The absolute stereochemistry was arbitrarily assigned for Example 31A and Example 31B.

Intermediate 38

2-bromo-5,6-dihydro-8H-imidazo[2,1-c][1,4]oxazine

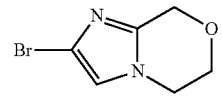

Step 1: 5,6-dihydro-8H-imidazo[2,1-c][1,4]oxazine was synthesized according to a procedure in WO 2016138821.

Step 2: To a stirred solution of 5,6-dihydro-8H-imidazo[2,1-c][1,4]oxazine (3 g, 24.16 mmol) in CH$_3$CN (30 mL), was added NBS (9.04 g, 50.80 mmol) portion-wise at 0° C. The reaction was stirred at 0° C. for 2 h. After completion by TLC, the reaction was concentrated. The crude mixture was triturated with CCl$_4$ (5×30 mL), filtered and the filtrate was concentrated under vacuum to afford 2,3-dibromo-5,6-dihydro-8H-imidazo[2,1-c][1,4]oxazine (3 g, 44%) as a white solid. MS (ESI) 281.1 [M+H]$^+$.

Step 3: To a stirred solution of 2,3-dibromo-5,6-dihydro-8H-imidazo[2,1-c][1,4]oxazine (500 mg, 1.76 mmol) in dry THF was added 1.6 M iPrMgCl (1.65 mL, 2.85 mmol) drop-wise at 0° C. The reaction was stirred at 0° C. for 2 h. After completion by TLC, the reaction was quenched with water (25 mL) and extracted with EtOAc (2×30 mL). The combined organic layers were dried (Na$_2$SO$_4$) and evaporated under reduced pressure. The residue was purified by flash chromatography (SiO$_2$, 3% MeOH/DCM) to afford Intermediate 38 (280 mg, 77%) as an off-white solid. MS (ESI) m/z 203.3 [M+H]$^+$.

Intermediate 39

2-allyl-1-(5,6-dihydro-8H-imidazo[2,1-c][1,4]oxazin-2-yl)-6-(methylthio)-1,2-dihydro-3H-pyrazolo[3,4-d]pyrimidin-3-one

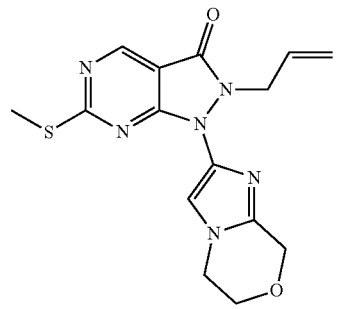 [SMILES: C=CCn1c(=O)c2cnc(SC)nc2n1-c1cn2c(n1)COCC2]

Intermediate 39 was prepared following a procedure described for Intermediate 3 using Intermediate 1 and Intermediate 38. The mixture was degassed for 20 min and then heated in the microwave at 100° C. for 2 h. MS (ESI) 345.5 [M+H]$^+$.

Example 32

2-allyl-1-(5,6-dihydro-8H-imidazo[2,1-c][1,4]oxazin-2-yl)-6-((4-(4-methylpiperazin-1-yl)phenyl)amino)-1,2-dihydro-3H-pyrazolo[3,4-d]pyrimidin-3-one

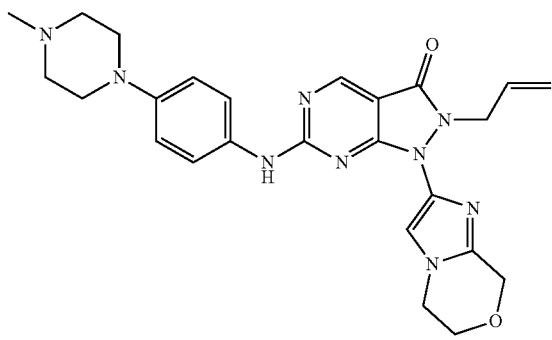 [SMILES: C=CCn1c(=O)c2cnc(Nc3ccc(N4CCN(C)CC4)cc3)nc2n1-c1cn2c(n1)COCC2]

Example 32 (5 mg) was prepared by following a procedure described for Examples 2A and 2B using Intermediate 39. $^1$H NMR (400 MHz, DMSO-$d_6$) δ 9.94 (s, 1H), 8.77 (s, 1H), 7.53-7.48 (m, 3H), 6.86 (d, J=8.8 Hz, 1H), 5.76 (s, 1H), 5.73-5.71 (m, 1H), 5.11 (d, J=10.8 Hz, 1H), 5.03 (d, J=17.6 Hz, 1H), 4.71 (s, 2H), 4.24 (s, 2H), 4.10-4.05 (m, 4H), 3.06 (t, J=4.4 Hz, 4H), 2.50-2.42 (m, 4H), 2.21 (s, 3H); MS (ESI) m/z 488.2 [M+H]$^+$.

Intermediate 40

2-iodo-6-methyl-5,6-dihydro-7H-pyrrolo[3,4-b]pyridin-7-one

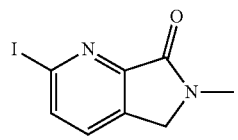

Step 1: To a stirred solution of methyl 6-chloro-3-methylpicolinate (10 g, 54 mmol) in CH$_3$CN (50 mL) was added NaI (40 g, 270 mmol) followed by TMS-Cl (36 mL, 270 mmol)) at rt. The reaction was refluxed for 8 h. After completion by TLC, the solvent was evaporated, the residue was diluted with water (100 mL), and extracted with EtOAc (3×100 mL). The combined organic layers were dried over (Na$_2$SO$_4$), filtered and concentrated under reduced pressure. The residue was purified by flash chromatography (SiO$_2$, 50% EtOAc/pet ether) to afford 6-iodo-3-methylpicolinic acid (8 g, 57%) as an off-white solid. $^1$H NMR (300 MHz, DMSO-$d_6$) δ 13.50 (br s, 1H), 7.72 (d, J=3 Hz, 2H), 2.41 (s, 3H).

Step 2: To a stirred solution of 6-iodo-3-methylpicolinic acid (8 g, 30 mmol) in MeOH (80 mL) was added H$_2$SO$_4$ (4.8 ml, 91 mmol) drop-wise at 0° C. The ice bath was removed and the mixture was stirred at reflux for 12 h. After completion by TLC, the solvent was evaporated, the residue was diluted with water (100 mL). The pH was adjusted to 9 using saturated NaHCO$_3$ and the reaction was extracted with EtOAc (3×50 mL). The combined extracts were washed with water (100 mL), brine (100 mL), dried (Na$_2$SO$_4$), filtered and concentrated under reduced pressure. The residue was purified by flash chromatography (SiO$_2$, 20% EtOAc/pet ether) to afford methyl 6-iodo-3-methylpicolinate (7 g, 83%) as a pale yellow solid. MS (ESI) 278.3 [M+H]$^+$.

Step 3: To a stirred solution of methyl 6-iodo-3-methylpicolinate (8.5 g, 30 mmol) in CCl$_4$ (100 mL), was added NBS (7.1 g, 39 mmol), AIBN (492 mg, 3 mmol). The reaction was heated at 65° C. for 16 h. After completion by TLC, the solvent was evaporated and the residue was suspended in water (100 mL). The mixture was extracted with DCM (3×50 mL). The combined extracts were dried (Na$_2$SO$_4$), filtered and concentrated under reduced pressure. The residue was purified by flash chromatography (SiO$_2$, 15% EtOAc/pet ether) to afford methyl 3-(bromomethyl)-6-iodopicolinate (4.31 g, 40%) as a brown liquid. MS (ESI) 356.1 [M+H]$^+$.

Step 4: To a stirred, rt solution methyl 3-(bromomethyl)-6-iodopicolinate (3 g, 8.4 mmol) in THF (10 mL) was added 2.0 M methylamine in THF (42 mL, 84 mmol). The reaction was stirred at rt for 24 h. After completion by TLC, the solvent was evaporated and the residue was diluted with water (30 mL). The resulting precipitate was filtered and dried to afford Intermediate 40 (1.3 g, 56%) as an off-white solid. MS (ESI) 275.2 [M+H]$^+$.

Intermediate 41

2-allyl-1-(6-methyl-7-oxo-6,7-dihydro-5H-pyrrolo[3,4-b]pyridin-2-yl)-6-(methylthio)-1,2-dihydro-3H-pyrazolo[3,4-d]pyrimidin-3-one

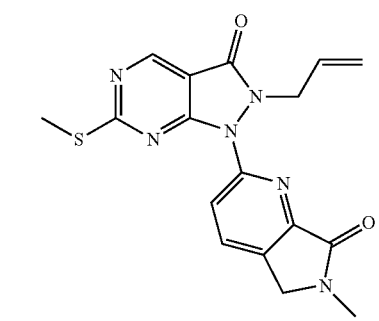 [SMILES: C=CCn1c(=O)c2cnc(SC)nc2n1-c1ccc2c(n1)C(=O)N(C)C2]

Intermediate 41 was prepared following a procedure described for Intermediate 3 using Intermediate 1 and Intermediate 40. The mixture was degassed for 20 min and then heated in the microwave at 100° C. for 2 h. MS (ESI) 369.4 [M+H]$^+$.

Example 33

2-allyl-1-(6-methyl-7-oxo-6,7-dihydro-5H-pyrrolo[3,4-b]pyridin-2-yl)-6-((4-(4-methylpiperazin-1-yl)phenyl)amino)-1,2-dihydro-3H-pyrazolo[3,4-d]pyrimidin-3-one

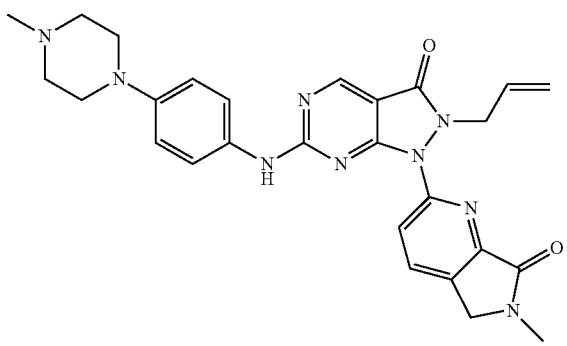 [SMILES: C=CCn1c(=O)c2cnc(Nc3ccc(N4CCN(C)CC4)cc3)nc2n1-c1ccc2c(n1)C(=O)N(C)C2]

Example 33 (150 mg) was prepared by following a procedure described for Examples 2A and 2B using Intermediate 41. $^1$H NMR (400 MHz, DMSO-d$_6$) δ 10.11 (s, 1H), 8.85 (s, 1H), 8.33 (d, J=7.2 Hz, 1H), 8.06 (d, J=8 Hz, 1H), 7.58 (br s, 2H), 6.94 (d, J=8.8 Hz, 2H), 5.73-5.66 (m, 1H), 5.00 (d, J=10 Hz, 1H), 4.86 (d, J=17.2 Hz, 1H), 4.63-4.61 (m, 2H), 4.55 (s, 2H), 3.13 (s, 3H), 3.11-3.09 (m, 4H), 2.47-2.44 (m, 4H), 2.22 (s, 3H); MS (ESI) 512.3 [M+H]$^+$.

Intermediate 42

6-(tert-butyl)-2-iodo-5,6-dihydro-7H-pyrrolo[3,4-b]pyridin-7-one

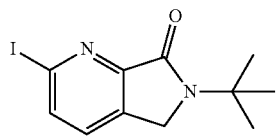

To a stirred, rt solution methyl 3-(bromomethyl)-6-iodopicolinate (500 mg, 1.4 mmol) in THF (5 mL), was added tert-butylamine (256 mg, 3.50 mmol). The reaction was stirred at rt for 16 h. After completion by TLC, the solvent was evaporated and the residue was diluted with water (30 mL). The precipitated solid was filtered and dried to afford Intermediate 42 (220 mg, 49%) as an off-white solid. $^1$H NMR (400 MHz, DMSO-d$_6$) δ 7.96 (d, J=8.0 Hz, 1H), 7.77 (d, J=8.0 Hz, 1H), 4.54 (s, 2H), 1.49 (s, 9H).

Intermediate 43

2-allyl-1-(6-(tert-butyl)-7-oxo-6,7-dihydro-5H-pyrrolo[3,4-b]pyridin-2-yl)-6-(methylthio)-1,2-dihydro-3H-pyrazolo[3,4-d]pyrimidin-3-one

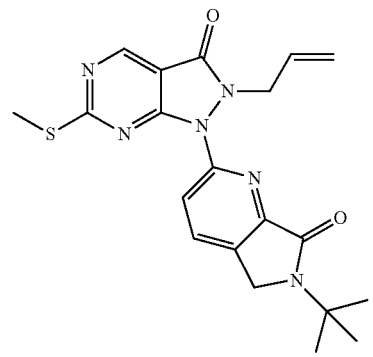 [SMILES: C=CCn1c(=O)c2cnc(SC)nc2n1-c1ccc2c(n1)C(=O)N(C(C)(C)C)C2]

Intermediate 43 was prepared following a procedure described for Intermediate 3 using Intermediate 1 and Intermediate 42. The mixture was degassed for 20 min and then heated in the microwave at 100° C. for 2 h. MS (ESI) 411.14 [M+H]$^+$.

Example 34

2-allyl-6-((4-(4-methylpiperazin-1-yl)phenyl)amino)-1-(7-oxo-6,7-dihydro-5H-pyrrolo[3,4-b]pyridin-2-yl)-1,2-dihydro-3H-pyrazolo[3,4-d]pyrimidin-3-one

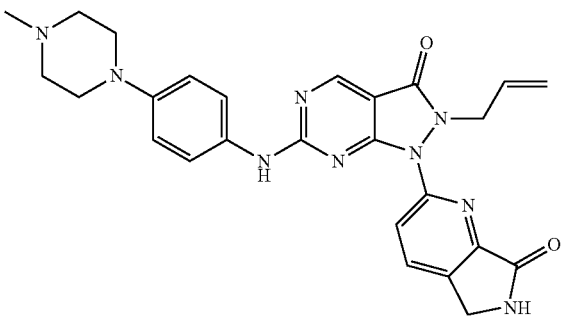 [SMILES: C=CCn1c(=O)c2cnc(Nc3ccc(N4CCN(C)CC4)cc3)nc2n1-c1ccc2c(n1)C(=O)NC2]

Step 1: 2-allyl-1-(6-(tert-butyl)-7-oxo-6,7-dihydro-5H-pyrrolo[3,4-b]pyridin-2-yl)-6-((4-(4-methylpiperazin-1-yl)phenyl)amino)-1,2-dihydro-3H-pyrazolo[3,4-d]pyrimidin-3-one (150 mg) was prepared by following a procedure described for Examples 2A and 2B using Intermediate 43. MS (ESI) 554.0 [M+H]$^+$.

Step 2: To a stirred solution of 2-allyl-1-(6-(tert-butyl)-7-oxo-6,7-dihydro-5H-pyrrolo[3,4-b]pyridin-2-yl)-6-((4-(4-methylpiperazin-1-yl)phenyl)amino)-1,2-dihydro-3H-pyrazolo[3,4-d]pyrimidin-3-one (150 mg, 7.05 mmol) was added trifluoromethanesulfonic acid (0.7 mL) at 0° C. The ice bath was removed and the reaction was stirred at rt for 2 h. After completion by TLC, the reaction was neutralized with NaHCO$_3$ and then extracted with EtOAc (3×20 mL). The combined organic layers were dried (Na$_2$SO$_4$), filtered and concentrated under reduced pressure. The residue was purified by reverse phase HPLC (H₂O/CH₃CN gradient) to afford Example 34 (10 mg) as an off-white solid. ¹H NMR (400 MHz, DMSO-d₆) δ 10.20 (br s, 1H), 9.09 (br s, 1H), 8.85 (s, 1H), 8.32 (d, J=7.2 Hz, 1H), 8.07 (d, J=8.4 Hz, 1H), 7.58 (br s, 2H), 6.94 (d, J=8.4 Hz, 2H), 5.74-5.67 (m, 1H), 5.01 (d, J=10.0 Hz, 1H), 4.80 (d, J=18.0 Hz, 1H), 4.63 (br s, 2H), 4.46 (br s, 2H), 3.10 (s, 4H), 2.47-2.45 (m, 4H), 2.22 (s, 3H); MS (ESI) 498.2 [M+H]⁺.

Intermediate 44

5-bromo-3-methyl-2,3-dihydrofuro[2,3-b]pyridin-3-ol

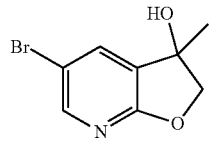

Step 1: To a stirred solution of ethyl 2-hydroxyacetate (27.67 g, 266.14 mmol) in DME (200 mL) was added 60% NaH (8.744 g, 380.2 mmol) at 0° C. portion-wise. The ice bath was removed and the reaction was stirred for 30 min. Ethyl 5-bromo-2-chloronicotinate (20 g, 76.04 mmol) was added and the reaction was refluxed for 16 h. After completion by TLC, the reaction was concentrated under reduced pressure and the residue was dissolved in water (150 mL). The mixture was adjusted to pH 4 using acetic acid. The mixture was extracted with EtOAc (3×80 mL). The combined organic layers were dried (Na₂SO₄), filtered and concentrated under reduced pressure. The residue was purified by flash chromatography (SiO₂, 30% EtOAc/pet ether) to afford ethyl 5-bromo-3-oxo-2,3-dihydrofuro[2,3-b]pyridine-2-carboxylate (8.5 g, 30%) as an off-white solid. MS (ESI) 285.9 [M+H]⁺.

Step 2: A mixture of ethyl 5-bromo-3-oxo-2,3-dihydrofuro[2,3-b]pyridine-2-carboxylate (9 g, 31.57 mmol) and 50% aqueous H₂SO₄ (90 mL) was heated to 60° C. and stirred for 16 h. After completion by TLC, the reaction mixture was diluted with ice-cold water (200 mL) and extracted with EtOAc (2×200 mL). The combined organic layers were washed with water (150 mL), brine (200 mL), dried (Na₂SO₄), filtered and concentrated under reduced pressure to afford 5-bromofuro[2,3-b]pyridin-3(2H)-one (4.5 g, 66%) as a pale brown solid. MS (ESI) 213.8 [M+H]⁺.

Step 3: To a stirred solution of 5-bromofuro[2,3-b]pyridin-3(2H)-one (4 g, 18.77 mmol) in diethyl ether (40 mL) was added 3.0 M CH₃MgI in DEE (31 mL, 93.85 mmol) at 0° C. The ice bath was removed and the reaction was stirred at rt for 1 h. The reaction mixture was quenched sat. NH₄Cl (50 mL) and extracted with EtOAc (3×50 mL). The organic layer was dried (Na₂SO₄), filtered and concentrated under reduced pressure. The residue was purified by flash chromatography (SiO₂, 20% EtOAc/pet ether) to afford Intermediate 44 (2.0 g, 46%) as a brown solid. MS (ESI) 229.9 [M+H]⁺.

Intermediate 45

2-allyl-1-(3-hydroxy-3-methyl-2,3-dihydrofuro[2,3-b]pyridin-5-yl)-6-(methylthio)-1,2-dihydro-3H-pyrazolo[3,4-d]pyrimidin-3-one

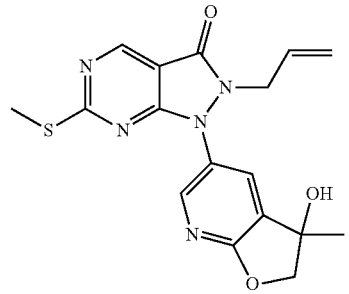

Intermediate 45 was prepared following a procedure described for Intermediate 3 using Intermediate 1 and Intermediate 44. The mixture was degassed for 20 min and then heated in the microwave at 100° C. for 6 h. MS (ESI) 372.4 [M+H]⁺.

Example 35A 2-allyl-1-(3-hydroxy-3-methyl-2,3-dihydrofuro[2,3-b]pyridin-5-yl)-6-((4-(4-methylpiperazin-1-yl)phenyl)amino)-1,2-dihydro-3H-pyrazolo[3,4-d]pyrimidin-3-one

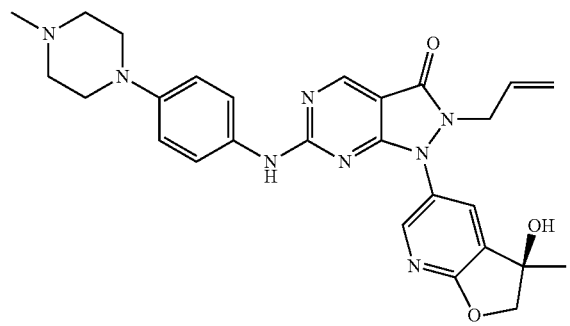

Example 35B (S)-2-allyl-1-(3-hydroxy-3-methyl-2,3-dihydrofuro[2,3-b]pyridin-5-yl)-6-((4-(4-methylpiperazin-1-yl)phenyl)amino)-1,2-dihydro-3H-pyrazolo[3,4-d]pyrimidin-3-one

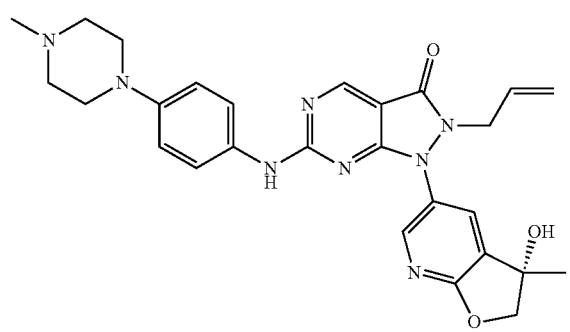

Examples 35A and 35B were prepared by following a procedure described for Examples 2A and Examples 2B using Intermediate 45 to give racemic 2-allyl-1-(3-hydroxy-3-methyl-2,3-dihydrofuro[2,3-b]pyridin-5-yl)-6-((4-(4-methylpiperazin-1-yl)phenyl)amino)-1,2-dihydro-3H-pyrazolo[3,4-d]pyrimidin-3-one (150 mg). The enantiomers were separated by chiral SFC chromatography (Chiral Pak AD-H, (35.0% (0.5% isopropylamine in IPA)) to give Peak 1 (Example 35A, 48 mg) and Peak 2 (Example 35B, 46 mg). Example 35A: yellow solid; $^1$H NMR (400 MHz, DMSO-d$_6$) δ10.30 (br s, 1H), 8.81 (s, 1H), 8.18 (d, J=2.4 Hz, 1H), 7.83 (br s, 1H), 7.49 (d, J=8.4 Hz, 2H), 6.84 (d, J=8.8 Hz, 2H), 5.83 (s, 1H), 5.73-5.64 (m, 1H), 5.11 (d, J=10.4 Hz, 1H), 4.97 (d, J=17.2 Hz, 1H), 4.44 (s, 2H), 4.23 (br s, 2H), 3.09-3.01 (m, 4H), 2.46-2.41 (m, 4H), 2.21 (s, 3H), 1.57 (s, 3H); MS (ESI) 515.2 [M+H]$^+$. Example 35B: yellow solid; $^1$H NMR (400 MHz, DMSO-d$_6$) δ 10.04 (br s, 1H), 8.81 (s, 1H), 8.17 (d, J=2.4 Hz, 1H), 7.83 (br s, 1H), 7.49 (d, J=8.4 Hz, 2H), 6.83 (d, J=8.4 Hz, 2H), 5.83 (s, 1H), 5.74-5.65 (m, 1H), 5.11 (d, J=10.4 Hz, 1H), 4.97 (d, J=17.2 Hz, 1H), 4.44 (s, 2H), 4.23 (br s, 2H), 3.09-3.01 (m, 4H), 2.47-2.39 (m, 4H), 2.21 (s, 3H), 1.57 (s, 3H); MS (ESI) 515.2 [M+H]$^+$. The absolute stereochemistry was arbitrarily assigned for Example 35A and Example 35B.

Intermediate 46

2-bromo-7-methyl-6,7-dihydro-5H-pyrrolo[1,2-a]imidazol-7-ol

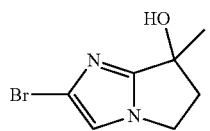

Step 1: 5,6-dihydro-7H-pyrrolo[1,2-a]imidazol-7-one was prepared according to U.S. Publication No. 2012/0214762.

Step 2: To a 0° C. solution of 5,6-dihydro-7H-pyrrolo[1,2-a]imidazol-7-one (15 g, 123.0 mmol) in THF (150 mL) was added 3M MeMgBr (49 mL, 147.0 mmol) drop-wise. The ice bath was removed and the reaction was stirred at rt for 5 h. After completion by TLC, the reaction was quenched with sat. NH$_4$Cl solution at 0° C. The mixture was extracted 10% MeOH/DCM (2×200 mL). The combined organic layers were dried (Na$_2$SO$_4$) and evaporated under reduced pressure. The residue was purified by flash chromatography (SiO$_2$, 3% MeOH/DCM) to afford 7-methyl-6,7-dihydro-5H-pyrrolo[1,2-a]imidazol-7-ol (5.1 g, 30%) as a yellow solid. MS (ESI) 139.1 [M+H]$^+$.

Step 3: To a 0° C. solution of 7-methyl-6,7-dihydro-5H-pyrrolo[1,2-a]imidazol-7-ol (14 g, 0.101 mol) in DCM (140 mL) was added NaHCO$_3$ (0.111 mmol), and NBS (37.7 g, 0.212 mol) portion-wise over 10 min. The ice bath was removed and the reaction was stirred at rt for 3 h. After completion by TLC, the reaction was concentrated under reduced pressure. The residue was purified by flash chromatography (SiO$_2$, 3% MeOH/DCM) to afford 2,3-dibromo-7-methyl-6,7-dihydro-5H-pyrrolo[1,2-a]imidazol-7-ol (7 g, 23%) as yellow solid. MS (ESI) 296.8 [M+H]$^+$.

Step 4: To a 0° C. of 2,3-dibromo-7-methyl-6,7-dihydro-5H-pyrrolo[1,2-a]imidazol-7-ol (7 g, 23.7 mmol) in THF (70 mL), was added 1.3 M i-PrMgCl in THF (29 mL, 37.9 mmol) drop-wise. The ice bath was removed and the reaction was stirred at rt for 2 h. After completion by TLC, the reaction was quenched with sat. NH$_4$Cl (100 mL) and extracted with EtOAc (2×300 mL). The combined organic layers were dried (Na$_2$SO$_4$) and the solvent was evaporated under reduced pressure. The residue was purified by flash chromatography (SiO$_2$, 3% MeOH/DCM) to afford Intermediate 46 (3.5 g, 68%) as an off-white solid. MS (ESI) 217.3 [M+H]$^+$.

Intermediate 47

2-allyl-1-(7-hydroxy-7-methyl-6,7-dihydro-5H-pyrrolo[1,2-a]imidazol-2-yl)-6-(methylthio)-1,2-dihydro-3H-pyrazolo[3,4-d]pyrimidin-3-one

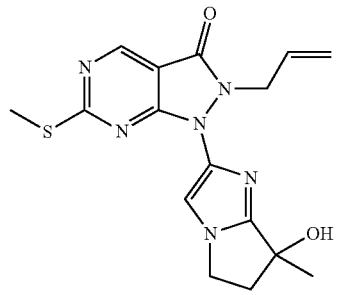 [SMILES: C=CCn1c(=O)c2cnc(SC)nc2n1-c1cn2c(n1)C(C)(O)CC2]

Intermediate 47 was prepared following a procedure described for Intermediate 3 using Intermediate 1 and Intermediate 46. MS (ESI) 359.1 [M+H]$^+$.

Example 36A (S)-2-allyl-1-(7-hydroxy-7-methyl-6,7-dihydro-5H-pyrrolo[1,2-a]imidazol-2-yl)-6-((4-(4-methylpiperazin-1-yl)phenyl)amino)-1,2-dihydro-3H-pyrazolo[3,4-d]pyrimidin-3-one

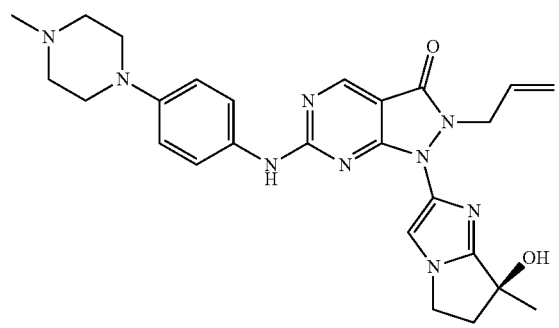 [SMILES: C=CCn1c(=O)c2cnc(Nc3ccc(N4CCN(C)CC4)cc3)nc2n1-c1cn2c(n1)[C@@](C)(O)CC2]

Example 36B (R)-2-allyl-1-(7-hydroxy-7-methyl-6,7-dihydro-5H-pyrrolo[1,2-a]imidazol-2-yl)-6-((4-(4-methylpiperazin-1-yl)phenyl)amino)-1,2-dihydro-3H-pyrazolo[3,4-d]pyrimidin-3-one

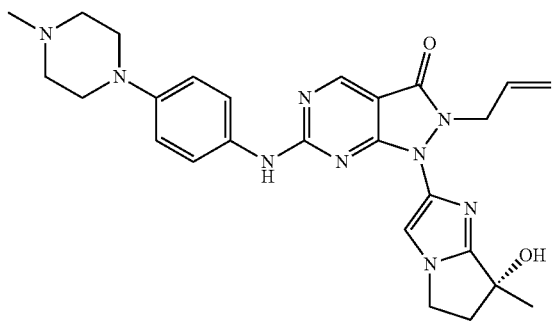 [SMILES: C=CCn1c(=O)c2cnc(Nc3ccc(N4CCN(C)CC4)cc3)nc2n1-c1cn2c(n1)[C@](C)(O)CC2]

Examples 36A and 36B were prepared by following a procedure described for Examples 2A and Examples 2B using Intermediate 47 to give racemic 2-allyl-1-(7-hydroxy-7-methyl-6,7-dihydro-5H-pyrrolo[1,2-a]imidazol-2-yl)-6-((4-(4-methylpiperazin-1-yl)phenyl)amino)-1,2-dihydro-3H-pyrazolo[3,4-d]pyrimidin-3-one (250 mg). The enantiomers were separated by chiral SFC chromatography (Chiralpak OJ-H, 10.0% (0.5% DEA in Ethanol)) to give Peak 1 (Example 36A, 53 mg) and Peak 2 (Example 36B, 66 mg). Example 36A: yellow solid; $^1$H NMR (400 MHz, DMSO-$d_6$) δ 9.92 (br s, 1H), 8.77 (s, 2H), 7.50 (d, J=8.4 Hz, 2H), 7.45 (s, 1H), 6.85 (d, J=7.2 Hz, 2H), 5.75-5.68 (m, 1H), 5.55 (s, 1H), 5.10 (d, J=10.0 Hz, 1H), 5.02 (d, J=17.2 Hz, 1H), 4.24 (s, 2H), 4.12-4.02 (m, 2H) 3.05 (s, 4H), 2.44 (s, 1H) 2.43 (s, 4H), 2.21 (s, 3H), 1.49 (s, 3H); MS (ESI) 502.2 [M+H]$^+$. Example 36B: yellow solid; $^1$H NMR (400 MHz, DMSO-$d_6$) δ 9.92 (br s, 1H), 8.77 (s, 2H), 7.50 (d, J=8.4 Hz, 2H), 7.45 (s, 1H), 6.85 (d, J=7.2 Hz, 2H), 5.75-5.68 (m, 1H), 5.55 (s, 1H), 5.10 (d, J=10.0 Hz, 1H), 5.02 (d, J=17.2 Hz, 1H), 4.24 (s, 2H), 4.12-4.02 (m, 2H), 3.06 (s, 4H), 2.46 (s, 1H), 2.45 (s, 4H), 2.21 (s, 3H), 1.50 (s, 3H); MS (ESI) 502.3 [M+H]$^+$. The absolute stereochemistry was arbitrarily assigned for Example 36A and Example 36B.

Intermediate 48

3-bromo-5-methyl-6,7-dihydro-5H-cyclopenta[c]pyridin-5-ol

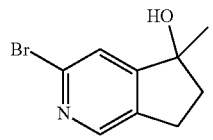

Step 1: 3-amino-6,7-dihydro-5H-cyclopenta[c]pyridin-5-one was prepared according to Sakairi, M., Arzneimittel Forschung, 62(11), 537-544; 2012.

Step 2: To a 0° C. solution of 3-amino-6,7-dihydro-5H-cyclopenta[c]pyridin-5-one (200 mg, 1.34 mmol) in dibromoethane (2 mL) was added CuBr$_2$ (0.149 g, 0.668 mmol) portion-wise. Isoamyl nitrite (0.179 g, 1.49 mmol) was then added drop-wise. The reaction mixture was warmed to rt and stirred for 16 h. The reaction was quenched with water (50 mL), basified with sat. NaHCO$_3$ and extracted with DCM (2×50 mL). The combined organic layers were dried (Na$_2$SO$_4$) and concentrated under reduced pressure. The residue was purified by flash chromatography (SiO$_2$, 30% EtOAc/pet ether) to afford 3-bromo-6,7-dihydro-5H-cyclopenta[c]pyridin-5-one (60 mg, 21%) as a brown solid. MS (ESI) 212.3 [M+H]$^+$.

Step 3: To a 0° C. solution of 3-bromo-6,7-dihydro-5H-cyclopenta[c]pyridin-5-one (50 mg, 0.23 mmol.) in Et$_2$O (2 mL) was added 3.0 M MeMgBr in Et$_2$O (0.4 mL, 1.15 mmol.). The ice bath was removed and the reaction was stirred at rt for 16 h. After completion by TLC, the reaction was poured in to ice water (15 mL) and extracted with EtOAc (2×20 mL). The organic layer was dried (Na$_2$SO$_4$) and concentrated under reduced pressure. The residue was purified by flash chromatography (SiO$_2$, 30% EtOAc/pet ether) to afford Intermediate 48 (15 mg, 28%) as a brown solid. MS (ESI) 228.4 [M+H]$^+$.

Intermediate 49

2-allyl-1-(5-hydroxy-5-methyl-6,7-dihydro-5H-cyclopenta[c]pyridin-3-yl)-6-(methylthio)-1,2-dihydro-3H-pyrazolo[3,4-d]pyrimidin-3-one

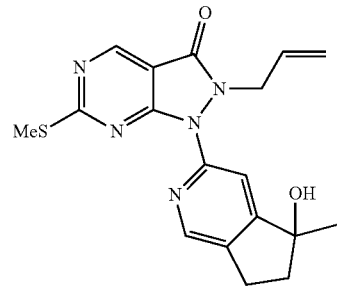 [SMILES: C=CCn1c(=O)c2cnc(SC)nc2n1-c1cc2c(cn1)CCC2(C)O]

Intermediate 49 was prepared following a procedure described for Intermediate 3 using Intermediate 1 and Intermediate 48. MS (ESI) 370.4 [M+H]$^+$.

Example 37A (S)-2-allyl-1-(5-hydroxy-5-methyl-6,7-dihydro-5H-cyclopenta[c]pyridin-3-yl)-6-((4-(4-methylpiperazin-1-yl)phenyl)amino)-1,2-dihydro-3H-pyrazolo[3,4-d]pyrimidin-3-one

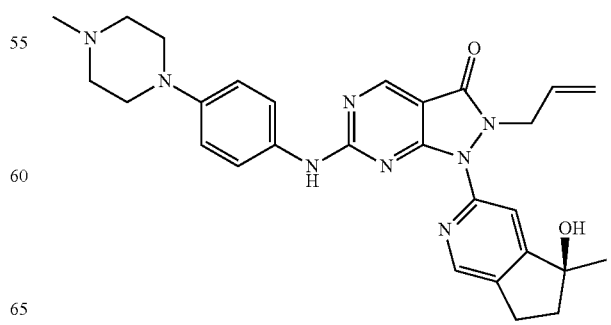

Example 37B (R)-2-allyl-1-(5-hydroxy-5-methyl-6,7-dihydro-5H-cyclopenta[c]pyridin-3-yl)-6-((4-(4-methylpiperazin-1-yl)phenyl)amino)-1,2-dihydro-3H-pyrazolo[3,4-d]pyrimidin-3-one

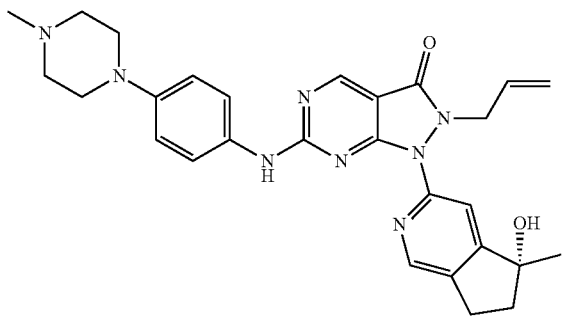

Examples 37A and 37B were prepared by following a procedure described for Examples 9A and Examples 9B using Intermediate 49 to give racemic 2-allyl-1-(5-hydroxy-5-methyl-6,7-dihydro-5H-cyclopenta[c]pyridin-3-yl)-6-((4-(4-methylpiperazin-1-yl)phenyl)amino)-1,2-dihydro-3H-pyrazolo[3,4-d]pyrimidin-3-one (25 mg). The enantiomers were separated by chiral SFC chromatography (Chiralpak AD-H 20.0% (0.5% DEA in Methanol)) to give Peak 1 (Example 37A, 10 mg) and Peak 2 (Example 37B, 10 mg). Example 37A: yellow solid; $^1$H NMR (400 MHz, DMSO-$d_6$) δ 10.14 (br s, 1H), 8.81 (s, 1H), 8.37 (s, 1H), 7.75 (br s, 1H), 7.58 (br s, 2H), 6.93 (d, J=8.8 Hz, 2H), 5.70-5.61 (m, 1H), 5.49 (s, 1H), 5.02 (d, J=10 Hz, 1H), 4.86 (d, J=17.2 Hz, 1H), 4.65-4.45 (m, 2H), 3.07-3.03 (m, 4H), 3.02-2.81 (m, 2H), 2.46-2.43 (m, 4H), 2.22 (s, 3H), 2.16 (t, J=7.6 Hz, 2H), 1.45 (s, 3H); MS (ESI) 513.4 [M+H]$^+$. Example 37B: yellow solid; $^1$H NMR (400 MHz, DMSO-$d_6$) δ 10.14 (br s, 1H), 8.81 (s, 1H), 8.37 (s, 1H), 7.75 (br s, 1H), 7.58 (br s, 2H), 6.93 (d, J=12.4 Hz, 2H), 5.70-5.61 (m, 1H), 5.49 (s, 1H), 5.02 (d, J=9.6 Hz, 1H), 4.86 (d, J=17.2 Hz, 1H), 4.65-4.45 (m, 2H), 3.08-3.06 (m, 4H), 3.04-2.81 (m, 2H), 2.46-2.43 (m, 4H), 2.22 (s, 3H), 2.16 (t, J=7.6 Hz, 2H), 1.45 (s, 3H); MS (ESI) 513.7 [M+H]$^+$. The absolute stereochemistry was arbitrarily assigned for Example 37A and Example 37B.

Intermediate 50

2-bromo-7-(1,1-difluoroethyl)-6,7-dihydro-5H-cyclopenta[b]pyridin-7-ol

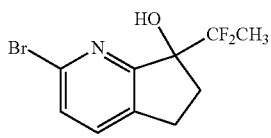

Step 1: To a stirred solution of 2-bromo-5,6-dihydro-7H-cyclopenta[b]pyridin-7-one (5 g, 23.58 mmol) in THF (50 mL) was added iPrMgCl 0.5 M in THF (70.7 mL, 35.37 mmol) drop-wise at 0° C. The reaction was stirred at rt for 16 h. Upon completion, the reaction was cooled to 0° C. and quenched with sat. NH$_4$Cl (100 mL) solution and extracted with EtOAc (2×200 mL). The combined extracts were washed with brine (200 mL), dried (Na$_2$SO$_4$) and evaporated to dryness. The residue was purified by flash chromatography (SiO$_2$, 15% EtOAc/Hexanes) to afford 2-bromo-7-(prop-1-en-2-yl)-6,7-dihydro-5H-cyclopenta[b]pyridin-7-ol (1.7 g, 28%) as yellow liquid. MS (ESI) 254.1 [M+H]$^+$.

Step 2: To a stirred solution of 2-bromo-7-(prop-1-en-2-yl)-6,7-dihydro-5H-cyclopenta[b]pyridin-7-ol (2.5 g, 9.82 mmol) in THF (25 mL) was added 60% NaH (590 mg, 14.76 mmol) at 0° C. The mixture was stirred for 30 min. and acetic anhydride (1.39 mL, 14.76 mmol) drop-wise at 0° C. The reaction was stirred at rt for 16 h. After completion by TLC, the reaction was quenched with ice water and extracted EtOAc (2×100 mL). The combined extracts were washed with water (100 mL), brine (100 mL), dried (Na$_2$SO$_4$) and evaporated to dryness. The residue was purified by flash chromatography (neutral alumina, 10% EtOAc/Pet. ether) to afford 2-bromo-7-(prop-1-en-2-yl)-6,7-dihydro-5H-cyclopenta[b]pyridin-7-yl acetate (1.7 g, 58%) as yellow liquid. MS (ESI) 296.0 [M+H]$^+$.

Step 3: Ozone gas purged through a stirred solution of 2-bromo-7-(prop-1-en-2-yl)-6,7-dihydro-5H-cyclopenta[b]pyridin-7-yl acetate (3.4 g, 11.5 mmol) in MeOH (40 mL) at −78° C. for 30 min. Upon completion by TLC, the reaction was quenched with 1 mL of dimethylsulfide at −78° C. and stirred at rt for 1 h. The reaction mixture was concentrated and diluted with water (100 mL) and EtOAc (200 mL). The organic layer was separated, dried (Na$_2$SO$_4$) and evaporated under reduced pressure to afford 7-acetyl-2-bromo-6,7-dihydro-5H-cyclopenta[b]pyridin-7-yl acetate (2.1 g, 61%) as white solid. MS (ESI) m/z 298.1 [M+H].

Step 4: In a sealed tube, to 7-acetyl-2-bromo-6,7-dihydro-5H-cyclopenta[b]pyridin-7-yl acetate (800 mg, 2.69 mmol) was added DAST (8.9 mL, 67.34 mmol) and the reaction was stirred at rt for 2 days. Upon completion the reaction mixture was added drop-wise to crushed ice and extracted with EtOAc (2×100 mL). The organic layer was separated, washed with water (2×50 mL), dried (Na$_2$SO$_4$) and evaporated under reduced pressure. The residue was purified by flash chromatography (SiO$_2$, 10% EtOAc/Hexanes) to afford 2-bromo-7-(1,1-difluoroethyl)-6,7-dihydro-5H-cyclopenta[b]pyridin-7-yl acetate (85 mg, 10%) as brown oil. MS (ESI) 320.1 [M+H]$^+$.

Step 5: To a stirred solution of afford 2-bromo-7-(1,1-difluoroethyl)-6,7-dihydro-5H-cyclopenta[b]pyridin-7-yl acetate (300 mg, 0.937 mmol) in MeOH (5 mL) was added K$_2$CO$_3$ (259 mg, 1.88 mmol) at 0° C. The ice bath was removed and the reaction was stirred at rt for 3 h. Upon completion by TLC, the reaction mixture was concentrated under reduced pressure. Water (20 mL) was added and the mixture was extracted with EtOAc (2×50 mL). The combined organic layers were washed with water (2×50 mL), dried (Na$_2$SO$_4$) and evaporated under reduced pressure to afford (2-bromo-7-(1,1-difluoroethyl)-6,7-dihydro-5H-cyclopenta[b]pyridin-7-ol (230 mg, 0.83 mmol, 88%) as brown liquid. MS (ESI) 278.0 [M+H]$^+$.

Intermediate 51

2-allyl-1-(7-(1,1-difluoroethyl)-7-hydroxy-6,7-dihydro-5H-cyclopenta[b]pyridin-2-yl)-6-(methylthio)-1,2-dihydro-3H-pyrazolo[3,4-d]pyrimidin-3-one

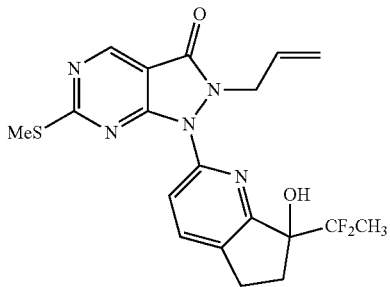

Intermediate 51 was prepared following a procedure described for Intermediate 3 using Intermediate 1 and Intermediate 50. MS (ESI) 420.2 [M+H]$^+$.

Example 38A (S)-2-allyl-1-(7-(1,1-difluoroethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

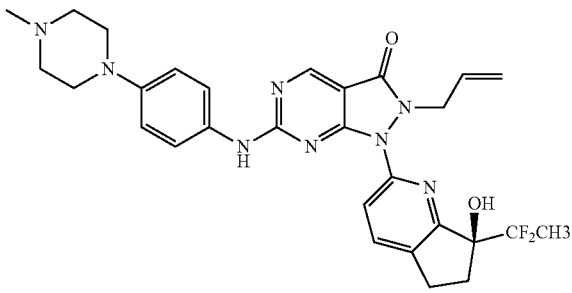

Example 38B (R)-2-allyl-1-(7-(1,1-difluoroethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one

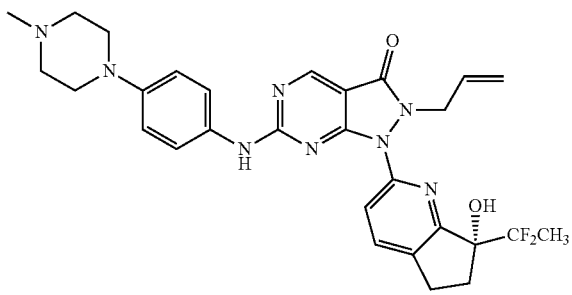

Examples 38A and 38B were prepared by following a procedure described for Examples 9A and 9B using Intermediate 51 to give racemic 2-allyl-1-(7-(1,1-difluoroethyl)-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (105 mg). The enantiomers were separated by chiral SFC chromatography (Chiral Pak AD-H, (30.0% (0.5% DEA in MeOH)) to give Peak 1 (Example 38A, 10 mg) and Peak 2 (Example 38B, 20 mg). Example 38A: $^1$H NMR (400 MHz, DMSO-d$_6$) δ 10.03 (br s, 1H), 8.82 (s, 1H), 8.01 (br s, 1H), 7.81 (d, J=8.0 Hz, 1H), 7.57 (br s, 2H), 6.92 (d, J=8.8 Hz, 2H), 6.12 (s, 1H), 5.6-5.62 (m, 1H), 4.99 (d, J=9.6 Hz, 1H), 4.86-4.77 (m, 2H), 4.5 (m, 1H), 3.09 (s, 5H), 3.01-2.99 (m, 1H), 2.98-2.89 (m, 1H), 2.50-2.46 (m, 4H), 2.22 (s, 3H), 2.20-2.10 (m, 1H), 1.92 (t, J=19.6 Hz, 3H); MS (ESI) 563.5 [M+H]$^+$. Example 38B: $^1$H NMR (400 MHz, DMSO-d$_6$) δ 10.03 (br s, 1H), 8.82 (s, 1H), 8.01 (br s, 1H), 7.81 (d, J=8.0 Hz, 1H), 7.57 (br s, 2H), 6.92 (d, J=8.8 Hz, 2H), 6.12 (s, 1H), 5.66-5.64 (m, 1H), 5.00-4.97 (d, J=9.6 Hz, 1H), 4.85-4.81 (m, 2H), 4.57 (m, 1H), 3.09-2.86 (m, 5H), 2.89-2.88 (m, 1H), 2.57-2.50 (m, 5H), 2.22 (s, 3H), 2.15-2.05 (m, 1H) 1.92 (t, J=19.6 Hz, 3H); MS (ESI) 563.5 [M+H]$^+$. The absolute stereochemistry was arbitrarily assigned for Example 38A and Example 38B.

Intermediate 52

1-(1-methylpiperidin-4-yl)-1H-indol-5-amine

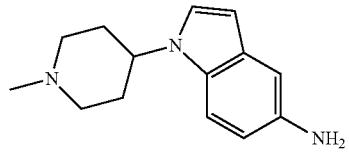 [SMILES: CN1CCC(n2ccc3cc(N)ccc32)CC1]

Intermediate 52 was prepared following a procedure described in EP 2141163. MS (ESI) 230.6 [M+H]$^+$.

Example 39A (S)-2-allyl-1-(7-ethyl-7-hydroxy-6,7-dihydro-5H-cyclopenta[b]pyridin-2-yl)-6-((1-(1-methylpiperidin-4-yl)-1H-indol-5-yl)amino)-1,2-dihydro-3H-pyrazolo[3,4-d]pyrimidin-3-one

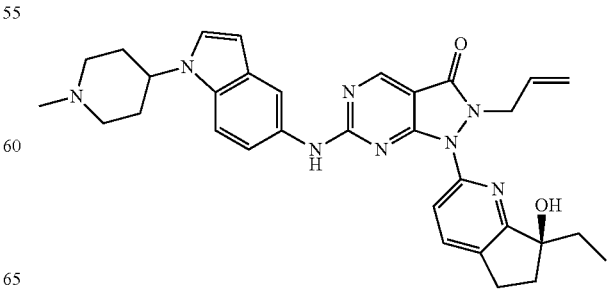

Example 39B (R)-2-allyl-1-(7-ethyl-7-hydroxy-6,7-dihydro-5H-cyclopenta[b]pyridin-2-yl)-6-((1-(1-methylpiperidin-4-yl)-1H-indol-5-yl)amino)-1,2-dihydro-3H-pyrazolo[3,4-d]pyrimidin-3-one

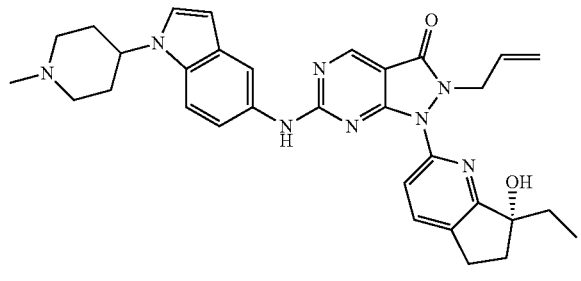 [SMILES: C=CCn1c(=O)c2cnc(Nc3ccc4c(ccn4C4CCN(C)CC4)c3)nc2n1-c1ccc2c(n1)[C@@](O)(CC)CC2]

Examples 39A and 39B were prepared by following a procedure described for Examples 9A and 9B using Intermediate 17 and Intermediate 52 to give racemic 2-allyl-1-(7-ethyl-7-hydroxy-6,7-dihydro-5H-cyclopenta[b]pyridin-2-yl)-6-((1-(1-methylpiperidin-4-yl)-1H-indol-5-yl)amino)-1,2-dihydro-3H-pyrazolo[3,4-d]pyrimidin-3-one (240 mg). The enantiomers were separated by chiral SFC chromatography (Chiral Pak AD-H, (30.0% (0.5% DEA in MeOH)) to give Peak 1 (Example 39A, 69 mg) and Peak 2 (Example 39B, 67 mg). Example 39A: yellow solid; $^1$H NMR (400 MHz, DMSO-$d_6$) δ 10.21 (br s, 1H), 8.84 (s, 1H), 8.09 (br s, 1H), 7.90 (d, J=7.6 Hz, 1H), 7.77 (d, J=8.0 Hz, 1H), 7.49-7.46 (m, 2H), 7.40-7.30 (m, 1H), 6.43 (d, J=3.2 Hz, 1H), 5.73-5.63 (m, 1H), 5.06 (s, 1H), 4.99 (d, J=10.4 Hz, 1H), 4.86 (d, J=16.4 Hz, 1H), 4.83-4.70 (m, 1H), 4.60-4.50 (m, 1H), 4.35-4.25 (m, 1H), 3.01-2.89 (m, 3H), 2.82-2.75 (m, 1H), 2.24 (s, 3H), 2.24-2.12 (m, 3H), 2.03-1.86 (m, 6H), 1.73-1.68 (m, 1H), 0.87 (t, J=7.4 Hz, 3H); MS (ESI) 565.5 [M+H]$^+$. Example 39B: yellow solid; $^1$H NMR (400 MHz, DMSO-$d_6$) δ 10.21 (br s, 1H), 8.84 (s, 1H), 8.09 (br s, 1H), 7.90 (d, J=7.6 Hz, 1H), 7.77 (d, J=8.4 Hz, 1H), 7.49-7.46 (m, 2H), 7.40-7.30 (m, 1H), 6.43 (d, J=3.2 Hz, 1H), 5.71-5.63 (m, 1H), 5.06 (s, 1H), 4.99 (d, J=10.4 Hz, 1H), 4.86 (d, J=17.6 Hz, 1H), 4.83-4.70 (m, 1H), 4.60-4.55 (m, 1H), 4.35-4.25 (m, 1H), 3.00-2.89 (m, 3H), 2.82-2.75 (m, 1H), 2.24 (s, 3H), 2.24-2.12 (m, 6H), 2.03-1.86 (m, 6H), 1.73-1.68 (m, 1H), 0.87 (t, J=7.4 Hz, 3H); MS (ESI) 565.4 [M+H]$^+$. The absolute stereochemistry was arbitrarily assigned for Example 39A and Example 39B.

Intermediate 53

3-methyl-4-(1-methyl-1,2,3,6-tetrahydropyridin-4-yl)aniline

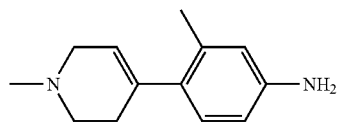

Intermediate 53 was prepared following an analogous procedure described in WO Publication No. 2014/134308. MS (ESI) 203.4 [M+H]$^+$.

Example 40A

S)-2-allyl-1-(7-ethyl-7-hydroxy-6,7-dihydro-5H-cyclopenta[b]pyridin-2-yl)-6-((3-methyl-4-(1-methyl-1,2,3,6-tetrahydropyridin-4-yl)phenyl)amino)-1,2-dihydro-3H-pyrazolo[3,4-d]pyrimidin-3-one

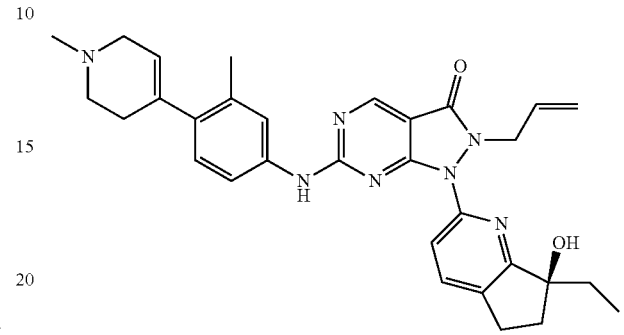

Example 40B (R)-2-allyl-1-(7-ethyl-7-hydroxy-6,7-dihydro-5H-cyclopenta[b]pyridin-2-yl)-6-((3-methyl-4-(1-methyl-1,2,3,6-tetrahydropyridin-4-yl)phenyl)amino)-1,2-dihydro-3H-pyrazolo[3,4-d]pyrimidin-3-one

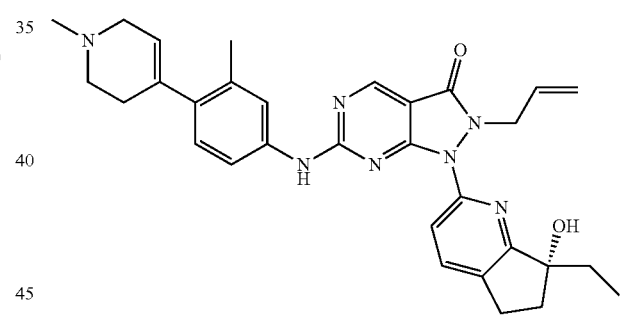

Examples 40A and 40B were prepared by following a procedure described for Examples 9A and 9B using Intermediate 17 and Intermediate 53 to give racemic 2-allyl-1-(7-ethyl-7-hydroxy-6,7-dihydro-5H-cyclopenta[b]pyridin-2-yl)-6-((3-methyl-4-(1-methyl-1,2,3,6-tetrahydropyridin-4-yl)phenyl)amino)-1,2-dihydro-3H-pyrazolo[3,4-d]pyrimidin-3-one (217 mg). The enantiomers were separated by chiral SFC chromatography (Chiral Pak AD-H, (30.0% (0.5% DEA in MeOH)) to give Peak 1 (Example 40A, 35 mg) and Peak 2 (Example 40B, 33 mg). Example 40A: yellow solid; $^1$H NMR (400 MHz, DMSO-$d_6$) δ 10.20 (br s, 1H), 8.88 (s, 1H), 7.90 (d, J=8.4 Hz, 1H), 7.72 (d, J=8.0 Hz, 1H), 7.65 (brs, 1H), 7.45 (dd, J=8.4 Hz, 2.0 Hz, 1H), 7.01 (d, J=8.4 Hz, 1H), 5.51-5.50 (m, 1H), 5.50 (s, 1H), 5.05 (s, 1H), 4.99 (d, J=10 Hz, 1H), 4.85 (d, J=17.2 Hz, 1H), 4.74-4.59 (m, 2H), 2.97-2.95 (m, 3H), 2.82-2.80 (m, 1H), 2.56-2.50 (m, 2H), 2.28-2.19 (m, 9H), 2.01-1.69 (m, 3H), 0.86 (t, J=7.6 Hz, 3H); MS (ESI) 538.2 [M+H]$^+$. Example 40B: yellow solid; $^1$H NMR (400 MHz, DMSO-$d_6$) δ 10.20 (br s, 1H), 8.88 (s, 1H), 7.90 (d, J=8.4 Hz, 1H), 7.72 (d, J=8.0 Hz, 1H), 7.65 (brs, 1H), 7.45 (dd, J=8.4 Hz, 2.0 Hz, 1H), 7.01 (d, J=8.4 Hz, 1H), 5.51-5.50 (m, 1H), 5.50 (s, 1H), 5.05 (s, 1H), 4.99 (d, J=10 Hz, 1H), 4.85 (d, J=17.2 Hz, 1H), 4.74-4.59 (m, 2H), 2.97-2.95 (m, 3H), 2.82-2.80 (m, 1H), 2.56-2.50 (m, 2H), 2.28-2.19 (m, 9H), 2.01-1.69 (m, 3H), 0.86 (t, J=7.6 Hz, 3H); MS (ESI) 538.2 [M+H]$^+$. The absolute stereochemistry was arbitrarily assigned for Example 40A and Example 40B.

Intermediate 54

N-(2-bromo-8-methyl-5,6,7,8-tetrahydroquinolin-8-yl)acetamide

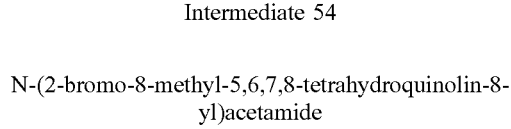

To a stirred solution of Intermediate 31 (250 mg, 1.037 mmol) in acetonitrile (6 mL) was added chlorosulfonic acid (0.2 mL) at rt and stirred for 2 h. The reaction was concentrated under reduced pressure, diluted in water (10 mL), extracted with EtOAc (2×10 mL), dried (Na$_2$SO$_4$), filtered and concentrated under reduced pressure. The above reaction was repeated 3×250 mg scale. The combined residues were purified by flash chromatography (SiO$_2$, 40% EtOAc/Pet ether) to afford to afford Intermediate 54 (480 mg, 41%) as an off-white solid. MS (ESI) 283.1 [M+1]$^+$.

Intermediate 55

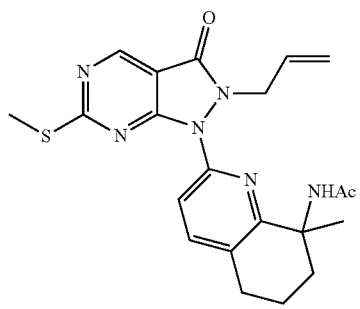

Intermediate 55 was prepared following a procedure described for Intermediate 3 using Intermediate 1 and Intermediate 54. MS (ESI) 425.1 [M+H]$^+$.

Example 41A (S)—N-(2-(2-allyl-6-((4-(4-methylpiperazin-1-yl)phenyl)amino)-3-oxo-2,3-dihydro-1H-pyrazolo[3,4-d]pyrimidin-1-yl)-8-methyl-5,6,7,8-tetrahydroquinolin-8-yl)acetamide

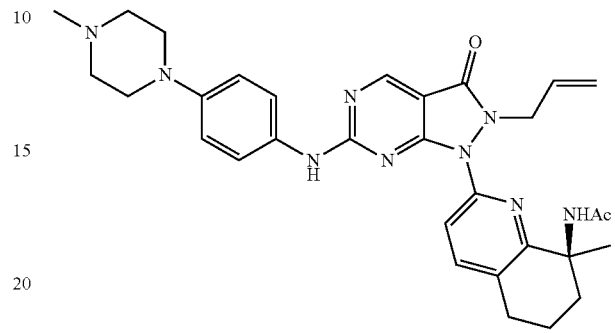

Example 41B (R)—N-(2-(2-allyl-6-((4-(4-methylpiperazin-1-yl)phenyl)amino)-3-oxo-2,3-dihydro-1H-pyrazolo[3,4-d]pyrimidin-1-yl)-8-methyl-5,6,7,8-tetrahydroquinolin-8-yl)acetamide

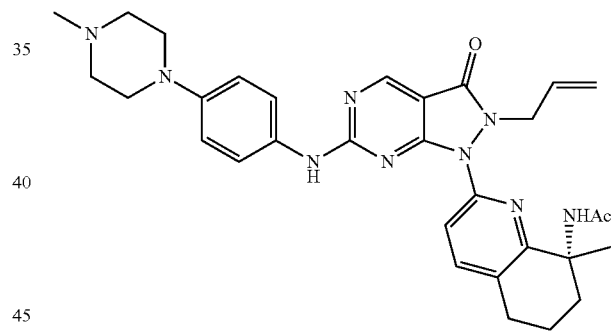

Examples 41A and 41B were prepared by following a procedure described for Examples 9A and 9B using Intermediate 17 and Intermediate 55 to give racemic N-(2-(2-allyl-6-((4-(4-methylpiperazin-1-yl)phenyl)amino)-3-oxo-2,3-dihydro-1H-pyrazolo[3,4-d]pyrimidin-1-yl)-8-methyl-5,6,7,8-tetrahydroquinolin-8-yl)acetamide (220 mg). The enantiomers were separated by chiral SFC chromatography (Chiralpak IC, (40.0% (0.5% DEA in MeOH)) to give Peak 1 (Example 41A, 70 mg) and Peak 2 (Example 41B, 50 mg). Example 41A: yellow solid; $^1$H NMR (400 MHz, DMSO-d$_6$) δ 10.12 (brs, 1H), 8.80 (s, 1H), 8.18 (s, 1H), 7.71 (d, J=7.6 Hz, 1H), 7.60 (d, J=8.0 Hz, 3H), 6.96 (d, J=8.8 Hz, 2H), 5.60-5.55 (m, 1H), 4.97 (d, J=10.0 Hz, 1H), 4.87 (d, J=17.2 Hz, 1H), 4.75-4.70 (m, 1H), 4.53-4.51 (m, 1H), 3.30-3.10 (m, 4H), 2.93-2.76 (m, 6H), 2.68-2.58 (m, 4H), 1.86-1.68 (m, 6H), 1.40 (s, 3H); MS (ESI) 568.2 [M+H]$^+$. Example 41B: yellow solid; $^1$H NMR (400 MHz, DMSO-d$_6$) δ 10.12 (brs, 1H), 8.79 (s, 1H), 8.17 (s, 1H), 7.71 (d, J=7.6 Hz, 1H), 7.60 (d, J=8.0 Hz, 3H), 6.92 (d, J=8.8 Hz, 2H), 5.60-5.55 (m, 1H), 4.97 (d, J=10.4 Hz, 1H), 4.87 (d, J=17.2 Hz, 1H), 4.73-4.69 (m, 1H), 4.53-4.48 (m, 1H), 3.10 (s, 4H), 2.79 (m, 2H), 2.63-2.58 (m, 1H), 2.47-2.44 (m, 4H), 2.22 (s, 3H), 1.84-1.68 (m, 6H), 1.40 (s, 3H); MS (ESI) 568.2 [M+H]$^+$. The absolute stereochemistry was arbitrarily assigned for Example 41A and Example 41B.

Example 42

2-allyl-1-(8-amino-8-methyl-5,6,7,8-tetrahydroquinolin-2-yl)-6-((4-(4-methylpiperazin-1-yl)phenyl)amino)-1,2-dihydro-3H-pyrazolo[3,4-d]pyrimidin-3-one

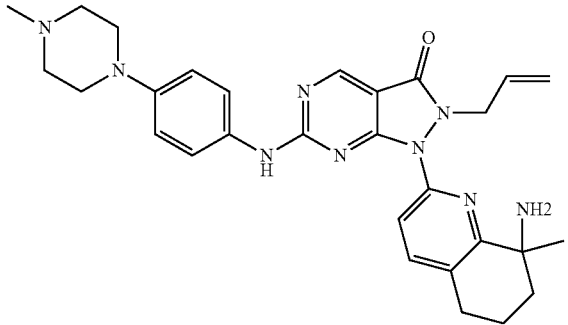

To a stirred solution of N-(2-(2-allyl-6-((4-(4-methylpiperazin-1-yl)phenyl)amino)-3-oxo-2,3-dihydro-1H-pyrazolo[3,4-d]pyrimidin-1-yl)-8-methyl-5,6,7,8-tetrahydroquinolin-8-yl)acetamide (500 mg, 0.881 mmol) in a pressure tube was added 1,4-dioxane (10 mL) and 6M HCl (10 mL). The reaction was heated at 100° C. for 16 h. The reaction was concentrated under reduced pressure and the pH was adjusted to 8 with 1 M NaOH. The mixture was extracted with 10% MeOH/DCM (3×50 mL). The combined organic layers were dried (Na$_2$SO$_4$), filtered and concentrated under reduced pressure. The crude residue was purified by HPLC chromatography (C18, water/CH$_3$CN) to afford Example 42 (90 mg, 19%) as a pale yellow solid. $^1$H NMR (300 MHz, DMSO-d$_6$) δ 10.15 (brs, 1H), 8.81 (s, 1H), 7.74 (d, J=8.1 Hz, 1H), 7.65-7.52 (m, 3H), 6.92 (d, J=9.3 Hz, 2H), 5.76-5.60 (m, 1H), 5.00 (d, J=10.2 Hz, 1H), 4.86 (d, J=17.1 Hz, 1H), 4.74-4.60 (m, 2H), 3.15-3.05 (m, 4H), 2.85-2.75 (m, 2H), 2.48-2.43 (m, 4H), 2.25 (s, 3H), 1.90-1.75 (m, 6H), 1.35 (s, 3H); MS (ESI) 526.2 [M+H]$^+$.

Procedure A
Wee1 Binding Assay

Wee 1 kinase was determined by using Fluorescence Resonance Energy Transfer (FRET) assay. In 384-well plates, Wee1 kinase (2 nM final concentration) was mixed with AlexaFluor labeled tracer 178 (50 nM final concentration, K$_d$=24 nM), Eu-anti-GST antibody (2 nM final concentration) and then inhibitor (0.003 to 10 micromolar) in a final volume of 16 µl kinase buffer (50 mM HEPES pH 7.5, 0.01% BRIJ-35, 10 mM MgCl$_2$, 1 mM EGTA). The plate was shaken for 30 seconds, incubated for 60 min at RT, and recorded on fluorescence plate reader. The results are shown in Table 1.

Procedure B
H23 Cellular Proliferation Assay

H23[ATCC (CRL-5800™)] cells were grown and maintained in RPMI-1640 medium with 10% FBS and 1% penicillin-streptomycin. Cells were treated with compounds diluted in DMSO and a 9 point 5-fold serial dilutions. Plates were placed in 37° C., 5% CO$_2$ for to incubate for 4 days. Before they were developed by adding 100 µL of CellTiter-Glo reagent (Promega) to the assay plate, plates were shaken briefly for 2 mins and allowed to incubate at rt for 10 mins. The plates are read with a M5e plate reader according to CellTiter-Glo protocol. The GraphPad Prism software is used to get IC$_{50}$ values. The results are shown in Table 1.

TABLE 1

Wee1 Enzymatic and cellular data

| Example # | Wee1 enzymatic (nM) | H23 (nM) |
|---|---|---|
| AZD1775 | A | B |
| 1A | A | C |
| 1B | A | — |
| 2A | A | C |
| 2B | A | B |
| 3A | A | C |
| 3B | A | B |
| 4A | A | C |
| 4B | A | C |
| 5A | — | C |
| 5B | — | B |
| 6A | — | C |
| 6B | — | B |
| 7 | A | C |
| 8 | A | B |
| 9A | A | B |
| 9B | A | B |
| 10A | A | B |
| 10B | A | B |
| 11A | A | C |
| 11B | A | B |
| 12A | A | B |
| 12B | A | A |
| 13A | — | B |
| 13B | — | A |
| 14 | — | B |
| 15A | A | C |
| 15B | A | B |
| 16A | — | B |
| 16B | A | B |
| 17A | — | B |
| 17B | — | B |
| 18A | — | B |
| 18B | — | B |
| 19A | — | C |
| 19B | — | B |
| 20A | — | C |
| 20B | — | B |
| 21A | A | C |
| 21B | A | B |
| 22A | B | C |
| 22B | A | B |
| 23A | — | B |
| 23B | — | A |
| 24A | — | B |
| 24B | — | B |
| 25A | A | B |
| 25B | A | B |
| 26A | A | C |
| 26B | A | A |
| 27A | A | B |
| 27B | A | B |
| 28A | — | B |
| 28B | — | B |
| 30A | A | B |
| 30B | A | B |
| 31A | — | A |
| 31B | — | A |
| 32 | B | C |
| 33 | B | C |
| 34 | A | — |
| 35A | B | C |
| 35B | B | C |
| 36A | B | C |
| 36B | C | C |
| 37A | — | C |

TABLE 1-continued

Wee1 Enzymatic and cellular data

| Example # | Wee1 enzymatic (nM) | H23 (nM) |
|---|---|---|
| 37B | — | C |
| 38A | — | C |
| 38B | — | B |
| 39A | — | B |
| 39B | — | B |
| 40A | — | B |
| 40B | — | A |
| 41A | — | C |
| 41B | — | C |

For Wee1 enzymatic $IC_{50}$: A = a single $IC_{50}$ ≤10 nM; B = a single $IC_{50}$ >10 nM and <100 nM; C = a single $IC_{50}$ ≥100 nM. For H23 CTG $IC_{50}$: A = a single $IC_{50}$ ≤100 nM; B = a single $IC_{50}$ >100 nM and <1000 nM; C = a single $IC_{50}$ ≥1000 nM.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

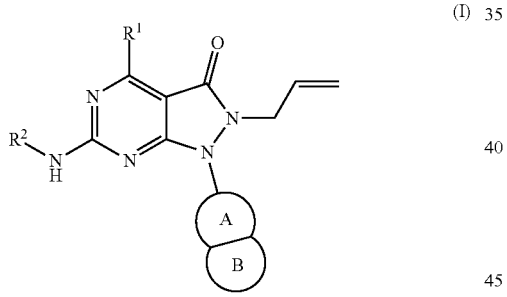

(I)

wherein:

$R^1$ is selected from the group consisting of hydrogen, halogen and a substituted or unsubstituted $C_1$-$C_6$ alkyl;

Ring A is selected from the group consisting of a substituted or unsubstituted phenyl and a substituted or unsubstituted 5-6 membered monocyclic heteroaryl;

Ring B is selected from the group consisting of a substituted or unsubstituted monocyclic 5-7 membered carbocyclyl and a substituted or unsubstituted 5-7 membered monocyclic heterocyclyl;

$R^2$ is selected from the group consisting of

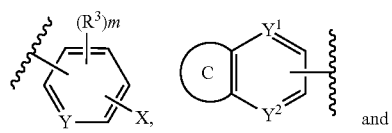 and

-continued

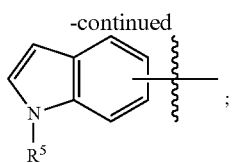;

m is 0, 1, 2 or 3;

$R^3$ is selected from the group consisting of halogen and a substituted or unsubstituted $C_1$-$C_6$ alkyl;

X is selected from the group consisting of hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl;

Y is CH or N;

$Y^1$ is $CR^{4A}$ or N;

$Y^2$ is $CR^{4B}$ or N;

Ring C is selected from the group consisting of a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl;

$R^{4A}$ and $R^{4B}$ are independently selected from the group consisting of hydrogen, halogen and an unsubstituted $C_{1-4}$ alkyl; and $R^5$ is a substituted or unsubstituted 5-7 membered monocyclic heterocyclyl.

2. The compound of claim 1, wherein $R^1$ is hydrogen.

3. The compound of claim 1, wherein Ring A is a substituted or unsubstituted 5-6 membered monocyclic heteroaryl.

4. The compound of claim 3, wherein

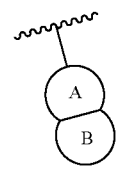

is selected from the group consisting of:

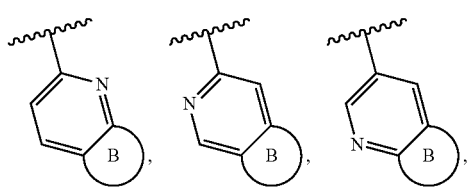

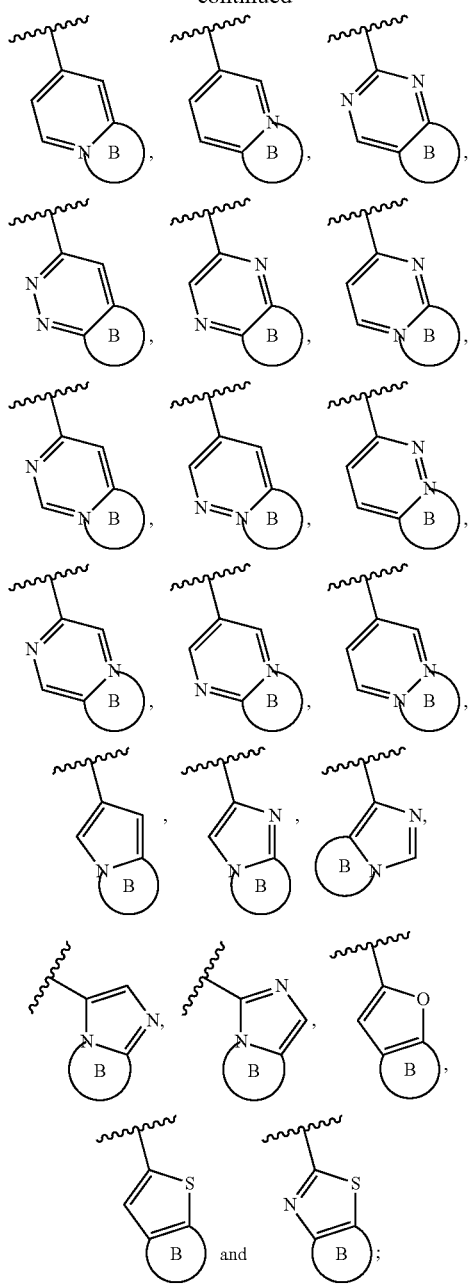

wherein each of the aforementioned groups are substituted or unsubstituted.

5. The compound of claim 3, wherein Ring A is unsubstituted.

6. The compound of claim 1, wherein Ring B is a substituted or unsubstituted monocyclic 5-7 membered carbocyclyl.

7. The compound of claim 6, wherein Ring B is a substituted monocyclic 5 membered carbocyclyl.

8. The compound of claim 6, wherein Ring B is substituted with 1, 2 or 3 substituents independently selected from the group consisting of fluoro, hydroxy, amino, an unsubstituted —NHC(O)$C_1$-$C_6$ alkyl, an unsubstituted $C_1$-$C_6$ haloalkyl and an unsubstituted $C_1$-$C_6$ alkyl.

9. The compound of claim 1, wherein $R^2$ is

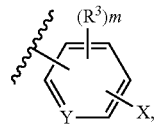

wherein Y is CH.

10. The compound of claim 9, wherein X is a substituted or unsubstituted 4-6 membered monocyclic heterocyclyl.

11. The compound of claim 10, wherein X is selected from the group consisting of a substituted or unsubstituted azetidine, a substituted or unsubstituted oxetane, a substituted or unsubstituted diazetidine, a substituted or unsubstituted azaoxetane, a substituted or unsubstituted pyrrolidine, a substituted or unsubstituted tetrahydrofuran, a substituted or unsubstituted imidazoline, a substituted or unsubstituted pyrazolidine, a substituted or unsubstituted piperidine, a substituted or unsubstituted tetrahydropyran, a substituted or unsubstituted piperazine, a substituted or unsubstituted morpholine and a substituted or unsubstituted dioxane.

12. The compound of claim 10, wherein X is substituted.

13. The compound of claim 12, wherein X is substituted with 1 or 2 substituents independently selected from the group consisting of fluorine, an unsubstituted $C_1$-$C_6$ alkyl, an unsubstituted $C_1$-$C_6$ hydroxyalkyl, an unsubstituted amine($C_1$-$C_6$ alkyl) and an unsubstituted ($C_1$-$C_6$ alkyl)acyl.

14. The compound of claim 1, wherein $R^2$ is

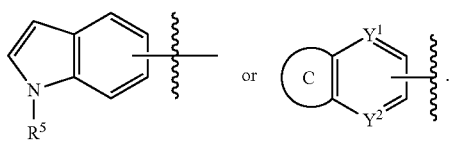

15. The compound of claim 9, wherein m is 0.

16. The compound of claim 1, wherein the compound is selected from the group consisting of:

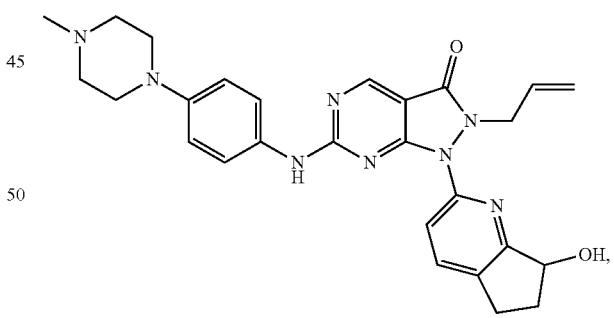

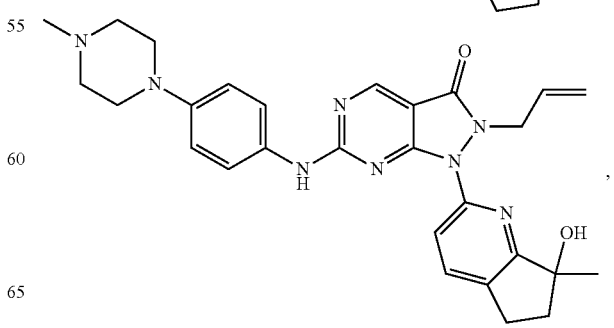

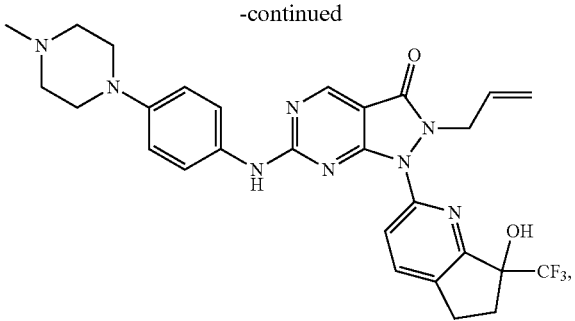
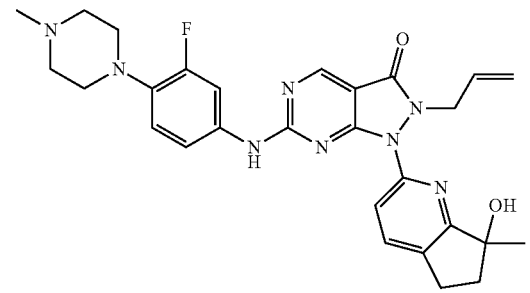
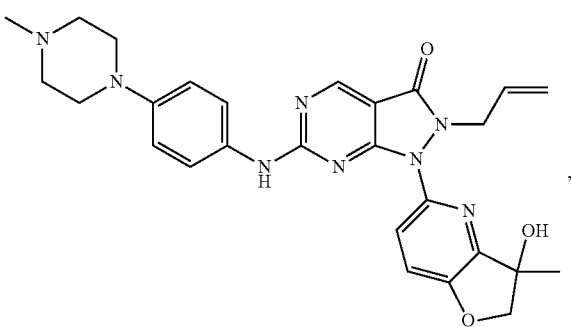
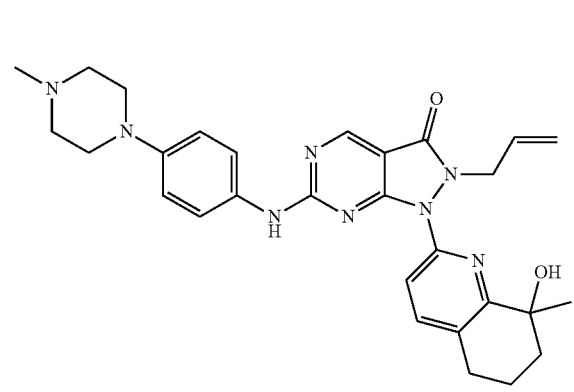
or a pharmaceutically acceptable salt of any of the foregoing.
17. The compound of claim 1, wherein the compound is selected from the group consisting of:
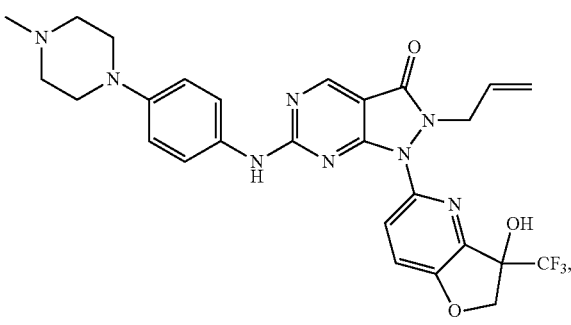
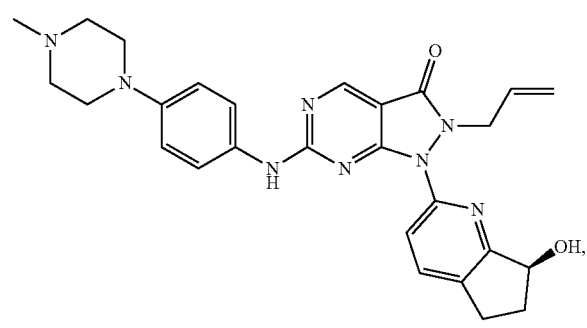
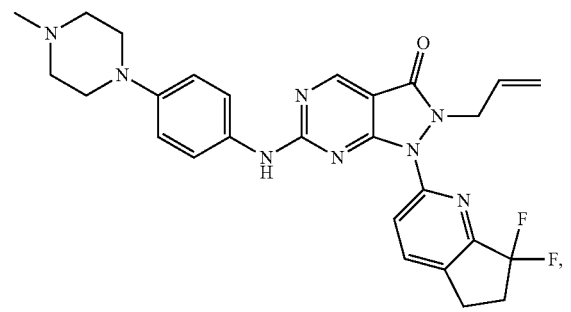
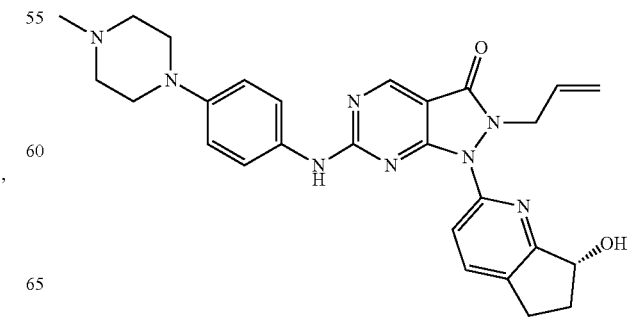

139
-continued
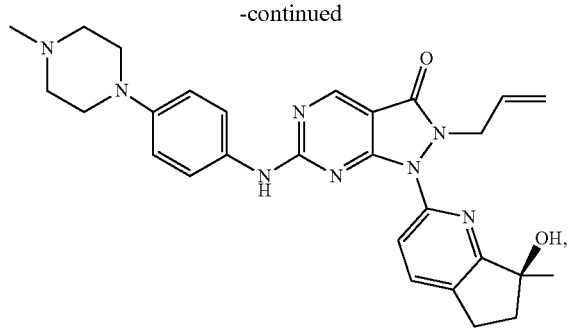
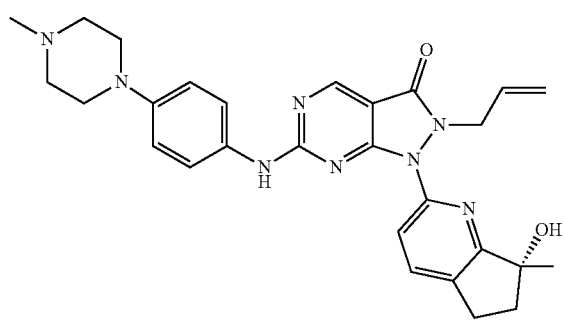
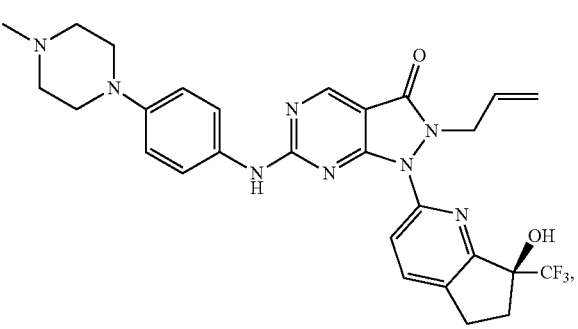
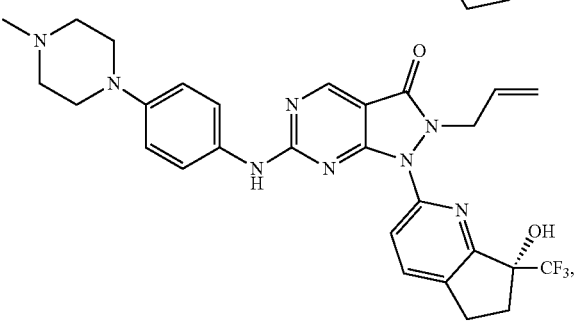
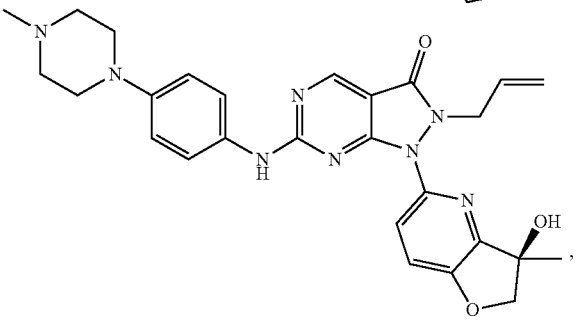
140
-continued
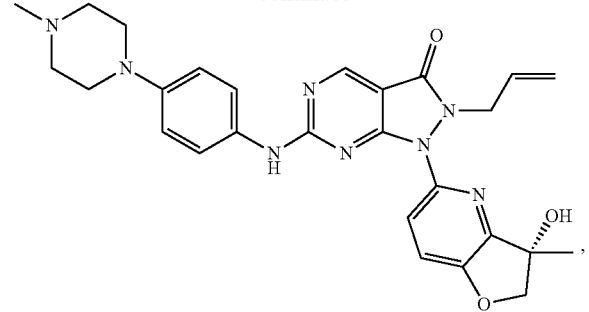
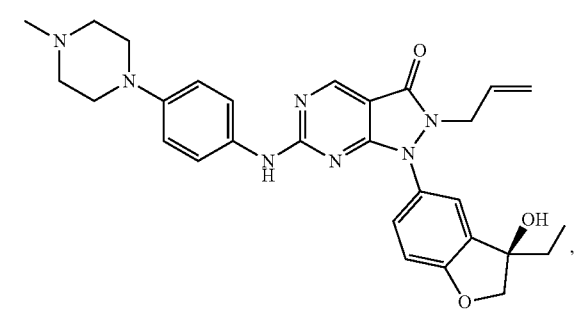
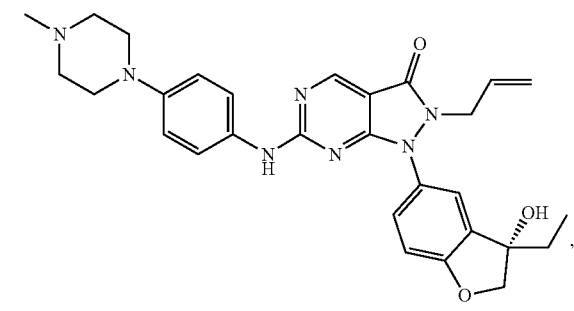
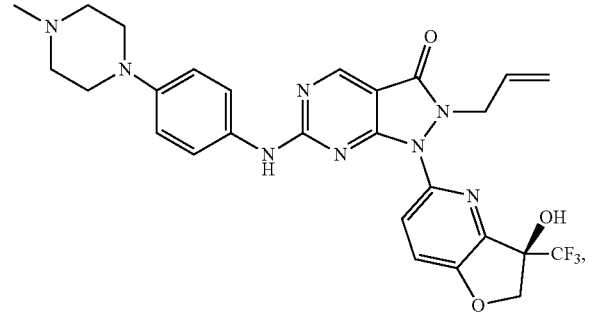
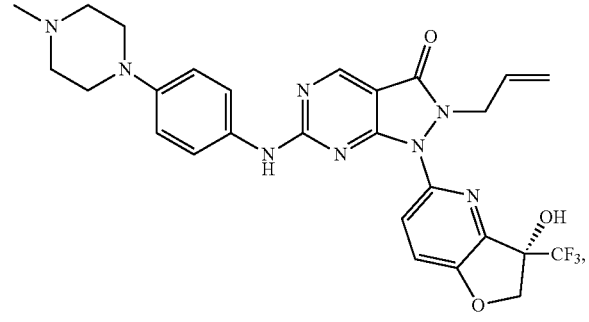

141
-continued
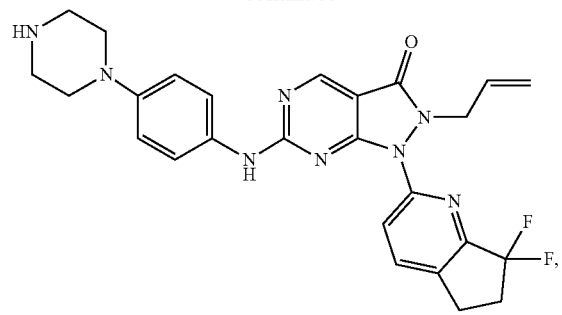
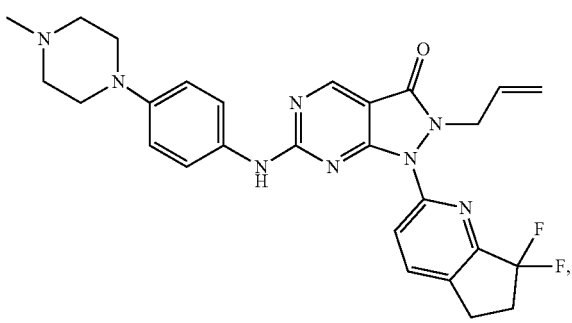
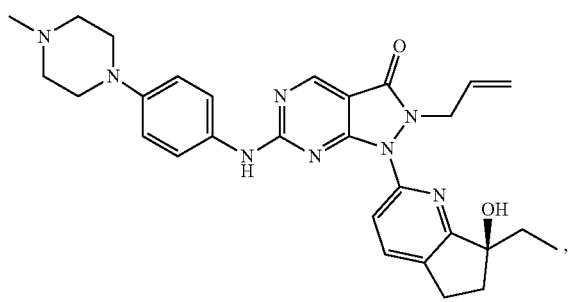
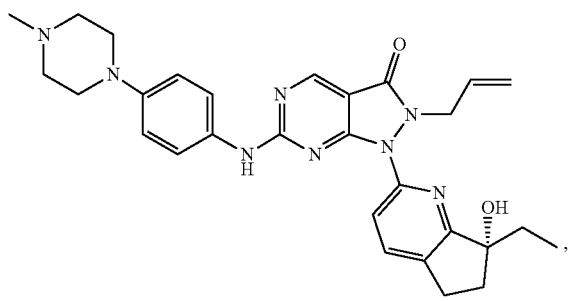
142
-continued
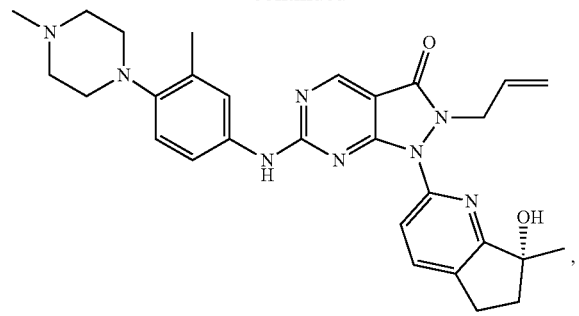
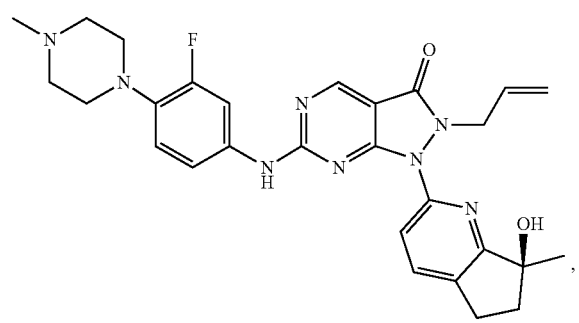
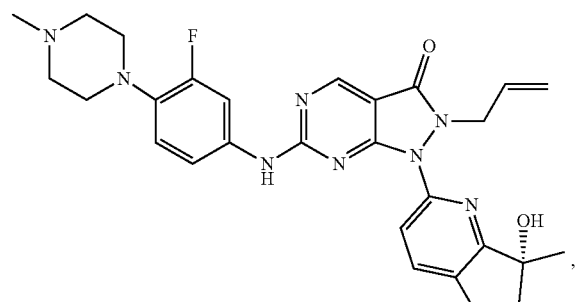
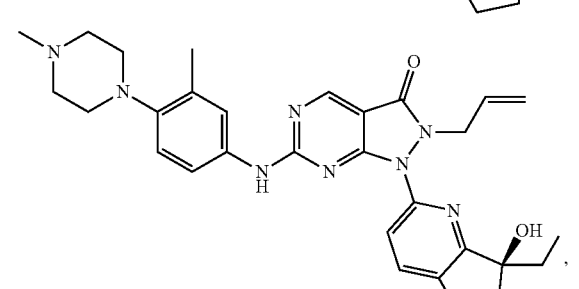
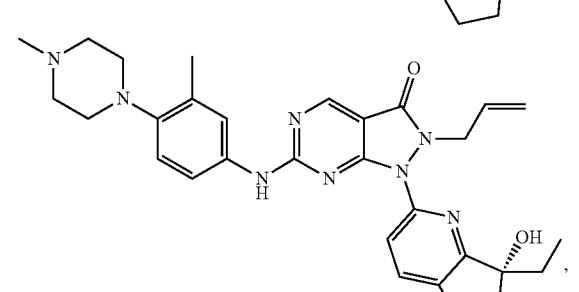

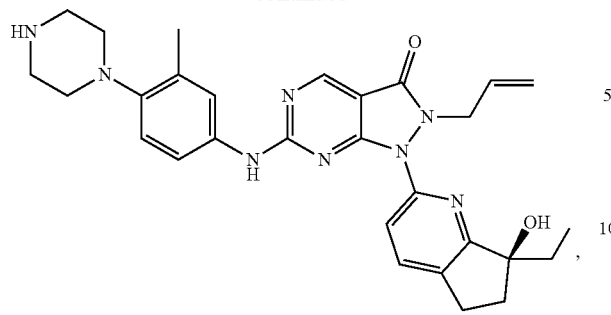
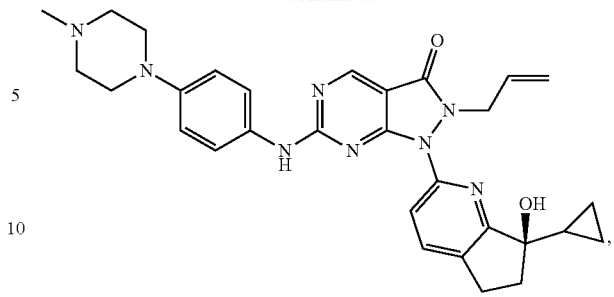
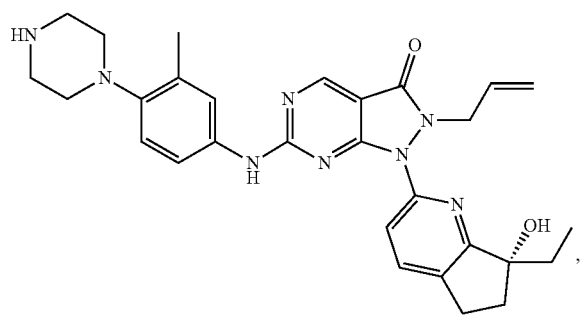
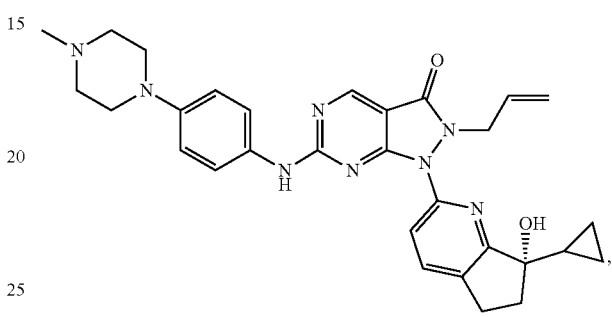
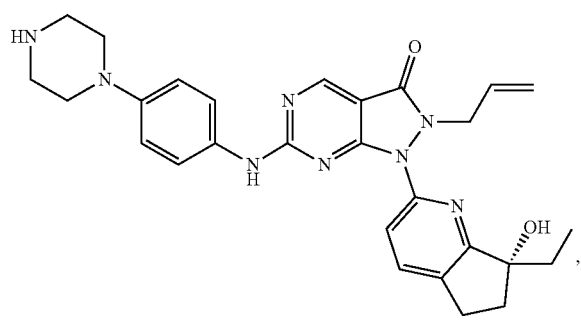
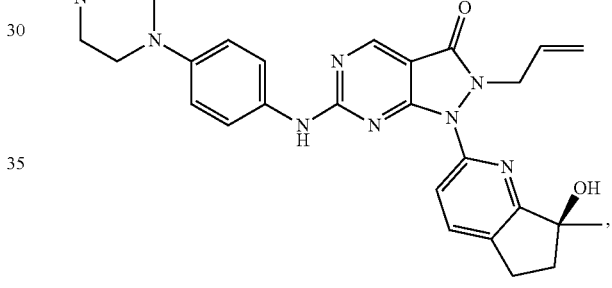
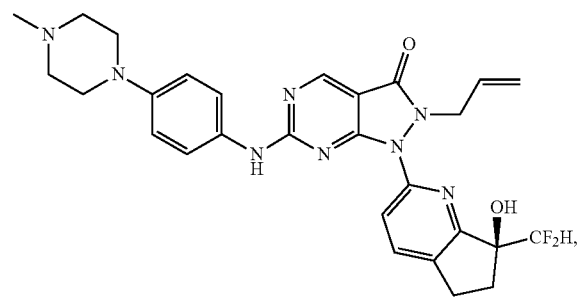
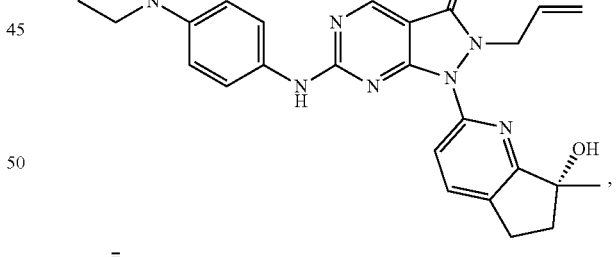
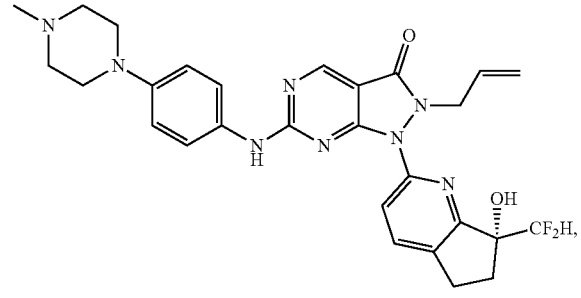
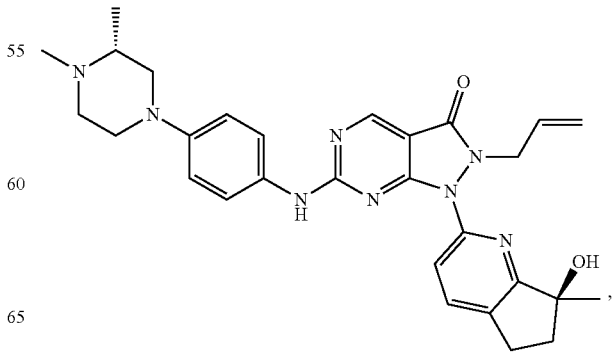

145
-continued
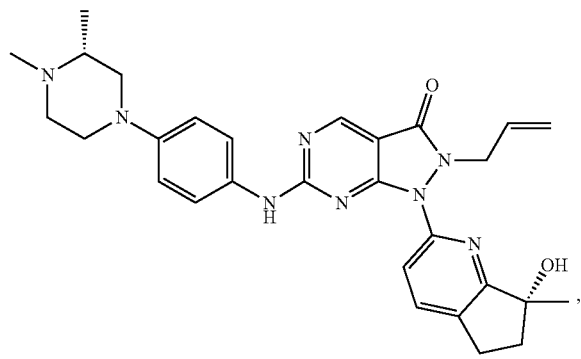
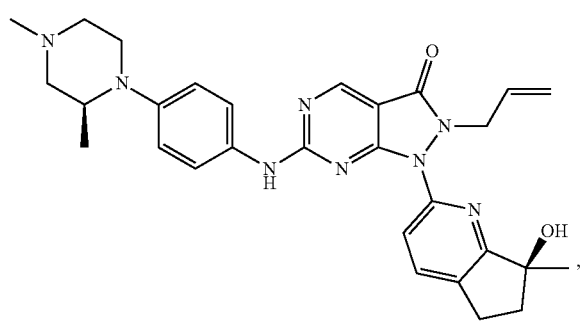
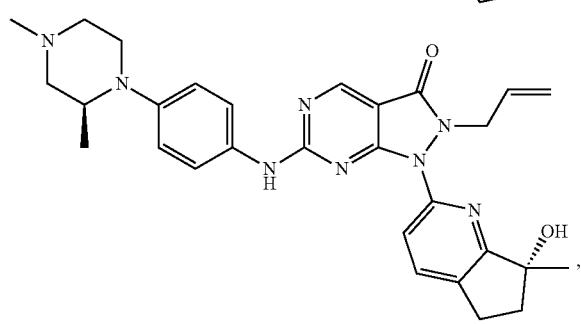
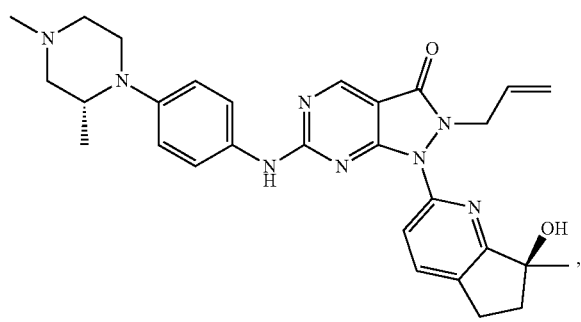
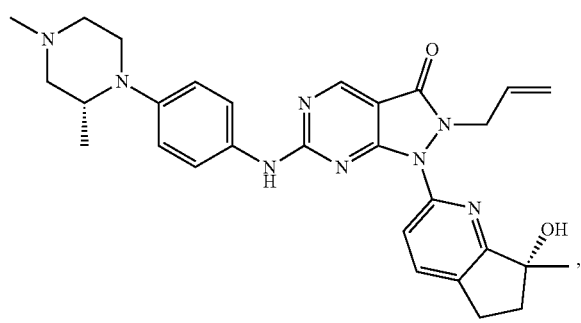
146
-continued
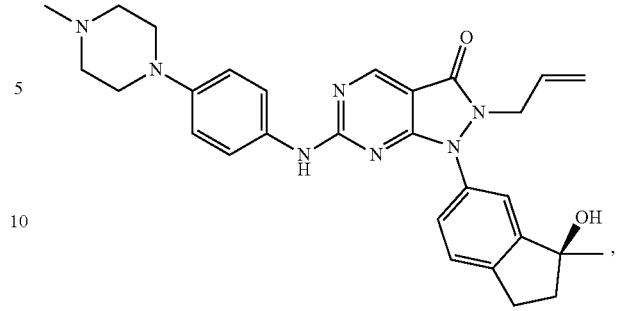

147
-continued
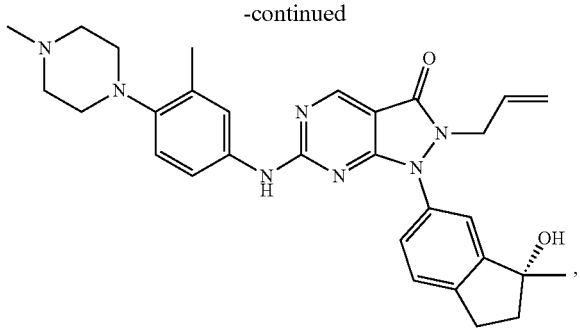
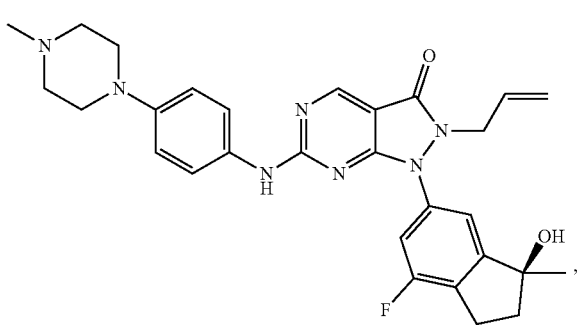
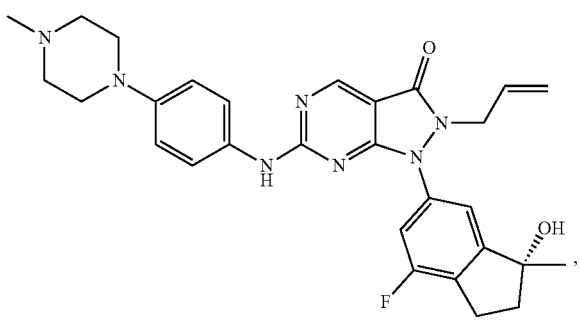
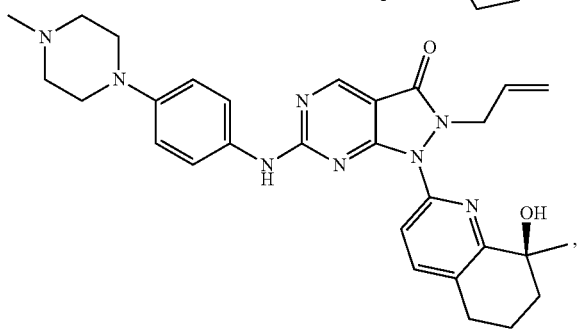
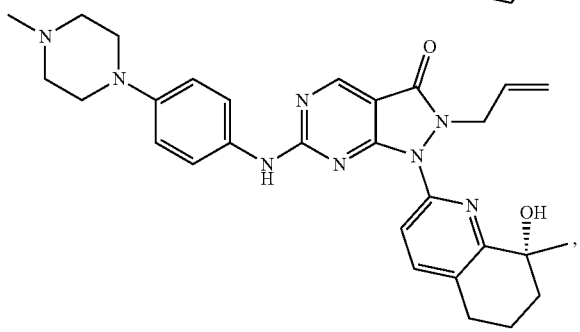
148
-continued
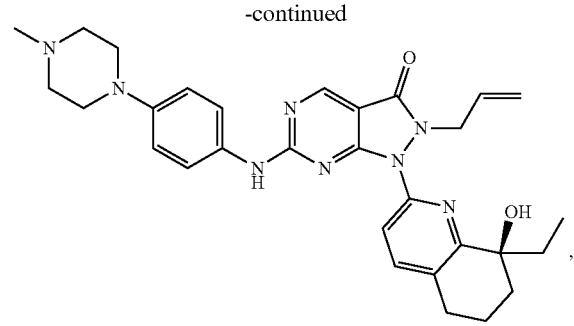
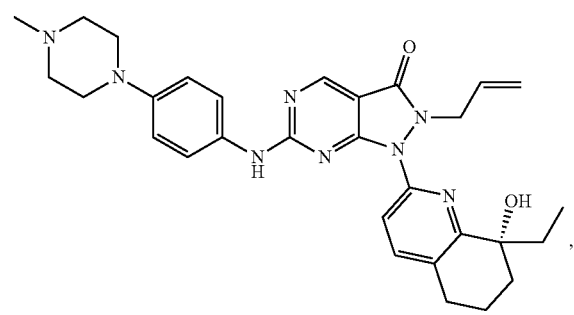
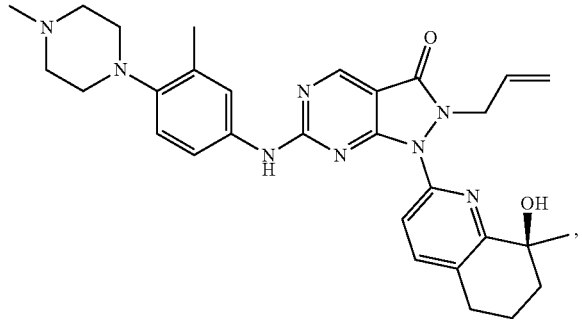
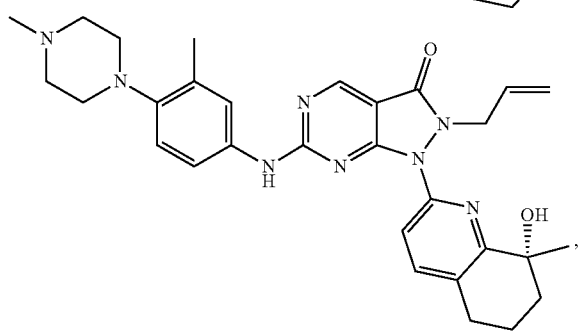
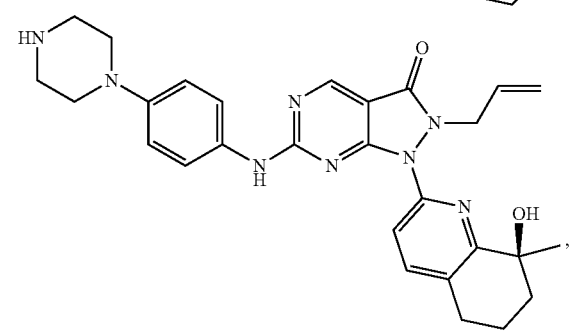

149
-continued
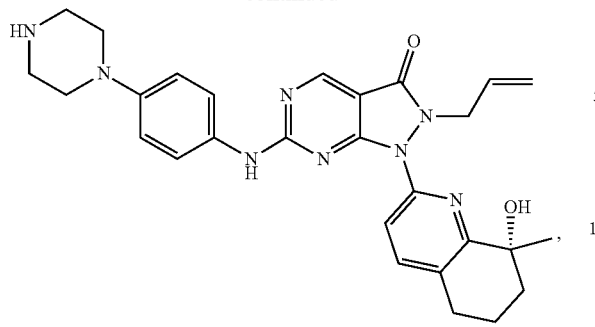
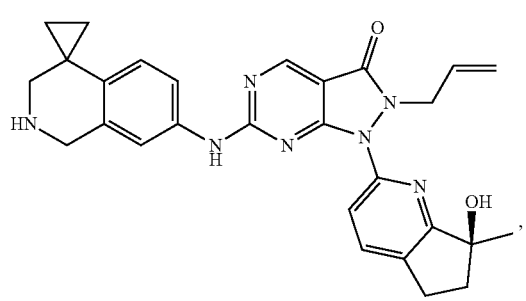
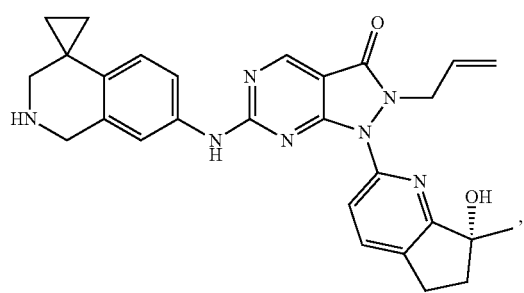
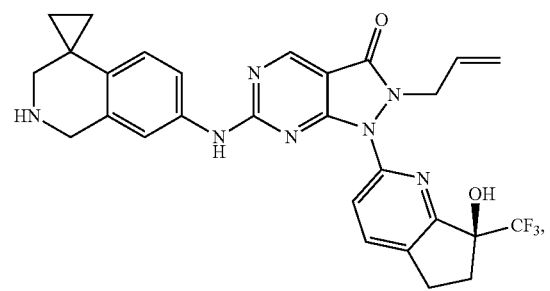
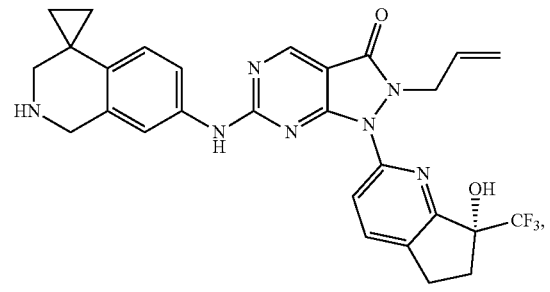
150
-continued
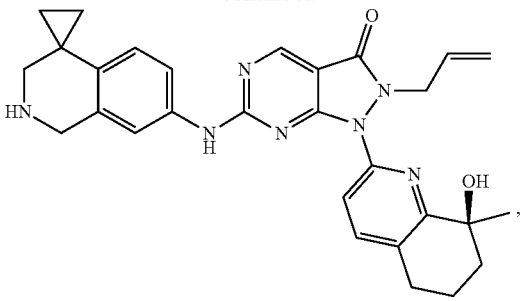
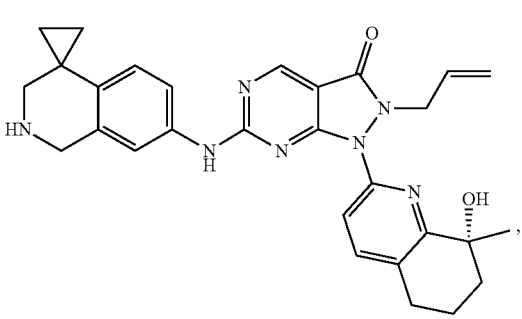
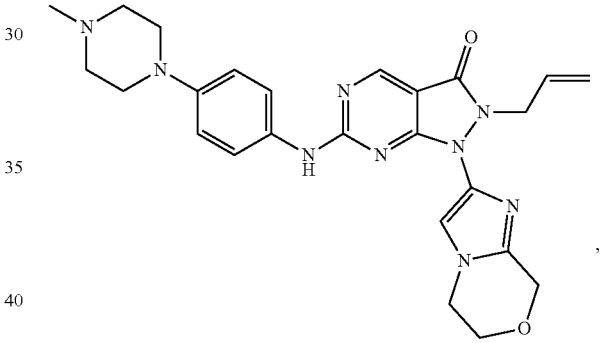
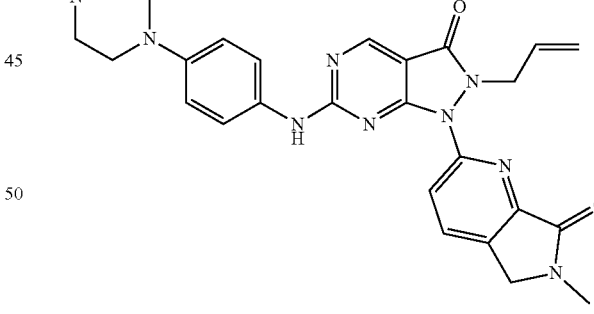
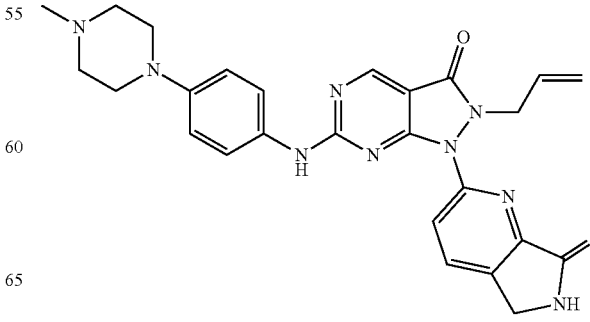

151
-continued
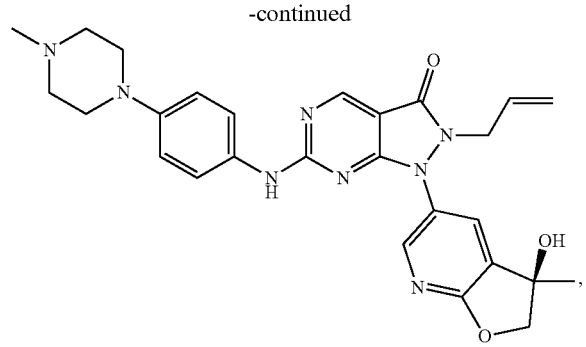
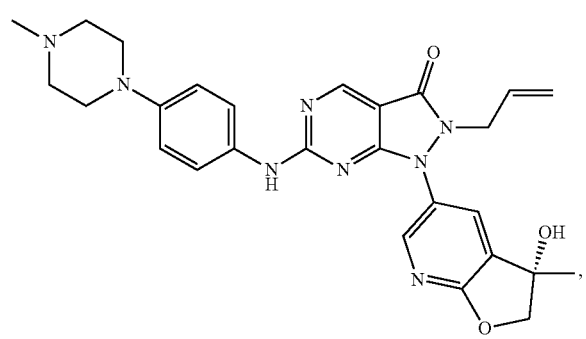
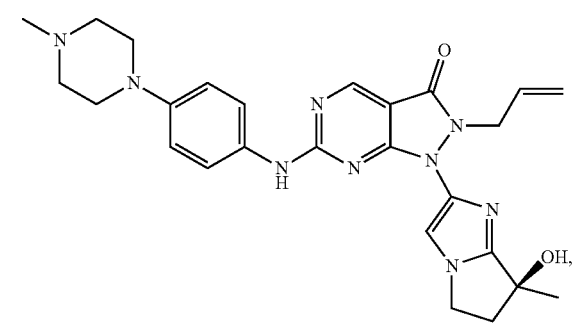
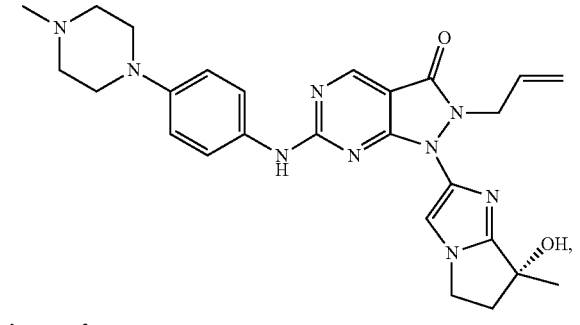
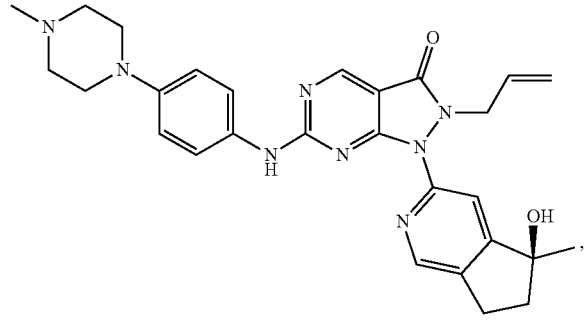
152
-continued
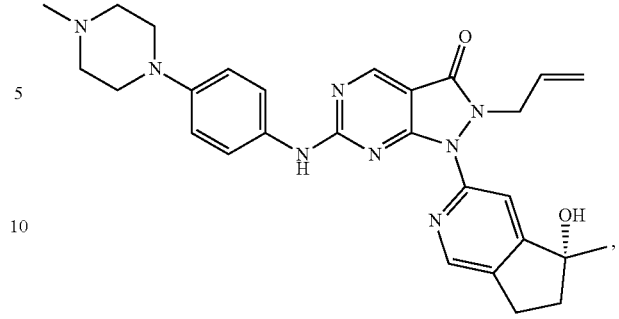
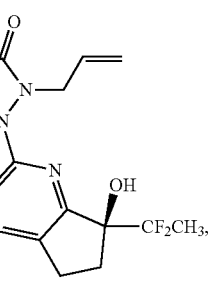
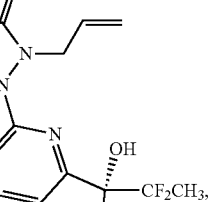
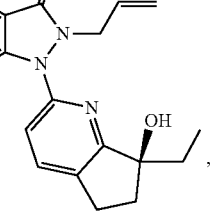
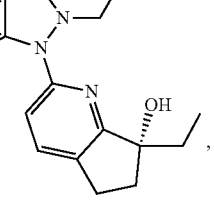
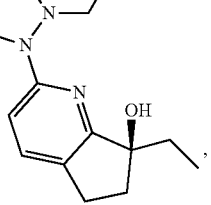

-continued

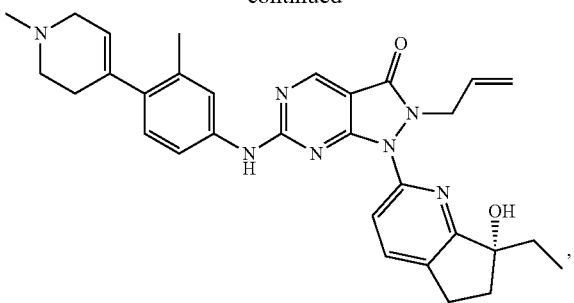

,

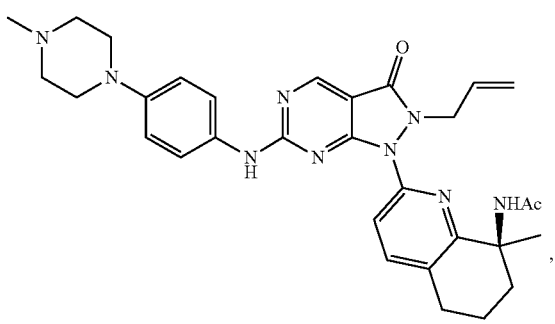

,

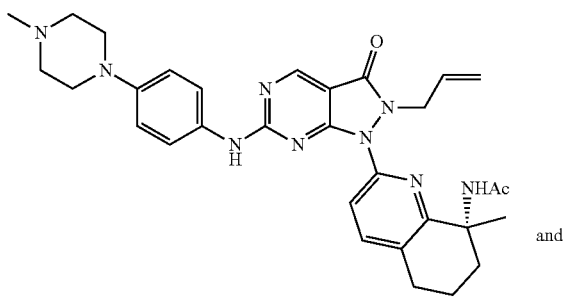

and

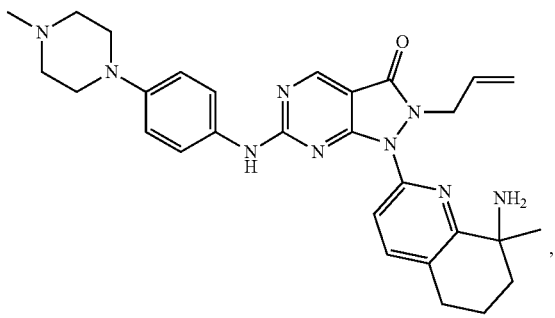

, or a pharmaceutically acceptable salt of any of the foregoing.

18. A pharmaceutical composition comprising an effective amount of the compound of claim 1, or a pharmaceutically acceptable salt thereof, and a pharmaceutically acceptable carrier, diluent, excipient or combination thereof.

19. A method for ameliorating or treating a cancer comprising administering an effective amount of claim 1, or a pharmaceutically acceptable salt thereof, to a subject having the cancer, wherein the cancer is selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

20. A method for inhibiting replication of a malignant growth or a tumor comprising contacting the malignant growth or the tumor with an effective amount of claim 1, or a pharmaceutically acceptable salt thereof, wherein the malignant growth or tumor is due to a cancer selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

21. A method for ameliorating or treating a malignant growth or a tumor comprising contacting the malignant growth or the tumor with an effective amount of claim 1, or a pharmaceutically acceptable salt thereof, wherein the malignant growth or tumor is due to a cancer selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

22. The compound of claim 16, wherein the compound is

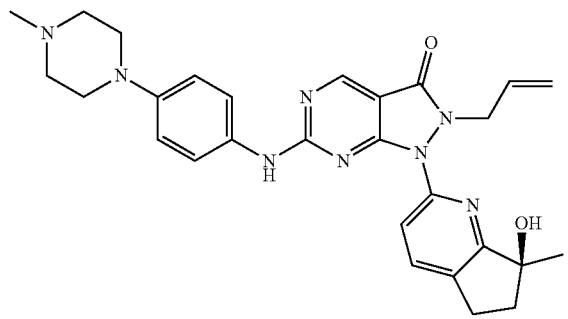

or a pharmaceutically acceptable salt thereof.

23. The compound of claim 16, wherein the compound is

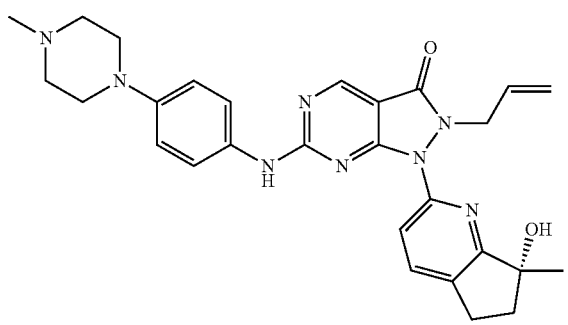

or a pharmaceutically acceptable salt thereof.

24. The compound of claim 16, wherein the compound is

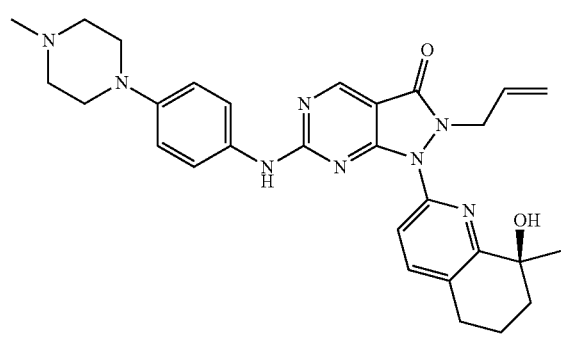

or a pharmaceutically acceptable salt thereof.

25. The compound of claim 16, wherein the compound is

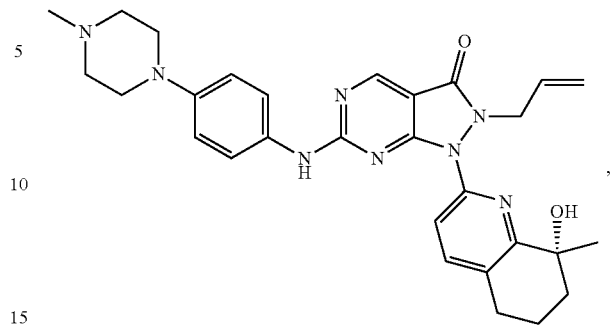

or a pharmaceutically acceptable salt thereof.

26. The compound of claim 17, wherein the compound is

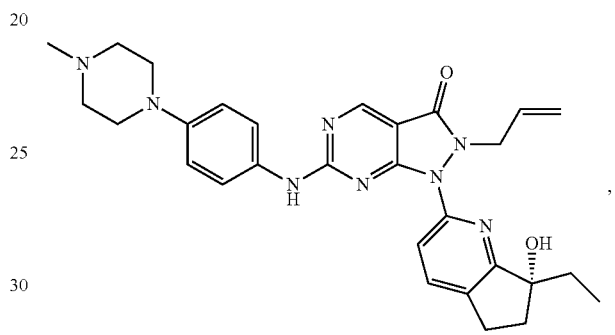

or a pharmaceutically acceptable salt thereof.

27. The compound of claim 17, wherein the compound is

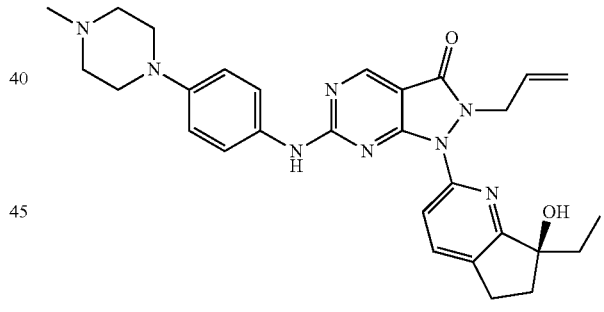

or a pharmaceutically acceptable salt thereof.

* * * * *